United States Patent
Lambert et al.

(10) Patent No.: US 8,927,729 B2
(45) Date of Patent: Jan. 6, 2015

(54) PESTICIDAL COMPOSITIONS

(71) Applicant: Dow AgroSciences LLC, Indianapolis, IN (US)

(72) Inventors: William T. Lambert, Westfield, IN (US); Gary D. Crouse, Noblesville, IN (US); Thomas C. Sparks, Greenfield, IN (US); Denise P. Cudworth, Indianapolis, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

(21) Appl. No.: 14/157,849

(22) Filed: Jan. 17, 2014

(65) Prior Publication Data

US 2014/0135364 A1 May 15, 2014

Related U.S. Application Data

(62) Division of application No. 13/389,062, filed as application No. PCT/US2010/044538 on Aug. 5, 2010, now Pat. No. 8,674,109.

(60) Provisional application No. 61/232,142, filed on Aug. 7, 2009.

(51) Int. Cl.
*A61K 31/44* (2006.01)
*C07D 401/00* (2006.01)
*A01N 47/18* (2006.01)
*C07D 249/10* (2006.01)
*C07D 409/12* (2006.01)
*C07D 417/12* (2006.01)
*C07D 401/12* (2006.01)
*A01N 47/20* (2006.01)
*C07D 413/12* (2006.01)
*C07H 13/12* (2006.01)
*C07D 405/12* (2006.01)
*C07D 403/12* (2006.01)

(52) U.S. Cl.
CPC ............... *A01N 47/20* (2013.01); *A01N 47/18* (2013.01); *C07D 249/10* (2013.01); *C07D 409/12* (2013.01); *C07D 417/12* (2013.01); *C07D 401/12* (2013.01); *C07D 413/12* (2013.01); *C07H 13/12* (2013.01); *C07D 405/12* (2013.01); *C07D 403/12* (2013.01)
USPC ....................................... 546/272.4; 514/346

(58) Field of Classification Search
None
See application file for complete search history.

(56) References Cited

U.S. PATENT DOCUMENTS

| 4,833,158 A | 5/1989 | Twydell et al. |
|---|---|---|
| 8,178,658 B2 | 5/2012 | Crouse et al. |
| 2007/0066617 A1 | 3/2007 | Mita et al. |
| 2012/0053216 A1 | 3/2012 | Creemer et al. |
| 2012/0172217 A1 | 7/2012 | Brown et al. |
| 2012/0202687 A1 | 8/2012 | Crouse et al. |
| 2012/0202688 A1 | 8/2012 | Crouse et al. |
| 2013/0019348 A1 | 1/2013 | Crouse et al. |

FOREIGN PATENT DOCUMENTS

| EP | 10807152.3 | 2/2013 |
|---|---|---|
| WO | WO98/47894 A1 | 10/1998 |
| WO | WO00/24735 A1 | 5/2000 |
| WO | WO2007/125984 A1 | 11/2007 |
| WO | WO2009/102736 A1 | 8/2009 |

OTHER PUBLICATIONS

U.S. Appl. No. 13/747,497, filed Jan. 23, 2013 by Dow AgroSciences LLC.
U.S. Appl. No. 13/746,621, filed Jan. 22, 2013 by Dow AgroSciences LLC.
Kagabu S and Medej S, "Stability Comparison of Imidacloprid and Related Compounds under Simulated Sunlight, Hydrolysis Conditions, and to Oxygen" Biosci. Biotech. Biochem., 59 (6), 980-985, (1995).
Kagabu S, Murata N, Hibino R, Hanzawa M, and Nishimura K, "Insecticidal and Neuroblocking Activities of Thiamethoxam-Type Compounds in the American Cockroach (*Periplaneta americana* L.)" J. Pesticide Sci. 30 (2), 111-115 (2005).
Kollmeyer, WD, Flattum RF, Foster JP, Powell JE, Schroeder ME, and Soloway SB, "Discovery of the Nitromethylene Heterocycle Insecticides" Nicotinoid Insecticides and the Nicotinic Acetylcholine Receptor (pp. 71-89) Eds Yamamoto I, and Casida JE.
Shiga Y, Okada I, and Fukuchi T, "Synthesis and Acaricidal Activity of N-(1,3,4-Thiadiazol-2-yl) cyclopropanecarboxamides" J. Pesticide Sci. 28, 61-63 (2003).
Sparks TC, Crouse GD, and Durst D, "Natural products as insecticides: the biology, biochemistry and quantitative structure-activity relationships of spinosyns and spinosoids" Pest Manag Sci 57:896-905 (2001).
Wakita T, Kinoshita K, Kodaka K, Yasui N, Naoi A, and Banba S "Synthesis and Structure Activity Relationships of Dinotefuran Derivatives: Modification in the Tetrahydro-3-furylmethyl Part" J. Pesticide Sci. 29 (4), 356-363 (2004).
Ertl P. "Cheminformatics Analysis of Organic Substituents: Identification of the Most Common Substituents, Calculation of Substituents Properties, and Automatic Identification of Drug-like Bioisosteric Groups" J. Chem Inf. Comput. Sci. 2003, 43, 374-380.

*Primary Examiner* — Heidi Reese
(74) *Attorney, Agent, or Firm* — Carl D. Corvin

(57) ABSTRACT

Pesticidal compositions and their uses are disclosed.

4 Claims, No Drawings

PESTICIDAL COMPOSITIONS

CROSS-REFERENCE TO RELATED APPLICATIONS

This Application claims is a divisional of U.S. patent application Ser. No. 13/389,062, filed 8 Mar. 2012, which is a national stage of international application PCT/US2010/044538, filed 5 Aug. 2010, which claims the benefit of U.S. provisional application Ser. No. 61/232,142 filed on 7 Aug. 2009, the entire disclosures of which are hereby incorporated by reference.

FIELD OF THE INVENTION

The invention disclosed in this document is related to the field of pesticides and their use in controlling pests.

BACKGROUND OF THE INVENTION

Pests cause millions of human deaths around the world each year. Furthermore, there are more than ten thousand species of pests that cause losses in agriculture. These agricultural losses amount to billions of U.S. dollars each year. Termites cause damage to various structures such as homes. These termite damage losses amount to billions of U.S. dollars each year. As a final note, many stored food pests eat and adulterate stored food. These stored food losses amount to billions of U.S. dollars each year, but more importantly, deprive people of needed food.

There is an acute need for new pesticides. Insects are developing resistance to pesticides in current use. Hundreds of insect species are resistant to one or more pesticides. The development of resistance to some of the older pesticides, such as DDT, the carbamates, and the organophosphates, is well known. But resistance has even developed to some of the newer pesticides. Therefore, a need exists for new pesticides and particularly for pesticides that have new modes of action.

Substituents

Non-Exhaustive List

The examples given for the substituents are (except for halo) non-exhaustive and must not be construed as limiting the invention disclosed in this document.

"alkenyl" means an acyclic, unsaturated (at least one carbon-carbon double bond), branched or unbranched, substituent consisting of carbon and hydrogen, for example, vinyl, allyl, butenyl, pentenyl, hexenyl, heptenyl, octenyl, nonenyl, and decenyl.

"alkenyloxy" means an alkenyl further consisting of a carbon-oxygen single bond, for example, allyloxy, butenyloxy, pentenyloxy, hexenyloxy, heptenyloxy, octenyloxy, nonenyloxy, and decenyloxy.

"alkoxy" means an alkyl further consisting of a carbon-oxygen single bond, for example, methoxy, ethoxy, propoxy, isopropoxy, 1-butoxy, 2-butoxy, isobutoxy, tert-butoxy, pentoxy, 2-methylbutoxy, 1,1-dimethylpropoxy, hexoxy, heptoxy, octoxy, nonoxy, and decoxy.

"alkyl" means an acyclic, saturated, branched or unbranched, substituent consisting of carbon and hydrogen, for example, methyl, ethyl, propyl, isopropyl, 1-butyl, 2-butyl, isobutyl, tert-butyl, pentyl, 2-methylbutyl, 1,1-dimethylpropyl, hexyl, heptyl, octyl, nonyl, and decyl.

"alkynyl" means an acyclic, unsaturated (at least one carbon-carbon triple bond, and any double bonds), branched or unbranched, substituent consisting of carbon and hydrogen, for example, ethynyl, propargyl, butynyl, pentynyl, hexynyl, heptynyl, octynyl, nonynyl, and decynyl.

"alkynyloxy" means an alkynyl further consisting of a carbon-oxygen single bond, for example, pentynyloxy, hexynyloxy, heptynyloxy, octynyloxy, nonynyloxy, and decynyloxy.

"aryl" means a cyclic, aromatic substituent consisting of hydrogen and carbon, for example, phenyl, naphthyl, and biphenyl.

"cycloalkenyl" means a monocyclic or polycyclic, unsaturated (at least one carbon-carbon double bond) substituent consisting of carbon and hydrogen, for example, cyclobutenyl, cyclopentenyl, cyclohexenyl, cycloheptenyl, cyclooctenyl, cyclodecenyl, norbornenyl, bicyclo[2.2.2]octenyl, tetrahydronaphthyl, hexahydronaphthyl, and octahydronaphthyl.

"cycloalkenyloxy" means a cycloalkenyl further consisting of a carbon-oxygen single bond, for example, cyclobutenyloxy, cyclopentenyloxy, cyclohexenyloxy, cycloheptenyloxy, cyclooctenyloxy, cyclodecenyloxy, norbornenyloxy, and bicyclo[2.2.2]octenyloxy.

"cycloalkyl" means a monocyclic or polycyclic, saturated substituent consisting of carbon and hydrogen, for example, cyclopropyl, cyclobutyl, cyclopentyl, cyclohexyl, cycloheptyl, cyclooctyl, cyclodecyl, norbornyl, bicyclo[2.2.2]octyl, and decahydronaphthyl.

"cycloalkoxy" means a cycloalkyl further consisting of a carbon-oxygen single bond, for example, cyclopropyloxy, cyclobutyloxy, cyclopentyloxy, cyclohexyloxy, cycloheptyloxy, cyclooctyloxy, cyclodecyloxy, norbornyloxy, and bicyclo[2.2.2]octyloxy.

"halo" means fluoro, chloro, bromo, and iodo.

"haloalkyl" means an alkyl further consisting of, from one to the maximum possible number of, identical or different, halos, for example, fluoromethyl, difluoromethyl, trifluoromethyl, 1-fluoroethyl, 2-fluoroethyl, 2,2,2-trifluoroethyl, chloromethyl, trichloromethyl, and 1,1,2,2-tetrafluoroethyl.

"heterocyclyl" means a cyclic substituent that may be fully saturated, partially unsaturated, or fully unsaturated, where the cyclic structure contains at least one carbon and at least one heteroatom, where said heteroatom is nitrogen, sulfur, or oxygen, for example, benzofuranyl, benzoisothiazolyl, benzoisoxazolyl, benzoxazolyl, benzothienyl, benzothiazolyl cinnolinyl, furanyl, indazolyl, indolyl, imidazolyl, isoindolyl, isoquinolinyl, isothiazolyl, isoxazolyl, 1,3,4-oxadiazolyl, oxazolinyl, oxazolyl, phthalazinyl, pyrazinyl, pyrazolinyl, pyrazolyl, pyridazinyl, pyridyl, pyrimidinyl, pyrrolyl, quinazolinyl, quinolinyl, quinoxalinyl, 1,2,3,4-tetrazolyl, thiazolinyl, thiazolyl, thienyl, 1,2,3-triazinyl, 1,2,4-triazinyl, 1,3,5-triazinyl, 1,2,3-triazolyl, and 1,2,4-triazolyl.

DETAILED DESCRIPTION OF THE INVENTION

The compounds of this invention have the following formula:

$$Ar_1-Het-Ar_2-\underset{R_4}{\underset{|}{N_1}}-\underset{X_2}{\overset{X_1}{C}}-\underset{R_3}{\overset{R_2}{\underset{|}{C_1}}}-R_1$$

wherein:
(a) $Ar_1$ is
(1) furanyl, phenyl, pyridazinyl, pyridyl, pyrimidinyl, thienyl, or
(2) substituted furanyl, substituted phenyl, substituted pyridazinyl, substituted pyridyl, substituted pyrimidinyl, or substituted thienyl, wherein said substituted furanyl, substituted phenyl, substituted pyridazinyl, substituted pyridyl, substituted pyrimidinyl, and substituted thienyl, have one or more substituents independently selected from H, F, Cl, Br, I, CN, $NO_2$, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)H$, $C(=O)NR_xR_y$, $(C_1$-$C_6$ alkyl)$NR_xR_y$, $C(=O)(C_1$-$C_6$ alkyl), $C(=O)O(C_1$-$C_6$ alkyl), $C(O)(C_1$-$C_6$ haloalkyl), $C(=O)O(C_1$-$C_6$ haloalkyl), $C(O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(=O)O(C_1$-$C_6$ alkyl), phenyl, phenoxy, substituted phenyl and substituted phenoxy wherein such substituted phenyl and substituted phenoxy have one or more substituents independently selected from H, F, Cl, Br, I, CN, $NO_2$, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)H$, $C(=O)NR_xR_y$, $(C_1$-$C_6$ alkyl)$NR_xR_y$, $C(=O)(C_1$-$C_6$ alkyl), $C(O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(O)O(C_1$-$C_6$ alkyl)phenyl, and phenoxy;

(b) Het is a 5 or 6 membered, saturated or unsaturated, heterocyclic ring, containing one or more heteroatoms independently selected from nitrogen, sulfur, or oxygen, and where $Ar_1$ and $Ar_2$ are not ortho to each other (but may be meta or para, such as, for a five membered ring they are 1,3 and for a 6 membered ring they are either 1, 3 or 1,4), and where said heterocyclic ring may also be substituted with one or more substituents independently selected from H, F, Cl, Br, I, CN, $NO_2$, oxo, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(O)_n(C_1$-$C_6$ haloalkyl), $OSO_2(C_1$-$C_6$ alkyl), $OSO_2(C_1$-$C_6$ haloalkyl), $C(=O)H$, $C(=O)NR_xR_y$, $(C_1$-$C_6$ alkyl)$NR_xR_y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(=O)O(C_1$-$C_6$ alkyl), phenyl, phenoxy, substituted phenyl and substituted phenoxy wherein such substituted phenyl and substituted phenoxy have one or more substituents independently selected from H, F, Cl, Br, I, CN, $NO_2$, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)H$, $C(=O)NR_xR_y$, $(C_1$-$C_6$ alkyl)$NR_xR_y$, $C(=O)(C_1$-$C_6$ alkyl), $C(=O)O(C_1$-$C_6$ alkyl), $C(=O)(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl), $C(=O)O(C_1$-$C_6$ alkyl), phenyl, and phenoxy;

(c) $Ar_2$ is
(1) furanyl, phenyl, pyridazinyl, pyridyl, pyrimidinyl, thienyl, or
(2) substituted furanyl, substituted phenyl, substituted pyridazinyl, substituted pyridyl, substituted pyrimidinyl, or substituted thienyl, wherein said substituted furanyl, substituted phenyl, substituted pyridazinyl, substituted pyridyl, substituted pyrimidinyl, and substituted thienyl, have one or more substituents independently selected from H, F, Cl, Br, I, CN, $NO_2$, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)H$, $C(=O)NR_xR_y$, $(C_1$-$C_6$ alkyl)$NR_xR_y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(O)(C_1$-$C_6$ alkyl)$C(=O)O(C_1$-$C_6$ alkyl), phenyl, phenoxy, substituted phenyl and substituted phenoxy (wherein such substituted phenyl and substituted phenoxy have one or more substituents independently selected from H, F, Cl, Br, I, CN, $NO_2$, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)H$, $C(=O)NR_xR_y$, $(C_1$-$C_6$ alkyl)$NR_xR_y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_1$-$C_6$ haloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(=O)O(C_1$-$C_6$ alkyl), phenyl, and phenoxy;

(d) $X_1$ is O or S;
(e) $X_2$ is O or S;
(f) R4 is H, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)H$, $C(=O)NR_xR_y$, $(C_1$-$C_6$ alkyl)$NR_xR_y$, $C(=O)(C_1$-$C_6$ alkyl), $C(=O)O(C_1$-$C_6$ alkyl), $C(=O)(C_1$-$C_6$ haloalkyl), $C(=O)O(C_1$-$C_6$ haloalkyl), $C(=O)(C_3$-$C_6$ cycloalkyl), $C(=O)O(C_3$-$C_6$ cycloalkyl), $C(=O)(C_2$-$C_6$ alkenyl), $C(=O)O(C_2$-$C_6$ alkenyl), $(C_1$-$C_6$ alkyl)$O(C_1$-$C_6$ alkyl), $(C_1$-$C_6$ alkyl)$S(C_1$-$C_6$ alkyl), $C(=O)(C_1$-$C_6$ alkyl)$C(=O)O(C_1$-$C_6$ alkyl), phenyl, phenoxy, wherein each alkyl, haloalkyl, cycloalkyl, halocycloalkyl, cycloalkoxy, halocycloalkoxy, alkoxy, haloalkoxy, alkenyl, alkynyl, phenyl, and phenoxy are optionally substituted with one or more substituents independently selected from F, Cl, Br, I, CN, $NO_2$, oxo, $C_1$-$C_6$ alkyl, $C_1$-$C_6$ haloalkyl, $C_1C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_2$-$C_6$ alkynyl, $S(=O)_n(C_1$-$C_6$ alkyl), $S(=O)_n(C_1$-$C_6$ haloalkyl), $OSO_2(C_1$-$C_6$ alkyl), $OSO_2(C_1$-$C_6$ haloalkyl), $C(=O)H$, $C(=O)NR_xR_y$, $(C_1$-$C_6$ alkyl)$NR_xR_y$, $C(=O)(C_1$-$C_6$ alkyl), $C(=O)O(C_1$-$C_6$ alkyl), C(=O)($C_1$-$C_6$ haloalkyl), C(=O)O($C_1$-$C_6$ haloalkyl), C(=O)($C_3$-$C_6$ cycloalkyl), C(=O)O($C_3$-$C_6$ cycloalkyl), C(=O)($C_2$-$C_6$ alkenyl), C(=O)O($C_2$-$C_6$ alkenyl), ($C_1$-$C_6$ alkyl)O($C_1$-$C_6$ alkyl), ($C_1$-$C_6$ alkyl)S($C_1$-$C_6$ alkyl), C(=O)($C_1$-$C_6$ alkyl)C(=O)O($C_1$-$C_6$ alkyl), phenyl, and phenoxy;

(g) n=0, 1, or 2;

(h) $R_x$ and $R_y$ are independently selected from H, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_2$-$C_6$ alkynyl, S(=O)$_n$($C_1$-$C_6$ alkyl), S(O)$_n$($C_1$-$C_6$ haloalkyl), OSO$_2$($C_1$-$C_6$ alkyl), OSO$_2$($C_1$-$C_6$ haloalkyl), C(=O)H, C(O)($C_1$-$C_6$ alkyl), C(=O)O($C_1$-$C_6$ alkyl), C(=O)($C_1$-$C_6$ haloalkyl), C(=O)O($C_1$-$C_6$ haloalkyl), C(=O)($C_3$-$C_6$ cycloalkyl), C(=O)O($C_3$-$C_6$ cycloalkyl), C(=O)($C_2$-$C_6$ alkenyl), C(=O)O($C_2$-$C_6$ alkenyl), ($C_1$-$C_6$ alkyl)O($C_1$-$C_6$ alkyl), ($C_1$-$C_6$ alkyl)S($C_1$-$C_6$ alkyl), C(=O)($C_1$-$C_6$ alkyl)C(=O)O($C_1$-$C_6$ alkyl), phenyl, and phenoxy; and (i) R1, R2, and R3 are independently selected from H, F, Cl, Br, I, CN, NO$_2$, $C_1$-$C_6$ alkyl, $C_1$-$C_6$ haloalkyl, $C_3$-$C_6$ cycloalkyl, $C_3$-$C_6$ halocycloalkyl, $C_2$-$C_6$ alkenyl, $C_2$-$C_6$ alkynyl, C(=O)H, C(O)NR$_x$R$_y$, ($C_1$-$C_6$ alkyl)NR$_x$R$_y$, C(=O)($C_1$-$C_6$ alkyl), C(=O)O($C_1$-$C_6$ alkyl), ($C_1$-$C_6$ alkyl)O($C_1$-$C_6$ alkyl)O($C_1$-$C_6$ alkyl), C(O)($C_1$-$C_6$ haloalkyl), C(=O)O($C_1$-$C_6$ haloalkyl), C(=O)($C_3$-$C_6$ cycloalkyl), C(=O)O($C_3$-$C_6$ cycloalkyl), C(=O)($C_2$-$C_6$ alkenyl), C(=O)O($C_2$-$C_6$ alkenyl), ($C_1$-$C_6$ alkyl)O($C_1$-$C_6$ alkyl), ($C_1$-$C_6$ alkyl)S($C_1$-$C_6$ alkyl), C(=O)($C_1$-$C_6$ alkyl)C(=O)O($C_1$-$C_6$ alkyl), C(=O) phenyl, phenyl, $C_1$-$C_6$ alkylphenyl, C(=O)phenoxy, phenoxy, $C_1$-$C_6$ alkylphenoxy, C(=O)Het-1, Het-1, or $C_1$-$C_6$ alkylHet-1, wherein Het-1 is a 5- or 6-membered, saturated or unsaturated, heterocyclic ring, containing one or more heteroatoms independently selected from nitrogen, sulfur or oxygen, and wherein each alkyl, haloalkyl, cycloalkyl, halocycloalkyl, cycloalkoxy, halocycloalkoxy, alkoxy, haloalkoxy, alkenyl, alkynyl, phenyl, phenoxy, and Het-1, are optionally substituted with one or more substituents independently selected from F, Cl, Br, I, CN, NO$_2$, oxo, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_2$-$C_6$ alkynyl, S(=O)$_n$($C_1$-$C_6$ alkyl), S(=O)$_n$($C_1$-$C_6$ haloalkyl), OSO$_2$($C_1$-$C_6$ alkyl), OSO$_2$($C_1$-$C_6$ haloalkyl), C(=O)H, C(=O)NR$_x$R$_y$, ($C_1$-$C_6$ alkyl)NR$_x$R$_y$, ($C_1$-$C_6$ alkenyl)NR$_x$R$_y$, ($C_1$-$C_6$ alkynyl)NR$_x$R$_y$, C(=O)($C_1$-$C_6$ alkyl), C(=O)O($C_1$-$C_6$ alkyl), C(=O)($C_1$-$C_6$ haloalkyl), C(O)O($C_1$-$C_6$ haloalkyl), C(=O)($C_3$-$C_6$ cycloalkyl), C(=O)O($C_3$-$C_6$ cycloalkyl), C(=O)($C_2$-$C_6$ alkenyl), C(=O)O($C_2$-$C_6$ alkenyl), ($C_1$-$C_6$ alkyl)O($C_1$-$C_6$ alkyl), ($C_1$-$C_6$ alkyl)S($C_1$-$C_6$ alkyl), C(=O)($C_1$-$C_6$ alkyl)C(=O)O($C_1$-$C_6$ alkyl), phenyl, phenoxy, and Het-1, wherein R1 and R2 together can optionally form a 3- to 12-membered saturated or unsaturated cyclic group which may contain one or more heteroatoms selected from nitrogen, sulfur, and oxygen (with the proviso that there is preferably not a $C_1$—O— bond in such cyclic group) wherein said cyclic group may have one or more substituents independently selected from F, Cl, Br, I, CN, NO$_2$, oxo, $C_1$-$C_6$ alkyl, $C_1$-$C_6$ haloalkyl, $C_3$-$C_6$ cycloalkyl, $C_3$-$C_6$ halocycloalkyl, $C_3$-$C_6$ cycloalkoxy, $C_3$-$C_6$ halocycloalkoxy, $C_1$-$C_6$ alkoxy, $C_1$-$C_6$ haloalkoxy, $C_2$-$C_6$ alkenyl, $C_2$-$C_6$ alkynyl, S(=O)$_n$($C_1$-$C_6$ alkyl), S(=O)$_n$($C_1$-$C_6$ haloalkyl), OSO$_2$($C_1$-$C_6$ alkyl), OSO$_2$($C_1$-$C_6$ haloalkyl), C(=O)H, C(=O)NR$_x$R$_y$, ($C_1$-$C_6$ alkyl)NR$_x$R$_y$, C(=O)($C_1$-$C_6$ alkyl), C(=O)O($C_1$-$C_6$ alkyl), C(=O)($C_1$-$C_6$ haloalkyl), C(=O)O($C_1$-$C_6$ haloalkyl), C(=O)($C_3$-$C_6$ cycloalkyl), C(=O)O($C_3$-$C_6$ cycloalkyl), C(=O)($C_2$-$C_6$ alkenyl), C(=O)O($C_2$-$C_6$ alkenyl), ($C_1$-$C_6$ alkyl)O($C_1$-$C_6$ alkyl), ($C_1$-$C_6$ alkyl)S($C_1$-$C_6$ alkyl), C(=O)($C_1$-$C_6$ alkyl)C(=O)O($C_1$-$C_6$ alkyl), phenyl, phenoxy, and Het-1.

In another embodiment Ar$_1$ is a substituted phenyl wherein said substituted phenyl, has one or more substituents independently selected from $C_1$-$C_6$ haloalkyl and $C_1$-$C_6$ haloalkoxy.

In another embodiment Het is a triazolyl.

In another embodiment Ar$_2$ is a phenyl.

In another embodiment R4 is H or $C_1$-$C_6$ alkyl.

In another embodiment R1, R2, and R3 are independently selected from H, CN, $C_1$-$C_6$ alkyl, $C_1$-$C_6$ haloalkyl, $C_3$-$C_6$ cycloalkyl, $C_2$-$C_6$ alkenyl, $C_2$-$C_6$ alkynyl, C(=O)O($C_1$-$C_6$ alkyl), phenyl, and Het-1.

In another embodiment R1, R2, and R3 are independently selected from $C_1$-$C_6$ alkyl, $C_1$-$C_6$ haloalkyl, $C_3$-$C_6$ cycloalkyl, $C_2$-$C_6$ alkenyl, $C_2$-$C_6$ alkynyl, C(=O)O($C_1$-$C_6$ alkyl), phenyl, and Het-1. are substituted with one or more substituents independently selected from F, Cl, Br, I, CN, NO$_2$, $C_1$-$C_6$ alkyl, $C_1$-$C_6$ haloalkyl, $C_1$-$C_6$ alkoxy, S(=O)$_n$ ($C_1$-$C_6$ alkyl), ($C_1$-$C_6$ alkyl)NR$_x$R$_y$, ($C_1$-$C_6$ alkenyl)NR$_x$R$_y$, ($C_1$-$C_6$ alkynyl)NR$_x$R$_y$, C(=O)O($C_1$-$C_6$ alkyl), and phenyl.

In another embodiment when R1, R2, and R3 are Het-1 they are independently selected from pyrimidinyl, pyridyl, quinolinyl, thiazolyl, thienyl, furanyl, isoxazolyl, each of which may be optionally substituted.

In another embodiment Het and Het-1 when they have a ring nitrogen include (N$^+$—O$^-$) group.

While these embodiments have been expressed, other embodiments and combinations of these expressed embodiments and other embodiments are possible.

Preparation of Triaryl-Intermediates

Compounds of this invention are prepared by linking the X$_2$(C$_1$)R1R2R3 to a triaryl intermediate, Ar$_1$-Het-Ar$_2$, by means of a carbamate or thiocarbamate linkage N$_1$(C=X$_1$) (defined above). A wide variety of triaryl precursors can be used to prepare compounds of this invention, provided that they contain a suitable functional group on Ar$_2$. Suitable functional groups include an amino, or carboxylic acid group. These triaryl-intermediates can be prepared by methods previously described in the chemical literature. Several of these methods are described below.

Intermediates wherein 'Het' is a disubstituted pyridine, pyrimidine, pyrazine or pyridizine can be made by coupling of a halo- or alkylthio-substituted pyridine, pyrimidine or pyrazine with an aryl boronic acid or borate ester, under Suzuki arylation conditions. See, for example, the following.

For pyridines: Couve-Bonnaire et al. *Tetrahedron* 2003, 59, 2793 and Puglisi et al. *Eur. J. Org. Chem.* 2003, 1552.

For pyrazines: Schultheiss and Bosch *Heterocycles* 2003, 60, 1891.

For pyrimidines: Qing et al. *J. Fluorine Chem.* 2003, 120, 21 and Ceide and Montalban *Tetrahedron Lett.* 2006, 47, 4415.

For 2,4-diaryl pyrimidines: Schomaker and Delia *J. Org. Chem.* 2001, 66, 7125.

Thus, successive palladium-catalyzed arylations, using 4-formylphenyl boronic acid and 4-trifluoromethoxyphenyl boronic acid, can generate virtually any particular substitution pattern, as shown in the scheme below:

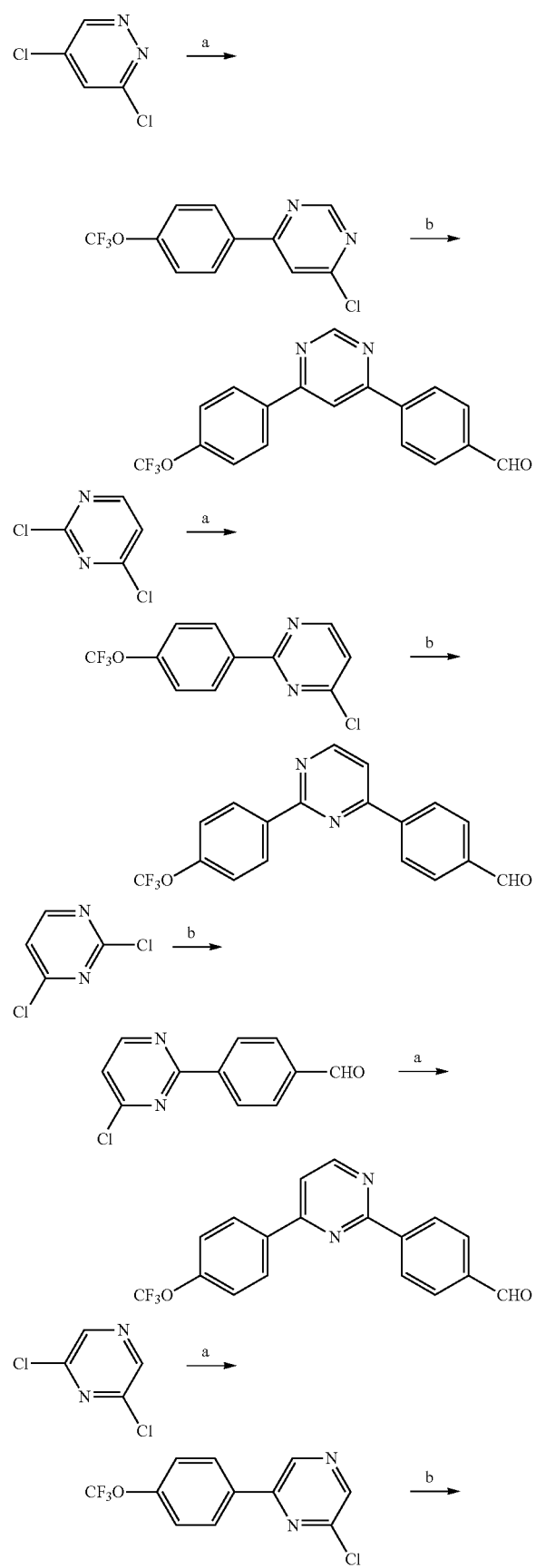
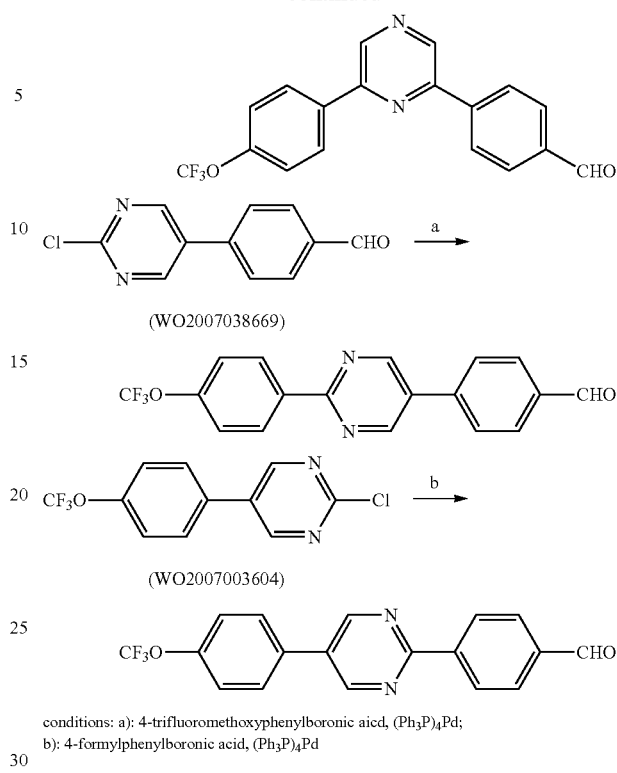
conditions: a): 4-trifluoromethoxyphenylboronic aicd, (Ph$_3$P)$_4$Pd;
b): 4-formylphenylboronic acid, (Ph$_3$P)$_4$Pd
Similarly, diaryl pyridines and pyrazines and other dihalogenated heterocyclic aromatic compounds can be prepared from dihalogenated pyridines and pyrazines and other dihalogenated heterocyclic aromatic compounds using the same protocol:
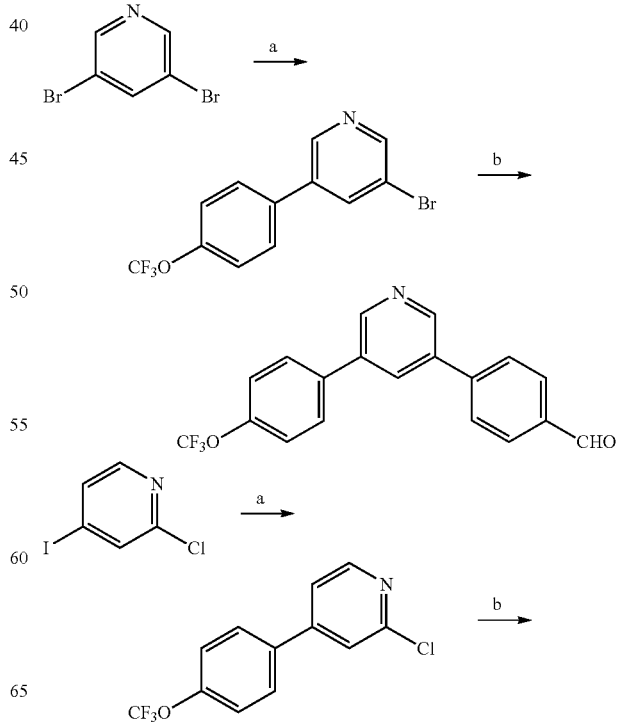

Srogl *Org. Lett.* 2002, 4, 979) to give 2-phenyl pyrimidines, which then were reduced to the corresponding anilines using, for example, a palladium on carbon (Pd/C) catalyst in EtOH under a hydrogen atmosphere.

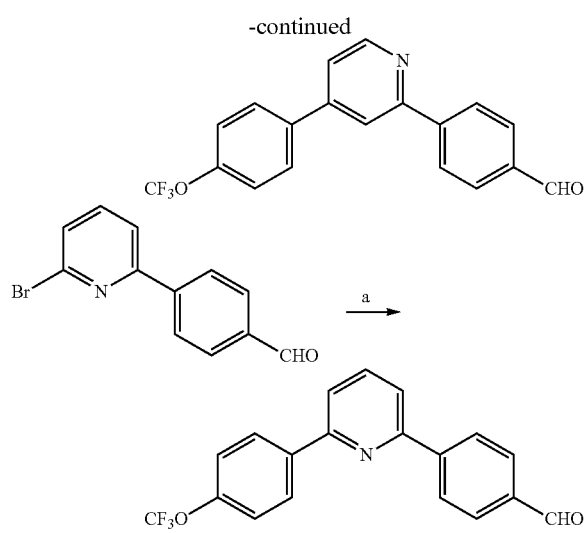

(*EJC* 2003, 8, 1152-1558)

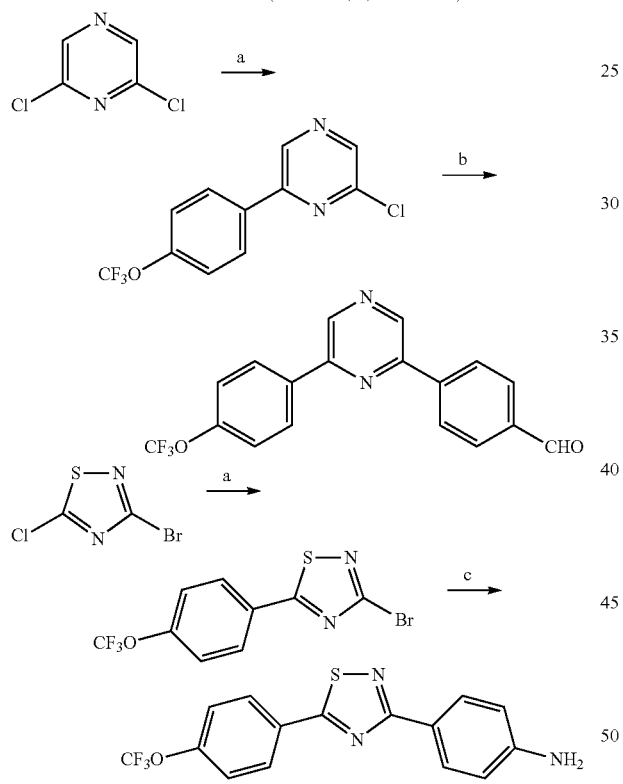

conditions: a): 4-trifluoromethoxyphenylboronic acid, (Ph₃P)₄Pd;
b) 4-formylphenylboronic acid, (Ph₃P)₄Pd;
c) 4-aminophenyl boronic acid, (Ph₃P)₄Pd The halo- or alkylthio-pyrimidine and pyridine precursors are either commercially available, or may be synthesized by routes described in the literature (Rorig and Wagner U.S. Pat. No. 3,149,109, 1964; Kreutzberger and Tesch *Arzneim.-Forsch.* 1978, 28, 235).

Compounds where 'Het' is a 1,3-diaryl-6-perfluoroalkyl pyrimidine can be prepared according to the following scheme. The 2-methylthio-substituted pyrimidine was arylated under modified Suzuki conditions (Liebeskind and

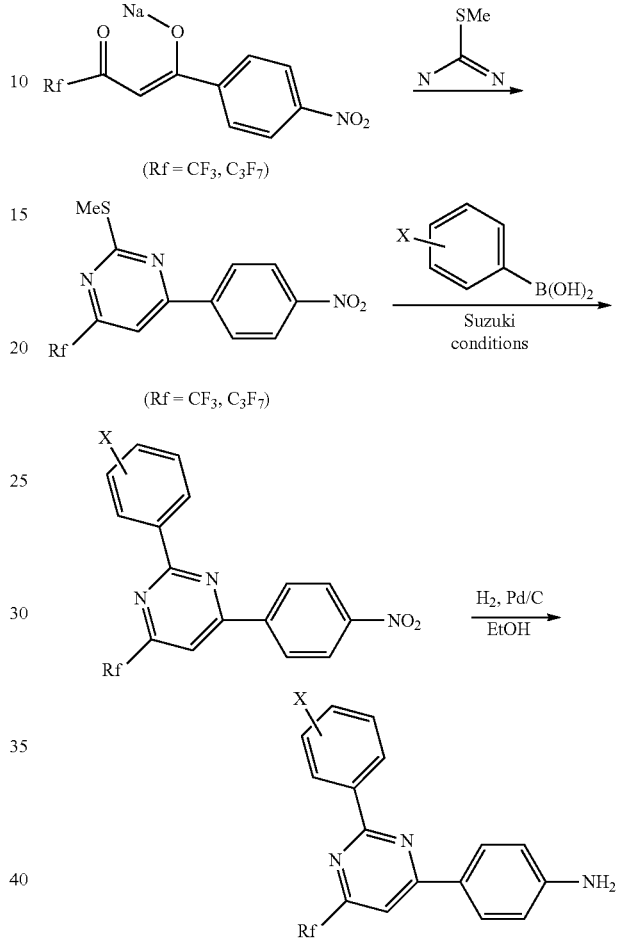

Intermediate compounds wherein 'Het' is a 1,3-disubstituted 1,2,4-triazole can be prepared according to one of the following schemes.

Route A: 1,3-Diaryl 1,2,4-triazoles were prepared from the corresponding —NH 3-aryl 1,2,4-triazoles by following a published route for N-arylation of imidazoles (Lin et al. *J. Org. Chem.* 1979, 44, 4160). Coupling of 1,2,4-triazoles to aryl halides was done under thermal or, preferably, microwave conditions (Antilla et al. *J. Org. Chem.* 2004, 69, 5578).

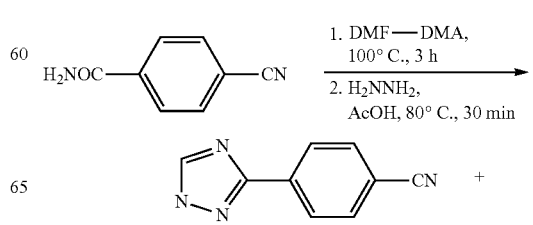

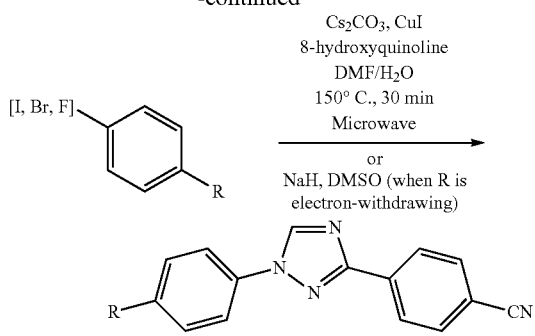

Route B: Bromination of hydrazones followed by treatment of the bromohydrazone with tetrazole results in formation of the 1,3-diaryl 1,2,4-triazole (Butler and Fitzgerald *J. Chem. Soc., Perkin Trans.* 1 1988, 1587).

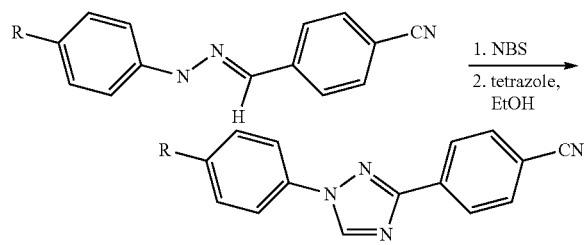

Route C. 1,2,4-Triazole compounds in which the 5-position is further substituted with an alkyl or substituted alkyl group can be prepared according to the following scheme (Paulvannan and Hale *Tetrahedron* 2000, 56, 8071):

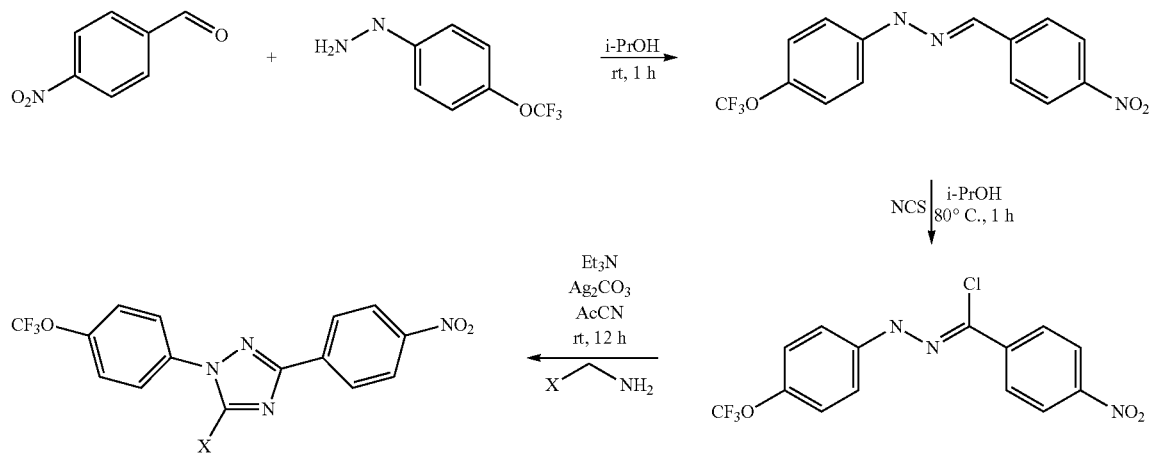

Compounds where 'Het' is an imidazole can be prepared according to one of the following schemes:

Route A (Step 1: Lynch et al. *J. Am. Chem. Soc.* 1994, 116, 11030. Step 2: Liu et al. *J. Org. Chem.* 2005, 70, 10135):

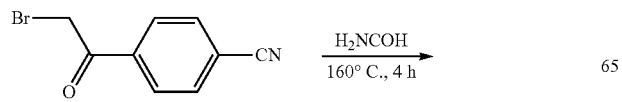

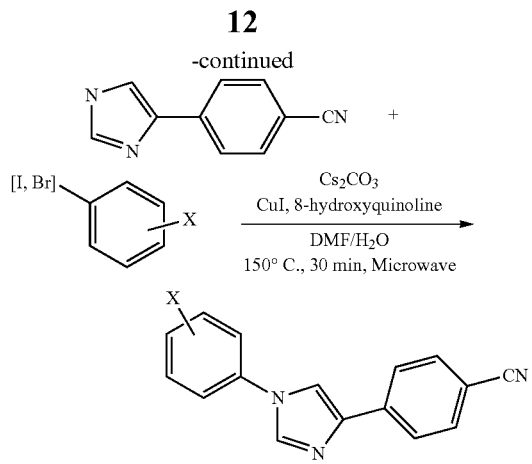

Route B. For halo-aryl groups that also contain an activating group such as nitro or cyano, displacement of an aryl halide with an imidazole, using a base such as potassium carbonate in a polar aprotic solvent, such as N,N-dimethylformamide (DMF) or dimethyl sulfoxide (DMSO), can be accomplished in the following manner (Bouchet et al. *Tetrahedron* 1979, 35, 1331):

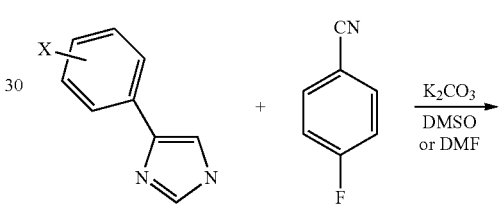

-continued

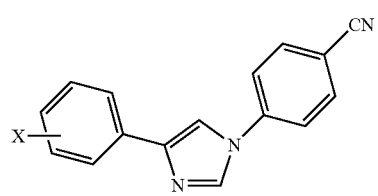

Route C: Following a procedure first described by Porretta et al. (*Farmaco, Edizione Scientifica* 1985, 40, 404), an N-phenacyl aniline is treated with potassium thiocyanate in acidic medium (HCl), and the resulting 2-mercapto imidazole is then converted into the desulfurized diaryl imidazole by treatment with nitric acid in acetic acid.

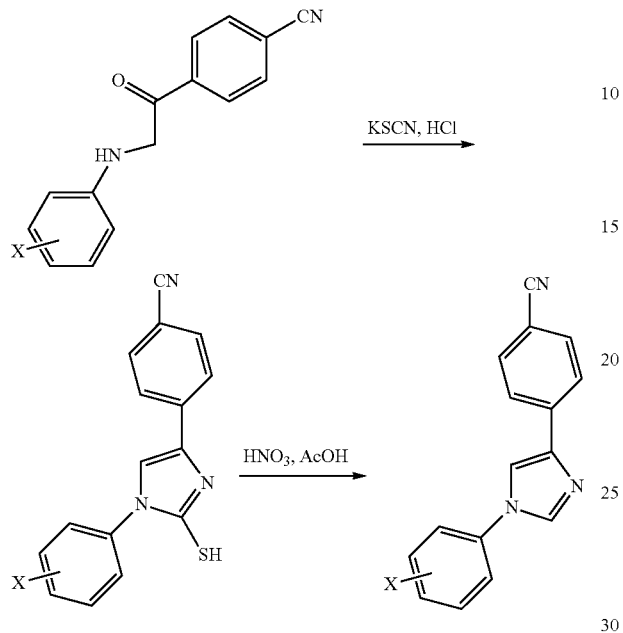

Route D. N-Arylation of 4-bromoimidazole under microwave irradiation conditions (Route A, Step 2) furnished the intermediate 1-aryl-4-bromoimidazole, which was converted into triaryl-intermediates by treatment with aryl boronic acids under palladium-catalyzed conditions.

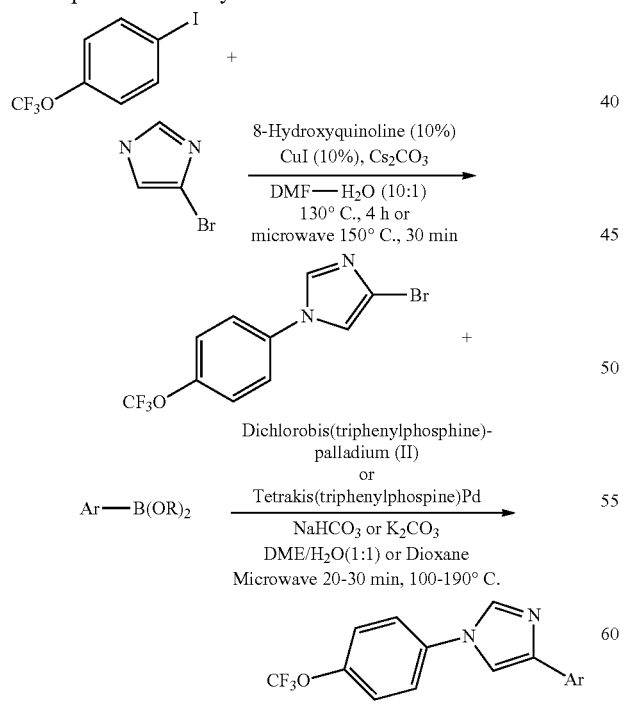

Compounds where 'Het' is a 1,4-disubstituted 1,2,3-triazole can be prepared according to the following scheme (Feldman et al. *Org Lett.* 2004, 6, 3897):

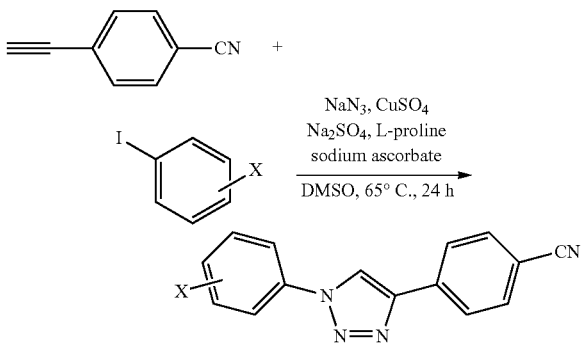

Compounds where 'Het' is a 3,5-disubstituted 1,2,4-triazole can be prepared according to the following scheme (Yeung et al. *Tetrahedron Lett.* 2005, 46, 3429):

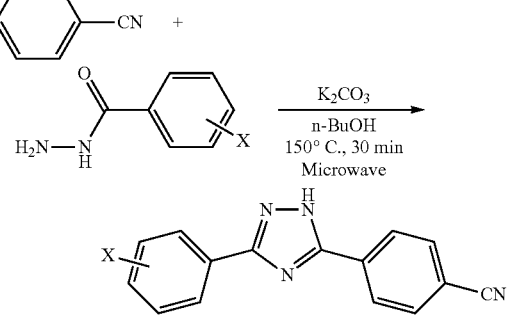

Compounds where 'Het' is a 1,3-disubstituted 1,2,4-triazolin-5-one can be prepared according to the following scheme (Pirrung and Tepper *J. Org. Chem.* 1995, 60, 2461 and Lyga *Synth. Commun.* 1986, 16, 163). (DPPA is diphenyl phosphoryl azide.):

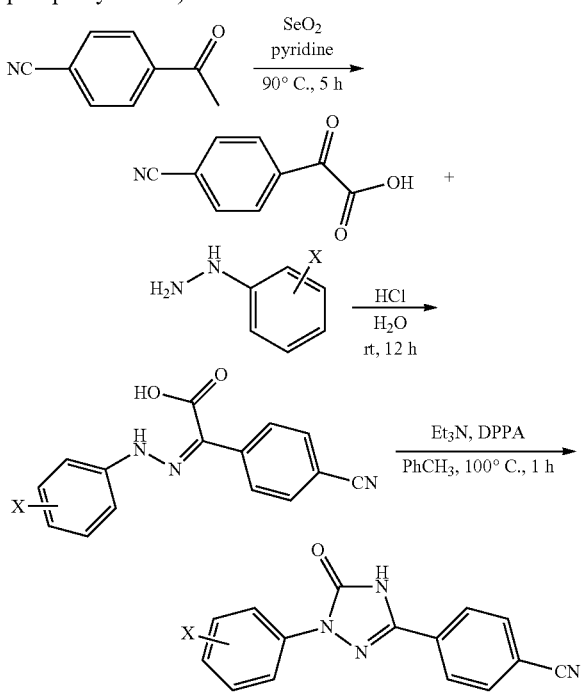

Compounds where 'Het' is a 1,3-diaryl pyrazoline can be prepared according to the following scheme. The monohydrazone of terephthalaldehyde is treated with N-chlorosuccinimide (NCS) in i-PrOH, and the resulting chlorohydrazone intermediate is treated directly with base and a substituted olefin to generate the pyrazoline:

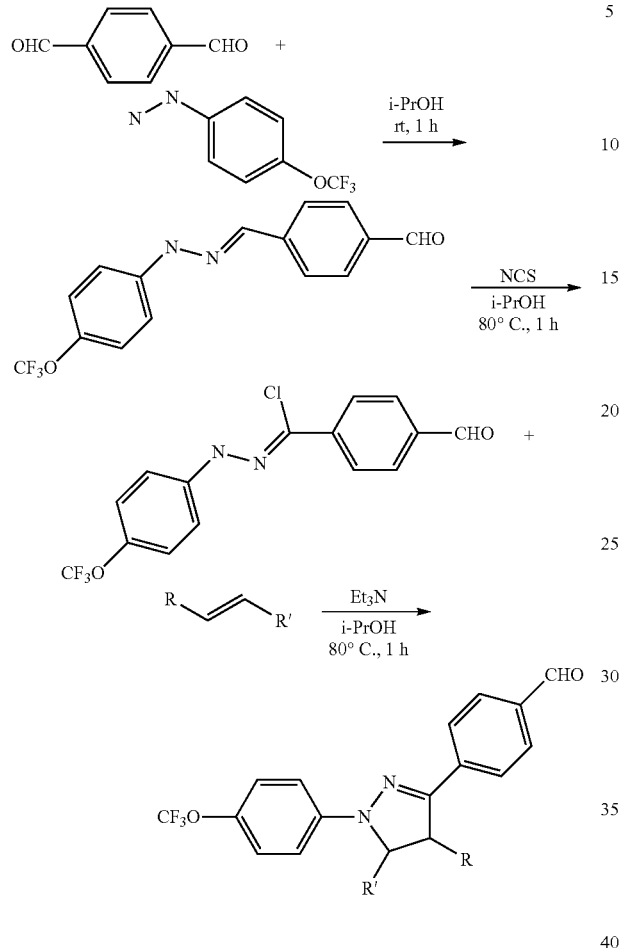

Compounds where 'Het' is a 3,5-disubstituted isoxazole can be prepared according to the following scheme:

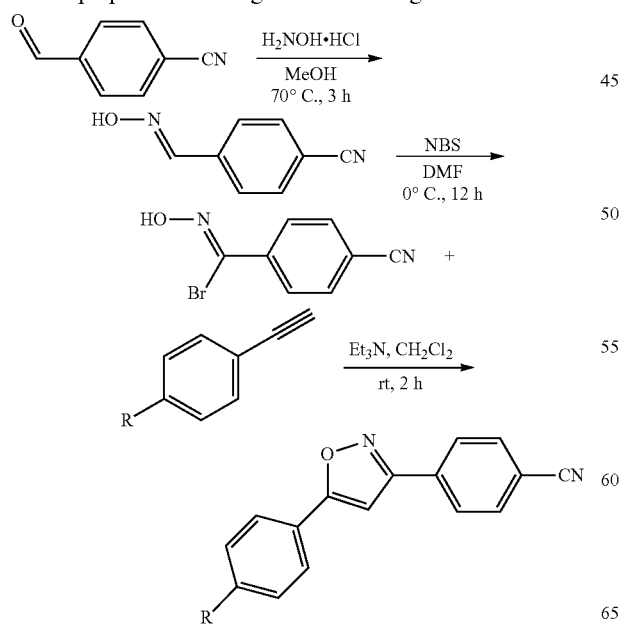

Compounds where 'Het' is a 1,3-disubstituted pyrazole can be prepared according to the following scheme. Coupling of the pyrazole to halogenated aromatics was accomplished using microwave conditions described by Liu et al., Route A, Step 2 above. (DMA is dimethyl acetal.)

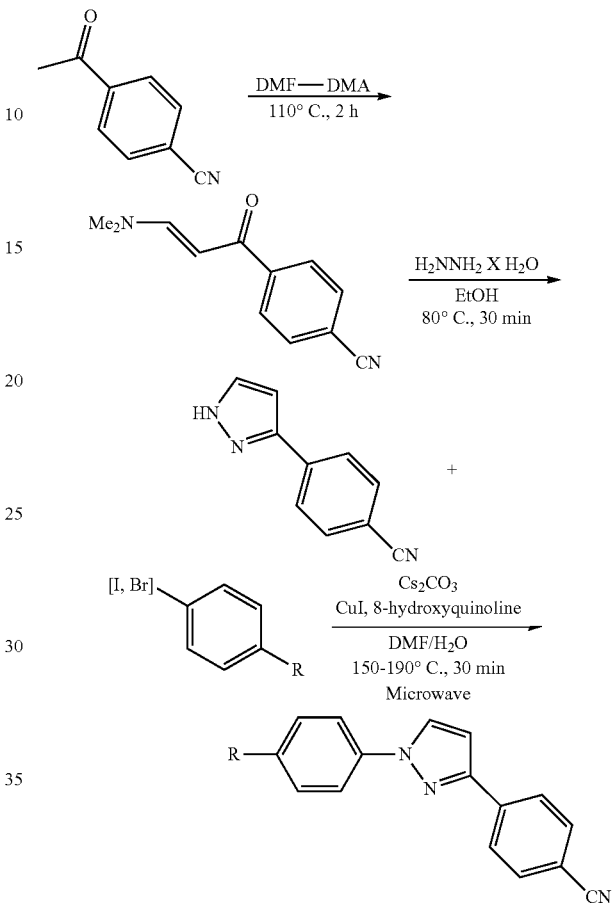

Compounds where 'Het' is a 2,4-disubstituted thiazole are prepared by condensation of a thioamide to an α-halo acetophenone in a protic solvent such as ethanol (for example, Potts and Marshall *J. Org. Chem.* 1976, 41, 129).

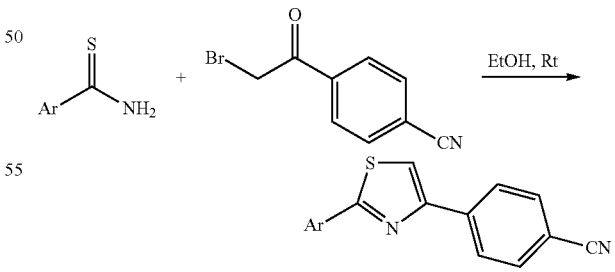

Compounds where 'Het' is a 1,4-disubstituted 1,2,4-triazolin-5-one are prepared according to the following scheme (Henbach DE 2724819 A1, 1978 with slight modification to two steps):

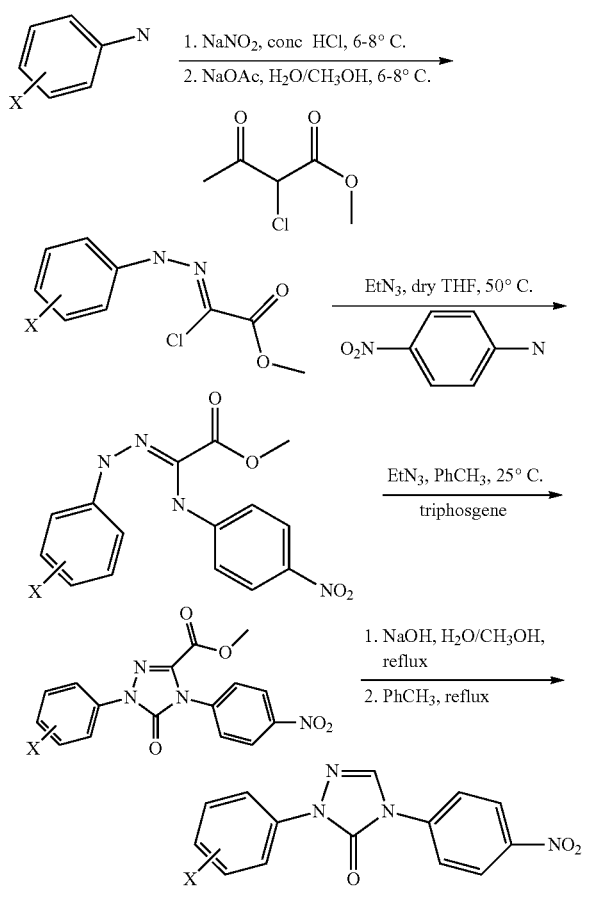

Compounds where 'Het' is a 2,4-disubstituted oxazoline are prepared starting from the α-bromoacetophenone according to the following scheme (Periasamy et al. *Synthesis* 2003, 1965 and Liu et al. *J. Am. Chem. Soc.* 2007, 129, 5834).

Compounds where 'Het' is a 2,5-disubstituted oxazoline are prepared according to the following scheme (Favretto et al. *Tetrahedron Lett.* 2002, 43, 2581 and Liu et al. *J. Am. Chem. Soc.* 2007, 129, 5834):

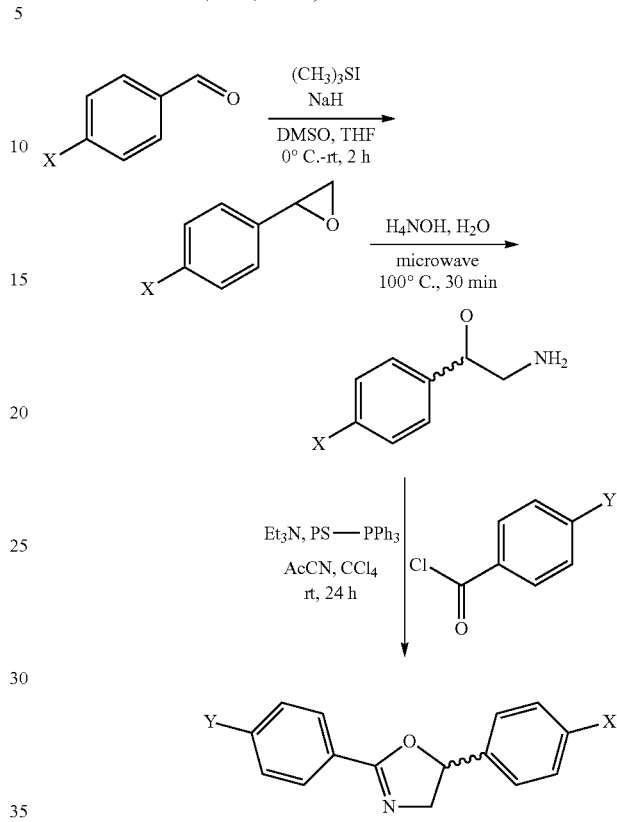

Compounds where 'Het' is a 1,4-disubstituted piperazine are prepared according to the following scheme (Evans et al. *Tetrahedron Lett.* 1998, 39, 2937):

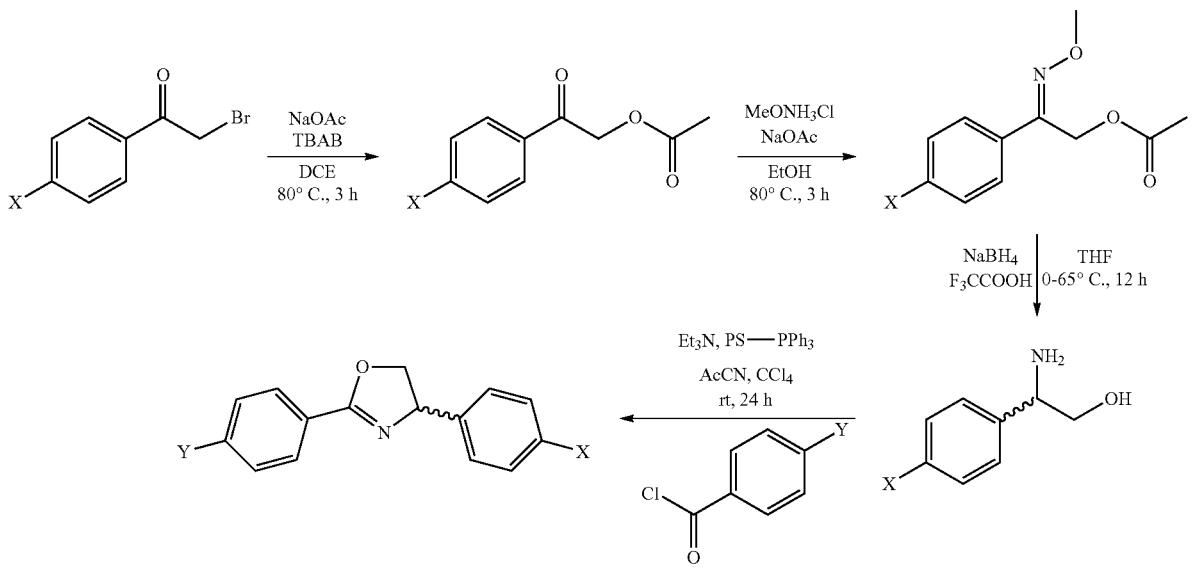

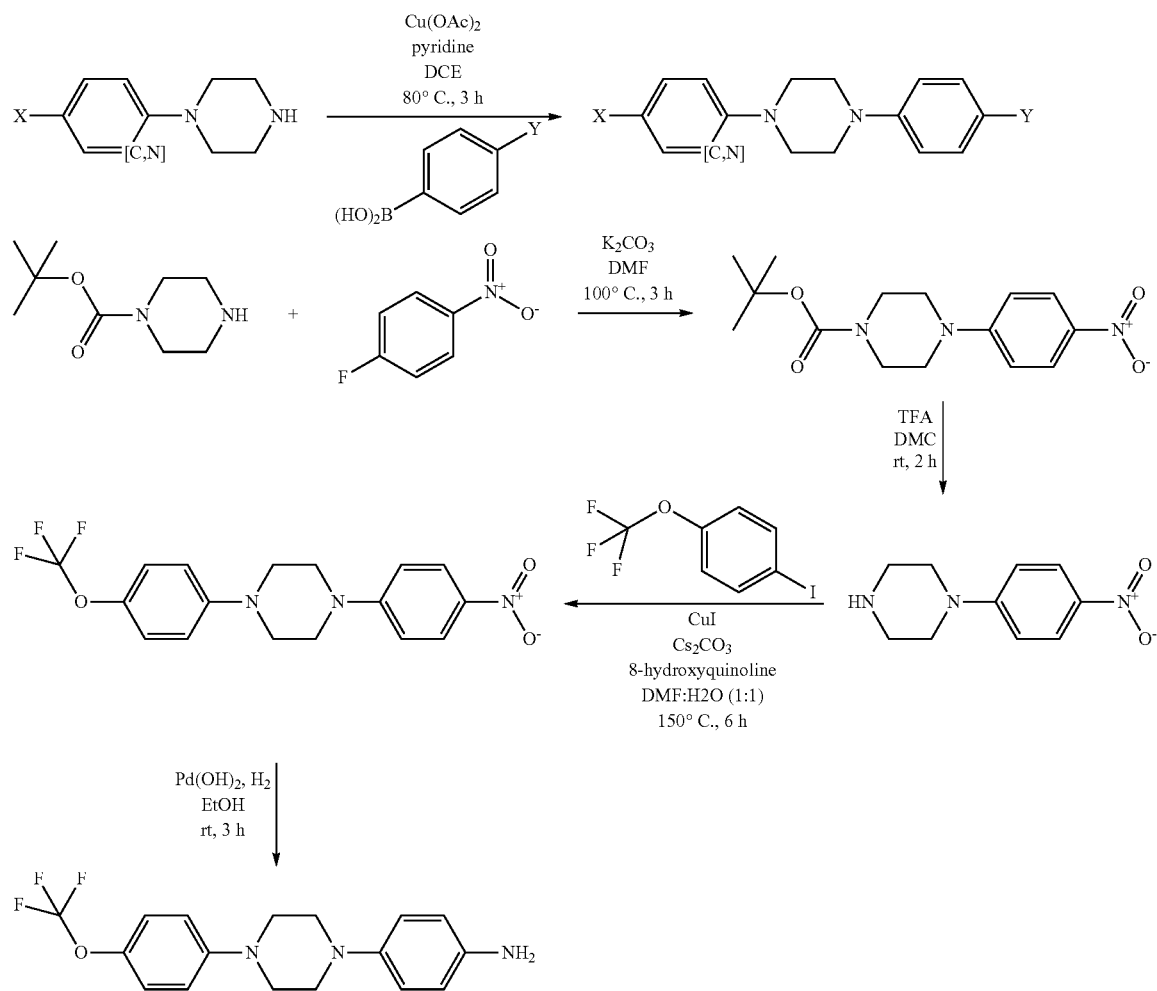

Compounds where 'Het' is a 1,3-disubstituted pyrazoline are prepared by addition of an aryl hydrazine to a β-dimethylamino propiophenone as shown in the following scheme, which is described in Linton et al. *Tetrahedron Lett.* 2007, 48, 1993, and Wheatley et al. *J. Am. Chem. Soc.* 1954, 76, 4490. In addition to the pyrazoline, a minor amount of bis-addition leads to the corresponding dimethylaminomethylpyrazoline. These materials can be separated chromatographically.

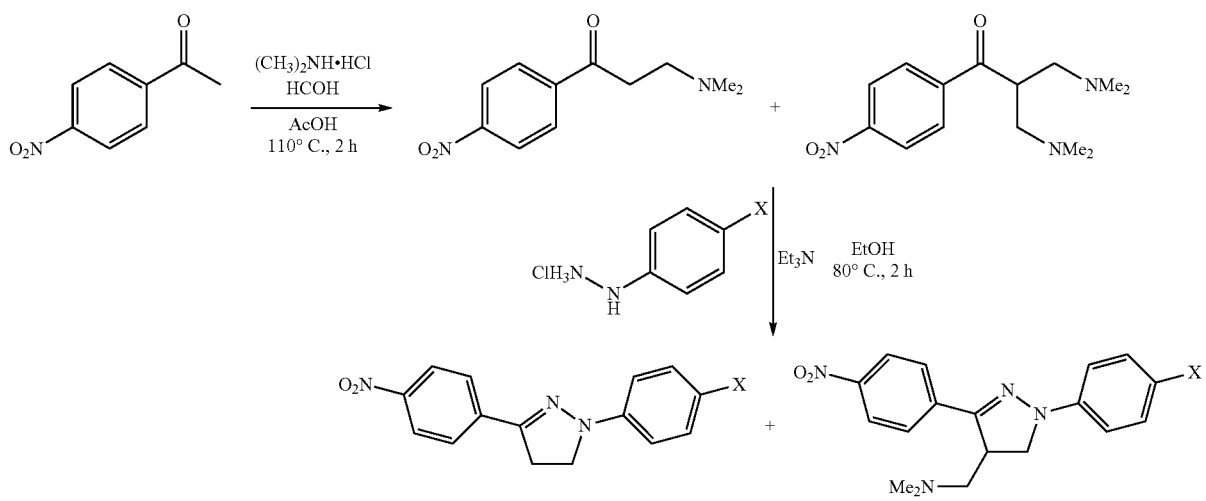

Compounds where 'Het' is a 3,5-disubstituted 1,2,4-triazine are prepared according to the following scheme (Reid et al. *Bioorg. Med. Chem. Lett.* 2008, 18, 2455 and Saraswathi and Srinivasan *Tetrahedron Lett.* 1971, 2315):

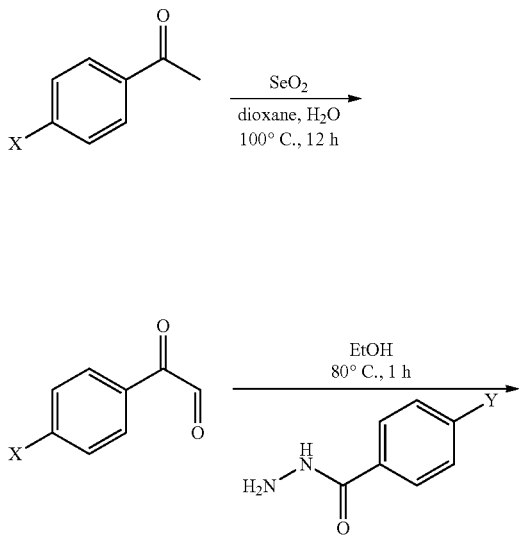

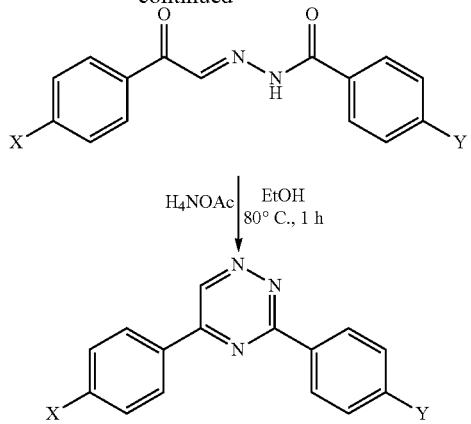

Compounds where 'Het' is a 2-ketopiperazine or 2,5-diketopiperazine are prepared as in the following scheme. The nitrophenyl glycine ester can be acylated using chloroacetyl chloride, and the intermediate N-chloroacetylated glycine ester, upon treatment with an aniline, undergoes displacement and ring closure at from 120 to 180° C. to form a diketopiperazine. Alternatively, monoketo saturated or unsaturated piperazines can be formed from the acetal intermediate below, by hydrolysis and ring closure.

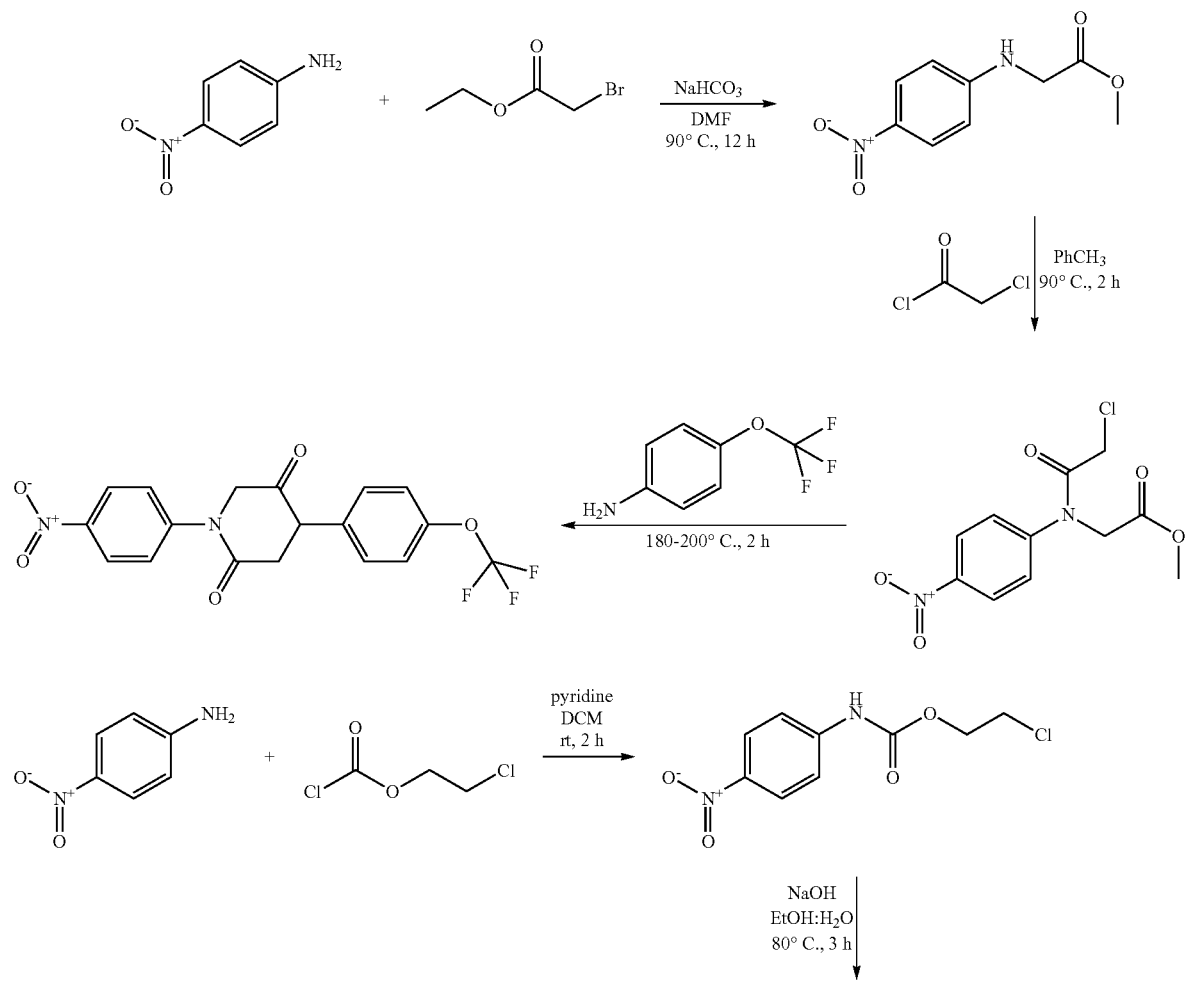

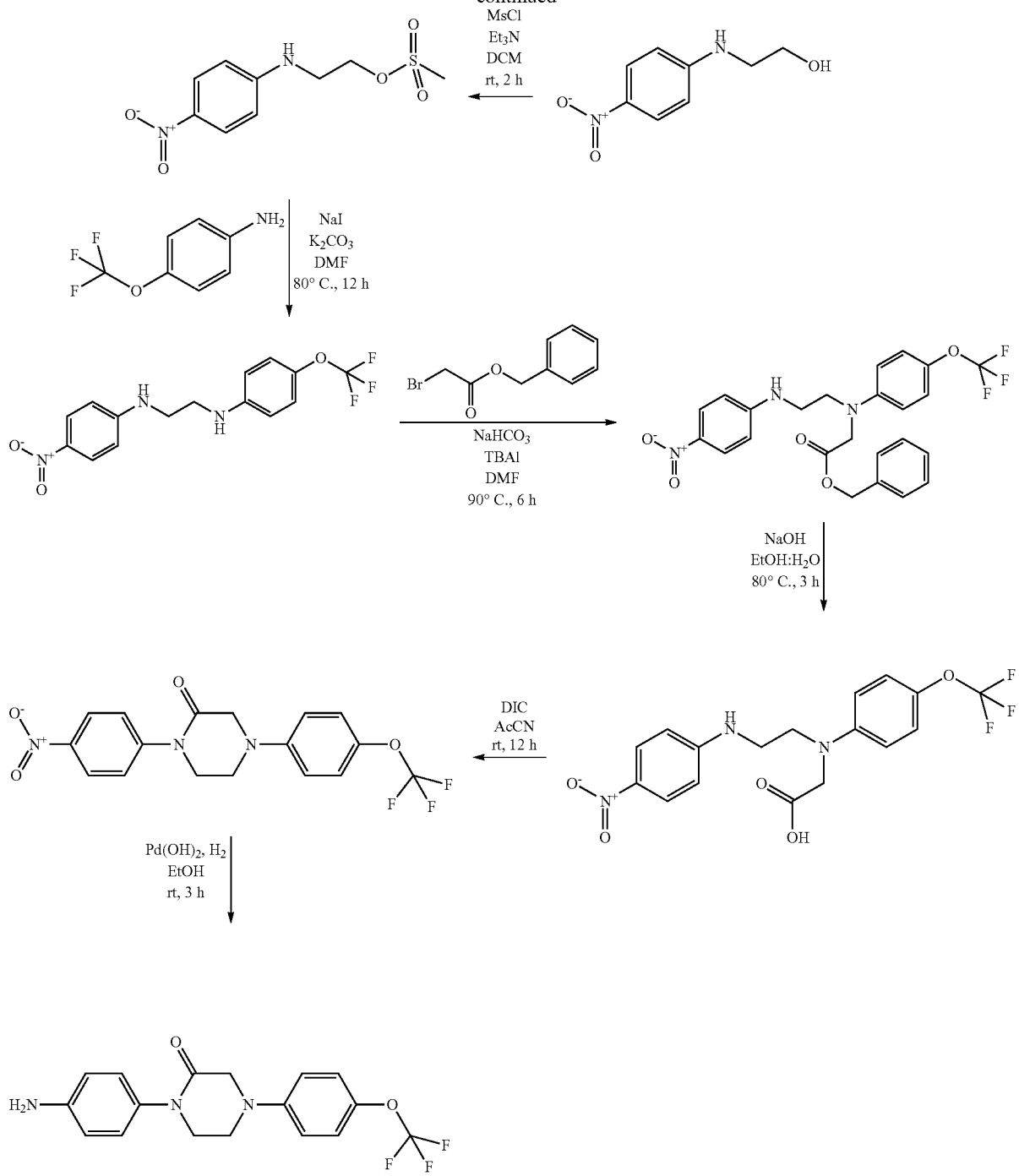

55

Preparation of (Thio)Carbamate-Linked Compounds

Carbamate- or thio-carbamate linked compounds can be prepared from the corresponding aryl amines by conversion into either an isocyanate, isothiocyanate or p-nitrophenyl carbamate, followed by treatment with the appropriate alcohol (ROH) and an organic or inorganic base in a suitable solvent such as tetrahydrofuran (THF), at temperatures between 0 and 100° C. Alternatively, the carbamate can be formed from a chloroformate, generated from the alcohol (ROH) by treatment with triphosgene in the presence of a base such as pyridine, followed by reaction with an appropriate amine.

An isocyanate intermediate can be generated from the carboxylic acid by treating with a source of azide such as diphenylphosphoryl azide (DPPA). The acyl azide then can be made to undergo a Curtius rearrangement by heating to 110° C. in toluene, and the resulting isocyanate treated with an appropriate alcohol and a base as described above to generate the carbamate. The precursor carboxylic acids can be prepared via oxidation of an aldehyde, using conditions described in Example 18, via basic hydrolysis of a nitrile (for example 4-(1-(4-trifluoromethoxyphenyl)-1,2,4-triazol-3- yl)-benzonitrile as described in Example 10), or via acidic hydrolysis of a nitrile using any of a variety of conditions described in the literature.

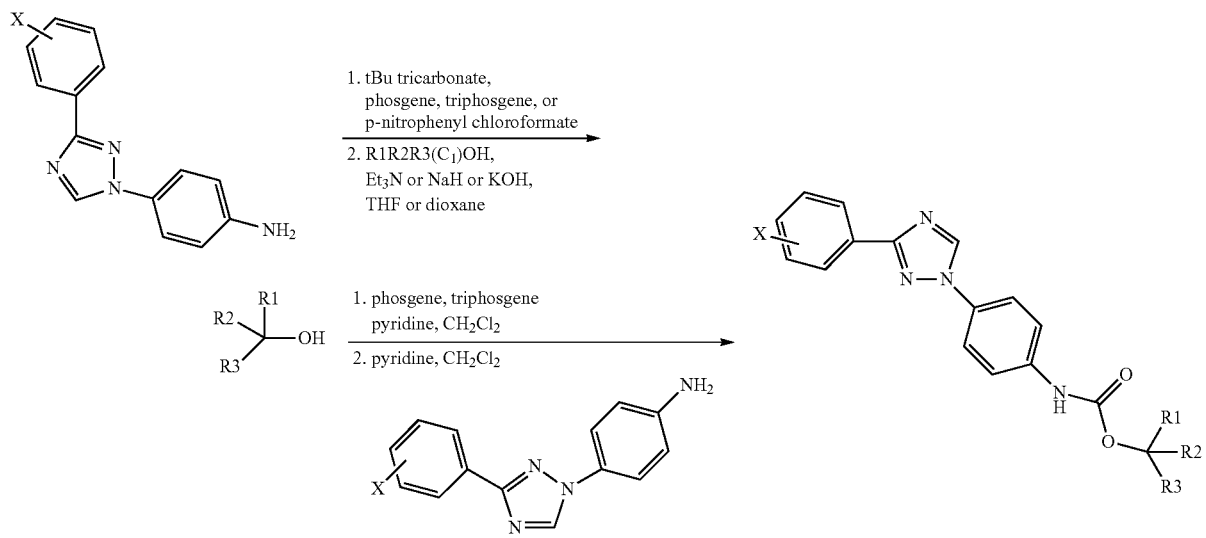

Carbamates can also be prepared via nitrophenyl carbonates as shown below and demonstrated in McClure and Sieber *Heteroat. Chem.* 2000, 11, 192. Reaction of a tertiary carbinol with potassium metal, followed by addition of p-nitrophenyl chloroformate, provides the desired p-nitrophenyl carbonate. Subsequent reaction of the carbonate with an amine in the presence of sodium carbonate in DMF affords the carbamate.

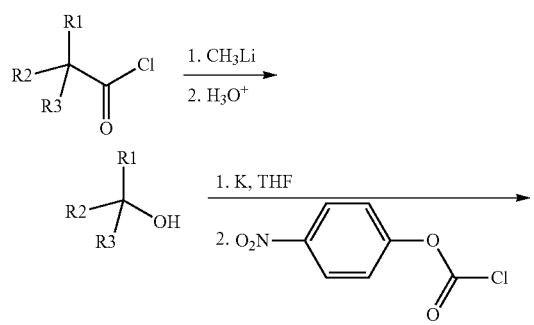

-continued

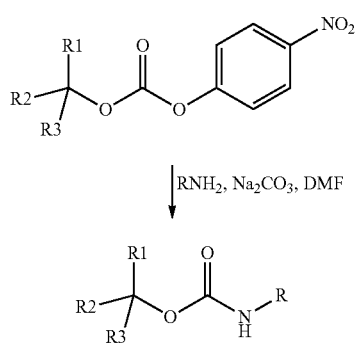

Alkynyl carbamates can be further functionalized by deprotonation with a base, such as n-butyl lithium, in a polar aprotic solvent, such as THF, followed by reaction with ethyl chloroformate to provide the substituted alkyne.

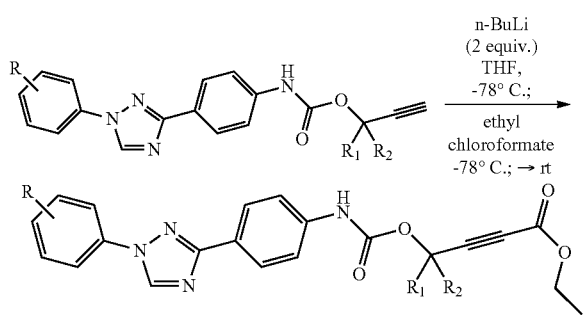

Alkene-containing carbamates can be further functionalized via hydroboration-oxidation with borane-dimethyl sulfide complex, followed by treatment with sodium perborate tetrahydrate.

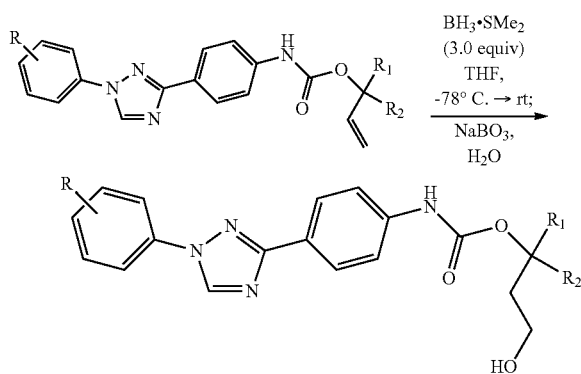

EXAMPLES

The examples are for illustration purposes and are not to be construed as limiting the invention disclosed in this document to only the embodiments disclosed in these examples.

Starting materials, reagents and solvents which were obtained from commercial sources were used without further purification. Anhydrous solvents were purchased as Sure/Seal™ from Aldrich and were used as received. Melting points were obtained on a Thomas Hoover Unimelt capillary melting point apparatus or an OptiMelt Automated Melting Point System from Sanford Research Systems and are uncorrected.

Examples 1-55 illustrate the preparation of additional molecules useful in making various embodiments of this invention.

Example 1

Preparation of 4-[1-(4-trifluoromethoxyphenyl)-1H-pyrrol-3-yl]-benzaldehyde

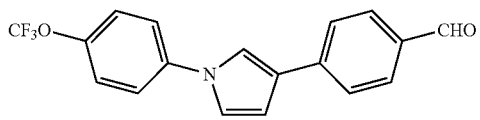

Step 1. 1-(4-Trifluoromethoxyphenyl)-1H-pyrrole. The compound was prepared according to Colotta et al. *J. Med. Chem.* 2006, 49, 6015. A solution of 4-trifluoromethoxyphenyl amine (500 milligrams (mg), 2.82 millimoles (mmol), 1.00 equivalent (eq)) and 2,5-diethoxy tetrahydrofuran (452 mg, 2.82 mmol, 1.00 eq) in glacial acetic acid (20 milliliters (mL)) was heated at 90° C. for 1 hour (h) before being dried onto silica gel. The residue was then slurried in refluxing hexane, filtered hot, and concentrated to dryness affording the desired intermediate (519 mg, 81%).

Step 2. 3-Bromo-1-(4-trifluoromethoxyphenyl)-1H-pyrrole. The compound was prepared according to Bray et al. *J. Org. Chem.* 1990, 55, 6317. To a solution of 1-(4-trifluoromethoxyphenyl)-1H-pyrrole (519 mg, 2.29 mmol, 1.00 eq) in THF (250 mL) at −78° C. was added a 0.05 M solution of N-bromosuccinimide (NBS; 408 mg, 2.29 mmol, 1.00 eq) in THF over 45 minutes (min). The vessel was slowly warmed to room temperature before concentration to afford the crude bromopyrrole, which was shown to consist of 55% desired intermediate by GC-MS. The material was used in the subsequent reaction without further purification.

Step 3. 4-[1-(4-Trifluoromethoxyphenyl)-1H-pyrrol-3-yl]-benzaldehyde. A suspension of crude 3-bromo-1-(4-trifluoromethoxyphenyl)-1H-pyrrole (356 mg, 1.26 mmol, 1.00 eq), 4-formylphenylboronic acid (283 mg, 1.89 mmol, 1.50 eq), bis(triphenylphosphine)palladium(II) dichloride (27 mg, 0.04 mmol, 0.03 eq), 2 M $Na_2CO_3$ (aq) (1.26 mL, 2.52 mmol, 2.0 eq), and 1,4-dioxane (5 mL) were heated at 150° C. in a microwave reaction vessel for 45 min. The cooled solution was then diluted with EtOAc (20 mL), filtered over Celite®, concentrated to dryness, and purified via chromatography (2:2:1, hexane:EtOAc:acetone) to afford the desired intermediate (79 mg, 21%).

Example 2

Preparation of 4-[1-(4-trifluoromethoxyphenyl)-4,5-dihydro-1H-pyrazol-3-yl]-benzaldehyde

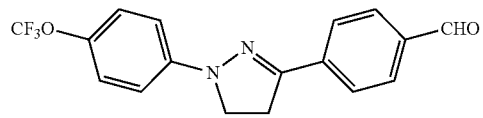

Step 1. 1-(4-Trifluoromethoxyphenyl)-pyrazolidin-3-one: The compound was prepared according to Rees and Tsoi *Chem. Commun.* 2000, 415. A suspension of (4-trifluoromethoxyphenyl)-hydrazine hydrochloride (300 mg, 1.32 mmol, 1.00 eq), 3-chloropropionyl chloride (167 mg, 1.32 mmol, 1.00 eq), and PS-DIEA (1.30 grams (g), 5.28 mmol, 4.00 eq) in THF (20 mL) was stirred at ambient temperature for 12 h. The solution was then filtered, concentrated to dryness, and purified via chromatography (2:2:1, hexane:EtOAc:acetone) to afford the desired intermediate (120 mg, 37%).

Step 2. 3-Chloro-1-(4-trifluoromethoxyphenyl)-4,5-dihydro-1H-pyrazole: The general procedure was taken from Wang et al. *Tetrahedron Lett.* 2005, 46, 2631. To a solution of 1-(4-trifluoromethoxyphenyl)-pyrazolidin-3-one (120 mg, 0.49 mmol, 1.00 eq) in toluene (20 mL) was slowly added phosphoryl chloride (22.5 mg, 1.47 mmol, 3.00 eq). The mixture was then heated at 80° C. for 1 h before cooling to room temperature and quenching with $H_2O$ (10 mL). The vessel was stirred under an atmosphere of nitrogen ($N_2$) for 8 h before the product was extracted into EtOAc (200 mL), dried (MgSO$_4$), and concentrated under reduced pressure. GC-MS proved 88% formation of the desired intermediate, which was used in subsequent reactions without further purification.

Step 3. 4-[1-(4-Trifluoromethoxyphenyl)-4,5-dihydro-1H-pyrazol-3-yl]-benzaldehyde: A suspension of 3-chloro-1-(4-trifluoromethoxyphenyl)-4,5-dihydro-1H-pyrazole (114 mg, 0.43 mmol, 1.00 eq), 4-formylphenylboronic acid (97 mg, 0.65 mmol, 1.50 eq), bis(triphenylphosphine)palladium (II) dichloride (10 mg, 0.01 mmol, 0.03 eq), 2 M Na$_2$CO$_3$ (aq) (0.43 mL, 0.86 mmol, 2.0 eq), and 1,4-dioxane (5 mL) were heated at 150° C. in a microwave reaction vessel for 45 min. The cooled solution was then diluted with EtOAc (20 mL), filtered over Celite®, concentrated to dryness, and purified via chromatography (2:2:1, hexane:EtOAc:acetone) to afford the desired intermediate (50 mg, 0.15 mmol, 31%).

Example 3

Preparation of 4-[1-(5-bromo-2-chlorophenyl)-1H-imidazol-4-yl]-benzonitrile

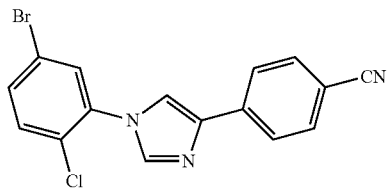 [SMILES: N#Cc1ccc(-c2cn(-c3cc(Br)ccc3Cl)cn2)cc1]

The compound was prepared according to Liu et al. *J. Org. Chem.* 2005, 70, 10135. 4-(1H-Imidazol-4-yl)-benzonitrile (75 mg, 0.44 mmol; prepared from 4-(2-bromo-acetyl)-benzonitrile using the method of Lynch et al. *J. Am. Chem. Soc.* 1994, 116, 11030), 4-bromo-1-chloro-2-iodobenzene (169 mg, 0.532 mmol), Cs$_2$CO$_3$ (577 mg, 1.77 mmol), CuI (3 mg, 0.013 mmol), 8-hydroxyquinoline (2 mg, 0.013 mmol), and DMF/H$_2$O (2 mL; 10:1 solution) were combined in a 10 mL CEM Microwave reaction vessel fitted with magnetic stir bar and subjected to microwave irradiation at 150° C. for 30 min. The contents were then filtered and concentrated to dryness affording intermediate 5-bromo-2-chlorophenyl)-1H-imidazol-4-yl]-benzonitrile (68 mg, 43%).

Example 4

Preparation of 4-[5-(4-propylphenyl)-isoxazol-3-yl]-benzonitrile

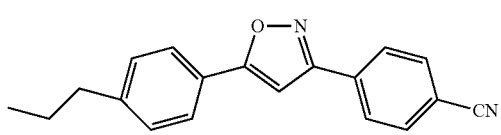 [SMILES: CCCc1ccc(-c2cc(-c3ccc(C#N)cc3)no2)cc1]

Step 1. 4-(Hydroxyiminomethyl)-benzonitrile. The compound was prepared according to Biasotti et al. *Bioorg. Med. Chem.* 2003, 11, 2247. A suspension of 4-formylbenzonitrile (500 mg, 3.81 mmol, 1.00 eq), hydroxylamine hydrochloride (290 mg, 4.19 mmol, 1.10 eq), and sodium acetate (1.56 g, 19.05 mmol, 5.00 eq) in MeOH (50 mL) was heated at 70° C. for 4 h before concentration to dryness. The residue was then slurried in Et$_2$O, filtered, and concentrated to afford the desired intermediate (496 mg, 3.39 mmol, 89%).

Step 2. 4-(Hydroxyimino-bromomethyl)-benzonitrile. The compound was prepared according to Tanaka et al. *Bull. Chem. Soc. Jpn.* 1984, 57, 2184. A 0.05 M solution of NBS (724 mg, 4.07 mmol, 1.20 eq) in CH$_2$Cl$_2$ was added dropwise to a 0° C. solution of 4-(hydroxyiminomethyl)-benzonitrile (496 mg, 3.39 mmol, 1.00 eq) in CH$_2$Cl$_2$ (50 mL). The solution was warmed to room temperature before being volumetrically partitioned between two different reaction vials. Each vial was then concentrated and the crude residues were used without further purification.

Step 3. 4-[5-(4-Propylphenyl)-isoxazol-3-yl]-benzonitrile. A solution of 4-(hydroxyimino-bromomethyl)-benzonitrile (381 mg, 1.70 mmol), triethylamine (0.71 mL, 5.10 mmol, 3.0 eq), and 1-ethynyl-4-propylbenzene (1.23 g, 8.50 mmol, 5.0 eq) in toluene (20 mL) was heated at 100° C. for 1 h before concentration to dryness. Purification via normal phase chromatography afforded the desired intermediate (108 mg, 22%).

Example 5

Preparation of 4-{1-[4-(1-hydroxypropyl)-phenyl]-1H-pyrazol-3-yl}-benzonitrile

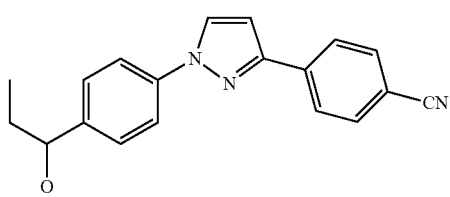 [SMILES: CCC(O)c1ccc(-n2ccc(-c3ccc(C#N)cc3)n2)cc1]

Step 1. 3-(4-Cyanophenyl)pyrazole. To a round bottom flask equipped with stir bar and reflux condenser were added p-cyanoacetophenone (5 g, 34.44 mmol) and dimethylformamide dimethylacetal (DMF-DMA; 40 mL). The mixture was stirred at reflux for 5 h before concentration under reduced pressure afforded the crude dimethylamino-acryloylbenzonitrile intermediate. The residue was then suspended in a minimal volume of EtOH (~20 mL), charged with hydrazine monohydrate (1.67 mL, 34.4 mmol), and heated at 80° C. for 30 min before concentration. The crude 3-(4-cyanophenyl)pyrazole material (5.59 g, 33 mmol, 96%) which was isolated was of sufficient purity for use in the subsequent reaction.

Step 2. 4-[1-(4-Propionyl-phenyl)-1H-pyrazol-3-yl]-benzonitrile. 4-(1H-Pyrazol-3-yl)-benzonitrile (100 mg, 0.591 mmol), 1-(4-bromophenyl)-propan-1-one (126 mg, 0.591 mmol), Cs$_2$CO$_3$ (770 mg, 2.364 mmol), CuI (4 mg, 0.018 mmol), 8-hydroxyquinoline (3 mg, 0.018 mmol), and DMF/H$_2$O (2 mL; 10:1 solution) were combined in a 10 mL CEM Microwave reaction vessel fitted with magnetic stir bar and subjected to microwave irradiation at 150° C. for 30 min. The contents were then filtered and concentrated to dryness affording the nitrile (158 mg, 0.508 mmol, 86%).

Example 6

Preparation of 5-(4-formylphenyl)-2-(4-trifluoromethoxyphenyl)-3,4-dihydro-2H-pyrazole-3,4-dicarboxylic acid diethyl ester

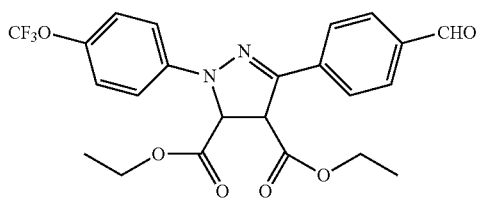

Step 1. Preparation of 4-[(4-trifluoromethoxyphenyl)-hydrazonomethyl]-benzaldehyde. The compound was prepared according to Paulvannan et al. *Tetrahedron*. 2000, 56, 8071. To a stirred solution of benzene-1,4-dicarbaldehyde (1.50 g, 11.2 mmol, 1.0 eq) in i-PrOH (250 mL) was added 4-trifluoromethoxy)phenylhydrazine hydrochloride (2.55 g, 11.2 mmol, 1.0 eq) portionwise over 5 min. The solution was stirred at ambient temperature for 1 h before concentration to dryness and purification via chromatography (2:2:1 hexane:EtOAc:acetone) to afford the intermediate (2.48 g, 72%).

Step 2. Chlorohydrazone synthesis. The intermediate was prepared according to Lokanatha Rai and Hassner *Synth. Commun.* 1989, 19, 2799. A solution of 4-[(4-trifluoromethoxyphenyl)-hydrazonomethyl]-benzaldehyde (2.48 g, 8.05 mmol, 1.00 eq) and N-chlorosuccinimide (1.61 g, 12.08 mmol, 1.5 eq) in i-PrOH (100 mL) was heated at 80° C. for 1 h. The solution was then cooled and volumetrically partitioned evenly between six different reaction vessels to each contain 1.34 mmol of the intermediate.

Step 3. Pyrazoline synthesis. The compounds were prepared according to Paulvannan et al. *Tetrahedron* 2000, 56, 8071. To each reaction vessel were added triethylamine (0.56 mL, 4.02 mmol, 3.00 eq) and the respective acrylates (6.70 mmol, 5.00 eq). The reaction mixtures were then heated at 70° C. for 90 min before concentration to dryness and purification via chromatography (2:2:1 hexane:EtOAc:acetone).

Example 7

Preparation of 4-{1-[4-(2,2,2-trifluoroethoxy)-phenyl]-1H-imidazol-4-yl}-benzonitrile

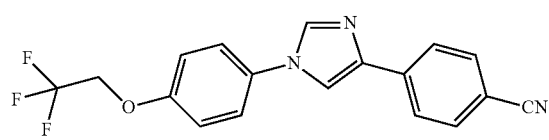 [SMILES: N#Cc1ccc(-c2cn(-c3ccc(OCC(F)(F)F)cc3)cn2)cc1]

4-(2-Bromoacetyl)-benzonitrile (58 mg, 0.21 mmol) and 4-(2,2,2-trifluoroethoxy)-phenylamine (50 mg, 0.21 mmol) were combined in a 100 mL Erlenmeyer flask fitted with magnetic stir bar. The contents were dissolved in EtOH (1 mL) and stirred at ambient temperature for 2 h. The crude intermediate was then transferred to a 100 mL round bottom flask containing KSCN (21 mg, 0.21 mmol) and conc. HCl (18 μL, 0.21 mmol). The vessel was heated at 80° C. for 1 h before its contents were poured into 5 mL of a 1:1 H$_2$O/NH$_4$OH solution. The solution was allowed to stand for 24 h, and then the solid was filtered and washed with ether to afford the intermediate imidazolethiol (32 mg, 0.086 mmol, 33%). An aqueous solution of HNO$_3$ (1.35 mL, 0.387 mmol) and KNO$_3$ (1 mg, 0.003 mmol) was then added dropwise over 10 min to a suspension of the imidazolethiol in acetic acid (2 mL). After stirring for 2 h at ambient temperature the solution was poured into crushed ice and neutralized (pH=7) with 0.1 N sodium hydroxide (NaOH, aq). The nitrile was isolated by vacuum filtration and dried in a 45° C. vacuum oven for 12 h (23 mg, 78%), mp 179° C.

Example 8

Preparation of 4-[1-(4-propylphenyl)-1H-imidazol-4-yl]-benzonitrile

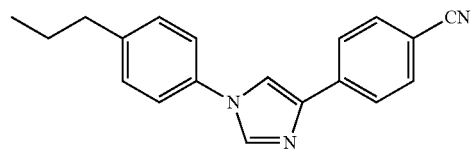 [SMILES: CCCc1ccc(-n2cnc(-c3ccc(C#N)cc3)c2)cc1]

4-Propylaniline (2.70 g, 20 mmol) was added dropwise to a solution of 4-cyanophenacyl bromide (2.20 g, 10 mmol) in DMF (5 mL). This solution was then added to hot (180° C.) formamide (20 mL) over 5 min, and the combined solution was allowed to stir at 180° C. for 2 h. The cooled solution was then poured onto ice (100 mL), and extracted with ether (2×75 mL). After drying and concentrating, the resulting dark oil was purified by chromatography (3:1:2 hexanes:EtOAc:CH$_2$Cl$_2$). The first product (510 mg) was identified as 4-(5-propyl-1H-indol-3-yl)-benzonitrile, mp 140° C. The second fraction (275 mg) was identified as the desired imidazole: mp 133° C.; $^1$H NMR (400 MHz, CDCl$_3$) δ 7.95 (d, J=6 Hz, 2H), 7.90 (s, 1H), 7.70 (d, J=6 Hz, 2H), 7.68 (s, 1H), 7.38 (d, J=4 Hz, 2H), 7.31 (d, J=4 Hz, 2H), 2.69 (t, J=8.9 Hz, 2H), 1.68 (m, 2H), 0.98 (t, J=7.5 Hz, 3H); ESIMS m/z 288.1 (M+H).

Example 9

Preparation of 4-[1-(4-trifluoromethoxyphenyl)-1H-imidazol-4-yl]-benzonitrile

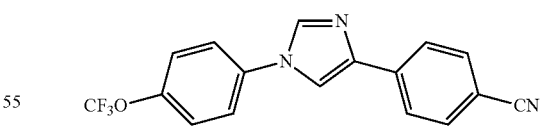

4-Trifluoromethoxyaniline (2.20 g, 12.4 mmol) was added dropwise to a solution of 4-cyanophenacyl bromide (1.50 g, 6.7 mmol) in DMF (5 mL). This solution was then added to hot (180° C.) formamide (20 mL) over 5 min, and the combined solution was allowed to stir at 180° C. for 2 h. The cooled solution was then poured onto ice (100 mL), and extracted with ether (2×75 mL). After drying and concentrating, the resulting semi-solid was crystallized from MeOH/H$_2$O. A second recrystallization from MeOH/H$_2$O removed traces of the formanilide impurity and furnished pure product (200 mg): mp 155° C. Anal. Calcd. for $C_{17}H_{10}F_3N_3O$: C, 62.01; H, 3.06; N, 12.76. Found: C, 61.53; H, 3.13; N, 12.55.

Example 10

Preparation of 4-[1-(4-trifluoromethoxyphenyl)-1H-imidazol-4-yl]-benzoic acid

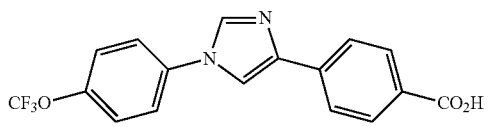

A solution of the nitrile (1.1 g, 3.3 mmol) in EtOH (5 mL) and water (2 mL) was treated with NaOH (1 g, 20 mmol), and the solution was heated to reflux for 6 h. It was then cooled and made acidic with 1 N HCl, and the resulting white solid was filtered and air-dried to give the acid (1.1 g) as a light grey solid: mp 230° C.; $^1$H NMR (400 MHz, CDCl$_3$) δ 11.4 (s, 1H), 7.90 (d, J=6.4 Hz, 2H), 7.89 (s, 1H), 7.80 (d, J=8.6 Hz, 2H), 7.63 (d, J=1.3 Hz, 1H), 7.49 (d, J=9.3 Hz, 2H), 7.38 (d, J=8.9 Hz, 2H).

Example 11

Preparation of 4-[4-(4-trifluoromethylphenyl)-1H-imidazol-1-yl]-benzonitrile

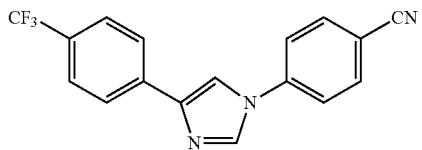 [SMILES: N#Cc1ccc(-n2cnc(-c3ccc(C(F)(F)F)cc3)c2)cc1]

4-Trifluoromethylphenyl imidazole (4.0 g, 19 mmol), 4-fluorobenzonitrile (1.2 g, 8.5 mmol) and potassium carbonate (1.5 g, 10.9 mmol) were combined in DMSO (15 mL) and heated at 100° C. for 6 h. The cooled solution was then poured onto water (100 mL), and the resulting solid was filtered and air-dried to give the imidazole nitrile (4.65 g) as a white solid: mp 252° C.; $^1$H NMR (300 MHz, CDCl$_3$) δ 8.05 (s, 1H), 7.95 (d, J=8 Hz, 2H), 7.85 (d, 2H), 7.72 (s, 1H), 7.72 (d, J=8 Hz, 2H), 7.62 (d, J=8 Hz, 2H); ESIMS m/z 314.1 (M+H). Anal. Calcd. for $C_{16}H_{10}F_3N_3O_2$: C, 65.18; H, 3.22; N, 13.41. Found: C, 64.49; H, 3.23; N, 13.08.

Example 12

Preparation of 4-bromo-1-(4-trifluoromethoxyphenyl)-1H-imidazole

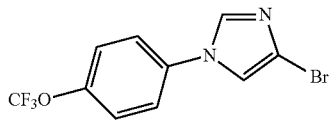

A round bottom flask was charged with 4-bromoimidazole (1.15 g, 7.81 mmol), CuI (0.07 g, 0.36 mmol), 8-hydroxyquinoline (0.05 g, 0.36 mmol), cesium carbonate (3.39 g, 10.4 mmol) and 4-trifluoromethoxyiodobenzene (1.50 g, 5.21 mmol). A 10:1 mixture of DMF (15 mL) and H$_2$O (1.5 mL) was added to the reaction mixture, and the solution was heated to 130° C. for 4 h. The reaction mixture was then diluted with EtOAc and washed sequentially with water, ammonium chloride (saturated), water and sodium bicarbonate. The organics were dried over MgSO$_4$, filtered and purified on a reverse phase column to give the imidazole (820 mg) as a white solid: mp 139-141° C.; ESIMS m/z 308.0 (M+H).

Example 13

Preparation of 4-methoxy-2-[1-(4-trifluoromethoxyphenyl)-1H-imidazol-4-yl]-benzaldehyde

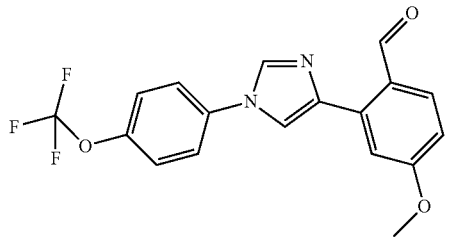 [SMILES: COc1ccc(C=O)c(-c2cn(-c3ccc(OC(F)(F)F)cc3)cn2)c1]

4-Bromo-1-(4-trifluoromethoxyphenyl)-1H-imidazole (100 mg, 0.326 mmol), 2-formyl-5-methoxyphenylboronic acid (73 mg, 0.41 mmol), bis(triphenylphosphine)palladium dichloride (2 mg, 0.003 mmol), sodium bicarbonate (49 mg, 0.59 mmol) and 1:1 DME/H$_2$O (8:8 mL) were combined and added to a microwave vessel. The reaction mixture was heated in the microwave with stirring at 100° C. for 12 min. The microwave took 5 min to reach 100° C., then maintained at 100° C. for 12 min, and then cooled. TLC (1:1 EtOAc: cyclohexane) showed the presence of starting materials, thus the sample was heated to 100° C. for another 8 min. Upon cooling a precipitate formed; this was filtered and washed with water to give a grey solid (86 mg): ESIMS m/z 363.0 (M+H).

The following intermediate was also prepared using this procedure:

Example 14

Preparation of 2-fluoro-4-[1-(4-trifluoromethoxyphenyl)-1H-imidazol-4-yl]-benzaldehyde

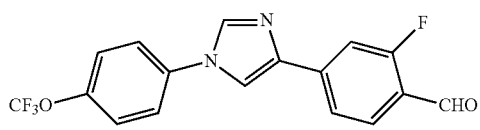

ESIMS m/z 351.0 (M+H).

Example 15

Preparation of 4-[1-(4-trifluoromethoxyphenyl)-1H-[1,2,4]triazol-3-yl]benzonitrile

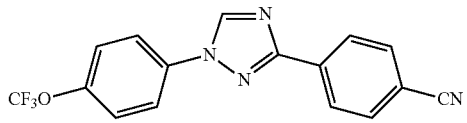

Step 1. 4-(1H-[1,2,4]Triazol-3-yl)-benzonitrile. The general procedure outlined by Lin et. al. (*J. Org. Chem.* 1979, 44, 4163) for preparation of 3-(4-nitrophenyl)-1H-[1,2,4]triazole was used. 4-Cyanobenzamide (21.63 g, 0.148 mol) was dissolved in DMF-DMA (100 mL) and was stirred at reflux under $N_2$ for 8 h. The mixture was concentrated to dryness and suspended in AcOH (50 mL). The vessel was then charged with hydrazine monohydrate (7.18 mL, 0.148 mmol) and stirred at reflux for 1 h before concentration. The desired 4-(1H-[1,2,4]triazol-3-yl)-benzonitrile was obtained in 98% purity by trituration with $Et_2O$ followed by filtration (12.17 g, 0.072 mol, 48%).

Step 2. 4-[1-(4-Trifluoromethoxyphenyl)-1H-[1,2,4]triazol-3-yl]-benzonitrile. The triazole (70 mg, 0.41 mmol), 1-iodo-4-trifluoromethoxybenzene (142 mg, 0.493 mmol), $Cs_2CO_3$ (535 mg, 1.644 mmol), CuI (3 mg, 0.012 mmol), 8-hydroxyquinoline (2 mg, 0.012 mmol), and $DMF/H_2O$ (2 mL; 10:1 solution) were combined in a 10 mL CEM Microwave reaction vessel fitted with magnetic stir bar and subjected to microwave irradiation at 150° C. for 30 min. The contents were then filtered and concentrated to dryness affording the 1,3-diphenyl triazole intermediate (18 mg, 13%).

Example 16

Preparation of 4-[1-(4-pentafluoroethylsulfanylphenyl)-1H-[1,2,4]triazol-3-yl]-benzonitrile

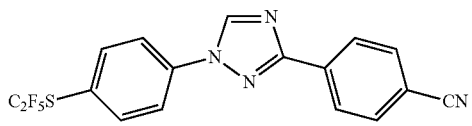

Step 1. 1-Bromo-4-pentafluoroethylsulfanylbenzene. The title compound was prepared using perfluoroalkylation conditions originally described by Popov et. al. *J. Fluorine Chem.* 1982, 21, 365. To a solution of 4-bromobenzenethiol (500 mg, 2.64 mmol, 1.00 eq) and triethylbenzyl ammonium chloride (60 mg, 0.26 mmol, 0.10 eq) in 10 mL of 1:1 $Et_2O$/NaOH (25% aq) at 0° C. was bubbled 1,1,1,2,2-pentafluoro-2-iodoethane gas for 30 min (>5 eq). During this time a UV lamp was directed at the reaction vessel while the temperature was maintained below 10° C. by intermittent use of an ice bath. The contents were then warmed to room temperature, extracted into $Et_2O$ (300 mL), dried ($MgSO_4$), and concentrated under reduced pressure. A portion of this crude material was used in subsequent reactions without further purification (200 mg residue: 120 mg product, 0.39 mmol, 1.2 eq).

Step 2. 4-[1-(4-Pentafluoroethylsulfanylphenyl)-1H-[1,2,4]triazol-3-yl]-benzonitrile. Coupling with 4-(1H-[1,2,4]triazol-3-yl)-benzonitrile as described above gave 4-[1-(4-pentafluoroethylsulfanylphenyl)-1H-[1,2,4]triazol-3-yl]-benzonitrile (70 mg, 46%).

Example 17

Preparation of 4-[1-(4-pentafluoroethyloxy-phenyl)-1H-[1,2,4]triazol-3-yl]-benzaldehyde

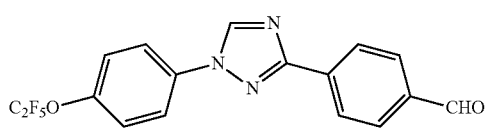

Step 1. A solution of 3-p-tolyl-1H-[1,2,4]triazole (4.85 g, 30.5 mmol), 4-bromophenyl pentafluoroethyl ether (10.0 g, 34.4 mmol), $Cs_2CO_3$ (25 g, 77 mmol), CuI (1.25 g, 6.5 mmol) and 8-hydroxyquinoline (0.35 g, 2.4 mmol) in 9:1 $DMF/H_2O$ (50 mL) was stirred vigorously and heated to 130° C. (internal temperature) for 20 h. The solution was then cooled, poured into water, and acidified with 2 N HCl to pH 2. Ether (250 mL) was then added and the solution was shaken and filtered before separating layers. The organic layer was dried and concentrated, and the resulting gummy solid was heated with hexanes (100 mL). The hot hexane layer was decanted from insoluble residue, the resulting solution cooled to 0° C. and the precipitated solid was filtered and air-dried to furnish 1-(4-pentafluoroethyloxy-phenyl)-3-p-tolyl-1H-[1,2,4]triazole (7.0 g, 61% based on starting triazole) as an off-white solid: mp 130-132° C.; ESIMS m/z 370.8 (M+H).

Step 2. The product from Step 1 (7.0 g, 18.7 mmol) was dissolved in acetonitrile (200 mL) and stirred at ambient temperature while ceric ammonium nitrate (32 g, 58 mmol) in water (60 mL) was added in portions over 10 min. The solution was then heated to reflux for 4 h, cooled, and diluted with water (200 mL). The solution was extracted with ether (2×200 mL), and the combined organic layer was dried and concentrated to give an orange oil. This material was dissolved in dioxane (40 mL) and treated with a solution of KOH (5 g, 90 mmol) in water (20 mL). The solution was heated to reflux for 2 h, then cooled and diluted with water (100 mL). The aldehyde precipitated and was collected by filtration. Recrystallization from $MeOH/H_2O$ gave the pure aldehyde as a white solid (2.2 g, 30%): mp 137-144° C. $^1H$ NMR (300 MHz, $CDCl_3$) δ 10.1 (s, 1H), 8.65 (s, 1H), 8.40 (d, J=8.4 Hz, 2H), 8.0 (d, J=8.4 Hz, 2H), 7.85 (d, J=9 Hz, 2H), 7.45 (d, J=9 Hz, 2H); ESIMS m/z 384.2 (M+H).

Example 18

Preparation of 4-[1-(4-pentafluoroethyloxy-phenyl)-1H-[1,2,4]triazol-3-yl]-benzoic acid

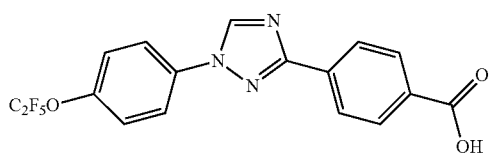

A solution of 4-[1-(4-pentafluoroethyloxy-phenyl)-1H-[1,2,4]triazol-3-yl]-benzaldehyde (1.7 g, 4.4 mmol), sodium bromate (2.1 g, 13.9 mmol) and sodium bisulfate (0.53 g, 4.5 mmol) in acetonitrile (50 mL) was heated to reflux for 5 h, during which time a voluminous precipitate formed. The solution was then cooled and poured into water (100 mL), filtered, and dried to furnish the acid (1.67 g) as a white solid: mp 225° C.; $^1$H NMR (300 MHz, CDCl$_3$) δ 10.1 (s, 1H), 8.63 (s, 1H), 8.35 (d, J=8.4 Hz, 2H), 8.5 (d, J=8.4 Hz, 2H), 7.85 (d, J=9 Hz, 2H), 7.43 (d, J=9 Hz, 2H); ESIMS m/z 399.2 (M+H$^+$).

extracted with EtOAc, dried, concentrated, and purified by chromatography (Biotage, 4:1 hexane:EtOAc) to give the triazole (0.42 g, 35%) as an off-white solid: mp 124° C.; $^1$H NMR (300 MHz, CDCl$_3$) δ 8.58 (s, 1H), 8.33 (d, J=8 Hz, 2H), 7.78 (d, J=8 Hz, 2H), 7.64 (d, J=8.2 Hz, 2H), 7.33 (d, J=8.2 Hz, 2H), 2.70 (t, J=7.8 Hz, 2H), 1.63 (m, 2H), 1.38 (m, 2H), 0.95 (t, J=7.5 Hz, 3H); ESIMS m/z 303.1.

Example 19

Preparation of 4-[1-(4-pentafluoroethyloxy-phenyl)-1H-[1,2,4]triazol-3-yl]-benzoyl azide

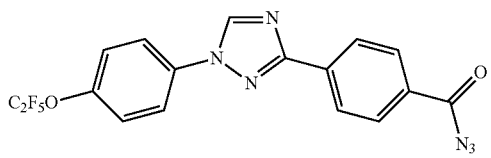

A solution of 4-[1-(4-pentafluoroethyloxy-phenyl)-1H-[1,2,4]triazol-3-yl]-benzoic acid (1.67 g, 4.2 mmol), diphenylphosphoryl azide (1.26 g, 4.58 mmol) and triethylamine (0.5 g, 5 mmol) in dry t-BuOH (10 mL) was heated to 75° C. for 90 min, resulting in dissolution of the starting acid and subsequent precipitation of the azide. The cooled solution was then poured onto ice (10 g), and the resulting mixture was filtered and dried to furnish the azide (0.80 g) as a white solid: mp 112-115° C. dec; $^1$H NMR (300 MHz, CDCl$_3$) δ 8.62 (s, 1H), 8.33 (d, J=8.4 Hz, 2H), 8.16 (d, J=8.4 Hz, 2H), 7.85 (d, J=9 Hz, 2H), 7.42 (d, J=9 Hz, 2H); ESIMS m/z 425 (M+H).

Example 20

Preparation of 4-[1-(4-butylphenyl)-1H-[1,2,4]triazol-3-yl]-benzonitrile

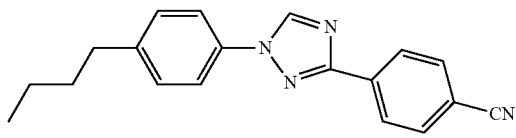 [SMILES: CCCCc1ccc(-n2cnc(-c3ccc(C#N)cc3)n2)cc1]

A solution of 4-n-butyl phenyl hydrazine (1.0 g, 5 mmol) and 4-cyanobenzaldehyde (0.8 g, 6.0 mmol) in i-PrOH (15 mL) was heated on a steam bath for 2 h and then was cooled and diluted with water (5 mL). The resulting orange solid was filtered and air-dried to give the hydrazone (1.30 g) as a yellow solid, mp 107° C. A solution of this hydrazone (1.1 g, 4.0 mmol) and NCS (0.67 g, 5 mmol) in i-PrOH (20 mL) was stirred under nitrogen at ambient temperature for 2 h, during which time the original solid dissolved and a new solid formed. The resulting orange solution was then treated with tetrazole (0.45 g, 6.4 mmol) and triethylamine (960 µL, 7.0 mmol). The orange-brown solution was heated at reflux for 2 h. The solution was then cooled, diluted with water (25 mL),

Example 21

Preparation of 4-[1-(4-pentafluoroethyl-phenyl)-1H-[1,2,4]triazol-3-yl]-benzaldehyde

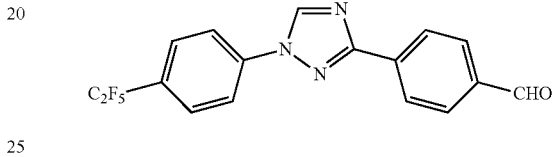

Step 1. 1-(4-Pentafluoroethyl-phenyl)-3-p-tolyl-1H-[1,2,4]triazole. Pentafluoroethyl iodide (521 mg, 2.12 mmol) was condensed into a vial containing 1-bromo-4-iodobenzene (300 mg, 1.06 mmol), copper(0) powder (135 mg, 2.12 mmol), and DMSO (5 mL). The vial was then sealed and subjected to microwave irradiation at 150° C. for 60 min. GC-MS proved consumption of the starting material yielding both 1-bromo-4-pentafluoroethylbenzene and 1-iodo-4-pentafluoroethylbenzene intermediates. The mixture (1.06 mmol) was transferred to a 250 mL round bottom flask and 3-p-tolyl-1H-[1,2,4]triazole (169 mg, 1.06 mmol), Cs$_2$CO$_3$ (1.38 g, 4.24 mmol), CuI (202 mg, 1.06 mmol), 8-hydroxyquinoline (2 mg, 0.011 mmol), and DMF/H$_2$O (12 mL; 10:1 solution) were added. The solution was stirred at reflux at 160° C. for 6 h. Upon completion, the cooled contents were poured into H$_2$O and precipitation was allowed for 1 h. The precipitate was collected by vacuum filtration and dried overnight in a 45° C. vacuum oven. The crude 1-(4-pentafluoroethylphenyl)-3-p-tolyl-1H-[1,2,4]triazole intermediate was used in step 2 without further purification.

Step 2. Oxidation to the aldehyde. Ammonium cerium(IV) nitrate (3.32 g, 4.24 mmol) and the intermediate from Step 1 were combined in a round bottom flask with acetonitrile and water (20 mL; 1:1). The solution was stirred at reflux at 110° C. for 4 h, affording a mixture of the 3-(4-nitrooxymethyl-phenyl)-1-(4-pentafluoroethyl-phenyl)-1H-[1,2,4]triazole and 4-[1-(4-pentafluoroethyl-phenyl)-1H-[1,2,4]triazol-3-yl]-benzaldehyde intermediates. The acetonitrile was removed under vacuum and the crude intermediate precipitates were collected by filtration. The material was then combined with powdered KOH (178 mg, 3.18 mmol) in dioxane and water (10 mL; 1:1) and was stirred at reflux at 105° C. for 90 min before the dioxane was removed under vacuum allowing precipitation of the intermediate from water. The 4-[1-(4-pentafluoroethyl-phenyl)-1H-[1,2,4]triazol-3-yl]-benzaldehyde intermediate was collected by filtration (35 mg, 0.095 mmol, 9% overall from 4-tolyl triazole).

Example 22

Preparation of trifluoromethanesulfonic acid 4-[3-(4-formyl-phenyl)-[1,2,4]triazol-1-yl]-phenyl ester

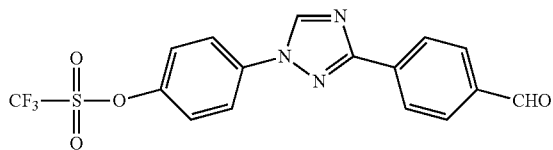 [SMILES: O=Cc1ccc(-c2ncn(-c3ccc(OS(=O)(=O)C(F)(F)F)cc3)n2)cc1]

Step 1. 1-(4-Methoxyphenyl)-3-p-tolyl-1H-[1,2,4]triazole was prepared by coupling 3-p-tolyl-1H-[1,2,4]triazole with 4-iodoanisole under conditions described in Step 1 of the previous example. This material was then demethylated using conditions described in Hitchcock et al. *Synlett* 2006, 2625. Boron tribromide (1 M solution in hexanes; 1.67 mL, 1.67 mmol) was added dropwise to a solution of 1-(4-methoxyphenyl)-3-p-tolyl-1H-[1,2,4]triazole (300 mg, 1.28 mmol) in $CH_2Cl_2$ (10 mL) at 0° C. under $N_2$. After addition was complete, the vessel was warmed to ambient temperature before refluxing at 40° C. for 6 h. The cooled contents were then quenched with $H_2O$ before removal of the $CH_2Cl_2$ and partitioning between EtOAc and water. The organic layer was collected, washed with brine, dried ($MgSO_4$), concentrated, and purified via chromatography (3:1:1, hexanes:EtOAc:acetone) to afford the 4-(3-p-tolyl-[1,2,4]triazol-1-yl)-phenol intermediate (219 mg, 0.872 mmol, 68%). Trifluoromethanesulfonic anhydride (0.16 mL, 0.96 mmol) was added dropwise to a solution of the phenol and 4-tert-butyl-2,6-dimethylpyridine (142 mg, 0.872 mmol) in $CH_2Cl_2$ (10 mL) at 0° C. under $N_2$. The vessel was warmed to ambient temperature before the solvent was removed under reduced pressure and the residue purified via chromatography (2:2:1, hexanes:EtOAc:acetone) affording the trifluoromethanesulfonic acid 4-(3-p-tolyl-[1,2,4]triazol-1-yl)-phenyl ester intermediate (304 mg, 0.794 mmol, 91%).

Step 2. Oxidation of the 4-methyl intermediate above to the corresponding aldehyde was carried out using ammonium cerium(IV) nitrate under conditions described in Step 2 of the previous example.

Example 23

Preparation of 4-[5-(4-trifluoromethylphenyl)-1H-[1,2,4]triazol-3-yl]-benzonitrile

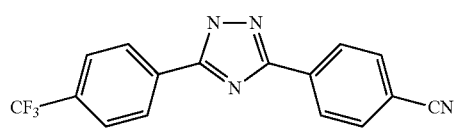 [SMILES: N#Cc1ccc(-c2n[nH]c(-c3ccc(C(F)(F)F)cc3)n2)cc1]

Terephthalonitrile (115 mg, 0.90 mmol), 4-trifluoromethylbenzoic acid hydrazide (92 mg, 0.450 mmol), $K_2CO_3$ (31 mg, 0.225 mmol), and n-butyl alcohol (~2 mL) were combined in a 10 mL CEM Microwave reaction vial fitted with magnetic stir bar and subjected to microwave irradiation at 150° C. for 30 min. The contents were then filtered and concentrated to dryness. Chromatography (3:1 hexanes/EtOAc) afforded the 1,2,4-triazole nitrile (72 mg, 0.230 mmol, 51%).

Example 24

Preparation of 4-[1-(3,4-dichlorophenyl)-5-oxo-4,5-dihydro-1H-[1,2,4]triazol-3-yl]-benzonitrile

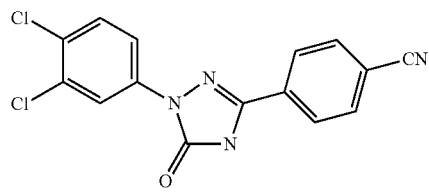 [SMILES: N#Cc1ccc(-c2nn(-c3ccc(Cl)c(Cl)c3)c(=O)[nH]2)cc1]

Step 1. 4-Cyanophenyl-oxo-acetic acid. A round bottom flask equipped with mechanical stirrer and reflux condenser was charged with p-cyanoacetophenone (5 g, 34.44 mol), $SeO_2$ (9.55 g, 86.1 mmol), and pyridine (~100 mL). The mixture was stirred at reflux for 6 h before precipitates were removed by filtration and the filtrate was charged with 10% HCl (aq) (20 mL). The filtrate was extracted into EtOAc (3×50 mL) and the combined organic layers were further extracted into nearly saturated $NaHCO_3$. The aqueous layer was then carefully made acidic (pH=1) with conc. HCl affording a small crop of the desired product. The remainder of the oxo acetic acid was obtained by extracting into EtOAc, drying ($MgSO_4$), and concentration (1.69 g, 28%).

Step 2. 4-[1-(3,4-Dichlorophenyl)-5-oxo-4,5-dihydro-1H-[1,2,4]triazol-3-yl]-benzonitrile. A suspension of 4-cyanophenyl-oxo-acetic acid (100 mg, 0.571 mmol), (3,4-dichlorophenyl)hydrazine hydrochloride (122 mg, 0.571 mmol), 12.1 N HCl (5 μL, 0.057 mmol), and $H_2O$ (~10 mL) in a 25 mL reaction vial was stirred vigorously at ambient temperature for 24 h. The hydrazone was obtained by vacuum filtration and placed into a 100 mL round bottom flask with a magnetic stir bar. The flask was then supplemented with triethylamine (0.08 mL, 0.571 mmol), diphenylphosphoryl azide (157 mg, 0.571 mmol), and toluene (20 mL) before heating at 110° C. for 1 h. Upon cooling the contents were quenched with 10% NaOH (aq) and made acidic (pH 1) with conc. HCl. Precipitation was allowed for 15 min before the intermediate was obtained by vacuum filtration and dried overnight in a 45° C. vacuum oven (16 mg, 8%).

Example 25

Preparation of 4-[1-(4-Chlorophenyl)-1H-[1,2,3]triazol-4-yl]-benzonitrile

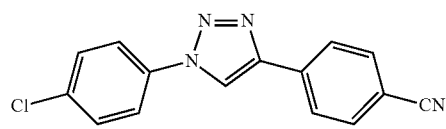 [SMILES: N#Cc1ccc(-c2cn(-c3ccc(Cl)cc3)nn2)cc1]

Following the procedure published by Feldman et al. (*Org Lett.* 2004, 6, 3897), a suspension of 4-ethynylbenzonitrile (50 mg, 0.393 mmol), 1-chloro-4-iodobenzene (94 mg, 0.393 mmol), L-proline (9 mg, 0.079 mmol), ascorbic acid (7 mg, 0.039 mmol), NaN$_3$ (31 mg, 0.472 mmol), CuSO$_4$ (3 mg, 0.020 mmol), and Na$_2$SO$_4$ (11 mg, 0.079 mmol) in DMSO (1.5 mL) was heated at 65° C. for 24 h. Upon cooling the mixture was diluted with H$_2$O and stirred for 30 min at ambient temperature. The intermediate 4-[1-(4-chlorophenyl)-1H[1,2,3]triazol-4-yl]-benzonitrile (54 mg, 48%) was then obtained by vacuum filtration after washing with copious volumes of H$_2$O and 20% NH$_4$OH (~20 mL).

Example 26

Preparation of 4-[5-(4-trifluoromethylphenyl)-tetrazol-2-yl]-benzaldehyde

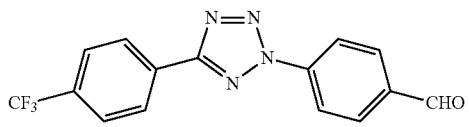 [SMILES: O=Cc1ccc(-n2nnc(-c3ccc(C(F)(F)F)cc3)n2)cc1]

This aldehyde was prepared from 4-trifluoromethylbenzaldehyde by following the route described in Roppe et al. *J. Med Chem.* 2004, 47, 4645.

Example 27

Preparation of 4-[5-(4-trifluoromethoxyphenyl)-pyridin-3-yl]-benzaldehyde

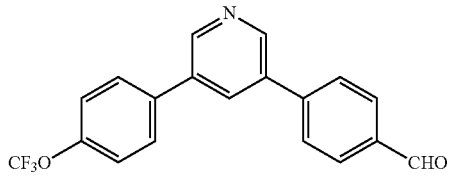

Step 1. 3,5-Dibromopyridine (4.4 mmol), 4-trifluoromethoxyphenyl boronic acid (5.1 mmol), tetrakis(triphenylphosphine)palladium(0) (0.04 mmol), 2 M potassium carbonate (8.44 mmol) and dioxane (21 mL) were combined in a vial and heated by microwave for 10 min at 150° C. The reaction mixture was taken up in ether and washed with brine. The ether layer was dried over magnesium sulfate, was filtered and the solvent removed in vacuo. The crude mixture was purified by silica gel chromatography to yield 3-bromo-5-(4-trifluoromethoxyphenye-pyridine (130 mg) as a yellow solid: $^1$H NMR (400 MHz, CDCl$_3$) δ 8.71 (m, 2H), 8.00 (t, J=2.1 Hz, 1H), 7.58 (d, J=8.8 Hz, 2H), 7.34 (d, J=8.0 Hz, 2H); ELMS m/z 317 (M$^+$).

Step 2. The compound was prepared by palladium-catalyzed arylation of the product of step 1 with 4-formylphenyl boronic acid.

Example 28

Preparation of 4-[4-(4-trifluoromethoxyphenyl)-pyridin-2-yl]-benzaldehyde

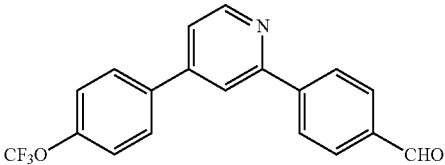

Step 1. The compound was prepared by palladium-catalyzed arylation of 2-chloro-4-iodopyridine with 4-trifluoromethoxyphenyl boronic acid.

Step 2. 2-Chloro-4-(4-trifluoromethoxyphenyl)-pyridine (0.55 mmol) starting from 2-chloro-4-iodopyridine, 4-formylphenyl boronic acid (0.82 mmol), tetrakis(triphenylphosphine)palladium(0) (0.005 mmol), 2 M potassium carbonate (0.55 mL) and dioxane (3 mL) were combined in a vial and irradiated by microwave for 15 min at 150° C. The reaction mixture was taken up in EtOAc and washed with brine. The organic layer was dried over magnesium sulfate, was filtered and the solvent removed in vacuo. Purification by silica gel chromatography (EtOAc/hexanes) yielded the product (120 mg) as an off-white solid: $^1$H NMR (400 MHz, CDCl$_3$) δ 10.11 (s, 1H), 8.81 (d, J=4.8 Hz, 1H), 8.24 (d, J=8.7 Hz, 2H), 8.03 (d, J=8.4 Hz, 2H), 7.96 (m, 1H), 7.73 (d, J=9.0 Hz, 2H), 7.49 (dd, J=5.3, 1.8 Hz, 1H), 7.37 (d, J=8.1 Hz, 2H); ELMS m/z 343 (M$^+$).

Example 29

Preparation of 4-[6-(4-trifluoromethoxyphenyl)-pyridin-2-yl]-benzaldehyde

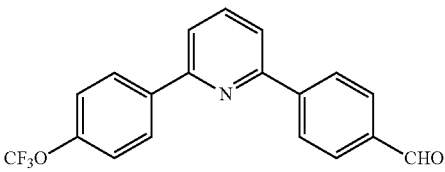

Step 1. 4-(6-Bromopyridin-2-yl)-benzaldehyde (0.31 mmol) was prepared as in Puglisi et al. *Eur. J. Org. Chem* 2003, 8, 1552-1558.

Step 2. 4-[6-(4-Trifluoromethoxyphenyl)-pyridin-2-yl]-benzaldehyde. 4-(6-Bromo-pyridin-2-yl)-benzaldehyde (0.31 mmol), 4-trifluoromethoxyphenyl boronic acid (0.46 mmol), tetrakis(triphenylphosphine)palladium(0) (0.003 mmol), 2 M potassium carbonate (0.31 mL) and dioxane (2 mL) were combined in a vial and irradiated by microwave for 10 min at 150° C. The reaction mixture was taken up in ether and washed with brine. The organic layer was dried over magnesium sulfate, was filtered and the solvent removed in vacuo. Purification by silica gel chromatography (EtOAc/hexanes) yielded the product (80 mg) as an off-white solid: mp 109-112° C.; $^1$H NMR (400 MHz, CDCl$_3$) δ 10.11 (s, 1H), 8.32 (d, J=8.5 Hz, 2H), 8.19 (d, J=8.1 Hz, 2H), 8.03 (d, J=8.4 Hz, 2H), 7.89 (t, J=7.9 Hz, 1H), 7.79 (d, J=7.7 Hz, 1H), 7.74 (d, J=8.0 Hz, 1H), 7.35 (d, J=8.3 Hz, 2H); EIMS m/z 343 (M$^+$).

Example 30

Preparation of 4-[6-(4-trifluoromethoxyphenyl)-pyrimidin-4-yl]-benzaldehyde

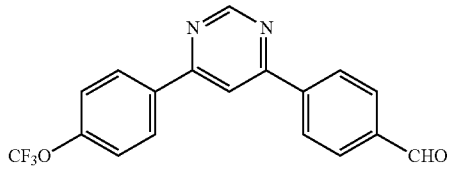

Step 1. 4-Chloro-6-(4-trifluoromethoxyphenyl)-pyrimidine was prepared by palladium-catalyzed arylation of 4,6-dichloropyrimidine and 4-trifluoromethoxyphenyl boronic acid: $^1$H NMR (400 MHz, CDCl$_3$) δ 9.05 (s, 1H), 8.14 (d, J=9.8 Hz, 2H), 7.74 (m, 1H), 7.36 (d, J=8.4 Hz, 2H); EIMS m/z 274 (M$^+$).

Step 2. The compound was prepared by palladium-catalyzed arylation of the product of step 1 with 4-formylphenyl boronic acid: $^1$H NMR (400 MHz, CDCl$_3$) δ 10.15 (s, 1H), 9.38 (d, J=0.9 Hz, 1H), 8.33 (d, J=8.4 Hz, 2H), 8.23 (d, J=8.5 Hz, 2H), 8.16 (d, J=0.8 Hz, 1H), 8.08 (d, J=8.8 Hz, 2H), 7.40 (d, J=8.1 Hz, 2H); EIMS m/z 344 (M$^+$).

Example 31

Preparation of 4-[2-(4-trifluoromethoxyphenyl)-pyrimidin-4-yl]-benzaldehyde

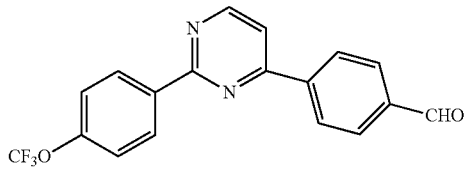

Step 1. 4-Chloro-2-(4-trifluoromethoxyphenyl)-pyrimidine. The title compound was prepared by palladium-catalyzed arylation of 2,4-dichloropyrimidine and 4-trifluoromethoxyphenyl boronic acid: mp 70-73° C.; $^1$H NMR (400 MHz, CDCl$_3$) δ 8.68 (d, J=5.6 Hz, 1H), 8.16 (d, J=9.1 Hz, 2H), 7.65 (d, J=5.3 Hz, 1H), 7.36 (dd, J=9.2, 0.9 Hz, 2H); ELMS m/z 274 (M$^+$).

Step 2. The compound was prepared by palladium-catalyzed arylation of the product of step 1 with 4-formylphenyl boronic acid: $^1$H NMR (400 MHz, CDCl$_3$) δ 10.13 (s, 1H), 8.91 (d, J=4.8 Hz, 1H), 8.74 (d, J=8.5 Hz, 2H), 8.28 (d, J=8.4 Hz, 2H), 8.03 (d, J=8.4 Hz, 2H), 7.65 (d, J=5.3 Hz, 1H), 7.39 (d, J=8.6 Hz, 2H); EIMS m/z 344 (M$^+$).

Example 32

Preparation of 4-[4-(4-trifluoromethoxyphenyl)-pyrimidin-2-yl]-benzaldehyde

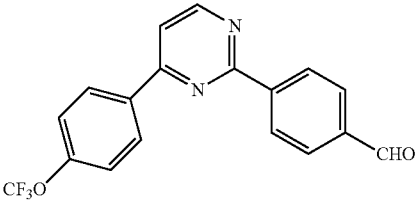

Step 1. 4-(4-Chloropyrimidin-2-yl)-benzaldehyde. The compound was prepared by palladium-catalyzed arylation of 2,4-dichloropyrimidine and 4-formylphenyl boronic acid: $^1$H NMR (400 MHz, CDCl$_3$) δ 10.13 (s, 1H), 8.74 (d, J=5.0 Hz, 1H), 8.27 (d, J=7.8 Hz, 2H), 8.04 (d, J=7.9 Hz, 2H), 7.74 (m, 1H); EIMS m/z 218 (M$^+$).

Step 2. The compound was prepared by palladium-catalyzed arylation of the product of Step 1 with 4-trifluoromethoxyphenyl boronic acid: $^1$H NMR (400 MHz, CDCl$_3$) δ 10.14 (s, 1H), 8.91 (d, J=4.2 Hz, 1H), 8.63 (d, J=8.5 Hz, 2H), 8.37 (d, J=8.4 Hz, 2H), 8.06 (d, J=8.8 Hz, 2H), 7.67 (d, J=5.4 Hz, 1H), 7.35 (d, J=8.7 Hz, 2H); EIMS m/z 344 (M$^+$).

Example 33

Preparation of 4-[6-(4-trifluoromethoxyphenyl)-pyrazin-2-yl]-benzaldehyde

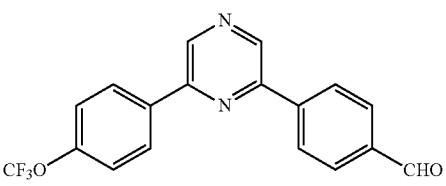

Step 1. 2-Chloro-6-(4-trifluoromethoxyphenyl)-pyrazine. The compound was prepared by palladium-catalyzed arylation of 2,6-dichloropyrazine and 4-trifluoromethoxyphenyl boronic acid: mp 58-60° C.; $^1$H NMR (400 MHz, CDCl$_3$) δ 8.94 (s, 1H), 8.57 (s, 1H), 8.10 (d, J=9.0 Hz, 2H), 7.37 (d, J=8.4 Hz, 2H); EIMS m/z 274 (M$^+$).

Step 2. The compound was prepared by palladium-catalyzed arylation of the product of step 1 with 4-formylphenyl boronic acid: $^1$H NMR (400 MHz, CDCl$_3$) δ 10.13 (s, 1H), 9.07 (s, 1H), 9.03 (s, 1H), 8.33 (d, J=8.1 Hz, 2H), 8.21 (d, J=8.7 Hz, 2H), 8.07 (d, J=7.6 Hz, 2H), 7.40 (d, J=8.3 Hz, 2H); EIMS m/z 344 (M$^+$).

Example 34

Preparation of 4-[2-(4-trifluoromethoxyphenyl)-pyrimidin-5-yl]-benzaldehyde

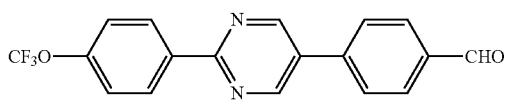

Step 1. 4-(2-Chloropyrimidin-5-yl)-benzaldehyde. The compound was prepared by palladium-catalyzed arylation of 2,5-dichloropyrimidine and 4-formylphenyl boronic acid.

Step 2. 4-(2-Chloropyrimidin-5-yl)-benzaldehyde (0.92 mmol), 4-trifluoromethoxyphenyl boronic acid (1.10 mmol), dichlorobis(triphenylphosphine)palladium(II) (0.01 mmol), 2 M potassium carbonate (0.92 mL) and dioxane (5 mL) were combined in a vial and irradiated by microwave for 10 min at 150° C. The organic layer from the reaction mixture was loaded directly onto silica and dried in vacuo. Purification by silica gel chromatography (EtOAc/hexanes) yielded the product (140 mg) as a white solid: $^1$H NMR (400 MHz, CDCl$_3$) δ 10.11 (s, 1H), 9.07 (s, 2H), 8.57 (d, J=9.0 Hz, 2H), 8.07 (d, J=8.5 Hz, 2H), 7.82 (d, J=8.3 Hz, 2H), 7.35 (d, J=8.3 Hz, 2H); EIMS m/z 344 (M$^+$).

Example 35

Preparation of 4-[5-(4-trifluoromethoxyphenyl)-pyrimidin-2-yl]-benzaldehyde

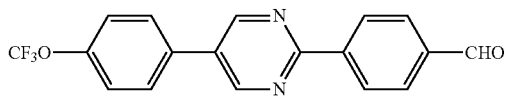

Step 1. 2-Chloro-5-(4-trifluoromethoxyphenyl)-pyrimidine. The compound was prepared by palladium-catalyzed arylation of 2,5-dichloropyrimidine with 4-trifluoromethoxyphenyl boronic acid.

Step 2. 2-Chloro-5-(4-trifluoromethoxyphenyl)-pyrimidine (4.22 mmol), 4-formylphenyl boronic acid (5.1 mmol), dichlorobis(triphenylphosphine)palladium(II) (0.05 mmol), 2 M potassium carbonate (4.2 mL) and dioxane (21 mL) were combined in a vial and irradiated by microwave for 20 min at 150° C. The organic layer from the reaction mixture was loaded directly onto silica and dried in vacuo. Purification by silica gel chromatography (EtOAc/hexanes) yielded the product (75 mg) as a white solid: $^1$H NMR (400 MHz, CDCl$_3$) 10.13 (s, 1H), 9.06 (s, 2H), 8.68 (d, J=8.8 Hz, 2H), 8.03 (d, J=8.3 Hz, 2H), 7.68 (d, J=8.8 Hz, 2H), 7.40 (d, J=8.7 Hz, 2H); EIMS m/z 344 (M$^+$).

Example 36

Preparation of 4-heptafluoropropyl-6-(4-nitrophenyl)-2-(4-trifluoromethylphenyl)-pyrimidine

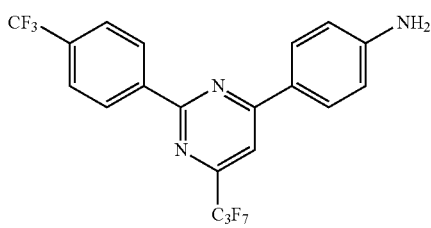

Step 1. 4-Heptafluoropropyl-6-(4-nitrophenyl)-2-(4-trifluoromethylphenyl)-pyrimidine. A solution of 4-heptafluoropropyl-2-methylsulfanyl-6-(4-nitrophenyl)-pyrimidine (1.20 g, 2.90 mmol; prepared from 1-(4-nitrophenyl-4,4,5,5,6,6,6-heptafluorohexane-1,3-dione according to Green et al. WO 200138311 A2), 4-trifluoromethylphenylboronic acid (0.608 g, 3.2 mmol), trifurylphosphine (114 mg, 0.49 mmol), and copper (II) 2-thiophenecarboxylate (750 mg, 3.9 mmol) were combined in dry THF (15 mL) and heated to 50° C. The catalyst tris(dibenzylideneacetone)dipalladium(0)-chloroform adduct (60 mg, cat) was then added in three portions over 3 h, and the solution was then allowed to stir at 50° C. overnight. Concentration and chromatography (Biotage, 5:1 hexane/CH$_2$Cl$_2$) furnished the title compound (0.60 g, 40%) as a light yellow solid: mp 191° C.; EIMS m/z 514.0 (M+H).

Step 2. 4-Heptafluoropropyl-6-(4-aminophenyl)-2-(4-trifluoromethylphenyl)-pyrimidine. A solution of 4-heptafluoropropyl-2-(4-trifluoromethylphenyl)-6-(4-nitrophenyl)-pyrimidine (0.18 g, 0.35 mmol), iron powder (0.20 g, 3.5 mmol), ferric ammonium sulfate (0.15 g, 0.3 mmol) in 3:1 EtOH/water was heated on a steam bath for 3 h. Then it was cooled, diluted with Et$_2$O (50 mL), filtered through Celite®, and concentrated to give the aniline as a yellow solid: $^1$H NMR (300 MHz, CDCl$_3$) δ 8.75 (d, J=8 Hz, 2H), 8.18 (d, J=8 Hz, 2H), 7.90 (s, 1H), 7.80 (d, J=8 Hz, 2H), 6.82 (d, J=8 Hz, 2H), 4.20 (s, 2H).

Example 37

Preparation of 4-trifluoromethyl-6-(4-aminophenyl)-2-(4-trifluoromethyl-phenyl)-pyrimidine

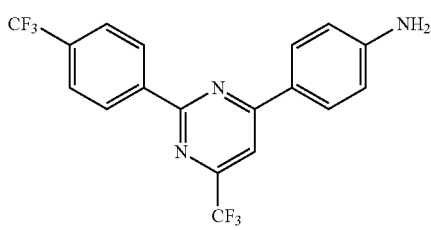

Step 1. 4-Trifluoromethyl-6-(4-nitrophenyl)-2-(4-trifluoromethylphenyl)-pyrimidine. A solution of 4-trifluoromethyl-2-methylsulfanyl-6-(4-nitrophenyl)-pyrimidine (1.25 g, 4.0 mmol; prepared from 1-(4-nitrophenyl-4,4,4-trifluorobutane-1,3-dione according to Green et al. WO 200138311 A2), 4-trifluoromethylphenylboronic acid (0.95 g, 5.0 mmol), trifurylphosphine (140 mg, 0.60 mmol), and copper (II) 2-thiophenecarboxylate (1.05 g, 5.0 mmol) were combined in dry THF (25 mL) and heated to 52° C. The catalyst tris(dibenzyl-idencacetone)dipalladium(0)-chloroform adduct (100 mg) was then added in three portions over 3 h, and the solution was then allowed to stir at 50° C. for 12 h. Concentration and chromatography (Biotage, 4:1 hexane/$CH_2Cl_2$) furnished the title compound (0.67 g, 41%) as a light yellow solid: mp 162° C.; $^1$H NMR (300 MHz, $CDCl_3$) δ 8.75 (d, J=8 Hz, 2H), 8.41 (s, 4H), 8.03 (s, 1H), 7.80 (d, J=8 Hz, 2H); EIMS m/z 414.1 (M+H).

Step 2. 4-Trifluoromethyl-6-(4-aminophenyl)-2-(4-trifluoromethylphenyl)-pyrimidine. A solution of 4-trifluoromethyl-2-(4-trifluoromethylphenyl)-6-(4-nitrophenyl)-pyrimidine (0.50 g, 1.2 mmol), iron powder (0.50 g, 9 mmol), ferric ammonium sulfate (0.5 g, 1.0 mmol) in 3:1 EtOH-water (30 mL) was heated on a steam bath for 3 h. Then it was cooled, diluted with diethyl ether (50 mL), filtered through Celite®, and concentrated. The crude amine was purified by Biotage column (4:1:1 Hexanes/EtOAc/$CH_2Cl_2$) to give pure aniline (0.22 g). This material was used directly in the formation of the corresponding carbamate: $^1$H NMR (300 MHz, $CDCl_3$) δ 8.75 (d, J=8 Hz, 2H), 8.16 (d, J=8 Hz, 2H), 7.81 (s, 1H), 7.77 (d, J=8 Hz, 2H), 6.82 (d, J=8 Hz, 2H), 4.15 (s, 2H).

Example 38

Preparation of 4-[2-(4-trifluoromethylphenyl)-pyrimidin-4-yl]-phenylamine

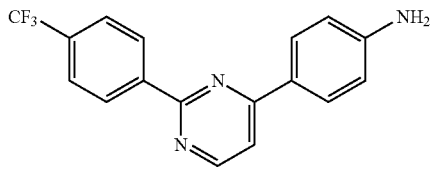 [SMILES: Nc1ccc(-c2ccnc(-c3ccc(C(F)(F)F)cc3)n2)cc1]

Step 1. 4-(4-Nitrophenyl)-2-(4-trifluoromethylphenyl)-pyrimidine. To sodium metal (82.7 mg, 3.60 mmol) dissolved in absolute EtOH (3 mL) was added 4-trifluoromethylbenzamidine hydrochloride dihydrate (938 mg, 3.60 mmol) followed by EtOH (4 mL). After 30 min, 3-dimethylamino-1-(4-nitrophenyl)-propenone (498 mg, 2.26 mmol) was added, and the mixture was heated at reflux approximately 66 h and was then allowed to cool. The mixture was concentrated to a tan solid which was triturated under saturated sodium bicarbonate. The solid was collected and air dried to give 937 mg. It was then dissolved in chloroform/EtOAc and was passed over silica gel eluting with 7:3 chloroform/EtOAc to afford the title compound (710 mg, 91%): mp 175-176.5° C.; $^1$H NMR δ 9.01 (d, J=5.3 Hz, 1H), 8.73 (d, J=8.2 Hz, 2H), 8.43 (s, 4H), 7.82 (d, J=8.1 Hz, 2H), 7.76 (d, J=5.2 Hz, 1H); EIMS m/z 345 (M+, 100), 299 (57). Anal. Calcd. for $C_{17}H_{10}F_3N_3O_2$: C, 59.13; H, 2.92; N, 12.17. Found: C, 58.82; H, 2.63; N, 11.98.

Step 2. 4-[2-(4-Trifluoromethylphenyl)-pyrimidin-4-yl]-phenylamine. A mixture of 4-(4-nitrophenyl)-2-(4-trifluoromethyl-phenyl)-pyrimidine (670 mg, 1.94 mmol) and 10% Pd/C (75 mg) in EtOH (30 mL) was placed on a Parr shaker at 40 psi hydrogen gas at room temperature. After 7 h the mixture was filtered through Celite® and the EtOH was removed in vacuo. The residue was partitioned between EtOAc and saturated $NaHCO_3$, and the organic phase was dried ($MgSO_4$). Concentration gave a solid which was dissolved in EtOAc and was filtered through a plug of silica gel. Concentration gave the title compound (500 mg, 82%): mp 166-167° C.; $^1$H NMR δ 8.75 (d, J=5.30 Hz, 1H), 8.67 (d, J=8.3 Hz, 2H), 8.10 (d, J=8.9 Hz, 2H), 7.75 (d, J=7.9 Hz, 2H), 7.54 (d, J=5.3 Hz, 1H), 6.80 (d, J=8.6 Hz, 2H), 4.03 (br s, 2H); MS (API-ES+) 316 ([M+H]+, 100). Anal. Calcd. for $C_{17}H_{12}F_3N_3$: C, 64.76; H, 3.84; N, 13.33. Found: C, 64.37; H, 3.71; N, 13.08.

Example 39

Preparation of 2-chloro-4-[3-(4-trifluoromethylphenyl)-[1,2,4]triazol-1-yl]-phenylamine

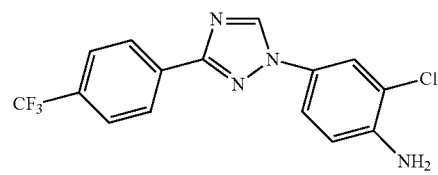 [SMILES: Nc1ccc(-n2cnc(-c3ccc(C(F)(F)F)cc3)n2)cc1Cl]

Step 1. 1-(3-Chloro-4-nitrophenyl)-3-(4-trifluoromethylphenyl)-1H-[1,2,4]triazole. A solution of NBS (180 mg, 1 mmol) in $CH_2Cl_2$ (4 mL) was stirred under nitrogen at 0° C. while dimethyl sulfide (110 mg, 1.8 mmol) was added via syringe. The solution, which forms a white solid, was then cooled to −20° C., and (N-(3-chloro-4-nitrophenyl)-N'-(4-trifluoromethyl-benzylidene)-hydrazine (200 mg, 0.58 mmol) in $CH_2Cl_2$ (4 mL) was added. The solution was allowed to warm to ambient temperature and stirred for an additional 2 h. The resulting orange solution was then diluted with $CH_2Cl_2$ (25 mL) and washed with water and brine before drying and concentrating. The resulting orange solid hydrazonyl bromide (150 mg) was then treated directly with tetrazole (25 mg, 0.35 mmol) and triethylamine (50 pt, 0.35 mmol) in absolute EtOH (5 mL). The resulting orange-brown solution was heated at reflux for 2 h. TLC showed that the initial bromide was first converted into two yellow intermediates, which then disappeared and were replaced by a single, colorless spot. The orange solution was then diluted with water (10 mL), yielding a tan-yellow solid which was filtered, air-dried, and recrystallized from toluene to give a yellow-tan solid (60 mg): mp 185° C. $^1$H NMR (300 MHz, $CDCl_3$) δ 8.60 (s, 1H), 8.41 (d, J=8.7 Hz, 1H), 8.33 (d, J=7.5 Hz, 2H), 7.90 (d, J=2 Hz, 1H), 7.70 (d, J=7.5 Hz, 2H), 7.65 (dd, J=8.7, 2 Hz, 1H); EIMS m/z 368.9. Anal. Calcd. for $C_{15}H_8ClF_3N_4O_2$: C, 48.86; H, 2.19; N, 15.20. Found: C, 48.39; H, 2.61; N, 14.91.

Step 2. 2-Chloro-4-[3-(4-trifluoromethylphenyl)-[1,2,4] triazol-1-yl]-phenylamine. A solution of the nitrophenyl derivative (0.75 g, 2.0 mmol) in MeOH (7 mL) and water (3 mL) was treated with iron powder (0.7 g, 12.5 mmol) and ferrous ammonium sulfate (hexahydrate; 0.7 g, 1.8 mmol). The solution was heated on a steam bath for 3 h, whereupon TLC showed complete conversion to a more polar, fluorescent product. The solution was cooled and filtered, and the filtrate was concentrated in vacuo. Purification by chromatography through a short plug of silica gel (7:2:1 hexane/EtOAc/$CH_2Cl_2$) gave the amine (0.55 g) as a light tan solid: mp 148° C.; $^1$H NMR (300 MHz, $CDCl_3$) δ 8.40 (s, 1H), 8.31 (d, J=8.4 Hz, 1H), 7.72 (d, J=8.4 Hz, 2H), 7.69 (d, J=2 Hz, 1H), 7.42 (dd, J=8.5, 2 Hz, 1H), 6.9 (d, J=8.4 Hz, 1H); EIMS Ink 340.4, 342.3 (M+H). Anal. Calcd. for $C_{15}H_{10}ClF_3N_4$: C, 53.19; H, 2.98; N, 16.83. Found: C, 52.90; H, 3.10; N, 16.83.

Example 40

Preparation of 4-[1-(4-trifluoromethoxyphenyl)-1H-[1,2,4]triazol-3-yl]-phenylamine

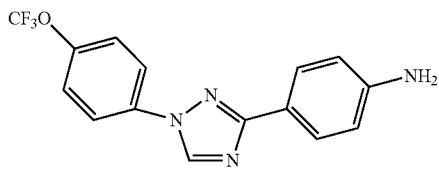

Step 1. 1-(4-Trifluoromethoxyphenyl)-3-(4-nitrophenyl)-1H-[1,2,4]triazole. A solution of NBS (0.70 g, 3.9 mmol) in CH$_2$Cl$_2$ (25 mL) was stirred under nitrogen at 0° C. while dimethyl sulfide (0.40 g, 6.5 mmol) was added via syringe. The solution, which forms a white solid, was then cooled to −20° C., and N-(4-nitrobenzylidene)-N'-(4-trifluoromethoxyphenyl)-hydrazine (0.70 g, 2.15 mmol) in CH$_2$Cl$_2$ (10 mL) was added. The solution was allowed to warm to ambient temperature and stirred an additional 2 h. The resulting orange solution was then diluted with CH$_2$Cl$_2$ (25 mL) and washed with water and brine before drying and concentrating. The resulting orange solid hydrazonyl bromide (0.9 g) was then treated directly with tetrazole (154 mg, 2.2 mmol) and triethylamine (280 μL, 0.23 mmol) in absolute EtOH (5 mL). The resulting orange-brown solution was heated at reflux for 2 h. TLC showed that the initial bromide was first converted into two yellow intermediates, which were replaced by a single, colorless spot. The orange solution was then concentrated and purified by chromatography (2:1:2 hexanes/EtOAc/CH$_2$Cl$_2$), yielding the title compound (0.30 g) as a light yellow solid: mp 147° C.; $^1$H NMR (300 MHz, CDCl$_3$) 8.68 (s, 1H), 8.40 (d, J=5 Hz, 2H), 8.35 (d, J=5 Hz, 2H), 7.85 (d, J=8 Hz, 2H), 7.42 (d, J=8 Hz, 2H); EIMS m/z 350 (M$^+$, 100), 299 (57).

Step 2. 4-[1-(4-Trifluoromethoxyphenyl)-1H-[1,2,4]triazol-3-yl]-phenylamine. Catalytic reduction using a Pd/C catalyst in EtOH under hydrogen atmosphere gave the corresponding aniline as a light grey solid: mp 160° C.; $^1$H NMR (300 MHz, CDCl$_3$) δ 8.50 (s, 1H), 8.00 (d, J=8.4 Hz, 2H), 7.78 (d, J=8.7 Hz, 2H), 7.35 (d, J=8 Hz, 2H), 6.76 (d, J=8.7 Hz, 2H), 3.9 (br s, 2H); EIMS m/z 321.

Example 41

Preparation of 4-[1-(4-pentafluoroethyloxyphenyl)-1H-[1,2,4]triazol-3-yl]-phenylamine

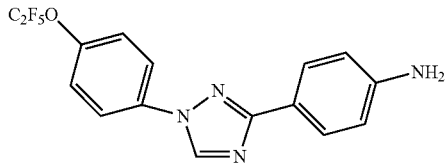

Step 1. 1-(4-Pentafluoroethyloxyphenyl)-3-(4-nitrophenyl)-1H-[1,2,4]triazole. A slurry of 3-(4-nitrophenyl)triazole (11.4 g, 60 mmol), 1-iodo-4-pentafluoroethoxybenzene (20 g, 60 mmol), cesium carbonate (39.0 g, 120 mmol), CuI (3.5 g, 18 mmol), 8-hydroxyquinoline (2.0 g, 13.8 mmol) and 9:1 DMF-H$_2$O (155 mL) was heated at 150° C. for 5 h and then cooled. The contents of the round-bottomed flask were poured onto water (150 mL) and extracted with Et$_2$O (2×100 mL). The organic layer was dried and concentrated, and the solid residue recrystallized from MeOH and water to give the nitrotriazole (11.8 g, 49%) as a tan solid: mp 170-175° C.; $^1$H NMR (300 MHz, CDCl$_3$) δ8.68 (s, 1H), 8.40 (d, J=5 Hz, 2H), 8.35 (d, J=5 Hz, 2H), 7.85 (d, J=8 Hz, 2H), 7.42 (d, J=5.2 Hz, 8 Hz, 2H); EIMS m/z 400 (M$^+$).

Step 2. 4-[1-(4-Pentafluoroethyloxyphenyl)-1H-[1,2,4]triazol-3-yl]-phenylamine. Catalytic reduction using a Pd/C catalyst in EtOH under hydrogen atmosphere gave the corresponding aniline as a light tan solid: mp 160° C.; $^1$H NMR (300 MHz, CDCl$_3$) δ 8.55 (s, 1H), 8.00 (d, J=7 Hz, 2H), 7.78 (d, J=8 Hz, 2H), 7.35 (d, J=8 Hz, 2H), 6.78 (d, J=8 Hz, 2H), 3.9 (br s, 2H); EIMS m/z 371.

Example 42

Preparation of 4-[1-(4-heptafluoropropyloxyphenyl)-1H-[1,2,4]triazol-3-yl]-phenylamine

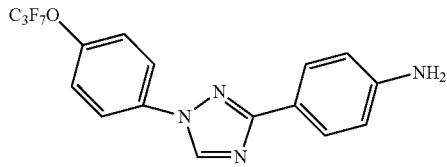

Step 1. 1-(4-Heptafluoropropyloxyphenyl)-3-(4-nitrophenyl)-1H-[1,2,4]triazole. A slurry of 3-(4-nitrophenyl)triazole (1.0 g, 5.2 mmol), 1-iodo-4-heptafluoropropyloxybenzene (6.1 g, 15.8 mmol), cesium carbonate (10.0 g, 30.7 mmol), CuI (900 mg, 4.7 mmol), and 8-hydroxyquinoline (500 mg, 3.4 mmol) in 9:1 DMF-H$_2$O (40 mL) was heated at 150° C. for 12 h, then cooled and the contents poured onto water (50 mL) and concentrated NH$_4$OH (50 mL). The blue solution was extracted with ether (100 mL), and the organic layer was separated and filtered to remove some insoluble material, then dried and concentrated. The solid residue was recrystallized from MeOH/water to furnish the nitrophenyl triazole (4.69 g) as a light tan solid: mp 114-116° C.; $^1$H NMR (300 MHz, CDCl$_3$) δ 8.66 (s, 1H), 8.40 (m, 4H), 7.85 (d, J=8 Hz, 2H), 7.42 (d, J=8 Hz, 2H); EIMS m/z 450.1 (M$^+$).

Step 2. 4-[1-(4-Heptafluoropropyloxyphenyl)-1H-[1,2,4]triazol-3-yl]-phenylamine. Catalytic reduction under the conditions described above gave the corresponding aniline as a light tan solid: mp 181-183° C.; $^1$H NMR (300 MHz, CDCl$_3$) δ 8.54 (s, 1H), 8.00 (d, J=8 Hz, 2H), 7.80 (d, J=8 Hz, 2H), 7.40 (d, J=8 Hz, 2H), 6.78 (d, J=8 Hz, 2H), 3.9 (br s, 2H); EIMS m/z 421.3 (M+1).

Example 43

Preparation of 4-[4-(4-trifluoromethylphenyl)-imidazol-1-yl]-phenylamine

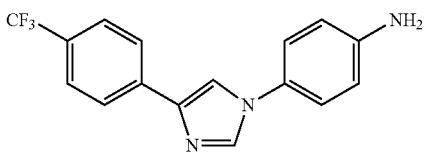 [SMILES: Nc1ccc(-n2cnc(-c3ccc(C(F)(F)F)cc3)c2)cc1]

Step 1. 4-[4-(4-Trifluoromethylphenyl)-1H-imidazol-1-yl]-nitrobenzene. 4-Trifluoromethylphenyl imidazole (1.43 g, 6.7 mmol), 4-fluoro nitrobenzene (1.2 g, 8.5 mmol) and potassium carbonate (1.5 g, 10.9 mmol) were combined in DMF (15 mL) and heated at 100° C. for 6 h. The cooled solution was then poured onto water (100 mL), and the resulting solid was filtered and air-dried to give the title imidazole (1.0 g) as a light yellow solid: mp 197° C. Anal. Calcd. for $C_{16}H_{10}F_3N_3O_2$: C, 57.66; H, 3.02; N, 12.61. Found: C, 57.69; H, 3.01; N, 12.48.

Step 2. 4-[4-(4-Trifluoromethylphenyl)-imidazol-1-yl]-phenylamine. Catalytic reduction using a Pd/C catalyst in EtOH under hydrogen atmosphere gave the corresponding aniline as a light grey solid: mp 142-143° C.; $^1$H NMR (400 MHz, CDCl$_3$) δ 7.90 (d, J=7 Hz, 2H), 7.75 (s, 1H), 7.65 (d, J=7 Hz, 2H), 7.52 (s, 1H), 7.19 (d, J=8 Hz, 2H), 6.75 (d, J=8 Hz, 2H), 3.8 (br s, 2H); EIMS m/z 302.0.

Example 44

Preparation of 4-[1-(4-trifluoromethylphenyl)-1H-imidazol-4-yl]phenylamine

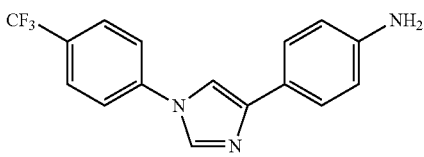 [SMILES: Nc1ccc(-c2cn(-c3ccc(C(F)(F)F)cc3)cn2)cc1]

Step 1. 4-[4-(4-Trifluoromethylphenyl)-1H-imidazol-1-yl]-nitrobenzene. Prepared as in step 1 of the preceding example.

Step 2. 4-[1-(4-Trifluoromethylphenyl)-1H-imidazol-4-yl]-phenylamine. Catalytic reduction using a Pd/C catalyst in EtOH under hydrogen atmosphere gave the corresponding aniline as a light grey solid: mp 191° C.; $^1$H NMR (400 MHz, CDCl$_3$) δ 7.92 (s, 1H), 7.76 (d, J=8 Hz, 2H), 7.66 (d, J=4.5 Hz, 2H), 7.55 (s, 1H), 6.75 (d, J=4.5 Hz, 2H), 3.8 (br s, 2H); EMS m/z 304.0. Anal. Calcd. for $C_{16}H_{12}F_3N_3$: C, 63.36; H, 3.99; N, 13.85. Found: C, 63.14; H, 4.07; N, 13.52.

Example 45

Preparation of 4-[1-(4-trifluoromethoxyphenyl)-1H-imidazol-4-yl]-phenylamine

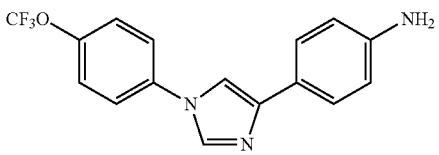

Step 1. 4-(4-Nitrophenyl)-1-(4-trifluoromethoxyphenyl)-1H-imidazole. The conditions described by Porretta et al. Farmaco, *Edizione Scientifica* 1985, 40, 404 were used to convert 4-trifluoromethoxyaniline (5.3 g, 30 mmol) and α-bromo-4-nitroacetophenone (3.7 g, 15 mmol) into the imidazole (2.1 g, 41%).

Step 2. 4-[1-(4-Trifluoromethoxyphenyl)-1H-imidazol-4-yl]-phenylamine. Catalytic reduction using a Pd/C catalyst in EtOH under hydrogen atmosphere gave the corresponding aniline as a light grey solid: mp 167° C.; $^1$H NMR (300 MHz, CDCl$_3$) δ 7.83 (s, 1H), 7.64 (d, J=4.8 Hz, 2H), 7.47 (d, J=4.4 Hz, 2H), 7.40 (s, 1H), 7.36 (d, J=4.8 Hz, 2H), 6.75 (d, J=4.4 Hz, 2H), 3.5 (br s, 2H); EIMS m/z 320. Anal. Calcd. for $C_{16}H_{12}F_3N_3O$: C, 60.19; H, 3.79; N, 13.16. Found: C, 59.91; H, 3.67; N, 13.03.

Example 46

Preparation of 4-(4-aminophenyl)-2-(4-trifluoromethoxyphenyl)-2,4-dihydro-[1,2,4]triazol-3-one

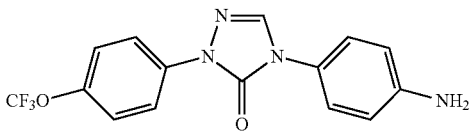

Step 1. 4-(4-Nitrophenyl)-2-(4-trifluoromethoxyphenyl)-2,4-dihydro-[1,2,4]triazol-3-one. The title compound was prepared according to the procedure in Henbach, DE 2724891 A1, 1978, with modifications to three steps: In the addition of the aniline, 4-nitroaniline was used instead of 3,5-dichloroaniline and dry THF was used as solvent instead of toluene. In the formation of the triazolinone ring, triphosgene (0.65 equiv) was used instead of phosgene: mp 136-140° C.; $^1$H NMR (300 MHz, CDCl$_3$) δ 8.40 (d, J=8.8 Hz, 2H), 8.05 (d, J=8.8 Hz, 2H), 7.99 (s, 1H), 7.89 (d, J=9.3 Hz, 2H), 7.32 (d, J=9.3 Hz, 2H); ESIMS m/z 367 (M+H).

Step 2. 4-(4-Aminophenyl)-2-(4-trifluoromethoxyphenyl)-2,4-dihydro-[1,2,4]triazol-3-one. The nitrophenyl triazolinone (0.037 g, 0.10 mmol) was dissolved in absolute EtOH (1 mL) under N$_2$. To this was added tin(II) chloride dihydrate (0.114 g, 0.51 mmol), and the mixture was stirred at reflux for 2 h. The mixture was cooled to 25° C., was poured onto ice-H$_2$O (25 mL), and the aqueous mixture was brought to pH 9-10 with 1 N NaOH. The mixture was extracted with Et$_2$O (3×25 mL), and the combined organic extracts were dried (MgSO$_4$), filtered and concentrated to give a dark brown solid (0.0297 g, 87%) that was used without further purification: mp 115-120° C.; $^1$H NMR (300 MHz, CDCl$_3$) δ 8.07 (d, J=9.7

Hz, 2H), 7.73 (s, 1H), 7.32-7.23 (m, 4H), 6.77 (d, J=8.5 Hz, 2H), 3.85 (br, 2H); ESIMS m/z 336 (M+).

Example 47

Preparation of 4-[5-(4-trifluoromethylphenyl)-4,5-dihydro-isoxazol-3-yl]-phenylamine

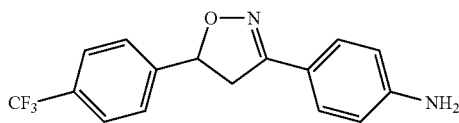 [SMILES: Nc1ccc(C2=NOC(c3ccc(C(F)(F)F)cc3)C2)cc1]

Step 1. {4-[5-(4-Trifluoromethylphenyl)-4,5-dihydro-isoxazol-3-yl]-phenyl}-carbamic acid tert-butyl ester. To a stirred solution of NCS (57 mg, 0.424 mmol) and pyridine (34) in chloroform (1.7 mL) was added 4-N-t-BOC-aminobenzaldehyde oxime (100 mg, 0.424 mmol). The reaction was stirred at room temperature for 10 min. 4-Trifluoromethylstyrene (78 μL, 0.53 mmol) was then added and the temperature was increased to 45° C. To this solution was added dropwise triethylamine (62 μL, 0.445 mmol) dissolved in chloroform (0.5 mL). The reaction was stirred at 45° C. for 5 h. The cooled solution was diluted with chloroform (10 mL) and washed with water (2×5 mL). The organic phase was then dried over $MgSO_4$, filtered and concentrated to give the isoxazoline (100 mg, 58%): $^1$H NMR (400 MHz, $CDCl_3$) δ 7.40-7.83 (m, 8H), 6.60 (br s, 1H), 5.76 (dd, J=11.0, 7.7 Hz, 1H), 3.81 (dd, J=16.5, 11.0 Hz, 1H), 3.29 (dd, J=16.5, 7.7 Hz, 1H); ELMS m/z 406 (M+).

Step 2. 4-[5-(4-Trifluoromethylphenyl)-4,5-dihydro-isoxazol-3-yl]-phenylamine. To a stirred solution of the N-BOC isoxazoline (prepared in step 1) in $CH_2Cl_2$ (2.5 mL) was added trifluoroacetic acid (6.16 mmol, 0.46 mL) and the reaction was stirred at room temperature for 3 h. The solution was concentrated and the residue was taken up in saturated $KHCO_3$ solution (5 mL) and stirred for 30 min. The mixture was then extracted with $CH_2Cl_2$ (3×10 mL). The organic phase was dried over $MgSO_4$, filtered and concentrated to afford the expected aniline (68 mg, 90%): $^1$H NMR (400 MHz, $CDCl_3$) δ 7.45-7.63 (m, 6H), 6.67 (d, J=8.6 Hz, 2H), 5.72 (dd, J=10.9, 7.6 Hz, 1H), 3.92 (br s, 2H), 3.78 (dd, J=16.7, 10.9 Hz, 1H), 3.25 (dd, J=16.7, 7.6 Hz, 1H); EIMS m/z 306 (M+).

Example 48

Preparation of 4-[3-(4-trifluoromethoxyphenyl)-4,5-dihydro-isoxazol-5-yl]-phenylamine

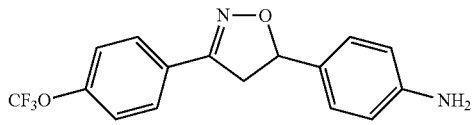

To a stirred solution of NCS (85 μL, 0.634 mmol) and pyridine (4 μL) in chloroform (2.5 mL) was added p-trifluoromethoxybenzaldehyde oxime (130 mg, 0.634 mmol). The reaction was heated at 50° C. for 3 h. 4-Aminostyrene (93 μL, 0.793 mmol) was then added followed by a solution of triethylamine (93 μL, 0.666 mmol) dissolved in chloroform (0.5 mL) dropwise. The reaction was stirred at 50° C. for 3 h. The cooled solution was diluted with chloroform (15 mL) and washed with water (2×10 mL). The organic phase was then dried over $MgSO_4$, filtered and concentrated. The residue was purified via radial chromatography using a 2:1 hexane/EtOAc solution as the eluent ($R_f$=0.18) to afford 4-[3-(4-trifluoromethoxyphenyl)-4,5-dihydro-isoxazol-5-yl]-phenylamine (125 mg; 61%): $^1$H NMR (400 MHz, $CDCl_3$) δ 7.73 (d, J=8.2 Hz, 2H), 7.25 (d, J=8.2 Hz, 2H), 7.17 (d, J=8.2 Hz, 2H), 6.68 (d, J=8.2 Hz, 2H), 5.65 (dd, J=10.9, 8.9 Hz, 1H), 3.55-3.75 (br s, 2H), 3.67 (dd, J=16.8, 10.9 Hz, 1H), 3.30 (dd, J=16.8, 8.9 Hz, 1H); EIMS m/z 322 (M+).

Example 49

Preparation of 1-(4-aminophenyl)-3-(4-trifluoromethoxyphenyl)-1,3-dihydroimidazol-2-one These compounds were prepared according to the procedure described in Bromidge et al. WO 2003057220 A1 with slight modifications.

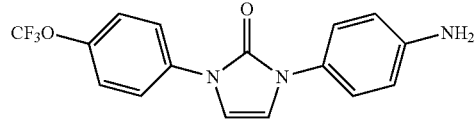

Step 1. (2,2-Dimethoxyethyl)-(4-trifluoromethoxyphenyl)amine. To a stirred solution of 4-trifluoromethoxyaniline (1 mL, 7.46 mmol) and glyoxaldehyde dimethyl acetal (60% v/v in water; 8.95 mmol, 1.6 mL) in EtOH (37 mL) was added 10% Pd/C (300 mg). The mixture was evacuated and flushed with nitrogen three times. Hydrogen was then added in a balloon apparatus and the mixture was stirred under 1 atm of hydrogen for 31 h. The mixture was filtered through a pad of Celite® and the pad was washed with EtOH (25 mL). The ethanol was removed under reduced pressure and the residue was diluted with $CH_2Cl_2$ (30 mL). The layers were separated and the organic phase was dried over $MgSO_4$, filtered and concentrated to give (2,2-dimethoxyethyl)-(4-trifluoromethoxyphenyl)amine (1.7 g, 86%): $^1$H NMR (400 MHz, $CDCl_3$) δ 7.04 (d, J=8.9 Hz, 2H), 6.59 (d, J=8.9 Hz, 2H), 4.56 (t, J=5.4 Hz, 1H), 3.92 (br s, 1H), 3.51 (d, J=5.4 Hz, 2H), 3.42 (s, 6H); EIMS m/z 265 (M+).

Step 2. 1-(2,2-Dimethoxyethyl)-3-(4-nitrophenyl)-1-(4-trifluoromethoxyphenyl)-urea. To a stirred solution of (2,2-dimethoxyethyl)-(4-trifluoromethoxyphenyl)amine (0.85 g, 3.2 mmol) dissolved in $CH_2Cl_2$ (32 mL) was added p-nitrophenyl isocyanate (0.58 g, 3.53 mmol) and the reaction mixture was stirred at room temperature overnight. The mixture was diluted with $CH_2Cl_2$ (50 mL) and was washed successively with $NaHCO_3$ (30 mL) and brine (30 mL). The organic phase was then dried over $MgSO_4$, filtered and concentrated. The residue was purified via radial chromatography using a 2:1 hexane/EtOAc solution as the eluent ($R_f$=0.32) to afford 1-(2,2-dimethoxyethyl)-3-(4-nitrophenyl)-1-(4-trifluoromethoxyphenyl)-urea (0.87 g, 63%): $^1$H NMR (400 MHz, $CDCl_3$) δ 8.15 (d, J=9.2 Hz, 2H), 7.50-7.30 (m, 6H), 7.02 (br s, 1H), 4.65 (t, J=5.4 Hz, 1H), 3.82 (d, J=5.4 Hz, 2H), 3.41 (s, 6H); EIMS m/z 429 (M+).

Step 3. 1-(4-Nitrophenyl)-3-(4-trifluoromethoxyphenyl)-1,3-dihydroimidazol-2-one. To a stirred solution of 1-(2,2-dimethoxyethyl)-3-(4-nitrophenyl)-1-(4-trifluoromethoxyphenyl)-urea (0.23 g, 0.53 mmol) dissolved in toluene (28 mL) was added concentrated HCl (2 drops). The reaction mixture was stirred at reflux for 3 h. The cooled solution was diluted with EtOAc (75 mL) and washed with saturated NaHCO$_3$ (25 mL) and brine (25 mL). The organic phase was then dried over MgSO$_4$, filtered and concentrated. The residue was purified via radial chromatography using a 2:1 hexane/EtOAc solution as the eluent (R$_f$=0.28) to afford 1-(4-nitrophenyl)-3-(4-trifluoromethoxyphenyl)-1,3-dihydroimidazol-2-one (134 mg, 71%): $^1$H NMR (400 MHz, CDCl$_3$) δ 8.35 (d, J=9.2 Hz, 2H), 7.93 (d, J=9.2 Hz, 2H), 7.67 (d, J=9.2 Hz, 2H), 7.34 (d, J=9.2 Hz, 2H), 6.87 (d, J=3.3 Hz, 1H), 6.81 (d, J=3.3 Hz, 1H); EIMS m/z/z 365 (M$^+$).

Step 4. 1-(4-Aminophenyl)-3-(4-trifluoromethoxyphenyl)-1,3-dihydro-imidazol-2-one. To a stirred solution of 1-(4-nitrophenyl)-3-(4-trifluoromethoxyphenyl)-1,3-dihydroimidazol-2-one (120 mg, 0.33 mmol) in EtOAc (3.5 mL) was added tin dichloride (371 mg, 1.64 mmol) and the reaction mixture was stirred at reflux for 3 h. The cooled solution was poured onto ice (15 mL) and the pH was adjusted to pH 7-8 by the addition of 10% NaHCO$_3$. The mixture was extracted with EtOAc (3×10 mL) and washed with brine (10 mL). The organic phase was then dried over MgSO$_4$, filtered and concentrated to obtain 1-(4-aminophenyl)-3-(4-trifluoromethoxyphenyl)-1,3-dihydroimidazol-2-one (102 mg, 92%): $^1$H NMR (400 MHz, CDCl$_3$) δ 7.72 (d, J=8.8 Hz, 2H), 7.37 (d, J=8.8 Hz, 2H), 7.32 (d, J=8.8 Hz, 2H), 6.76 (d, J=8.8 Hz, 2H), 6.69 (d, J=3.3 Hz, 1H), 6.65 (d, J=3.3 Hz, 1H); EIMS m/z 335 (M$^+$).

Example 50

Preparation of 1-(4-aminophenyl)-3-(4-trifluoromethoxyphenyl)-imidazolidin-2-one

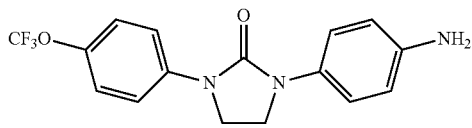

To a solution of 1-(4-nitrophenyl)-3-(4-trifluoromethoxyphenyl)-1,3-dihydroimidazol-2-one (144 mg, 0.395 mmol) in EtOH (40 mL) was added 10% Pd/C (100 mg). The mixture was evacuated and flushed with nitrogen three times. The Parr vessel was pressurized to 45 psi of hydrogen and shaken for 5 h. The depressurized solution was filtered through a pad of Celite® and the pad was washed with EtOH (25 mL). The ethanol was removed under reduced pressure to afford the title product (114 mg, 95%): $^1$H NMR (400 MHz, CDCl$_3$) δ 7.61 (d, J=9.2 Hz, 2H), 7.33 (d, J=9.2 Hz, 2H), 7.21 (d, J=8.6 Hz, 2H), 6.71 (d, J=9.2 Hz, 2H), 3.92 (s, 4H), 3.61 (br s, 2H); EIMS m/z 307 (M$^+$).

Example 51

Preparation of 4-[6-(4-trifluoromethoxyphenyl)-pyridazin-3-yl]-phenylamine

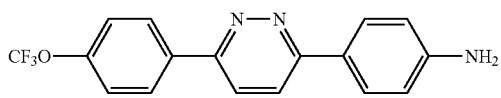

Step 1. 3-Chloro-6-(4-trifluoromethoxyphenyl)-pyridazine. To a solution containing 3,6-dichloropyridazine (0.3 g, 2.01 mmol), 4-trifluoromethoxyphenyl-boronic acid (0.50 g, 2.42 mmol) and 2 M K$_2$CO$_3$ (2 mL, 4.03 mmol) dissolved in dry 1,4-dioxane (11 mL) was added dichlorobis(triphenylphosphine)palladium(II) (14 mg, 0.02 mmol). The mixture was irradiated using a CEM Discover microwave at 190° C. for 30 min. The mixture was diluted with ether (100 mL) and washed with brine (30 mL). The organic phase was then dried over MgSO$_4$, filtered and concentrated. The residue was purified via radial chromatography using a 3:1 hexane/EtOAc solution as the eluent. Two fractions were isolated. The first fraction (R$_f$=0.63) was shown to be the bis-Suzuki product (95 mg, 12%). The second fraction isolated (R$_f$=0.34) was identified as 3-chloro-6-(4-trifluoromethoxyphenyl)-pyridazine (174 mg, 32%): NMR (400 MHz, CDCl$_3$) δ 8.10 (d, J=9.2 Hz, 2H), 7.83 (d, J=8.9 Hz, 2H), 7.60 (d, J=8.9 Hz, 2H), 7.37 (d, J=9.2 Hz, 2H); EIMS m/z 274 (M$^+$).

Step 2. 4-[6-(4-Trifluoromethoxyphenyl)-pyridazin-3-yl]-phenylamine. To a solution containing 3-chloro-6-(4-trifluoromethoxyphenyl)-pyridazine (157 mg, 0.57 mmol), 4-aminophenylboronic acid (118 mg, 0.86 mmol) and 2 M K$_2$CO$_3$ (0.57 mL, 1.14 mmol) dissolved in dry 1,4-dioxane (3.5 mL) was added dichlorobis(triphenylphosphine)palladium(II) (4 mg, 0.006 mmol). The mixture was irradiated using a CEM Discover microwave at 190° C. for 30 min. The mixture was diluted with ether (100 mL) and washed with brine (30 mL). The organic phase was then dried over MgSO$_4$, filtered and concentrated. The residue was purified via radial chromatography using a 97:3 CHCl$_3$/CH$_3$OH solution as the eluent (R$_f$=0.26) to afford the title compound (105 mg, 56%): $^1$H NMR (400 MHz, CDCl$_3$) δ 8.18 (d, J=8.6 Hz, 2H), 8.01 (d, J=8.6 Hz, 2H), 7.30-7.45 (m, 4H), 6.82 (d, J=8.6 Hz, 2H), 3.96 (br s, 2H); EIMS m/z 331 (Mt).

Example 52

Preparation of 4-[3-(4-trifluoromethoxyphenyl)-4,5-dihydro-[1,2,4]oxadiazol-5-yl]-benzaldehyde

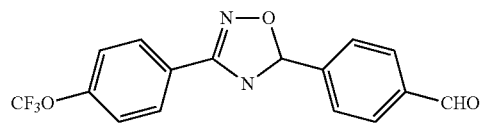

The compound was prepared according to the general procedure of Srivastava et al. *J. Heterocycl. Chem.* 1987, 24, 101 with slight modifications. To a stirred solution of 4-(trifluoromethoxy)benzamidoxime (Acros) (300 mg, 1.36 mmol) dissolved in acetic acid (1.4 mL) was added 1,4-terephthaldehyde (1.1 g, 8.18 mmol) and the reaction mixture was stirred at room temperature for 4 d. The mixture was then dissolved in CHCl$_3$ (20 mL) followed by addition of heptane (10 mL). This solution was concentrated under reduced pressure. This procedure was repeated twice. The residue was purified via radial chromatography using a 99:1 CHCl$_3$/CH$_3$OH solution as the eluent. Two fractions were isolated. The first fraction isolated (R$_f$=0.30) was shown to be starting material (20 mg). The second fraction isolated (R$_f$=0.17) was shown to be the title compound (23 mg, 5%): $^1$H NMR (400 MHz, CDCl$_3$) δ 10.02 (s, 1H), 7.91 (d, J=8.2 Hz, 2H), 7.77 (d, J=9.2 Hz, 2H), 7.70 (d, J=8.2 Hz, 2H), 7.27 (d, J=8.2 Hz, 2H), 6.64 (d, J=4.3 Hz, 1H), 5.18 (d, J=4.3 Hz, 1H); EIMS m/z 336 (M$^+$).

Example 53

Preparation of 4-[5-(4-trifluoromethoxyphenyl)-[1,2,4]oxadiazol-3-yl]-phenylamine

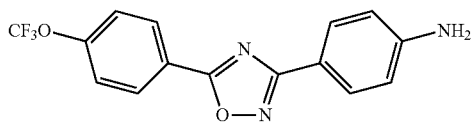

Step 1. {4-[5-(4-Trifluoromethoxyphenyl)-[1,2,4]oxadiazol-3-yl]-phenyl}-carbamic acid tert-butyl ester. To a stirred solution of tert-butyl-4-(N-hydroxycarbamimidoyl)-phenylcarbamate (Ace Synthesis) (500 mg, 1.99 mmol) dissolved in acetic acid (2.5 mL) was added 4-trifluoromethoxybenzaldehyde (1.7 mL, 11.94 mmol), and the reaction mixture was stirred at room temperature for 4 d. The mixture was diluted with CHCl$_3$ (20 mL) and filtered through a pad of Celite®. The pad was washed with CHCl$_3$ (20 mL). Heptane (20 mL) was then added to the solution and the solution was concentrated under reduced pressure. This procedure was repeated twice. The residue was purified via radial chromatography using a 3:1 hexane/EtOAc solution as the eluent. Two fractions were isolated. The first fraction isolated ($R_f$=0.42) was shown to be the title compound (127 mg, 15%): $^1$H NMR (300 MHz, CDCl$_3$) 8.26 (d, J=8.9 Hz, 2H), 8.09 (d, J=8.9 Hz, 2H), 7.52 (d, J=8.6 Hz, 2H), 7.39 (d, J=8.3 Hz, 2H), 6.70 (s, 1H), 1.54 (s, 9H); EIMS 421 (M$^+$). The second fraction isolated ($R_f$=0.11) was shown to be the 4,5-dihydro-1,2,4-oxadiazole (96 mg; 11%). $^1$H NMR (300 MHz, CDCl$_3$) δ 8.40 (d, J=8.9 Hz, 2H), 8.00 (d, J=8.9 Hz, 2H), 7.51 (d, J=8.9 Hz, 2H), 7.22-7.31 (m, 3H), 6.87 (s, 1H), 1.54 (s, 9H); EIMS m/z 423 (M$^+$).

Step 2. 4-[5-(4-Trifluoromethoxyphenyl)-[1,2,4]oxadiazol-3-yl]-phenylamine. To a stirred solution of {4-[5-(4-trifluoromethoxyphenyl)-[1,2,4]oxadiazol-3-yl]-phenyl}-carbamic acid tert-butyl ester (198 mg, 0.47 mmol) in CH$_2$Cl$_2$ (4.7 mL) was added trifluoroacetic acid (11.76 mmol, 0.87 mL) and the reaction mixture was stirred at room temperature for 3 h. The solution was concentrated and the residue was taken up in saturated KHCO$_3$ solution (10 mL) and stirred for 30 min. The mixture was then extracted with CH$_2$Cl$_2$ (3×10 mL). The organic phase was dried over MgSO$_4$, filtered and concentrated to afford 4-[5-(4-trifluoromethoxyphenyl)-[1,2,4]oxadiazol-3-yl]-phenylamine (127 mg; 84%): $^1$H NMR (300 MHz, CDCl$_3$) δ 8.26 (d, J=8.9 Hz, 2H), 7.97 (d, J=8.9 Hz, 2H), 7.39 (d, J=8.6 Hz, 2H), 6.77 (d, J=8.6 Hz, 2H), 3.40-3.80 (br s, 2H); EIMS m/z 321 (M$^+$).

Example 54

Preparation of 1-(4-aminophenyl)-4-(4-trifluoromethoxyphenyl)-piperazine-2,5-dione

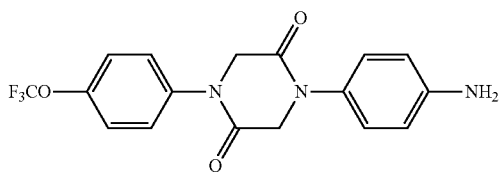

Step 1. 4-Nitrophenylamino acetic acid, methyl ester. To a solution of ethyl bromoacetate (60 g, 0.36 mol) and 4-nitroaniline (5 g, 0.036 mol) in DMF (100 mL) was added NaHCO$_3$ (60 g, 0.71 mol) and tetra-n-butylammonium iodide (500 mg, cat). The solution was heated to 90° C. for 16 h, and then it was cooled and poured onto water (300 mL). The resulting yellow solid was filtered and air-dried. Recrystallization from MeOH furnished the methyl ester (5 g) as a light yellow solid: mp 179-182° C.; $^1$H NMR (400 MHz, CDCl$_3$) δ 8.13 (d, J=8.4 Hz, 2H), 6.57 (d, J=8.4 Hz, 2H), 5.10 (s, 1H), 4.02 (s, 2H), 3.85 (s, 3H).

Step 2. [(2-Chloroacetyl)-(4-trifluoromethoxyphenyl)-amino]-acetic acid methyl ester. To a suspension of 4-nitrophenylamino acetic acid methyl ester (3.0 g, 14.2 mmol) in toluene (30 mL) was added chloroacetyl chloride (3 mL, excess). The solution was heated to 80° C. for 1 h, whereupon the solid dissolved. The solution was then cooled and concentrated, and then the residual solid was recrystallized from MeOH to give the ester (3.5 g) as a light yellow solid: mp 106-109° C.; $^1$H NMR (400 MHz, CDCl$_3$) δ 8.36 (d, J=8.4 Hz, 2H), 7.65 (d, J=8.4 Hz, 2H), 4.42 (s, 2H), 3.93 (s, 2H), 3.79 (s, 3H); MS m/z 286 (M$^+$).

Step 3. 1-(4-Aminophenyl)-4-(4-trifluoromethoxyphenyl)-piperazine-2,5-dione. The product of step 2 (0.6 g, 2.3 mmol) was combined with 4-trifluoromethoxyaniline (0.81 g, 4.6 mmol) and the materials were heated to 140° C. for 90 min. The residual solid was stirred with CH$_2$Cl$_2$ (50 mL) and filtered to remove the hydrochloride salt of the aniline, and then the residue was concentrated and purified. Chromatography (elution with EtOAc-hexanes) furnished the nitrophenyl piperazinedione (0.44 g) as a white solid, mp 223-224° C. Reduction of the nitro group using a Pd/C catalyst under conditions described above gave the title amine as a white solid: mp 250° C. dec; $^1$H NMR (400 MHz, CDCl$_3$) δ 7.4 (d, J=8.5 Hz, 2H), 7.33 (d, J=8.6 Hz, 2H), 7.12 (d, J=8.7 Hz, 2H), 6.75 (d, J=8.7 Hz, 2H), 4.5 (s, 2H), 4 45 (s, 2H); MS m/z 366.2 (M+H$^+$).

Example 55

Preparation of 5-(4-aminophenyl)-3-(4-trifluoromethylphenyl)-3H-[1,3,4]oxadiazol-2-one

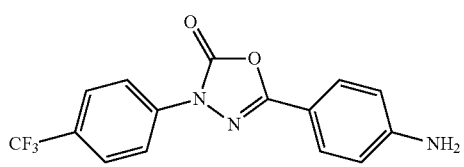 [SMILES: Nc1ccc(-c2nn(-c3ccc(C(F)(F)F)cc3)c(=O)o2)cc1]

5-(4-Nitrophenyl)-3-(4-trifluoromethylphenyl) 3H-[1,3,4]oxadiazole-2-one was prepared by treating the corresponding 4-nitrobenzoic acid N'-(4-trifluoromethylphenyl)-hydrazide with phosgene, using conditions described by Reimlinger et al. in *Chem. Ber.* 1970, 103, 1934. The nitro group was then reduced to the amine by treatment with hydrogen and Pd/C in EtOH: mp 160-163° C.; $^1$H NMR (400 MHz, CDCl$_3$) δ 8.1 (d, J=8.4 Hz, 2H), 7.75 (m, 4H), 6.75 (d, J=8.4 Hz, 2H), 4.1 (br s, 2H); MS m/z 322.6 (M+H$^+$).

Example 56

Preparation of {4-[1-(4-pentafluoroethyloxyphenyl)-1H-[1,2,4]triazol-3-yl]-phenyl}-carbamic acid tert-butyl ester (Compound 1)

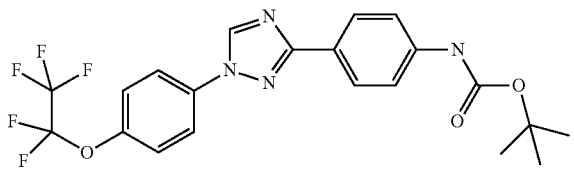 [SMILES: CC(C)(C)OC(=O)Nc1ccc(-c2ncn(-c3ccc(OC(F)(F)C(F)(F)F)cc3)n2)cc1]

A solution of 4-[1-(4-pentafluoroethyloxyphenyl)-1H-[1,2,4]triazol-3-yl]-phenylamine (1.0 g, 2.7 mmol) in dry THF (8 mL) was stirred while p-nitrophenyl chloroformate (0.60 g, 3 mmol) was added in one portion and the solution was allowed to stir for 3 h. The resulting solid was filtered and air-dried. A smaller portion of the p-nitrophenylcarbamate (152 mg, 0.28 mmol) was suspended in dry THF (3 mL). To this were added 2-methyl-2-propanol (41 mg, 0.32 mmol) in dry THF (1 mL) followed by NaH (60% mineral oil dispersion; 26 mg, 0.67 mmol) in one portion. Additional dry THF (1 mL) was used to rinse joints, etc. The solution was heated to 60° C. (external) for 1.5 h, at which point TLC (3:3:3:1 EtOAc/hexanes/CH$_2$Cl$_2$/acetone) showed no starting material. The mixture was cooled and allowed to stir at 25° C. for 20 h. The mixture was cooled, poured on to ice-water (50 mL), and extracted with EtOAc (3×50 mL). The combined extracts were washed with satd aq NaCl (75 mL), dried (Na$_2$SO$_4$), filtered and concentrated. RP-HPLC (acid-free medium water-acetonitrile gradient) provided the title compound (31 mg, 23%) as an off-white solid: mp 205-209° C.; $^1$H NMR (400 MHz, CDCl$_3$) δ 8.55 (s, 1H), 8.12 (d, J=9.0 Hz, 2H), 7.80 (d, J=9.3 Hz, 2H), 7.48 (d, J=8.8 Hz, 2H), 7.38 (d, J=9.0 Hz, 2H), 6.58 (s, 1H), 1.54 (s, 9H); ESIMS m/z 471 (M+H), 469 (M−H).

Compound 2 in Table 1 was synthesized as in Example 56.

Example 57

Preparation of {4-[1-(4-trifluoromethoxyphenyl)-1H-[1,2,4]triazol-3-yl]-phenyl}-carbamic acid 1-(5-ethoxy-pyrimidin-2-yl)-1-methyl-ethyl ester (Compound 3)

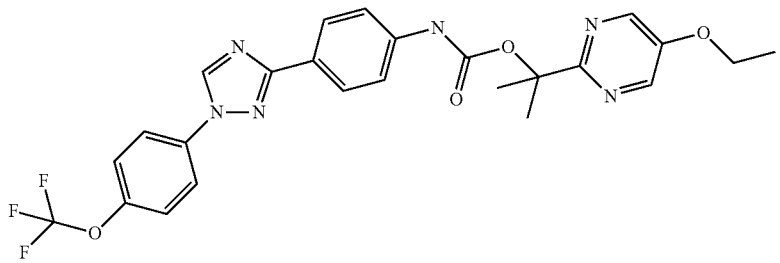 [SMILES: CCOc1cnc(C(C)(C)OC(=O)Nc2ccc(-c3ncn(-c4ccc(OC(F)(F)F)cc4)n3)cc2)nc1]

4-[1-(4-Trifluoromethoxyphenyl)-1H-[1,2,4]triazol-3-yl]-benzoyl azide (204 mg, 0.55 mmol) was taken up in dry toluene (2 mL), and the mixture was heated to 110° C. and stirred at that temperature for 1.5 h. Gas evolution was observed during the heating. The mixture was cooled, and then the alcohol (106 mg, 0.59 mmol) and NaH (60% in mineral oil dispersion; 76 mg, 1.9 mmol) were added. The mixture was stirred at 25° C. for 18 h. The mixture was poured onto H$_2$O (50 mL) and was extracted with EtOAc (3×50 mL). The combined organic extracts were dried over Na$_2$SO$_4$, filtered and concentrated to give a light tan residue. Silica gel column chromatography (3:3:3:1 cyclohexane:EtOAc: CH$_2$Cl$_2$:acetone) gave the title compound (97 mg, 34%) as a light tan solid: mp 168-171° C.; $^1$H NMR (400 MHz, CDCl$_3$) δ 8.52 (s, 1H), 8.37 (s, 2H), 8.08 (d, J=9.0 Hz, 2H), 7.77 (d, J=8.9 Hz, 2H), 7.42 (d, J=8.7 Hz, 2H), 7.36 (d, J=9.0 Hz, 2H), 6.91 (s, 1H), 4.12 (q, J=7.0 Hz, 2H), 1.87 (s, 6H), 1.44 (t, J=6.9 Hz, 3H); ESIMS m/z 529 (M+H), 527 (M−H); HRMS-ESI (m/z): [M]$^+$ calcd for C$_{25}$H$_{23}$F$_3$N$_6$O$_4$, 528.1727. found, 528.1730.

Compounds 4-8 in Table 1 were synthesized as in Example 57.

Example 58

Preparation of {4-[1-(4-trifluoromethoxyphenyl)-1H-[1,2,4]triazol-3-yl]-phenyl}-carbamic acid 1-methyl-pentyl ester (Compound 9)

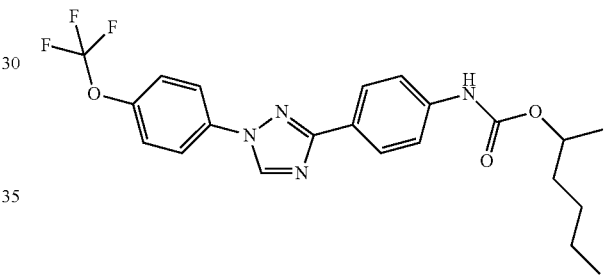

4-[1-(4-Trifluoromethoxyphenyl)-1H-[1,2,4]triazol-3-yl]-benzoyl azide (131 mg, 0.350 mmol) was suspended in dry toluene (1.0 mL). To the resulting slurry was added 2-hexanol (221 µL, 1.75 mmol) in one portion. The off-white slurry was then heated to 100° C. (external). Once UPLC analysis indicated complete consumption of the starting material, the clear yellow solution was cooled to 23° C. and concentrated. Silica gel chromatography (Biotage 10 g SNAP column, eluted with a 20% to 40% to 75% EtOAc/hexanes gradient) provided the title compound (134 mg, 85%) as a white solid: mp 111-113° C.; $^1$H NMR (300 MHz, CDCl$_3$) δ 8.54 (s, 1H), 8.13 (d, J=8.8 Hz, 2H), 7.78 (d, J=9.0 Hz, 2H), 7.51 (d, J=8.7 Hz, 2H), 7.37 (dd, J=9.0, 0.8 Hz, 2H), 6.76 (s, 1H), 5.00-4.83 (m, 1H), 1.76-1.44 (m, 2H), 1.44-1.31 (m, 4H), 1.29 (d, J=6.3

Hz, 3H), 0.91 (t, J=7.0 Hz, 3H); ESIMS m/z 449 (M+H), 447 (M−H); HRMS-ESI (m/z): [M]+ calcd for $C_{22}H_{23}F_3N_4O_3$, 448.172. found, 448.173.

Compound 10 in Table 1 was synthesized as in Example 58.

Example 59

Preparation of {4-[1-(4-trifluoromethoxyphenyl)-1H-[1,2,4]triazol-3-yl]-phenyl}-carbamic acid 1,1-dimethyl-2-phenyl-ethyl ester (Compound 11)

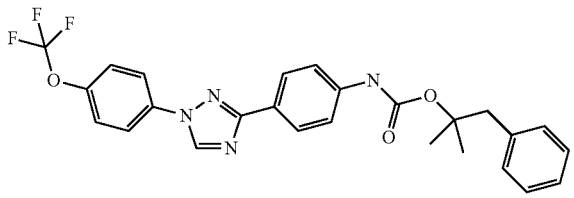 [SMILES: CC(C)(Cc1ccccc1)OC(=O)Nc1ccc(-c2ncn(-c3ccc(OC(F)(F)F)cc3)n2)cc1]

4-[1-(4-Trifluoromethoxyphenyl)-1H-[1,2,4]triazol-3-yl]-benzoyl azide (93 mg, 0.248 mmol) was suspended in dry toluene (0.71 mL). To the resulting slurry was added 2-methyl-1-phenyl-2-propanol (191 μL, 1.24 mmol) in one portion. The off-white slurry was then heated to 100° C. (external). Once UPLC analysis indicated complete consumption of the starting material, the yellow slurry was cooled to 23° C., filtered through a medium porosity frit, and concentrated. Silica gel chromatography (Biotage 10 g SNAP column, eluted with a 10% to 40% to 75% EtOAc/hexanes gradient) provided the title compound (71 mg, 58%) as a white solid: mp 153-155° C.; 1H NMR (300 MHz, CDCl3) δ 8.54 (s, 1H), 8.14 (d, J=8.7 Hz, 2H), 7.79 (d, J=9.0 Hz, 2H), 7.50 (d, J=8.5 Hz, 2H), 7.38 (d, J=8.6 Hz, 2H), 7.34-7.17 (m, 5H), 6.61 (s, 1H), 3.19 (s, 2H), 1.53 (s, 6H); ESIMS m/z 497 (M+H), 495 (M−H); HRMS-ESI (m/z): [M]+ calcd for $C_{26}H_{23}F_3N_4O_3$, 496.172. found, 496.172.

Example 60

Preparation of {4-[1-(4-trifluoromethoxyphenyl)-1H-[1,2,4]triazol-3-yl]-phenyl}-carbamic acid 1,1-dimethyl-prop-2-ynyl ester (Compound 12)

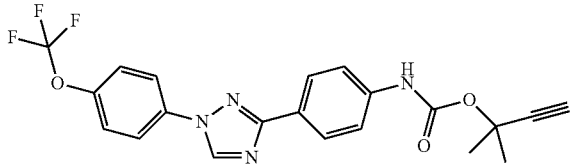 [SMILES: C#CC(C)(C)OC(=O)Nc1ccc(-c2ncn(-c3ccc(OC(F)(F)F)cc3)n2)cc1]

2-Methyl-3-butyn-2-ol (48 μL, 0.44 mmol) was added to a solution of triphosgene (42 mg, 0.14 mmol) and pyridine (38 μL, 0.47 mmol) in CH2Cl2 (1.0 mL) at 23° C. Gas evolution was observed during addition of the alcohol, and a precipitate was observed to form. The resulting slurry was stirred at 23° C. for 1 h. Stirring was ceased, the solid was allowed to settle to the bottom of the flask, and the supernatant was added via cannula to a slurry of 4-[1-(4-trifluoromethoxyphenyl)-1H-[1,2,4]triazol-3-yl]-phenylamine (100 mg, 0.312 mmol) and Pyridine (38 μL, 0.47 mmol) in CH2Cl2 (1.0 mL) at 23° C. A thick precipitate was observed to form. At this point, TLC analysis indicated some starting material remained, so an equivalent amount of triphosgene/pyridine/alcohol was combined as above, and the resulting supernatant was again added to the aniline mixture. After stirring for another 3 h at 23° C., the reaction mixture was diluted with 30% EtOAc/hexanes (10 mL), and a fine white precipitate was filtered on a coarse frit. The clear yellow filtrate was concentrated, and the resulting yellow oil was purified by silica gel chromatography (Biotage 10 g SNAP column, eluted with a 10% to 25% to 50% EtOAc/hexanes gradient) to provide the title compound (55 mg, 41%) as a white solid: mp 164-165° C.; 1H NMR (400 MHz, CDCl3) δ 8.54 (s, 1H), 8.13 (d, J=8.7 Hz, 2H), 7.79 (d, J=9.0 Hz, 2H), 7.53 (d, J=8.5 Hz, 2H), 7.38 (d, J=8.8 Hz, 2H), 6.73 (s, 1H), 2.61 (s, 1H), 1.77 (s, 6H); ESIMS m/z 431 (M+H); HRMS-ESI (m/z): [M]+ calcd for $C_{21}H_{17}F_3N_4O_3$, 430.125. found, 430.126.

Example 61

Preparation of {4-[1-(4-trifluoromethylphenyl)-1H-[1,2,4]triazol-3-yl]-phenyl}-carbamic acid 1,1-dimethyl-prop-2-ynyl ester (Compound 13)

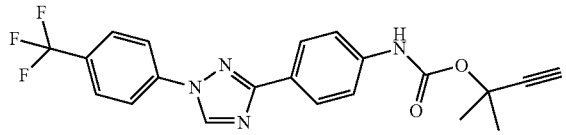 [SMILES: C#CC(C)(C)OC(=O)Nc1ccc(-c2ncn(-c3ccc(C(F)(F)F)cc3)n2)cc1]

4-[1-(4-Trifluoromethylphenyl)-1H-[1,2,4]triazol-3-yl]-benzoyl azide (137 mg, 0.383 mmol) was suspended in dry toluene (1.5 mL). To the resulting slurry was added 2-methyl-3-butyn-2-ol (187 μL, 1.91 mmol) followed by Et3N (264 μL, 1.91 mmol). The off-white slurry was then heated to 100° C. (external). Once UPLC analysis indicated complete consumption of the starting material, the yellow slurry was cooled to 23° C. and poured into 50% EtOAc/hexanes. The off-white slurry was then filtered through a medium porosity frit and concentrated. Silica gel chromatography (Biotage 10 g SNAP column, eluted with a 10% to 40% to 75% EtOAc/hexanes gradient) provided the title compound (20 mg, 13%) as a white solid: mp 187-189° C.; 1H NMR (400 MHz, CDCl3) δ 8.64 (s, 1H), 8.14 (d, J=8.7 Hz, 2H), 7.90 (d, J=8.4 Hz, 2H), 7.79 (d, J=8.6 Hz, 2H), 7.53 (d, J=8.6 Hz, 2H), 6.76 (s, 1H), 2.61 (s, 1H), 1.77 (s, 6H); ESIMS m/z 415 (M+H), 413 (M−H); HRMS-ESI (m/z): [M]+ calcd for $C_{21}H_{17}F_3N_4O_2$, 414.130. found, 414.131.

Example 62

Preparation of {4-[1-(4-trifluoromethoxyphenyl)-1H-[1,2,4]triazol-3-yl]-phenyl}-carbamic acid cyano-dimethyl-methyl ester (Compound 14)

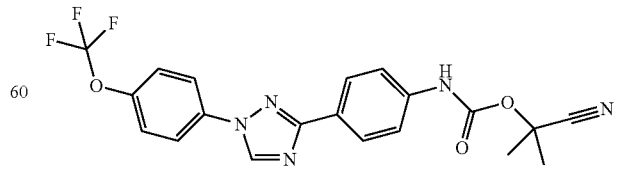

4-[1-(4-Trifluoromethoxyphenyl)-1H-[1,2,4]triazol-3-yl]-benzoyl azide (107 mg, 0.286 mmol) was suspended in dry toluene (1.0 mL). To the resulting slurry was added 2-cyano-2-propanol (78 µL, 0.858 mmol). The off-white slurry was then heated to 90° C. (external). Within 10 sec at this temperature, the slurry became homogenous and vigorous gas evolution was observed. Precipitate was observed to form after another 10 min at this temperature. Once UPLC analysis indicated complete consumption of the starting material, the yellow slurry was cooled to 23° C. and poured into hexanes. The off-white slurry was then filtered through a medium porosity frit and concentrated. Silica gel chromatography (Biotage 10 g SNAP column, eluted with a 20% to 40% to 75% EtOAc/hexanes gradient) provided the title compound (7 mg, 6%) as a light yellow solid: mp 172-175° C.; $^1$H NMR (300 MHz, CDCl$_3$) δ 8.55 (s, 1H), 8.16 (d, J=8.6 Hz, 2H), 7.79 (d, J=9.0 Hz, 2H), 7.52 (d, J=8.4 Hz, 2H), 7.38 (d, J=8.7 Hz, 2H), 6.79 (s, 1H), 1.84 (s, 6H); ESIMS m/z 432 (M+H), 430 (M−H).

Example 63

Preparation of 4{4-[1-(4-trifluoromethoxyphenyl)-1H-[1,2,4]triazol-3-yl]-phenyl}-carbamic acid 1-cyclopropyl-ethyl ester (Compound 15)

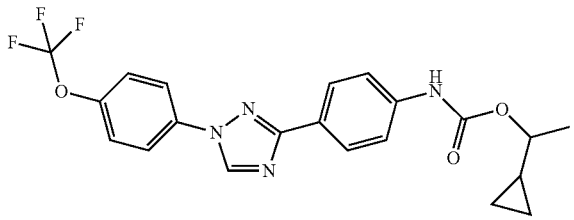 [SMILES: CC(OC(=O)Nc1ccc(-c2ncn(-c3ccc(OC(F)(F)F)cc3)n2)cc1)C1CC1]

4-[1-(4-Trifluoromethoxyphenyl)-1H-[1,2,4]triazol-3-yl]-benzoyl azide (84 mg, 0.225 mmol) was suspended in dry toluene (0.65 mL). To the resulting slurry was added 1-cyclopropylethyl alcohol (109 µL, 1.12 mmol). The off-white slurry was then heated to 90° C. (external). Within 10 sec at this temperature, the slurry became homogenous and vigorous gas evolution was observed. After 1 h, the slightly cloudy yellow solution was cooled to 23° C. and concentrated. Silica gel chromatography (Biotage 10 g SNAP column, eluted with a 10% to 25% to 50% EtOAc/hexanes gradient) provided recovered starting material (20 mg, 24%) as a white solid along with the title compound (67 mg, 69%) as a white solid: mp 123-124° C.; $^1$H NMR (400 MHz, CDCl$_3$) δ 8.54 (s, 1H), 8.13 (d, J=8.7 Hz, 2H), 7.78 (d, J=9.0 Hz, 2H), 7.51 (d, J=8.6 Hz, 2H), 7.37 (d, J=8.6 Hz, 2H), 6.85 (s, 1H), 4.34 (dq, J=12.7, 6.3 Hz, 1H), 1.38 (d, J=6.3 Hz, 3H), 1.14-0.95 (m, 1H), 0.67-0.42 (m, 3H), 0.29 (ddd, J=7.6, 6.5, 3.8 Hz, 1H); ESIMS m/z 433 (M+H), 431 (M−H).

Example 64

Preparation of 4-[1-(4-trifluoromethoxyphenyl)-1H-[1,2,4]triazol-3-yl]-phenyl}-carbamic acid 1-cyclohexyl-ethyl ester (Compound 16)

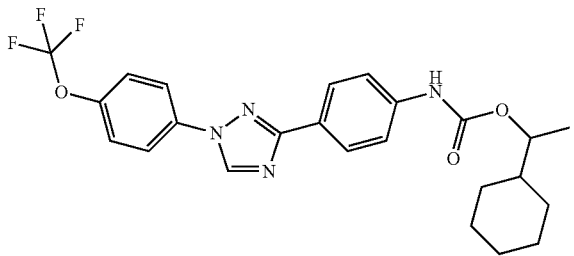 [SMILES: CC(OC(=O)Nc1ccc(-c2ncn(-c3ccc(OC(F)(F)F)cc3)n2)cc1)C1CCCCC1]

4-[1-(4-Trifluoromethoxyphenyl)-1H-[1,2,4]triazol-3-yl]-benzoyl azide (90 mg, 0.241 mmol) was suspended in dry toluene (0.70 mL). To the resulting slurry was added (1-cyclohexyl)ethyl alcohol (166 µL, 1.20 mmol). The off-white slurry was then heated to 90° C. (external). Within 10 sec at this temperature, the slurry became homogenous and vigorous gas evolution was observed. A small amount of precipitate was observed to form after another 10 min at this temperature. Once UPLC analysis indicated complete consumption of the starting material, the yellow slurry was cooled to 23° C. and poured into 25% EtOAc/hexanes. The off-white slurry was then filtered through a medium porosity frit and concentrated. Silica gel chromatography (Biotage 10 g SNAP column, eluted with a 15% to 30% to 50% EtOAc/hexanes gradient) provided the title compound (98 mg, 86%) as a white solid: mp 146-148° C.; $^1$H NMR (400 MHz, CDCl$_3$) δ 8.54 (s, 1H), 8.13 (d, J=8.7 Hz, 2H), 7.78 (d, J=9.0 Hz, 2H), 7.52 (d, J=8.5 Hz, 2H), 7.36 (d, J=8.4 Hz, 2H), 6.89 (s, 1H), 4.76 (p, J=6.3 Hz, 1H), 2.13-1.61 (m, 4H), 1.49 (tdd, J=11.8, 6.1, 3.1 Hz, 1H), 1.24 (d, J=6.4 Hz, 3H), 1.22-0.96 (m, 6H); ESIMS m/z 475 (M+H), 473 (M−H).

Example 65

Preparation of 4-methyl-4-{4-[1-(4-trifluoromethoxyphenyl)-1H-[1,2,4]triazol-3-yl]-phenylcarbamoyloxy-pent-2-ynoic acid ethyl ester (Compound 23)

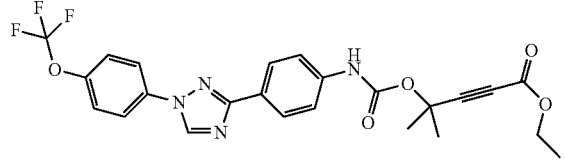 [SMILES: CCOC(=O)C#CC(C)(C)OC(=O)Nc1ccc(-c2ncn(-c3ccc(OC(F)(F)F)cc3)n2)cc1]

4-[1-(4-Trifluoromethylphenyl)-1H-[1,2,4]triazol-3-yl]-phenyl}-carbamic acid 1,1-dimethyl-prop-2-ynyl ester (Compound 13; 11981077; 88 mg, 0.20 mmol) was dissolved in dry THF (2.0 mL) and cooled to −78° C. n-BuLi (164 µL of a 2.5 M solution in hexanes, 0.410 mmol) was then added dropwise. The mixture was stirred for another 20 min at −78° C., and then ethyl chloroformate (24 µL, 0.25 mmol) was added in one portion. The mixture was stirred for another 30 min at −78° C. and was then warmed to 23° C. The mixture was quenched with half-saturated aqueous NH$_4$Cl and extracted with 50% EtOAc/hexanes. The combined organic layers were then washed with brine, dried over Na$_2$SO$_4$, and concentrated. Silica gel chromatography (Biotage 10 g SNAP column, eluted with a 15% to 30% to 50% to 75% EtOAc/hexanes gradient) followed by recrystallization from Et$_2$O/hexanes provided the title compound (10 mg, 10%) as a yellow solid: mp 183-188° C.; $^1$H NMR (300 MHz, CDCl$_3$) δ 8.57 (s, 1H), 8.27 (d, J=8.7 Hz, 2H), 7.80 (d, J=9.1 Hz, 2H), 7.40 (app d, J=8.7 Hz, 4H), 4.99 (s, 1H), 3.66 (q, J=7.1 Hz, 2H), 1.70 (s, 6H), 0.98 (t, J=7.1 Hz, 3H); ESIMS m/z 503 (M+H).

Example 66

Preparation of {4-[1-(4-trifluoromethoxyphenyl)-1H-[1,2,4]triazol-3-yl]-phenyl}-carbamic acid 2,2,3,3-pentafluoro-1-methyl-propyl ester (Compound 24)

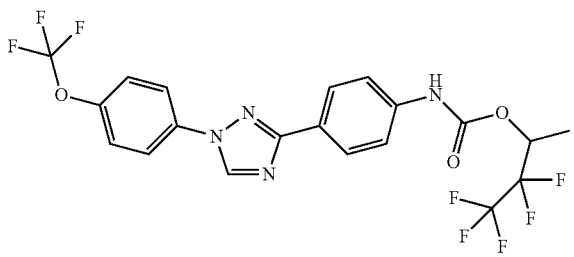 [SMILES: CC(OC(=O)Nc1ccc(-c2ncn(-c3ccc(OC(F)(F)F)cc3)n2)cc1)C(F)(F)C(F)(F)F]

4-[1-(4-Trifluoromethoxyphenyl)-1H-[1,2,4]triazol-3-yl]-benzoyl azide (77 mg, 0.206 mmol) was suspended in dry toluene (0.60 mL). To the resulting slurry was added 3,3,4,4,4-pentafluoro-2-butanol (120 µL, 1.03 mmol). The off-white slurry was then heated to 90° C. (external). Within 10 sec at this temperature, the slurry became homogenous and vigorous gas evolution was observed. A small amount of precipitate was observed to form after another 10 min at this temperature. Once UPLC analysis indicated complete consumption of the starting material, the yellow slurry was cooled to 23° C. and poured into 25% EtOAc/hexanes. The off-white slurry was filtered through a medium porosity frit and concentrated to provide the title compound (80 mg, 76%) as an off-white solid: mp 171-173° C.; $^1$H NMR (400 MHz, DMSO-$d_6$) δ 10.33 (s, 1H), 9.38 (s, 1H), 8.10-7.99 (m, 4H), 7.67-7.58 (m, 4H), 5.81-5.23 (m, 1H), 1.47 (d, J=6.3 Hz, 3H); ESIMS m/z 511 (M+H), 509 (M−H); HRMS-ESI (m/z): [M]$^+$ calcd for $C_{20}H_{14}F_8N_4O_3$, 510.0933. found 510.0998.

Example 67

Preparation of 2-{4-[1-(4-trifluoromethoxyphenyl)-1H-[1,2,4]triazol-3-yl]-phenylcarbamoyloxy}-hexanoic acid ethyl ester (Compound 26)

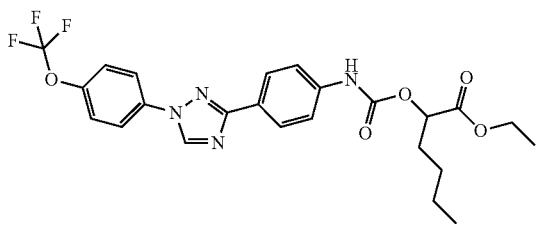 [SMILES: CCCCC(OC(=O)Nc1ccc(-c2ncn(-c3ccc(OC(F)(F)F)cc3)n2)cc1)C(=O)OCC]

4-[1-(4-Trifluoromethoxyphenyl)-1H-[1,2,4]triazol-3-yl]-benzoyl azide (90 mg, 0.241 mmol) was suspended in dry toluene (0.70 mL). The off-white slurry was then heated to 90° C. (external) and stirred for 30 min. Within 10 sec at this temperature, the slurry became homogenous and vigorous gas evolution was observed. The slightly cloudy yellow solution was cooled to 23° C. and ethyl 2-hydroxycaproate (52 µL, 1.20 mmol) was added. The mixture was stirred at 23° C. for 15 h more, and was then poured into 25% EtOAc/hexanes. The off-white slurry was filtered through a medium porosity frit and concentrated. Silica gel chromatography (Biotage 10 g SNAP column, eluted with a 15% to 30% to 50 to 75% EtOAc/hexanes gradient) provided the title compound (10 mg, 8%) as a white solid: mp 135-139° C.; $^1$H NMR (300 MHz, CDCl$_3$) δ 8.55 (s, 1H), 8.14 (d, J=8.7 Hz, 2H), 7.79 (d, J=9.0 Hz, 2H), 7.51 (d, J=8.8 Hz, 2H), 7.38 (dd, J=9.0, 0.8 Hz, 2H), 6.97 (s, 1H), 5.08 (dd, J=7.2, 5.4 Hz, 1H), 4.25 (q, J=7.1 Hz, 2H), 1.95-1.80 (m, 2H), 1.52-1.34 (m, 4H), 1.30 (t, J=7.1 Hz, 3H), 0.93 (t, J=7.2 Hz, 3H); ESIMS 507 (M+H), 505 (M−H).

Example 68

Preparation of 1-(4-(trifluoromethyl)phenyl)ethyl 4-(1-(4-(trifluoromethyl)phenyl)-1H-1,2,4-triazol-3-yl)-phenylcarbamate (Compound 27)

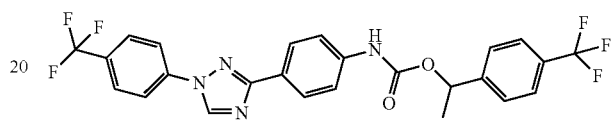

4-(1-(4-(Trifluoromethyl)phenyl)-1H-1,2,4-triazol-3-yl)benzoyl azide (62.5 mg, 0.174 mmol) was suspended in dry toluene (0.498 mL). To the resulting slurry was added 1-(4-(trifluoromethyl)phenyl)ethyl alcohol (36.5 mg, 0.192 mmol). The off-white slurry was heated to 100° C. (external) for 18 h and then cooled to ambient temperature. The reaction mixture was directly applied to a silica gel column, and elution with a 10% to 50% to 100% EtOAc/hexanes gradient provided the title compound (57.6 mg, 63%) as a white solid: mp 155.5-158.5° C.; $^1$H NMR (400 MHz, CDCl$_3$) δ 8.62 (s, 1H), 8.15 (d, J=8.8 Hz, 2H), 7.90 (d, J=8.5 Hz, 2H), 7.79 (d, J=8.5 Hz, 2H), 7.64 (d, J=8.2 Hz, 2H), 7.51 (app t, J=8.4 Hz, 4H), 6.79 (s, 1H), 5.95 (q, J=6.6 Hz, 1H), 1.63 (d, J=6.7 Hz, 3H); ESIMS 521 (M+H), 519 (M−H).

Example 69

Preparation of Carbamates—General Method A

The acyl azide was suspended in dry toluene (0.35 M). To the resulting slurry was added the appropriate alcohol (1.20 equiv). The slurry was heated to 100° C. (external) for 4-24 h and then cooled to ambient temperature. The product was isolated by vacuum filtration or purified by silica gel column chromatography (after applying the material directly to the column) eluting with EtOAc/hexanes gradient. In some instances, further purification by recrystallization was necessary. Typical solvents used include: chloroform-d, diethyl ether/hexanes, and diethyl ether/dichloromethane/hexanes mixtures.

Compounds 28-121 in Table 1 were synthesized as in Example 69.

Example 70

Preparation of Carbamates—General Method B

The acyl azide was suspended in dry toluene (0.35 M). To the resulting slurry was added the appropriate alcohol (1.20 equiv). The slurry was heated to 100° C. (external) for 4-24 h and then cooled to ambient temperature. Triethylamine (1.50 equiv) was added and the reaction mixture was stirred at ambient temperature for an additional 1 h. The product was isolated by vacuum filtration or purified by silica gel column chromatography (after applying the material directly to the column) eluting with EtOAc/hexanes gradient. Compounds 122-129 were synthesized as in Example 70.

Example 71

Preparation of 1-(6-(trifluoromethyl)pyridin-3-yl)ethyl ethyl(4-(1-(4-(trifluoromethoxy)phenyl)-1H-1,2,4-triazol-3-yl)phenyl)carbamate (Compound 130)

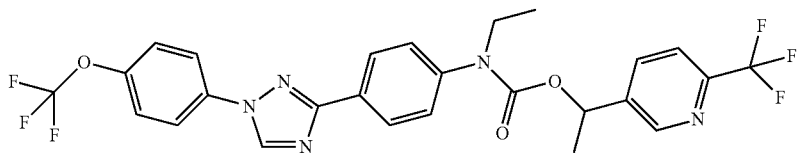 [SMILES: CCN(C(=O)OC(C)c1ccc(C(F)(F)F)nc1)c1ccc(-c2ncn(-c3ccc(OC(F)(F)F)cc3)n2)cc1]

1-(6-(Trifluoromethyl)pyridin-3-yl)ethyl 4-(1-(4-(trifluoromethoxy)phenyl)-1H-1,2,4-triazol-3-yl)phenylcarbamate (54 mg, 0.10 mmol) was dissolved in anhydrous DMF (0.5 mL) under $N_2$ and cooled to 0° C. NaH (60% suspension in mineral oil; 4.4 mg, 0.11 mmol) was added, and the mixture was stirred for 10 min at 0° C. Iodoethane (9 μL, 0.11 mmol) was added, and the mixture was warmed to ambient temperature and stirred for 1 h. Additional NaH (4 mg) and iodoethane (5 μL) were added at ambient temperature to promote complete consumption of the starting material. The mixture was quenched with aqueous $NH_4Cl$ and extracted with 80% EtOAc/hexanes (×3). The combined organic layers were washed with brine, dried over $Na_2SO_4$, and concentrated. The crude product was applied to a silica gel column, and elution with a 15% to 40% to 80% EtOAc/hexanes gradient provided the title compound (52.1 mg, 91%) as a light yellow oil: IR 3111, 2983, 2936, 1707, 1519, 1340, 1268, 1155 cm$^{-1}$; $^1$H NMR (300 MHz, CDCl$_3$) δ 8.62 (s, J=10.6 Hz, 1H), 8.58 (s, 1H), 8.21 (d, J=8.5 Hz, 2H), 7.81 (d, J=9.0 Hz, 2H), 7.73-7.58 (m, 2H), 7.40 (d, J=8.5 Hz, 2H), 7.30 (d, J=8.5 Hz, 2H), 5.95 (q, J=6.6 Hz, 1H), 3.84-3.70 (m, 2H), 1.53 (d, J=6.2 Hz, 3H), 1.19 (t, J=7.1 Hz, 3H); HRMS-FAB (m/z) [M+H]$^+$ calcd for $C_{26}H_{21}F_6N_5O_3$, 565.1549. found, 565.1568.

Example 72

Preparation of tert-butyl methyl(4-(1-(4-(trifluoromethoxy)phenyl)-1H-1,2,4-triazol-3-yl)phenyl)carbamate (Compound 131)

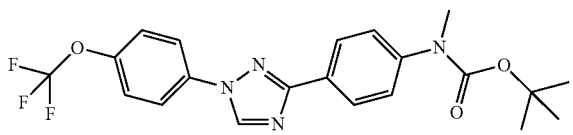 [SMILES: CN(C(=O)OC(C)(C)C)c1ccc(-c2ncn(-c3ccc(OC(F)(F)F)cc3)n2)cc1]

tert-Butyl (4-(1-(4-(trifluoromethoxy)phenyl)-1H-1,2,4-triazol-3-yl)phenyl)carbamate (120 mg, 0.286 mmol) was dissolved in anhydrous DMF (2.0 mL) under $N_2$ and cooled to 0° C. NaH (60% suspension in mineral oil; 15 mg, 0.372 mmol) was added, and the mixture was stirred for 10 min at 0° C. Iodomethane (23 μL, 0.372 mmol) was added, and the mixture was warmed to ambient temperature and stirred for 1 h. The mixture was quenched with aqueous $NH_4Cl$ and extracted with 80% EtOAc/hexanes (×3). The combined organic layers were washed with brine, dried over $Na_2SO_4$, and concentrated. The crude product was applied to a silica gel column, and elution with a 15% to 40% to 80% EtOAc/hexanes gradient provided the title compound (108.0 mg, 87%) as a white solid: mp 125-128° C.; $^1$H NMR (400 MHz, CDCl$_3$) δ 8.55 (s, 1H), 8.14 (d, J=8.6 Hz, 2H), 7.79 (d, J=8.9 Hz, 2H), 7.38 (d, J=9.8 Hz, 2H), 7.35 (d, J=8.8 Hz, 2H), 3.31 (s, 3H), 1.47 (s, 9H); HRMS-FAB (m/z) [M+H]$^+$ calcd for $C_{21}H_{21}F_3N_4O_3$, 434.156. found, 434.157.

Example 73

Preparation of O-methyl 4-(1-(4-(trifluoromethoxy)phenyl)-1H-1,2,4-triazol-3-yl)phenylcarbamothioate (Compound 132)

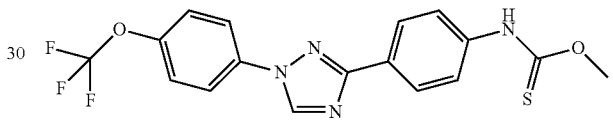

Step 1. 4-(1-(4-(Trifluoromethoxy)phenyl)-1H-1,2,4-triazol-3-yl)aniline was dissolved in THF (2.5 mL) to give a tan solution. Phenyl chlorothionoformate (0.205 mg, 1.19 mmol) was then added. A solid precipitated immediately and stirring became difficult. Additional THF (2.5 mL) was added to facilitate stirring. An additional portion of phenyl chlorothionoformate (0.205 mg, 1.19 mmol) was added followed by triethylamine (0.38 mL, 2.80 mmol). The reaction was quenched with satd aq NaHCO$_3$ and extracted with 50% EtOAc/hexanes. The organic layer was washed with aq NaHCO$_3$ solution and brine, dried over Na$_2$SO$_4$, and concentrated. Purification via silica gel chromatography (15% to 30% to 50% to 80% EtOAc/hexanes gradient) afforded N,N-bis(thionophenoxy)-4-(1-(4-(trifluoromethoxy)phenyl)-1H-1,2,4-triazol-3-yl)aniline (0.472 g, 80%) as a yellow solid: mp 142-144° C.; $^1$H NMR (400 MHz, CDCl$_3$) δ 8.58 (s, 1H), 8.34 (d, J=8.6 Hz, 2H), 7.80 (d, J=9.0 Hz, 2H), 7.66 (d, J=8.6 Hz, 2H), 7.49-7.34 (m, 6H), 7.34-7.28 (m, 2H), 7.26-7.13 (m, 4H); HRMS-FAB (m/z) [M+H]$^+$ calcd for $C_{29}H_{19}F_3N_4O_3S_2$, 592.085. found, 592.0861.

Step 2. To a solution of the product from Step 1 in MeOH (2.5 mL) and THF (2.5 mL) was added NaOH (2.5 mL of a 1 M aq solution). A thick yellow precipitate formed immediately. Additional THF, MeOH, and 1 M NaOH (2.5 mL each) were added and a clear yellow solution was obtained. The mixture was then poured into aq NaHCO$_3$ and extracted with 50% EtOAc/hexanes (×3). The combined organic layers were washed with brine, dried over Na₂SO₄, and concentrated to give a yellow solid. The solid was triturated with 20% EtOAc/hexanes to give the title compound (137 mg, 51%) as a white solid. The filtrate was concentrated and purified by silica gel chromatography (eluting with 15% to 40% to 80% EtOAc/hexanes gradient) to afford additional product (57.6 mg, 0.126 mmol, 22%): mp 192-194° C.; ¹H NMR (300 MHz, DMSO-d₆) δ 11.32 (s, 1H), 9.39 (s, 1H), 8.14-7.95 (m, 4H), 7.90-7.65 (br, 1H), 7.62 (app dd, J=9.0, 0.7 Hz, 2H), 7.60-7.40 (br, 1H), 4.01 (br s, 3H); HRMS-FAB (m/z) [M+H]⁺ calcd for $C_{17}H_{13}F_3N_4O_2S$, 394.071. found, 394.0712.

Example 74

Preparation of O-1-(6-(trifluoromethyl)pyridin-3-yl)ethyl 4-(1-(4-(trifluoromethoxy)phenyl)-1H-1,2,4-triazol-3-yl)phenylcarbamothioate (Compound 133)

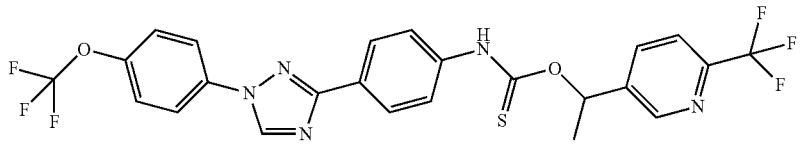 [SMILES: CC(OC(=S)Nc1ccc(-c2ncn(-c3ccc(OC(F)(F)F)cc3)n2)cc1)c1ccc(C(F)(F)F)nc1]

Under a N₂ atmosphere, thiophosgene (0.56 mmol) was added dropwise to cold dichloromethane cooled in an ice bath. To this solution was added a cold 0.2 mM (0.13 mmol) K₂CO₃ solution. The reaction was stirred for 10 min. 4-(1-(4-(Trifluoromethoxy)phenyl)-1H-1,2,4-triazol-3-yl)aniline (0.56 mmol) was dissolved in dichloromethane and added dropwise to the above mixture. The reaction was allowed to stir for another 10 min. A cold 0.6 mM (0.92 mmol) KOH solution was then added. After 30 min, the reaction mixture was diluted with dichloromethane and washed with water and brine. The organic layer was dried over MgSO₄ and concentrated. The crude isothiocyanate was used without further purification in the next step.

To a slurry of NaH (9.2 mg of a 60% suspension in mineral oil, 0.229 mmol) in THF (1 mL) at 0° C. was added 1-(6-(trifluoromethyl)pyridine-3-yl)ethanol (43.7 mg, 0.229 mmol) in PhCH₃ (0.4 mL). The mixture was warmed to ambient temperature and stirred for 15 min, and then the isothiocyanate from above (75.6 mg, 0.209 mmol) in THF (1 mL) was added via cannula. After stirring for 20 min, the mixture was quenched by addition of aq NH₄Cl solution and extracted with EtOAc (×3). The combined organic extracts were washed with brine, dried over Na₂SO₄, and concentrated. The crude product was applied to a silica gel column, and elution with a 15% to 40% to 65% EtOAc/hexanes gradient provided the title compound (88.2 mg, 77%) as an off-white solid: mp 186.5-188° C.; ¹H NMR (300 MHz, CDCl₃) δ 8.76 (s, 1H), 8.58 (s, 1H), 8.50 (s, 1H), 8.19 (d, J=8.7 Hz, 2H), 7.91-7.83 (m, 1H), 7.80 (d, J=9.1 Hz, 2H), 7.69 (d, J=8.1 Hz, 1H), 7.49-7.29 (m, 4H), 6.68 (q, J=6.7 Hz, 1H), 1.76 (d, J=6.6 Hz, 3H); HRMS-FAB (m/z) [M+H]⁺ calcd for $C_{24}H_{17}F_6N_5O_2S$, 553.101. found, 553.1006.

Example 75

Preparation of O-4-fluorophenyl 4-(1-(4-(trifluoromethoxy)phenyl)-1H-1,2,4-triazol-3-yl)phenylcarbamothioate (Compound 134)

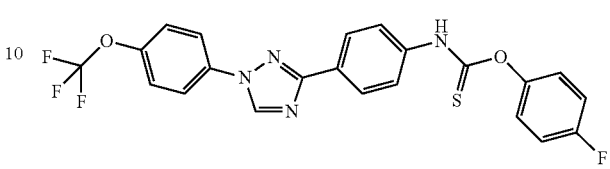

Into a 25 mL round-bottomed flask were added 4-(1-(4-(trifluoromethoxy)phenyl)-1H-1,2,4-triazol-3-yl)aniline (200 mg, 0.624 mmol), O-4-fluorophenyl carbonochloridothioate (238 mg, 1.249 mmol), and triethylamine (0.348 mL, 2.498 mmol) in THF (5 mL). The solution was stirred under ambient conditions for 2 h before the solvent was removed under reduced pressure. The crude product was added to a silica gel column and was eluted with EtOAc/hexanes gradient to afford the title compound (50 mg, 0.105 mmol, 17%) as a yellow solid: mp 164-169° C.; ¹H NMR (400 MHz, DMSO-d₆) δ 9.42 (s, 1H), 8.19-8.04 (m, 6H), 7.97 (br s, 1H), 7.66-7.57 (d, J=8.24 Hz, 2H), 7.33-7.19 (m, 4H); ESIMS m/z 475 (M+1).

Example 76

Preparation of methyl 4-(1-(4-(perfluoroethoxy)phenyl)-1H-1,2,4-triazol-3-yl)phenylcarbamate (Compound 135)

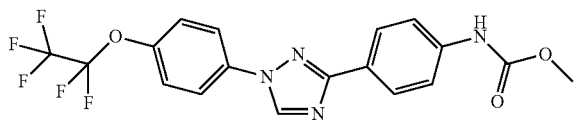 [SMILES: COC(=O)Nc1ccc(-c2ncn(-c3ccc(OC(F)(F)C(F)(F)F)cc3)n2)cc1]

4-Nitrophenyl 4-(1-(4-(perfluoroethoxy)phenyl)-1H-1,2,4-triazol-3-yl)phenylcarbamate (1.90 g, 3.55 mmol) was slurried in MeOH (15 mL) and cooled in a −10° C. dry ice/acetone bath. Sodium methoxide (1.33 mL of a 30 wt % solution in MeOH, 7.10 mmol) was added dropwise over 10 min. The resulting bright yellow slurry was warmed to ambient temperature and poured into ice water (150 mL). After stirring vigorously for 10 min, the mixture was filtered on a Büchner funnel. The tan solid was rinsed with water and dried in air. Recrystallization from MeOH/water provided the title compound (0.989 g, 65%) as a tan solid: mp 183-184.5° C.; $^1$H NMR (300 MHz, CDCl$_3$) δ 8.55 (s, 1H), 8.14 (d, J=8.7 Hz, 2H), 7.79 (d, J=9.0 Hz, 2H), 7.50 (d, J=8.6 Hz, 2H), 7.38 (d, J=8.9 Hz, 2H), 6.79 (s, 1H), 3.80 (s, 3H); HRMS-FAB (m/z) [M+H]$^+$ calcd for $C_{18}H_{13}F_5N_4O_3$, 428.0908. found, 428.0903.

Example 77

Preparation of methyl-{4-[1-(4-trifluoromethoxyphenyl)-1H-[1,2,4]triazol-3-yl]-phenyl}-carbamic acid 4-nitrophenyl ester (Compound 136)

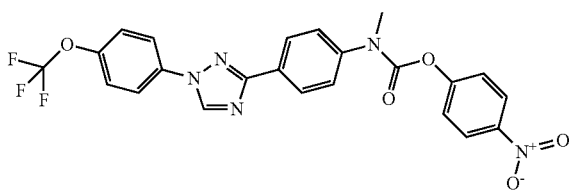 [SMILES: CN(C(=O)Oc1ccc([N+](=O)[O-])cc1)c1ccc(-c2ncn(-c3ccc(OC(F)(F)F)cc3)n2)cc1]

A suspension of 4-[1-(4-trifluoroethyloxyphenyl)-1H-[1,2,4]triazol-3-yl]-phenylamine (1.2 g, 3.7 mmol) in EtOH (4 mL) was treated with 1H-benzotriazole (0.48 g, 4.0 mmol) and formaldehyde (0.5 mL of 37% aqueous, 6 mmol), and the solution was heated to 40° C. for 10 min. Upon cooling, a solid formed, which was collected by filtration. There was obtained 1.33 g of the triazole adduct as a light yellow solid, mp 185-187° C. This material (1.2 g, 2.66 mmol) was dissolved in THF (20 mL) and treated with NaBH$_4$ (0.11 g, 2.9 mmol). The solution was stirred at ambient temperature for 30 min, then heated to reflux for 1 h. After cooling, the solution was poured onto water (30 mL) and extracted with ether. Drying and concentration, followed by silica gel chromatography (75:25 Hexanes:EtOAc) furnished methyl-{4-[1-(4-trifluoromethoxyphenyl)-1H-[1,2,4]triazol-3-yl]-phenyl}-amine (0.76 g, 86%) as a white solid, mp 121-123° C.; $^1$H NMR (300 MHz, CDCl$_3$) δ 8.51 (s, 1H), 8.02 (d, J=8.8 Hz, 2H), 7.78 (d, J=9.1 Hz, 2H), 7.37 (d, J=8.3 Hz, 2H), 6.68 (d, J=8.8 Hz, 2H), 3.96 (s, 1H), 2.91 (s, 3H); ELMS m/z 499 (M$^+$). A portion of this amine (0.11 g, 0.33 mmol) was dissolved in dry THF (2 mL) and treated with 4-nitrophenyl chloroformate (0.069 g, 0.34 mmol). The solid which formed over 10 min was collected by filtration and air-dried to give an off-white solid (0.10 g): mp 145-147° C.; $^1$H NMR (300 MHz, CDCl$_3$) δ 8.59 (s, 1H), 8.28 (d, J=8 Hz, 4H), 7.8 (d, J=8 Hz, 2H), 7.50-7.3 (m, 6H) 3.55 (s, 3H); EIMS m/z 499 (M$^+$).

The compounds were tested against beet armyworm and corn earworm using procedures described in the following examples and reported in Table 2.

In each case of Table 2, the rating scale is as follows:

| % Control (or Mortality) | Rating |
| --- | --- |
| 50-100 | A |
| Less than 50 | B |
| Not tested | C |

Example 78

Insecticidal Test for Beet Armyworm (*Spodoptera exigua*)

Bioassays on beet armyworm (BAW; *Spodoptera exigua*: Lepidoptera) were conducted using a 128-well diet tray assay. Three to five second instar BAW larvae were placed in each well (3 mL) of the diet tray that had been previously filled with 1 mL of artificial diet to which 50 μg/cm$^2$ of the test compound (dissolved in 50 μL of 90:10 acetone-water mixture) had been applied (to each of eight wells) and then allowed to dry. Trays were covered with a clear self-adhesive cover, and held at 25° C., 14:10 light-dark for six days. Percent mortality was recorded for the larvae in each well; activity in the eight wells was then averaged. The results for both bioassays are indicated in Table 2.

Example 79

Insecticidal Test for Corn Earworm (*Helicoverpa zea*)

Bioassays on corn earworm (CEW; *Helicoverpa zea*: Lepidoptera) were conducted using a 128-well diet tray assay. Three to five second instar CEW larvae were placed in each well (3 mL) of the diet tray that had been previously filled with 1 mL of artificial diet to which 50 μg/cm$^2$ of the test compound (dissolved in 50 μL of 90:10 acetone-water mixture) had been applied (to each of eight wells) and then allowed to dry. Trays were covered with a clear self-adhesive cover, and held at 25° C., 14:10 light-dark for six days. Percent mortality was recorded for the larvae in each well; activity in the eight wells was then averaged. The results for both bioassays are indicated in Table 2.

The compounds were also tested against green peach aphid using a procedure described in the following example and reported in Table 2.

In each case of Table 2, the rating scale is as follows:

| % Control (or Mortality) | Rating |
| --- | --- |
| 80-100 | A |
| Less than 80 | B |
| Not tested | C |

Example 80

Insecticidal Test for Green Peach Aphid (*Myzus persicae*) in Foliar Spray Assay Cabbage seedlings grown in 3-inch pots, with 2-3 small (3-5 cm) true leaves, were used as test substrate. The seedlings were infested with 20-50 green peach aphids (wingless adult and nymph) one day prior to chemical application. Four pots with individual seedlings were used for each treatment. Compounds (2 mg) were dissolved in 2 mL of acetone/methanol (1:1) solvent, forming stock solutions of 1000 ppm. The stock solutions were diluted 5× with 0.025% Tween 20 in H₂O to obtain the solution at 200 ppm. A hand-held Devilbiss sprayer was used for spraying a solution to both sides of cabbage leaves until runoff. Reference plants (solvent check) were sprayed with the diluent only. Treated plants were held in a holding room for three days at approximately 25° C. and 40% relative humidity (RH) prior to grading. Evaluation was conducted by counting the number of live aphids per plant under a microscope. Insecticidal activity was measured by using Abbott's correction formula are presented in Table 2:

Corrected % Control=100*(X−Y)/X where X=No. of live aphids on solvent check plants
Y=No. of live aphids on treated plants

Acid and Salt Derivatives and Solvates

The compounds disclosed in this invention can be in the form of pesticidally acceptable acid addition salts.

By way of non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxymethanesulfonic, and hydroxyethanesulfonic acids.

Additionally, by way of non-limiting example, an acid function can form salts including those derived from alkali or alkaline earth metals and those derived from ammonia and amines. Examples of preferred cations include sodium, potassium, magnesium, and aminium cations.

The salts are prepared by contacting the free base form with a sufficient amount of the desired acid to produce a salt. The free base forms may be regenerated by treating the salt with a suitable dilute aqueous base solution such as dilute aqueous NaOH, potassium carbonate, ammonia, and sodium bicarbonate. As an example, in many cases, a pesticide is modified to a more water soluble form e.g. 2,4-dichlorophenoxy acetic acid dimethyl amine salt is a more water soluble form of 2,4-dichlorophenoxy acetic acid, a well known herbicide.

The compounds disclosed in this invention can also form stable complexes with solvent molecules that remain intact after the non-complexed solvent molecules are removed from the compounds. These complexes are often referred to as "solvates".

Stereoisomers

Certain compounds disclosed in this document can exist as one or more stereoisomers. The various stereoisomers include geometric isomers, diastereomers, and enantiomers. Thus, the compounds disclosed in this invention include racemic mixtures, individual stereoisomers, and optically active mixtures. It will be appreciated by those skilled in the art that one stereoisomer may be more active than the others. Individual stereoisomers and optically active mixtures may be obtained by selective synthetic procedures, by conventional synthetic procedures using resolved starting materials, or by conventional resolution procedures.

Pests

In another embodiment, the invention disclosed in this document can be used to control pests.

In another embodiment, the invention disclosed in this document can be used to control pests of the Phylum Nematoda.

In another embodiment, the invention disclosed in this document can be used to control pests of the Phylum Arthropoda.

In another embodiment, the invention disclosed in this document can be used to control pests of the Subphylum Chelicerata.

In another embodiment, the invention disclosed in this document can be used to control pests of the Class Arachnida.

In another embodiment, the invention disclosed in this document can be used to control pests of the Subphylum Myriapoda.

In another embodiment, the invention disclosed in this document can be used to control pests of the Class Symphyla.

In another embodiment, the invention disclosed in this document can be used to control pests of the Subphylum Hexapoda.

In another embodiment, the invention disclosed in this document can be used to control pests of the Class Insecta.

In another embodiment, the invention disclosed in this document can be used to control Coleoptera (beetles). A non-exhaustive list of these pests includes, but is not limited to, *Acanthoscelides* spp. (weevils), *Acanthoscelides obtectus* (common bean weevil), *Agrilus planipennis* (emerald ash borer), *Agriotes* spp. (wireworms), *Anoplophora glabripennis* (Asian longhorned beetle), *Anthonomus* spp. (weevils), *Anthonomus grandis* (boll weevil), *Aphidius* spp., *Apion* spp. (weevils), *Apogonia* spp. (grubs), *Ataenius spretulus* (Black Turgrass Ataenius), *Atomaria linearis* (pygmy mangold beetle), *Aulacophore* spp., *Bothynoderes punctiventris* (beet root weevil), *Bruchus* spp. (weevils), *Bruchus pisorum* (pea weevil), *Cacoesia* spp., *Callosobruchus maculatus* (southern cow pea weevil), *Carpophilus hemipteras* (dried fruit beetle), *Cassida vittata, Cerosterna* spp., *Cerotoma* spp. (chrysomeids), *Cerotoma trifurcata* (bean leaf beetle), *Ceutorhynchus* spp. (weevils), *Ceutorhynchus assimilis* (cabbage seed-pod weevil), *Ceutorhynchus napi* (cabbage curculio), *Chaetocnema* spp. (chrysomelids), *Colaspis* spp. (soil beetles), *Conoderus scalaris, Conoderus stigmosus, Conotrachelus nenuphar* (plum curculio), *Cotinus nitidis* (Green June beetle), *Crioceris asparagi* (asparagus beetle), *Cryptolestes ferrugineus* (rusty grain beetle), *Cryptolestes pusillus* (flat grain beetle), *Cryptolestes turcicus* (Turkish grain beetle), *Ctenicera* spp. (wireworms), *Curculio* spp. (weevils), *Cyclocephala* spp. (grubs), *Cylindrocpturus adspersus* (sunflower stem weevil), *Deporaus marginatus* (mango leaf-cutting weevil), *Dermestes lardarius* (larder beetle), *Dermestes maculates* (hide beetle), *Diabrotica* spp. (chrysolemids), *Epilachna varivestis* (Mexican bean beetle), *Faustinus cubae, Hylobius pales* (pales weevil), *Hypera* spp. (weevils), *Hypera postica* (alfalfa weevil), *Hyperdoes* spp. (Hyperodes weevil), *Hypothenemus hampei* (coffee berry beetle), *Ips* spp. (engravers), *Lasioderma serricorne* (cigarette beetle), *Leptinotarsa decemlineata* (Colorado potato beetle), *Liogenys fuscus, Liogenys suturalis, Lissorhoptrus oryzophilus* (rice water weevil), *Lyctus* spp. (wood beetles/powder post beetles), *Maecolaspis joliveti, Megascelis* spp., *Melanotus communis, Meligethes* spp., *Meligethes aeneus* (blossom beetle), *Melolontha melolontha* (common European cockchafer), *Oberea brevis, Oberea linearis, Oryctes rhinoceros* (date palm beetle), *Oryzaephilus mercator* (merchant grain beetle), *Oryzaephilus surinamensis* (sawtoothed grain beetle), *Otiorhynchus* spp. (weevils), *Oulema melanopus* (cereal leaf beetle), *Oulema oryzae, Pantomorus* spp. (weevils), *Phyllophaga* spp. (May/June beetle), *Phyllophaga cuyabana, Phyllotreta* spp. (chrysomelids), *Phynchites* spp., *Popillia japonica* (Japanese beetle), *Prostephanus truncates* (larger grain borer), *Rhizopertha dominica* (lesser grain borer), *Rhizotrogus* spp. (European chafer), *Rhynchophorus* spp. (weevils), *Scolytus* spp. (wood beetles), *Shenophorus* spp. (Billbug), *Sitona lineatus* (pea leaf weevil), *Sitophilus* spp. (grain weevils), *Sitophilus granaries* (granary weevil), *Sitophilus oryzae* (rice weevil), *Stegobium paniceum* (drugstore beetle), *Tribolium* spp. (flour beetles), *Tribolium castaneum* (red flour beetle), *Tribolium confusum* (confused flour beetle), *Trogoderma variabile* (warehouse beetle), and *Zabrus tenebioides*.

In another embodiment, the invention disclosed in this document can be used to control Dermaptera (earwigs).

In another embodiment, the invention disclosed in this document can be used to control Dictyoptera (cockroaches). A non-exhaustive list of these pests includes, but is not limited to, *Blattella germanica* (German cockroach), *Blatta orientalis* (oriental cockroach), *Parcoblatta pennylvanica*, *Periplaneta americana* (American cockroach), *Periplaneta australoasiae* (Australian cockroach), *Periplaneta brunnea* (brown cockroach), *Periplaneta fuliginosa* (smokybrown cockroach), *Pyncoselus suninamensis* (Surinam cockroach), and *Supella longipalpa* (brownbanded cockroach).

In another embodiment, the invention disclosed in this document can be used to control Diptera (true flies). A non-exhaustive list of these pests includes, but is not limited to, *Aedes* spp. (mosquitoes), *Agromyza frontella* (alfalfa blotch leafminer), *Agromyza* spp. (leaf miner flies), *Anastrepha* spp. (fruit flies), *Anastrepha suspensa* (Caribbean fruit fly), *Anopheles* spp. (mosquitoes), *Batrocera* spp. (fruit flies), *Bactrocera cucurbitae* (melon fly), *Bactrocera dorsalis* (oriental fruit fly), *Ceratitis* spp. (fruit flies), *Ceratitis capitata* (Mediterranea fruit fly), *Chrysops* spp. (deer flies), *Cochliomyia* spp. (screwworms), *Contarinia* spp. (gall midges), *Culex* spp. (mosquitoes), *Dasineura* spp. (gall midges), *Dasineura brassicae* (cabbage gall midge), *Delia* spp., *Delia platura* (seedcorn maggot), *Drosophila* spp. (vinegar flies), *Fannia* spp. (filth flies), *Fannia canicularis* (little house fly), *Fannia scalaris* (latrine fly), *Gasterophilus intestinalis* (horse bot fly), *Gracillia perseae, Haematobia irritans* (horn fly), *Hylemyia* spp. (root maggots), *Hypoderma lineatum* (common cattle grub), *Liriomyza* spp. (leafminer flies), *Liriomyza brassica* (serpentine leafminer), *Melophagus ovinus* (sheep ked), *Musca* spp. (muscid flies), *Musca autumnalis* (face fly), *Musca domestica* (house fly), *Oestrus ovis* (sheep bot fly), *Oscinella frit* (frit fly), *Pegomyia betae* (beet leafminer), *Phorbia* spp., *Psila rosae* (carrot rust fly), *Rhagoletis cerasi* (cherry fruit fly), *Rhagoletis pomonella* (apple maggot), *Sitodiplosis mosellana* (orange wheat blossom midge), *Stomoxys calcitrans* (stable fly), *Tabanus* spp. (horse flies), and *Tipula* spp. (crane flies).

In another embodiment, the invention disclosed in this document can be used to control Hemiptera (true bugs). A non-exhaustive list of these pests includes, but is not limited to, *Acrosternum hilare* (green stink bug), *Blissus leucopterus* (chinch bug), *Calocoris norvegicus* (potato mind), *Cimex hemipterus* (tropical bed bug), *Cimex lectularius* (bed bug), *Dagbertus fasciatus, Dichelops furcatus, Dysdercus suturellus* (cotton stainer), *Edessa meditabunda, Eurygaster maura* (cereal bug), *Euschistus heros, Euschistus servus* (brown stink bug), *Helopeltis antonii, Helopeltis theivora* (tea blight plantbug), *Lagynotomus* spp. (stink bugs), *Leptocorisa oratorius, Leptocorisa varicornis, Lygus* spp. (plant bugs), *Lygus hesperus* (western tarnished plant bug), *Maconellicoccus hirsutus, Neurocolpus longirostris, Nezara viridula* (southern green stink bug), *Phytocoris* spp. (plant bugs), *Phytocoris californicus, Phytocoris relativus, Piezodorus guildingi, Poecilocapsus lineatus* (fourlined plant bug), *Psallus vaccinicola, Pseudacysta perseae, Scaptocoris castanea*, and *Triatoma* spp. (bloodsucking conenose bugs/kissing bugs).

In another embodiment, the invention disclosed in this document can be used to control Homoptera (aphids, scales, whiteflies, leafhoppers). A non-exhaustive list of these pests includes, but is not limited to, *Acrythosiphon pisum* (pea aphid), *Adelges* spp. (adelgids), *Aleurodes proletella* (cabbage whitefly), *Aleurodicus disperses, Aleurothrixus floccosus* (woolly whitefly), *Aluacaspis* spp., *Amrasca bigutella bigutella, Aphrophora* spp. (leafhoppers), *Aonidiella aurantii* (California red scale), *Aphis* spp. (aphids), *Aphis gossypii* (cotton aphid), *Aphis pomi* (apple aphid), *Aulacorthum solani* (foxglove aphid), *Bemisia* spp. (whiteflies), *Bemisia argentifolii, Bemisia tabaci* (sweetpotato whitefly), *Brachycolus noxius* (Russian aphid), *Brachycorynella asparagi* (asparagus aphid), *Brevennia rehi, Brevicoryne brassicae* (cabbage aphid), *Ceroplastes* spp. (scales), *Ceroplastes rubens* (red wax scale), *Chionaspis* spp. (scales), *Chrysomphalus* spp. (scales), *Coccus* spp. (scales), *Dysaphis plantaginea* (rosy apple aphid), *Empoasca* spp. (leafhoppers), *Eriosoma lanigerum* (woolly apple aphid), *Icerya purchasi* (cottony cushion scale), *Idioscopus nitidulus* (mango leafhopper), *Laodelphax striatellus* (smaller brown planthopper), *Lepidosaphes* spp., *Macrosiphum* spp., *Macrosiphum euphorbiae* (potato aphid), *Macrosiphum granarium* (English grain aphid), *Macrosiphum rosae* (rose aphid), *Macrosteles quadrilineatus* (aster leafhopper), *Mahanarva frimbiolata, Metopolophium dirhodum* (rose grain aphid), *Mictis longicornis, Myzus persicae* (green peach aphid), *Nephotettix* spp. (leafhoppers), *Nephotettix cinctipes* (green leafhopper), *Nilaparvata lugens* (brown planthopper), *Parlatoria pergandii* (chaff scale), *Parlatoria ziziphi* (ebony scale), *Peregrinus maidis* (corn delphacid), *Philaenus* spp. (spittlebugs), *Phylloxera vitifoliae* (grape phylloxera), *Physokermes piceae* (spruce bud scale), *Planococcus* spp. (mealybugs), *Pseudococcus* spp. (mealybugs), *Pseudococcus brevipes* (pine apple mealybug), *Quadraspidiptus perniciosus* (San Jose scale), *Rhapalosiphum* spp. (aphids), *Rhapalosiphum maida* (corn leaf aphid), *Rhapalosiphum padi* (oat bird-cherry aphid), *Saissetia* spp. (scales), *Saissetia oleae* (black scale), *Schizaphis graminum* (greenbug), *Sitobion avenae* (English grain aphid), *Sogatella furcifera* (white-backed planthopper), *Therioaphis* spp. (aphids), *Toumeyella* spp. (scales), *Toxoptera* spp. (aphids), *Trialeurodes* spp. (whiteflies), *Trialeurodes vaporariorum* (greenhouse whitefly), *Trialeurodes abutiloneus* (bandedwing whitefly), *Unaspis* spp. (scales), *Unaspis yanonensis* (arrowhead scale), and *Zulia entreriana*.

In another embodiment, the invention disclosed in this document can be used to control Hymenoptera (ants, wasps, and bees). A non-exhaustive list of these pests includes, but is not limited to, *Acromyrrmex* spp., *Athalia rosae, Atta* spp. (leafcutting ants), *Camponotus* spp. (carpenter ants), *Diprion* spp. (sawflies), *Formica* spp. (ants), *Iridomyrmex humilis* (Argentine ant), *Monomorium* ssp., *Monomorium minumum* (little black ant), *Monomorium pharaonis* (Pharaoh ant), *Neodiprion* spp. (sawflies), *Pogonomyrmex* spp. (harvester ants), *Polistes* spp. (paper wasps), *Solenopsis* spp. (fire ants), *Tapoinoma sessile* (odorous house ant), *Tetranomorium* spp. (pavement ants), *Vespula* spp. (yellow jackets), and *Xylocopa* spp. (carpenter bees).

In another embodiment, the invention disclosed in this document can be used to control Isoptera (termites). A nonexhaustive list of these pests includes, but is not limited to, *Coptotermes* spp., *Coptotermes curvignathus, Coptotermes frenchii, Coptotermes formosanus* (Formosan subterranean termite), *Cornitermes* spp. (nasute termites), *Cryptotermes* spp. (drywood termites), *Heterotermes* spp. (desert subterranean termites), *Heterotermes aureus, Kalotermes* spp. (drywood termites), *Incistitermes* spp. (drywood termites), *Macrotermes* spp. (fungus growing termites), *Marginitermes* spp. (drywood termites), *Microcerotermes* spp. (harvester termites), *Microtermes obesi, Procornitermes* spp., *Reticulitermes* spp. (subterranean termites), *Reticulitermes banyulensis, Reticulitermes grassei, Reticulitermes flavipes* (eastern subterranean termite), *Reticulitermes hageni, Reticulitermes hesperus* (western subterranean termite), *Reticulitermes santonensis, Reticulitermes speratus, Reticulitermes tibialis, Reticulitermes virginicus, Schedorhinotermes* spp., and *Zootermopsis* spp. (rotten-wood termites).

In another embodiment, the invention disclosed in this document can be used to control Lepidoptera (moths and butterflies). A non-exhaustive list of these pests includes, but is not limited to, *Achoea janata, Adoxophyes* spp., *Adoxophyes orana, Agrotis* spp. (cutworms), *Agrotis ipsilon* (black cutworm), *Alabama argillacea* (cotton leafworm), *Amorbia cuneana, Amyelosis transitella* (navel orangeworm), *Anacamptodes defectaria, Anarsia lineatella* (peach twig borer), *Anomis sabulifera* (jute looper), *Anticarsia gemmatalis* (velvetbean caterpillar), *Archips argyrospila* (fruit tree leafroller), *Archips rosana* (rose leaf roller), *Argyrotaenia* spp. (tortricid moths), *Argyrotaenia citrana* (orange tortrix), *Autographa gamma, Bonagota cranaodes, Borba cinnara* (rice leaf folder), *Bucculatrix thurberiella* (cotton leaf perforator), *Caloptilia* spp. (leaf miners), *Capua reticulana, Carposina niponensis* (peach fruit moth), *Chilo* spp., *Chlumetia transversa* (mango shoot borer), *Choristoneura rosaceana* (oblique banded leaf roller), *Chrysodeixis* spp., *Cnaphalocerus medinalis* (grass leafroller), *Colias* spp., *Conpomorpha cramerella, Cossus cossus* (carpenter moth), *Crambus* spp. (Sod webworms), *Cydia funebrana* (plum fruit moth), *Cydia molesta* (oriental fruit moth), *Cydia nignicana* (pea moth), *Cydia pomonella* (codling moth), *Darna diducta, Diaphania* spp. (stem borers), *Diatraea* spp. (stalk borers), *Diatraea saccharalis* (sugarcane borer), *Diatraea graniosella* (southwestern corn borer), *Earias* spp. (bollworms), *Earias insulata* (Egyptian bollworm), *Earias vitella* (rough northern bollworm), *Ecdytopopha aurantianum, Elasmopalpus lignosellus* (lesser cornstalk borer), *Epiphysias postruttana* (light brown apple moth), *Ephestia* spp. (flour moths), *Ephestia cautella* (almond moth), *Ephestia elutella* (tobacco moth), *Ephestia kuehniella* (Mediterranean flour moth), *Epimeces* spp., *Epinotia aporema, Erionota thrax* (banana skipper), *Eupoecilia ambiguella* (grape berry moth), *Euxoa auxiliaris* (army cutworm), *Feltia* spp. (cutworms), *Gortyna* spp. (stemborers), *Grapholita molesta* (oriental fruit moth), *Hedylepta indicata* (bean leaf webber), *Helicoverpa* spp. (noctuid moths), *Helicoverpa armigera* (cotton bollworm), *Helicoverpa zea* (bollworm/corn earworm), *Heliothis* spp. (noctuid moths), *Heliothis virescens* (tobacco budworm), *Hellula undalis* (cabbage webworm), *Indarbela* spp. (root borers), *Keiferia lycopersicella* (tomato pinworm), *Leucinodes orbonalis* (eggplant fruit borer), *Leucoptera malifoliella, Lithocollectis* spp., *Lobesia botrana* (grape fruit moth), *Loxagrotis* spp. (noctuid moths), *Loxagrotis albicosta* (western bean cutworm), *Lymantria dispar* (gypsy moth), *Lyonetia clerkella* (apple leaf miner), *Mahasena corbetti* (oil palm bagworm), *Malacosoma* spp. (tent caterpillars), *Mamestra brassicae* (cabbage armyworm), *Maruca testulalis* (bean pod borer), *Metisa plana* (bagworm), *Mythimna unipuncta* (true armyworm), *Neoleucinodes elegantalis* (small tomato borer), *Nymphula depunctalis* (rice caseworm), *Operophthera brumata* (winter moth), *Ostrinia nubilalis* (European corn borer), *Oxydia vesulia, Pandemis cerasana* (common currant tortrix), *Pandemis heparana* (brown apple tortrix), *Papilio demodocus, Pectinophora gossypiella* (pink bollworm), *Peridroma* spp. (cutworms), *Peridroma saucia* (variegated cutworm), *Perileucoptera coffeella* (white coffee leafminer), *Phthorimaea operculella* (potato tuber moth), *Phyllocnisitis citrella, Phyllonorycter* spp. (leafminers), *Pieris rapae* (imported cabbageworm), *Plathypena scabra, Plodia interpunctella* (Indian meal moth), *Plutella xylostella* (diamondback moth), *Polychrosis viteana* (grape berry moth), *Prays endocarpa, Prays oleae* (olive moth), *Pseudaletia* spp. (noctuid moths), *Pseudaletia unipunctata* (armyworm), *Pseudoplusia includens* (soybean looper), *Rachiplusia nu, Scirpophaga incertulas, Sesamia* spp. (stemborers), *Sesamia inferens* (pink rice stem borer), *Sesamia nonagrioides, Setora nitens, Sitotroga cerealella* (Angoumois grain moth), *Sparganothis pilleriana, Spodoptera* spp. (armyworms), *Spodoptera exigua* (beet armyworm), *Spodoptera frugiperda* (fall armyworm), *Spodoptera oridania* (southern armyworm), *Synanthedon* spp. (root borers), *Thecla basilides, Thermisia gemmatalis, Tineola bisselliella* (webbing clothes moth), *Trichoplusia ni* (cabbage looper), *Tuta absoluta, Yponomeuta* spp., *Zeuzera coffeae* (red branch borer), and *Zeuzera pyrina* (leopard moth).

In another embodiment, the invention disclosed in this document can be used to control Mallophaga (chewing lice). A non-exhaustive list of these pests includes, but is not limited to, *Bovicola ovis* (sheep biting louse), *Menacanthus stramineus* (chicken body louse), and *Menopon gallinea* (common hen louse).

In another embodiment, the invention disclosed in this document can be used to control Orthoptera (grasshoppers, locusts, and crickets). A non-exhaustive list of these pests includes, but is not limited to, *Anabrus simplex* (Mormon cricket), *Gryllotalpidae* (mole crickets), *Locusta migratoria, Melanoplus* spp. (grasshoppers), *Microcentrum retinerve* (angular winged katydid), *Pterophylla* spp. (katydids), *chistocerca gregaria, Scudderia furcata* (fork tailed bush katydid), and *Valanga nigricorni*.

In another embodiment, the invention disclosed in this document can be used to control Phthiraptera (sucking lice). A non-exhaustive list of these pests includes, but is not limited to, *Haematopinus* spp. (cattle and hog lice), *Linognathus ovillus* (sheep louse), *Pediculus humanus capitis* (human body louse), *Pediculus humanus humanus* (human body lice), and *Pthirus pubis* (crab louse), In another embodiment, the invention disclosed in this document can be used to control Siphonaptera (fleas). A non-exhaustive list of these pests includes, but is not limited to, *Ctenocephalides canis* (dog flea), *Ctenocephalides felis* (cat flea), and *Pulex irritans* (human flea).

In another embodiment, the invention disclosed in this document can be used to control Thysanoptera (thrips). A non-exhaustive list of these pests includes, but is not limited to, *Frankliniella fusca* (tobacco thrips), *Frankliniella occidentalis* (western flower thrips), *Frankliniella shultzei Frankliniella williamsi* (corn thrips), *Heliothrips haemorrhaidalis* (greenhouse thrips), *Riphiphorothrips cruentatus, Scirtothrips* spp., *Scirtothrips citri* (citrus thrips), *Scirtothrips dorsalis* (yellow tea thrips), *Taeniothrips rhopalantennalis*, and *Thrips* spp.

In another embodiment, the invention disclosed in this document can be used to control Thysanura (bristletails). A non-exhaustive list of these pests includes, but is not limited to, *Lepisma* spp. (silverfish) and *Thermobia* spp. (firebrats).

In another embodiment, the invention disclosed in this document can be used to control Acarina (mites and ticks). A non-exhaustive list of these pests includes, but is not limited to, *Acarapsis woodi* (tracheal mite of honeybees), *Acarus* spp. (food mites), *Acarus siro* (grain mite), *Aceria mangiferae* (mango bud mite), *Aculops* spp., *Aculops lycopersici* (tomato russet mite), *Aculops pelekasi, Aculus pelekassi, Aculus schlechtendali* (apple rust mite), *Amblyomma americanum* (lone star tick), *Boophilus* spp. (ticks), *Brevipalpus obovatus* (privet mite), *Brevipalpus phoenicis* (red and black flat mite), *Demodex* spp. (mange mites), *Dermacentor* spp. (hard ticks), *Dermacentor variabilis* (American dog tick), *Dermatophagoides pteronyssinus* (house dust mite), *Eotetranycus* spp., *Eotetranychus carpini* (yellow spider mite), *Epitimerus* spp., *Eriophyes* spp., *Ixodes* spp. (ticks), *Metatetranycus* spp., *Notoedres cati, Oligonychus* spp., *Oligonychus coffee, Oligonychus ilicus* (southern red mite), *Panonychus* spp., *Panonychus citri* (citrus red mite), *Panonychus ulmi* (European red mite), *Phyllocoptruta oleivora* (citrus rust mite), *Polyphagotarsonemun latus* (broad mite), *Rhipicephalus sanguineus* (brown dog tick), *Rhizoglyphus* spp. (bulb mites), *Sarcoptes scabiei* (itch mite), *Tegolophus perseaflorae, Tetranychus* spp., *Tetranychus urticae* (two-spotted spider mite), and *Varroa destructor* (honey bee mite).

In another embodiment, the invention disclosed in this document can be used to control Nematoda (nematodes). A non-exhaustive list of these pests includes, but is not limited to, *Aphelenchoides* spp. (bud and leaf & pine wood nematodes), *Belonolaimus* spp. (sting nematodes), *Criconemella* spp. (ring nematodes), *Dirofilaria immitis* (dog heartworm), *Ditylenchus* spp. (stem and bulb nematodes), *Heterodera* spp. (cyst nematodes), *Heterodera zeae* (corn cyst nematode), *Hirschmanniella* spp. (root nematodes), *Hoplolaimus* spp. (lance nematodes), *Meloidogyne* spp. (root knot nematodes), *Meloidogyne incognita* (root knot nematode), *Onchocerca volvulus* (hook-tail worm), *Pratylenchus* spp. (lesion nematodes), *Radopholus* spp. (burrowing nematodes), and *Rotylenchus reniformis* (kidney-shaped nematode).

In another embodiment, the invention disclosed in this document can be used to control Symphyla (symphylans). A non-exhaustive list of these pests includes, but is not limited to, *Scutigerella immaculata*.

For more detailed information consult "HANDBOOK OF PEST CONTROL—THE BEHAVIOR, LIFE HISTORY, AND CONTROL OF HOUSEHOLD PESTS" by Arnold Mallis, 9th Edition, copyright 2004 by GIE Media Inc.

Mixtures

The invention disclosed in this document can also be used with various insecticides, both for reasons of economy and synergy. Such insecticides include, but are not limited to, antibiotic insecticides, macrocyclic lactone insecticides (for example, avermectin insecticides, milbemycin insecticides, and spinosyn insecticides), arsenical insecticides, botanical insecticides, carbamate insecticides (for example, benzofuranyl methylcarbamate insecticides, dimethylcarbamate insecticides, oxime carbamate insecticides, and phenyl methylcarbamate insecticides), diamide insecticides, desiccant insecticides, dinitrophenol insecticides, fluorine insecticides, formamidine insecticides, fumigant insecticides, inorganic insecticides, insect growth regulators (for example, chitin synthesis inhibitors, juvenile hormone mimics, juvenile hormones, moulting hormone agonists, moulting hormones, moulting inhibitors, precocenes, and other unclassified insect growth regulators), nereistoxin analogue insecticides, nicotinoid insecticides (for example, nitroguanidine insecticides, nitromethylene insecticides, and pyridylmethylamine insecticides), organochlorine insecticides, organophosphorus insecticides, oxadiazine insecticides, oxadiazolone insecticides, phthalimide insecticides, pyrazole insecticides, pyrethroid insecticides, pyrimidinamine insecticides, pyrrole insecticides, tetramic acid insecticides, tetronic acid insecticides, thiazole insecticides, thiazolidine insecticides, thiourea insecticides, urea insecticides, as well as, other unclassified insecticides.

Some of the particular insecticides that can be employed beneficially in combination with the invention disclosed in this document include, but are not limited to, the following 1,2-dichloropropane, 1,3-dichloropropene, abamectin, acephate, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-endosulfan, amidithion, aminocarb, amiton, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, beta-cypermethrin, bifenthrin, bioallethrin, bioethanomethrin, biopermethrin, bioresmethrin, bistrifluoron, borax, boric acid, boric acid, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, chlorantraniliprole, chlorbicyclen, chlordane, chlordecone, chlordimeform, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclethrin, cycloprothrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinoprop, dinosam, dinotefuran, diofenolan, dioxabenzofos, dioxacarb, dioxathion, disulfoton, dithicrofos, d-limonene, DNOC, doramectin, ecdysterone, emamectin, EMPC, empenthrin, endosulfan, endothion, endrin, EPN, epofenonane, eprinomectin, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flonicamid, flubendiamide, flucofuron, flucycloxuron, flucythrinate, flufenerim, flufenoxuron, flufenprpx, fluvalinate, fonofos, formetanate, formothion, formparanate, fosmethilan, fospirate, fosthietan, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isoprocarb, isoprothiolane, isothioate, isoxathion, ivermectin, jasmolin I, jasmolin II, jodfenphos, juvenile hormone I, juvenile hormone II, juvenile hormone III, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfenfos, metaflumizone, methacrifos, methamidophos, methidathion, methiocarb, methocrotophos, methomyl, methoprene, methoxychlor, methoxyfenozide, methyl bromide, methylchloroform, methylene chloride, metofluthrin, metolcarb, metoxadiazone, mevinphos, mexacarbate, milbemectin, milbemycin oxime, mipafox, mirex, monocrotophos, morphothion, moxidectin, naftalofos, naled, naphthalene, nicotine, nifluridide, nitenpyram, nithiazine, nitrilacarb, novaluron, noviflumuron, omethoate, oxamyl, oxydemeton-methyl, oxydeprofos, oxydisulfoton, paradichlorobenzene, parathion, parathion-methyl, penfluoron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluthrin, promacyl, promecarb, propaphos, propetamphos, propoxur, prothidathion, prothiofos, prothoate, protrifenbute, pyraclofos, pyrafluprole, pyrazophos, pyresmethrin, pyrethrin I, pyrethrin II, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulfoxaflor, sulfluramid, sulfotep, sulfuryl fluoride, sulprofos, tau-fluvalinate, tazimcarb, TDE, tebufenozide, tebufenpyrad, tebupirimfos, teflubenzuron, tefluthrin, temephos, TEPP, teralethrin, terbufos, tetrachloroethane, tetrachlorvinphos, tetramethrin, theta-cypermethrin, thiacloprid, thiamethoxam, thicrofos, thiocarboxime, thiocyclam, thiodicarb, thiofanox, thiometon, thiosultap, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin, zolaprofos, and α-ecdysone.

Additionally, any combination of the above insecticides can be used.

The invention disclosed in this document can also be used, for reasons of economy and synergy, with acaricides, algicides, antifeedants, avicides, bactericides, bird repellents, chemosterilants, fungicides, herbicide safeners, herbicides, insect attractants, insect repellents, mammal repellents, mating disrupters, molluscicides, plant activators, plant growth regulators, rodenticides, synergists, defoliants, desiccants, disinfectants, semiochemicals, and virucides (these categories not necessarily mutually exclusive).

For more information consult "COMPENDIUM OF PESTICIDE COMMON NAMES" located at alanwood.net. Also consult "THE PESTICIDE MANUAL" 14th Edition, edited by C D S Tomlin, copyright 2006 by British Crop Production Council.

Synergistic Mixtures

The invention disclosed in this document can be used with other compounds such as the ones mentioned under the heading "Mixtures" to form synergistic mixtures where the mode of action of the compounds in the mixtures are the same, similar, or different.

Examples of mode of actions include, but are not limited to: acetylcholinesterase inhibitor; sodium channel modulator; chitin biosynthesis inhibitor; GABA-gated chloride channel antagonist; GABA and glutamate-gated chloride channel agonist; acetylcholine receptor agonist; MET I inhibitor; Mg-stimulated ATPase inhibitor; nicotinic acetylcholine receptor; Midgut membrane disrupter; oxidative phosphorylation disrupter, and ryanodine receptor (RyRs).

Additionally, the following compounds are known as synergists and can be used with the invention disclosed in this document: piperonyl butoxide, piprotal, propyl isome, sesamex, sesamolin, and sulfoxide.

Formulations

A pesticide is rarely suitable for application in its pure form. It is usually necessary to add other substances so that the pesticide can be used at the required concentration and in an appropriate form, permitting ease of application, handling, transportation, storage, and maximum pesticide activity. Thus, pesticides are formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra low volume solutions.

For further information on formulation types see "CATALOGUE OF PESTICIDE FORMULATION TYPES AND INTERNATIONAL CODING SYSTEM" Technical Monograph n° 2, 5th Edition by CropLife International (2002).

Pesticides are applied most often as aqueous suspensions or emulsions prepared from concentrated formulations of such pesticides. Such water-soluble, water-suspendable, or emulsifiable formulations, are either solids, usually known as wettable powders, or water dispersible granules, or liquids usually known as emulsifiable concentrates, or aqueous suspensions. Wettable powders, which may be compacted to form water dispersible granules, comprise an intimate mixture of the pesticide, a carrier, and surfactants. The concentration of the pesticide is usually from about 10% to about 90% by weight. The carrier is usually chosen from among the attapulgite clays, the montmorillonite clays, the diatomaceous earths, or the purified silicates. Effective surfactants, comprising from about 0.5% to about 10% of the wettable powder, are found among sulfonated lignins, condensed naphthalenesulfonates, naphthalenesulfonates, alkylbenzenesulfonates, alkyl sulfates, and non-ionic surfactants such as ethylene oxide adducts of alkyl phenols.

Emulsifiable concentrates of pesticides comprise a convenient concentration of a pesticide, such as from about 50 to about 500 grams per liter of liquid dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents, may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional anionic and non-ionic surfactants.

Aqueous suspensions comprise suspensions of water-insoluble pesticides dispersed in an aqueous carrier at a concentration in the range from about 5% to about 50% by weight. Suspensions are prepared by finely grinding the pesticide and vigorously mixing it into a carrier comprised of water and surfactants. Ingredients, such as inorganic salts and synthetic or natural gums, may also be added, to increase the density and viscosity of the aqueous carrier. It is often most effective to grind and mix the pesticide at the same time by preparing the aqueous mixture and homogenizing it in an implement such as a sand mill, ball mill, or piston-type homogenizer.

Pesticides may also be applied as granular compositions that are particularly useful for applications to the soil. Granular compositions usually contain from about 0.5% to about 10% by weight of the pesticide, dispersed in a carrier that comprises clay or a similar substance. Such compositions are usually prepared by dissolving the pesticide in a suitable solvent and applying it to a granular carrier which has been pre-formed to the appropriate particle size, in the range of from about 0.5 to about 3 mm. Such compositions may also be formulated by making a dough or paste of the carrier and compound and crushing and drying to obtain the desired granular particle size.

Dusts containing a pesticide are prepared by intimately mixing the pesticide in powdered form with a suitable dusty agricultural carrier, such as kaolin clay, ground volcanic rock, and the like. Dusts can suitably contain from about 1% to about 10% of the pesticide. They can be applied as a seed dressing or as a foliage application with a dust blower machine.

It is equally practical to apply a pesticide in the form of a solution in an appropriate organic solvent, usually petroleum oil, such as the spray oils, which are widely used in agricultural chemistry.

Pesticides can also be applied in the form of an aerosol composition. In such compositions the pesticide is dissolved or dispersed in a carrier, which is a pressure-generating propellant mixture. The aerosol composition is packaged in a container from which the mixture is dispensed through an atomizing valve.

Pesticide baits are formed when the pesticide is mixed with food or an attractant or both. When the pests eat the bait they also consume the pesticide. Baits may take the form of granules, gels, flowable powders, liquids, or solids. They are used in pest harborages.

Fumigants are pesticides that have a relatively high vapor pressure and hence can exist as a gas in sufficient concentrations to kill pests in soil or enclosed spaces. The toxicity of the fumigant is proportional to its concentration and the exposure time. They are characterized by a good capacity for diffusion and act by penetrating the pest's respiratory system or being absorbed through the pest's cuticle. Fumigants are applied to control stored product pests under gas proof sheets, in gas sealed rooms or buildings or in special chambers.

Pesticides can be microencapsulated by suspending the pesticide particles or droplets in plastic polymers of various types. By altering the chemistry of the polymer or by changing factors in the processing, microcapsules can be formed of various sizes, solubility, wall thicknesses, and degrees of penetrability. These factors govern the speed with which the active ingredient within is released, which in turn, affects the residual performance, speed of action, and odor of the product.

Oil solution concentrates are made by dissolving pesticide in a solvent that will hold the pesticide in solution. Oil solutions of a pesticide usually provide faster knockdown and kill of pests than other formulations due to the solvents themselves having pesticidal action and the dissolution of the waxy covering of the integument increasing the speed of uptake of the pesticide. Other advantages of oil solutions include better storage stability, better penetration of crevices, and better adhesion to greasy surfaces.

Another embodiment is an oil-in-water emulsion, wherein the emulsion comprises oily globules which are each provided with a lamellar liquid crystal coating and are dispersed in an aqueous phase, wherein each oily globule comprises at least one compound which is agriculturally active, and is individually coated with a monolamellar or oligolamellar layer comprising: (1) at least one non-ionic lipophilic surface-active agent, (2) at least one non-ionic hydrophilic surface-active agent and (3) at least one ionic surface-active agent, wherein the globules having a mean particle diameter of less than 800 nanometers. Further information on the embodiment is disclosed in U.S. patent publication 20070027034 published Feb. 1, 2007, having patent application Ser. No. 11/495,228. For ease of use this embodiment will be referred to as "OIWE".

For further information consult "INSECT PEST MANAGEMENT" 2nd Edition by D. Dent, copyright CAB International (2000). Additionally, for more detailed information consult "HANDBOOK OF PEST CONTROL—THE BEHAVIOR, LIFE HISTORY, AND CONTROL OF HOUSEHOLD PESTS" by Arnold Mallis, 9th Edition, copyright 2004 by GIE Media Inc.

Other Formulation Components

Generally, the invention disclosed in this document when used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, antifoam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulphate; sodium dioctyl sulfosuccinate; alkyl phenol ethoxylates; and aliphatic alcohol ethoxylates.

A dispersing agent is a substance which adsorbs onto the surface of a particles and helps to preserve the state of dispersion of the particles and prevents them from reaggregating. Dispersing agents are added to agrochemical formulations to facilitate dispersion and suspension during manufacture, and to ensure the particles redisperse into water in a spray tank. They are widely used in wettable powders, suspension concentrates and water-dispersible granules. Surfactants that are used as dispersing agents have the ability to adsorb strongly onto a particle surface and provide a charged or steric barrier to reaggregation of particles. The most commonly used surfactants are anionic, non-ionic, or mixtures of the two types. For wettable powder formulations, the most common dispersing agents are sodium lignosulfonates. For suspension concentrates, very good adsorption and stabilization are obtained using polyelectrolytes, such as sodium naphthalene sulfonate formaldehyde condensates. Tristyrylphenol ethoxylate phosphate esters are also used. Non-ionics such as alkylarylethylene oxide condensates and EO-PO block copolymers are sometimes combined with anionics as dispersing agents for suspension concentrates. In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulfonates; sodium naphthalene sulfonate formaldehyde condensates; tristyrylphenol ethoxylate phosphate esters; aliphatic alcohol ethoxylates; alkyl ethoxylates; EO-PO block copolymers; and graft copolymers.

An emulsifying agent is a substance which stabilizes a suspension of droplets of one liquid phase in another liquid phase. Without the emulsifying agent the two liquids would separate into two immiscible liquid phases. The most commonly used emulsifier blends contain alkylphenol or aliphatic alcohol with twelve or more ethylene oxide units and the oil-soluble calcium salt of dodecylbenzenesulfonic acid. A range of hydrophile-lipophile balance ("HLB") values from 8 to 18 will normally provide good stable emulsions. Emulsion stability can sometimes be improved by the addition of a small amount of an EO-PO block copolymer surfactant.

A solubilizing agent is a surfactant which will form micelles in water at concentrations above the critical micelle concentration. The micelles are then able to dissolve or solubilize water-insoluble materials inside the hydrophobic part of the micelle. The type of surfactants usually used for solubilization are non-ionics: sorbitan monooleates; sorbitan monooleate ethoxylates; and methyl oleate esters.

Surfactants are sometimes used, either alone or with other additives such as mineral or vegetable oils as adjuvants to spray-tank mixes to improve the biological performance of the pesticide on the target. The types of surfactants used for bioenhancement depend generally on the nature and mode of action of the pesticide. However, they are often non-ionics such as: alkyl ethoxylates; linear aliphatic alcohol ethoxylates; aliphatic amine ethoxylates.

A carrier or diluent in an agricultural formulation is a material added to the pesticide to give a product of the required strength. Carriers are usually materials with high absorptive capacities, while diluents are usually materials with low absorptive capacities. Carriers and diluents are used in the formulation of dusts, wettable powders, granules and water-dispersible granules.

Organic solvents are used mainly in the formulation of emulsifiable concentrates, ULV (ultra low volume) formulations, and to a lesser extent granular formulations. Sometimes mixtures of solvents are used. The first main groups of solvents are aliphatic paraffinic oils such as kerosene or refined paraffins. The second main group and the most common comprises the aromatic solvents such as xylene and higher molecular weight fractions of C9 and C10 aromatic solvents. Chlorinated hydrocarbons are useful as cosolvents to prevent crystallization of pesticides when the formulation is emulsified into water. Alcohols are sometimes used as cosolvents to increase solvent power.

Thickeners or gelling agents are used mainly in the formulation of suspension concentrates, emulsions and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. Examples of these types of materials, include, but are limited to, montmorillonite, e.g. bentonite; magnesium aluminum silicate; and attapulgite. Water-soluble polysaccharides have been used as thickening-gelling agents for many years. The types of polysaccharides most commonly used are natural extracts of seeds and seaweeds or are synthetic derivatives of cellulose. Examples of these types of materials include, but are not limited to, guar gum; locust bean gum; carrageenam; alginates; methyl cellulose; sodium carboxymethyl cellulose (SCMC); hydroxyethyl cellulose (HEC). Other types of anti-settling agents are based on modified starches, polyacrylates, polyvinyl alcohol and polyethylene oxide. Another good anti-settling agent is xanthan gum.

Microorganisms cause spoilage of formulated products. Therefore preservation agents are used to eliminate or reduce their effect. Examples of such agents include, but are not limited to: propionic acid and its sodium salt; sorbic acid and its sodium or potassium salts; benzoic acid and its sodium salt; p-hydroxybenzoic acid sodium salt; methyl p-hydroxybenzoate; and 1,2-benzisothiazalin-3-one (BIT).

The presence of surfactants, which lower interfacial tension, often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane while the non-silicone anti-foam agents are water-insoluble oils, such as octanol and nonanol, or silica. In both cases, the function of the anti-foam agent is to displace the surfactant from the air-water interface.

For further information, see "CHEMISTRY AND TECHNOLOGY OF AGROCHEMICAL FORMULATIONS" edited by D. A. Knowles, copyright 1998 by Kluwer Academic Publishers. Also see "INSECTICIDES IN AGRICULTURE AND ENVIRONMENT—RETROSPECTS AND PROSPECTS" by A. S. Perry, I. Yamamoto, I. Ishaaya, and R. Perry, copyright 1998 by Springer-Verlag.

Applications

The actual amount of pesticide to be applied to loci of pests is generally not critical and can readily be determined by those skilled in the art. In general, concentrations from about 0.01 grams of pesticide per hectare to about 5000 grams of pesticide per hectare are expected to provide good control.

The locus to which a pesticide is applied can be any locus inhabited by an pest, for example, vegetable crops, fruit and nut trees, grape vines, ornamental plants, domesticated animals, the interior or exterior surfaces of buildings, and the soil around buildings. Controlling pests generally means that pest populations, activity, or both, are reduced in a locus. This can come about when: pest populations are repulsed from a locus; when pests are incapacitated in or around a locus; or pests are exterminated, in whole or in part, in or around a locus. Of course a combination of these results can occur. Generally, pest populations, activity, or both are desirably reduced more than fifty percent, preferably more than 90 percent.

Generally, with baits, the baits are placed in the ground where, for example, termites can come into contact with the bait. Baits can also be applied to a surface of a building, (horizontal, vertical, or slant, surface) where, for example, ants, termites, cockroaches, and flies, can come into contact with the bait.

Because of the unique ability of the eggs of some pests to resist pesticides repeated applications may be desirable to control newly emerged larvae.

Systemic movement of pesticides in plants may be utilized to control pests on one portion of the plant by applying the pesticides to a different portion of the plant. For example, control of foliar-feeding insects can be controlled by drip irrigation or furrow application, or by treating the seed before planting. Seed treatment can be applied to all types of seeds, including those from which plants genetically transformed to express specialized traits will germinate. Representative examples include those expressing proteins toxic to invertebrate pests, such as *Bacillus thuringiensis* or other insecticidal toxins, those expressing herbicide resistance, such as "Roundup Ready" seed, or those with "stacked" foreign genes expressing insecticidal toxins, herbicide resistance, nutrition-enhancement or any other beneficial traits. Furthermore, such seed treatments with the invention disclosed in this document can further enhance the ability of a plant to better withstand stressful growing conditions. This results in a healthier, more vigorous plant, which can lead to higher yields at harvest time.

It should be readily apparent that the invention can be used with plants genetically transformed to express specialized traits, such as *Bacillus thuringiensis* or other insecticidal toxins, or those expressing herbicide resistance, or those with "stacked" foreign genes expressing insecticidal toxins, herbicide resistance, nutrition-enhancement or any other beneficial traits.

The invention disclosed in this document is suitable for controlling endoparasites and ectoparasites in the veterinary medicine sector or in the field of animal keeping. Compounds are applied in a known manner, such as by oral administration in the form of, for example, tablets, capsules, drinks, granules, by dermal application in the form of, for example, dipping, spraying, pouring on, spotting on, and dusting, and by parenteral administration in the form of, for example, an injection.

The invention disclosed in this document can also be employed advantageously in livestock keeping, for example, cattle, sheep, pigs, chickens, and geese. Suitable formulations are administered orally to the animals with the drinking water or feed. The dosages and formulations that are suitable depend on the species.

Before a pesticide can be used or sold commercially, such pesticide undergoes lengthy evaluation processes by various governmental authorities (local, regional, state, national, international). Voluminous data requirements are specified by regulatory authorities and must be addressed through data generation and submission by the product registrant or by another on the product registrant's behalf. These governmental authorities then review such data and if a determination of safety is concluded, provide the potential user or seller with product registration approval. Thereafter, in that locality where the product registration is granted and supported, such user or seller may use or sell such pesticide.

The headings in this document are for convenience only and must not be used to interpret any portion thereof.

TABLE 1

| # | Structure | IR (cm$^{-1}$) | MS | mp (° C.) | $^1$H NMR (CDCl$_3$, δ)$^1$ |
|---|---|---|---|---|---|
| 2 | 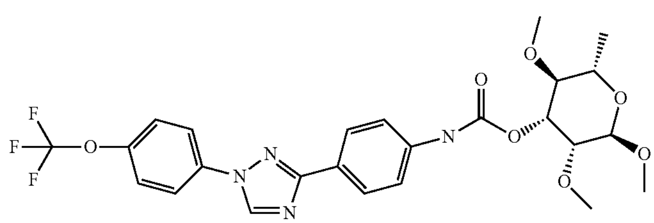 [SMILES: CO[C@@H]1O[C@@H](C)[C@H](OC)[C@@H](OC(=O)Nc2ccc(-c3ncn(-c4ccc(OC(F)(F)F)cc4)n3)cc2)[C@H]1OC] | | 551.1 (M − H) | 108-124 | 8.55 (s, 1H), 8.15 (d, J = 8.7 Hz, 2H), 7.80 (d, J = 9.0 Hz, 2H), 7.55 (d, J = 8.7 Hz, 2H), 7.39 (d, J = 8.7 Hz, 2H), 6.90 (s, 1H), 5.17 (dd, J = 9.5, 3.4 Hz, 1H), 4.73 (d, J = 1.9 Hz, 1H), 3.79-3.62 (m, 2H), 3.51 (s, 3H), 3.49 (s, 3H), 3.39 (s, 3H), 3.28 (t, J = 9.4 Hz, 1H), 1.35 (d, J = 6.3 Hz, 3H) |
| 4 | 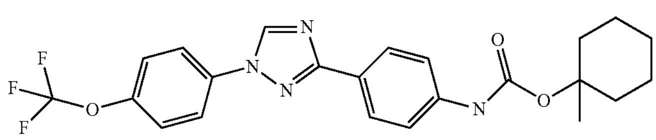 [SMILES: CC1(OC(=O)Nc2ccc(-c3ncn(-c4ccc(OC(F)(F)F)cc4)n3)cc2)CCCCC1] | | 459 (M − H) | 151-155 | 8.54 (s, 1H), 8.14 (d, J = 8.5 Hz, 2H), 7.79 (d, J = 8.9 Hz, 2H), 7.55-7.48 (m, 2H), 7.37 (d, J = 8.5 Hz, 2H), 6.77-6.73 (m, 1H), 2.18-1.06 (m, 10H), 1.00-0.93 (m, 3H) |
| 5 | 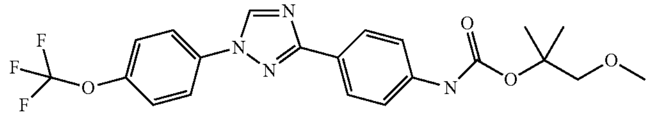 [SMILES: COCC(C)(C)OC(=O)Nc1ccc(-c2ncn(-c3ccc(OC(F)(F)F)cc3)n2)cc1] | | 449 (M − H) | 136-138 | 8.53 (s, 1H), 8.12 (d, J = 7.9 Hz, 2H), 7.79 (d, J = 9.0 Hz, 2H), 7.46 (d, J = 8.9 Hz, 2H), 7.37 (d, J = 9.1 Hz, 2H), 6.70 (s, 1H), 3.59 (s, 2H), 3.42 (s, 3H), 1.54 (s, 6H) |

TABLE 1-continued

| # | Structure | IR (cm$^{-1}$) | MS | mp (° C.) | $^1$H NMR (CDCl$_3$, δ)$^1$ |
|---|---|---|---|---|---|
| 6 | 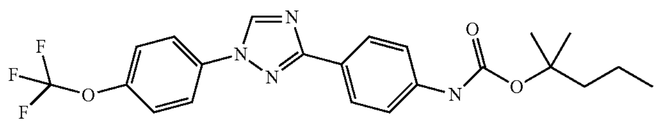 [SMILES: CCCC(C)(C)OC(=O)Nc1ccc(-c2ncn(-c3ccc(OC(F)(F)F)cc3)n2)cc1] | | 447 (M − H) | 161-164 | 8.53 (s, 1H), 8.12 (d, J = 8.7 Hz, 2H), 7.78 (d, J = 9.2 Hz, 2H), 7.47 (d, J = 8.3 Hz, 2H), 7.37 (d, J = 8.9 Hz, 2H), 6.61 (s, 1H), 1.84-1.77 (m, 2H), 1.51 (s, 6H), 1.46-1.32 (m, 2H), 0.95 (t, J = 7.3 Hz, 3H) |
| 7 | 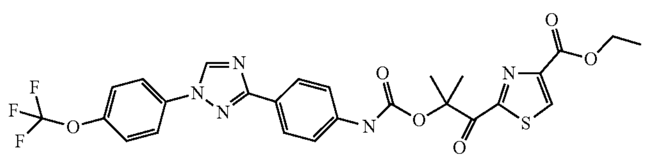 [SMILES: CCOC(=O)c1csc(C(=O)C(C)(C)OC(=O)Nc2ccc(-c3ncn(-c4ccc(OC(F)(F)F)cc4)n3)cc2)n1] | 3334, 1758, 1740, 1725, 1616, 1517 | 590 (M + H), 588 (M − H)$^-$ | | 8.60 (s, 1H), 8.16 (s, 1H), 8.05 (d, J = 9.1 Hz, 2H), 7.77 (d, J = 9.1 Hz, 2H), 7.57 (d, J = 9.0 Hz, 2H), 7.35 (d, J = 8.9 Hz, 2H), 5.81 (s, 1H), 4.37 (q, J = 7.1 Hz, 2H), 1.43 (s, 6H), 1.37 (t, J = 7.1 Hz, 3H) |
| 8 | 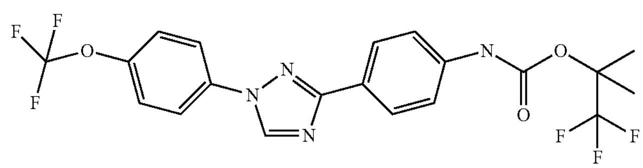 [SMILES: CC(C)(OC(=O)Nc1ccc(-c2ncn(-c3ccc(OC(F)(F)F)cc3)n2)cc1)C(F)(F)F] | | 473 (M − H) | 170-173 | 8.54 (s, 1H), 8.15 (d, J = 8.5 Hz, 2H), 7.79 (d, J = 9.1 Hz, 2H), 7.48 (d, J = 8.4 Hz, 2H), 7.37 (d, J = 8.9 Hz, 2H), 6.80 (br, 1H), 1.78 (s, 6H) |
| 10 | 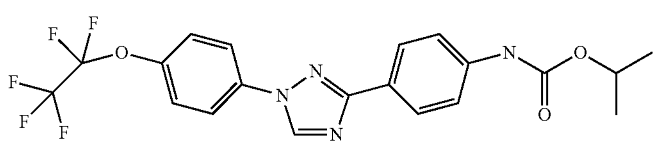 [SMILES: CC(C)OC(=O)Nc1ccc(-c2ncn(-c3ccc(OC(F)(F)C(F)(F)F)cc3)n2)cc1] | | 457 (M + H) | 203-207 | 8.55 (s, 1H), 8.14 (d, J = 8.7 Hz, 2H), 7.80 (d, J = 9.0 Hz, 2H), 7.50 (d, J = 8.8 Hz, 2H), 7.39 (d, J = 8.9 Hz, 2H), 6.65 (s, 1H), 5.17-4.92 (m, 1H), 1.32 (d, J = 6.3 Hz, 6H) |
| 17 | 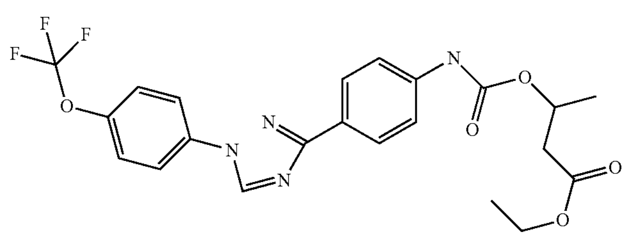 [SMILES: CCOC(=O)CC(C)OC(=O)Nc1ccc(C(=N)/N=C\Nc2ccc(OC(F)(F)F)cc2)cc1] | | 479 (M + H) | 88-90 | 8.55 (s, 1H), 8.13 (d, J = 8.7 Hz, 2H), 7.79 (d, J = 9.0 Hz, 2H), 7.51 (d, J = 8.5 Hz, 2H), 7.38 (d, J = 8.3 Hz, 2H), 6.87 (s, 1H), 5.41-5.21 (m, 1H), 4.16 (qd, J = 7.1, 1.2 Hz, 2H), 2.71 (dd, J = 15.4, 7.5 Hz, 1H), 2.57 (dd, J = 15.4, 5.6 Hz, 1H), 1.39 (d, J = 6.3 Hz, 3H), 1.26 (t, J = 7.1 Hz, 3H) |
| 18 | 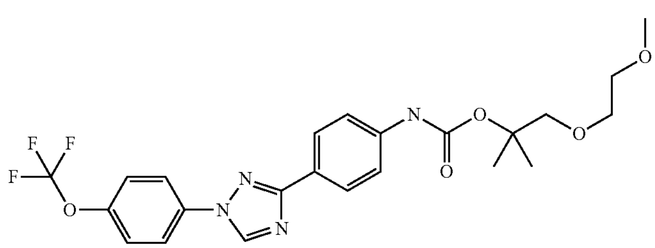 [SMILES: COCCOCC(C)(C)OC(=O)Nc1ccc(-c2ncn(-c3ccc(OC(F)(F)F)cc3)n2)cc1] | | 495 (M + H), 493 (M − H) | 72-75 | 8.54 (s, 1H), 8.12 (d, J = 8.7 Hz, 2H), 7.79 (d, J = 8.9 Hz, 2H), 7.48 (d, J = 8.7 Hz, 2H), 7.38 (d, J = 8.6 Hz, 2H), 6.79 (s, 1H), 3.69 (dd, J = 5.5, 3.9 Hz, 2H), 3.68 (s, 2H), 3.56 (dd, J = 5.8, 3.5 Hz, 2H), 3.37 (s, 3H), 1.54 (s, 6H) |

TABLE 1-continued

| # | Structure | IR (cm$^{-1}$) | MS | mp (° C.) | $^1$H NMR (CDCl$_3$, δ)$^1$ |
|---|---|---|---|---|---|
| 19 | 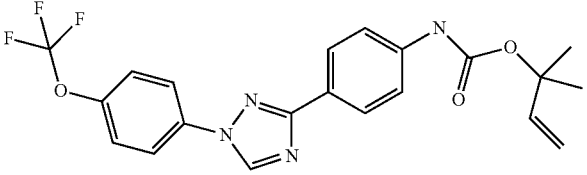 [SMILES: C=CC(C)(C)OC(=O)Nc1ccc(-c2ncn(-c3ccc(OC(F)(F)F)cc3)n2)cc1] | | 433 (M + H), 431 (M − H) | 163-165 | 8.53 (s, 1H), 8.10 (d, J = 8.6 Hz, 2H), 7.77 (d, J = 8.9 Hz, 2H), 7.48 (d, J = 8.5 Hz, 2H), 7.36 (d, J = 8.6 Hz, 2H), 6.77 (s, 1H), 6.18 (dd, J = 17.5, 10.9 Hz, 1H), 5.23 (d, J = 17.5 Hz, 1H), 5.13 (d, J = 10.9 Hz, 1H), 1.59 (s, 6H) |
| 20 | 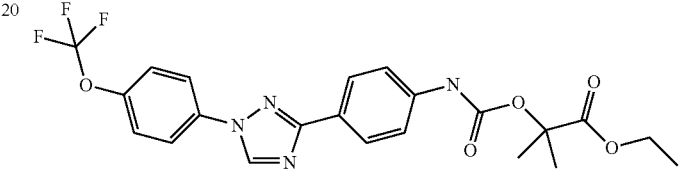 | | 479 (M + H), 477 (M − H) | 151-154 | 8.54 (s, 1H), 8.12 (d, J = 8.5 Hz, 2H), 7.78 (d, J = 8.9 Hz, 2H), 7.48 (d, J = 8.5 Hz, 2H), 7.37 (d, J = 8.6 Hz, 2H), 6.89 (s, 1H), 4.25 (q, J = 7.2 Hz, 2H), 1.64 (s, 6H), 1.28 (t, J = 7.1 Hz, 3H) |
| 21 | 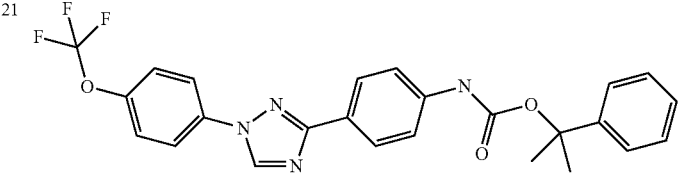 | | 483 (M + H) | 174-177 | 8.52 (s, 1H), 8.09 (d, J = 8.8 Hz, 2H), 7.77 (d, J = 9.0 Hz, 2H), 7.54-7.32 (m, 8H), 7.31-7.18 (m, 1H), 6.82 (s, 1H), 1.85 (s, 6H) |
| 22 | 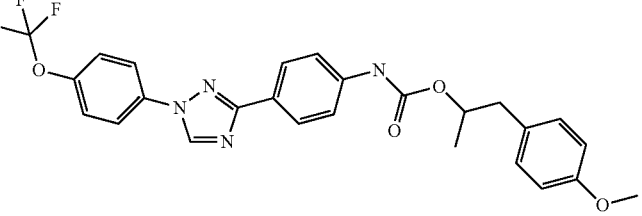 | | 513 (M + H), 511 (M − H) | 131-133 | 8.54 (s, 1H), 8.13 (d, J = 8.8 Hz, 2H), 7.78 (d, J = 9.2 Hz, 2H), 7.49 (d, J = 8.6 Hz, 2H), 7.38 (d, J = 8.2 Hz, 2H), 7.15 (d, J = 8.7 Hz, 2H), 6.84 (d, J = 8.7 Hz, 2H), 6.73 (s, 1H), 5.17-5.04 (m, 1H), 3.78 (s, 3H), 2.96 (dd, J = 13.8, 6.3 Hz, 1H), 2.77 (dd, J = 13.8, 6.7 Hz, 1H), 1.28 (d, J = 6.3 Hz, 3H) |
| 25 | 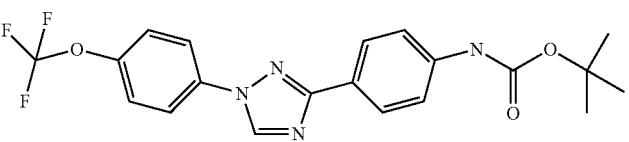 [SMILES: CC(C)(C)OC(=O)Nc1ccc(-c2ncn(-c3ccc(OC(F)(F)F)cc3)n2)cc1] | | 421 (M + H), 419 (M − H) | 177-179 | 8.54 (s, 1H), 8.11 (d, J = 8.7 Hz, 2H), 7.78 (d, J = 9.0 Hz, 2H), 7.48 (d, J = 8.7 Hz, 2H), 7.37 (d, J = 8.3 Hz, 2H), 6.64 (s, 1H), 1.53 (s, 9H) |
| 28 | 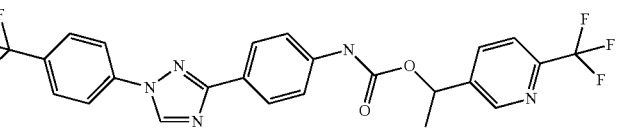 | | HRMS-FAB (m/z) [M + H]$^+$ calcd for C$_{24}$H$_{17}$F$_6$N$_5$O$_2$, 521.129; found, 521.1286 | 164.5-167.0 | 8.78 (d, J = 2.0 Hz, 1H), 8.63 (s, 1H), 8.14 (d, J = 8.8 Hz, 2H), 7.91 (m, 3H), 7.80 (d, J = 8.6 Hz, 2H), 7.71-7.66 (m, 1H), 7.49 (d, J = 8.7 Hz, 2H), 6.96 (s, 1H), 5.99 (q, J = 6.7 Hz, 1H), 1.66 (d, J = 6.7 Hz, 3H) |

TABLE 1-continued

| # | Structure | IR (cm$^{-1}$) | MS | mp (° C.) | $^1$H NMR (CDCl$_3$, δ)$^1$ |
|---|---|---|---|---|---|
| 29 | 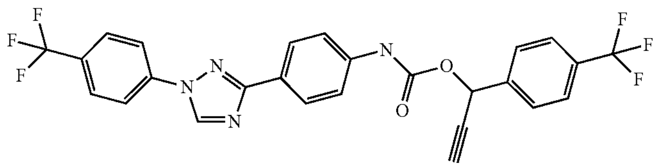 [SMILES: C#CC(OC(=O)Nc1ccc(-c2ncn(-c3ccc(C(F)(F)F)cc3)n2)cc1)c1ccc(C(F)(F)F)cc1] | | HRMS-FAB (m/z) [M + H]$^+$ calcd for C$_{26}$H$_{16}$F$_6$N$_4$O$_2$, 530.118; found, 530.1175 | 177.5-179.5 | 8.64 (s, 1H), 8.16 (d, J = 8.7 Hz, 2H), 7.90 (d, J = 8.5 Hz, 2H), 7.79 (d, J = 8.6 Hz, 2H), 7.75-7.64 (m, 4H), 7.51 (d, J = 8.7 Hz, 2H), 6.93 (s, 1H), 6.56 (d, J = 2.3 Hz, 1H), 2.77 (d, J = 2.3 Hz, 1H) |
| 30 | 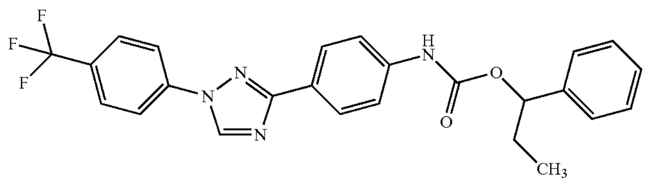 [SMILES: CCC(OC(=O)Nc1ccc(-c2ncn(-c3ccc(C(F)(F)F)cc3)n2)cc1)c1ccccc1] | | HRMS-FAB (m/z) [M + H]$^+$ calcd for C$_{25}$H$_{21}$F$_3$N$_4$O$_2$, 466.162; found, 466.1619 | 152-154 | 8.69 (s, 1H), 8.13 (d, J = 8.7 Hz, 2H), 7.90 (d, J = 8.5 Hz, 2H), 7.78 (d, J = 8.6 Hz, 2H), 7.50 (d, J = 8.7 Hz, 2H), 7.41-7.34 (m, 4H), 7.33-7.27 (m, 1H), 6.86 (s, 1H), 5.68 (t, J = 6.9 Hz, 1H), 2.01 (dq, J = 22.1, 7.4 Hz, 1H), 1.95-1.82 (m, 1H), 0.95 (t, J = 7.4 Hz, 3H) |
| 31 | 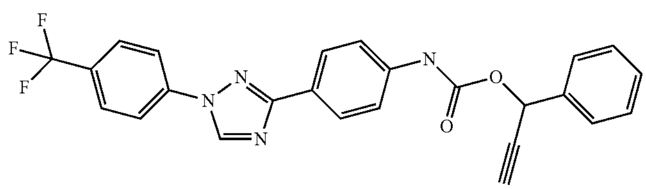 [SMILES: C#CC(OC(=O)Nc1ccc(-c2ncn(-c3ccc(C(F)(F)F)cc3)n2)cc1)c1ccccc1] | | HRMS-FAB (m/z) [M + H]$^+$ calcd for C$_{25}$H$_{17}$F$_3$N$_4$O$_2$, 462.130; found, 462.1305 | 170-173 | 8.63 (s, 1H), 8.15 (d, J = 8.7 Hz, 2H), 7.89 (d, J = 8.5 Hz, 2H), 7.78 (d, J = 8.6 Hz, 2H), 7.60 (dd, J = 7.7, 1.8 Hz, 2H), 7.51 (d, J = 8.6 Hz, 2H), 7.45-7.32 (m, 3H), 6.90 (s, 1H), 6.52 (d, J = 2.2 Hz, 1H), 2.73 (d, J = 2.3 Hz, 1H) |
| 32 | 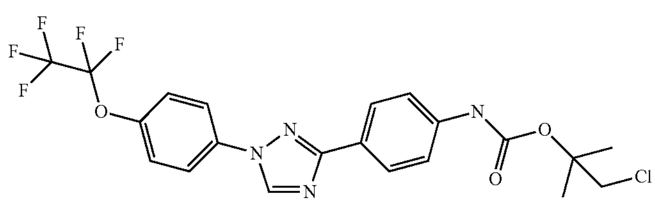 [SMILES: CC(C)(CCl)OC(=O)Nc1ccc(-c2ncn(-c3ccc(OC(F)(F)C(F)(F)F)cc3)n2)cc1] | | HRMS-FAB (m/z) [M + H]$^+$ calcd for C$_{21}$H$_{18}$ClF$_5$N$_4$O$_3$, 504.0988; found, 504.1002 | 181-184 | 8.55 (s, 1H), 8.13 (d, J = 8.7 Hz, 2H), 7.80 (d, J = 9.0 Hz, 2H), 7.48 (d, J = 8.7Hz, 2H), 7.38 (d, J = 8.9 Hz, 2H), 6.75 (s, 1H), 3.89 (s, 2H), 1.61 (s, 6H) |
| 33 | 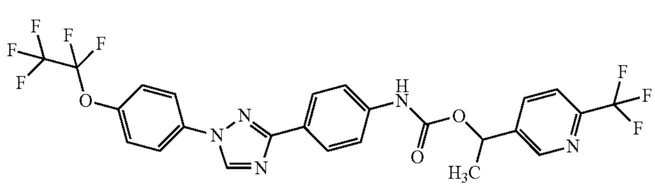 [SMILES: CC(OC(=O)Nc1ccc(-c2ncn(-c3ccc(OC(F)(F)C(F)(F)F)cc3)n2)cc1)c1ccc(C(F)(F)F)nc1] | | 588 ([M + H]$^+$), 586 ([M − H]$^-$) | 173-175 | 8.78 (d, J = 1.9 Hz, 1H), 8.55 (s, 1H), 8.14 (d, J = 8.8 Hz, 2H), 7.89 (dd, J = 8.1, 2.1 Hz, 1H), 7.79 (d, J = 9.1 Hz, 2H), 7.74-7.65 (m, 1H), 7.48 (d, J = 8.7 Hz, 2H), 7.38 (d, J = 9.0 Hz, 2H), 6.89 (s, 1H), 5.99 (q, J = 6.7 Hz, 1H), 1.66 (d, J = 6.7 Hz, 3H) |

TABLE 1-continued

| # | Structure | IR (cm$^{-1}$) | MS | mp (° C.) | $^1$H NMR (CDCl$_3$, δ)$^1$ |
|---|---|---|---|---|---|
| 34 | 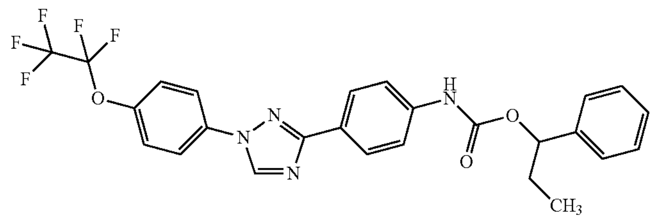 [SMILES: CCC(OC(=O)Nc1ccc(-c2ncn(-c3ccc(OC(F)(F)C(F)(F)F)cc3)n2)cc1)c1ccccc1] | (thin film) 3230, 3114, 3063, 2974, 2941, 1719, 1615, 1516, 1445, 1416, 1315, 1225, 1137, 1092, 1051, 985, 843 | HRMS-FAB (m/z) [M + H]$^+$ calcd for C$_{26}$H$_{21}$F$_5$N$_4$O$_3$, 532.153; found, 532.1539 | | 8.89 (s, 1H), 8.14 (d, J = 8.7 Hz, 2H), 7.85 (d, J = 9.0 Hz, 2H), 7.51 (d, J = 8.7 Hz, 2H), 7.38 (dd, J = 9.6, 6.7 Hz, 6H), 7.33-7.26 (m, 1H), 6.89 (s, 1H), 5.68 (t, J = 6.9 Hz, 1H), 2.08-1.94 (m, 1H), 1.94-1.81 (m, 1H), 0.94 (t, J = 7.4 Hz, 3H) |
| 35 | 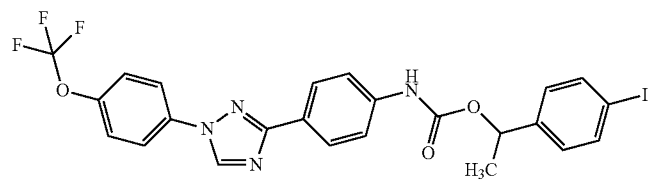 [SMILES: CC(OC(=O)Nc1ccc(-c2ncn(-c3ccc(OC(F)(F)F)cc3)n2)cc1)c1ccc(I)cc1] | | HRMS-FAB (m/z) [M + H]$^+$ calcd for C$_{24}$H$_{18}$F$_3$IN$_4$O$_3$, 594.0376; found, 594.0411 | 139-142.5 | 8.54 (s, 1H), 8.12 (d, J = 8.7 Hz, 2H), 7.78 (d, J = 9.0 Hz, 2H), 7.70 (d, J = 8.4 Hz, 2H), 7.48 (d, J = 8.6 Hz, 2H), 7.38 (d, J = 8.4 Hz, 2H), 7.15 (d, J = 8.3 Hz, 2H), 6.79 (s, 1H), 5.84 (q, J = 6.6 Hz, 1H), 1.59 (d, J = 6.7 Hz, 3H) |
| 36 | 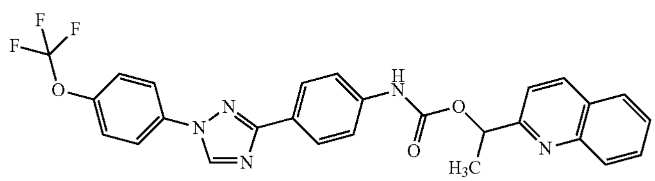 [SMILES: CC(OC(=O)Nc1ccc(-c2ncn(-c3ccc(OC(F)(F)F)cc3)n2)cc1)c1ccc2ccccc2n1] | | HRMS-FAB (m/z) [M + H]$^+$ calcd for C$_{27}$H$_{20}$F$_3$N$_5$O$_3$, 519.1518; found, 519.1527 | 157.5-159 | 8.53 (s, 1H), 8.19 (d, J = 8.5 Hz, 1H), 8.12 (app d, J = 8.7 Hz, 3H), 7.81 (d, J = 8.1 Hz, 1H), 7.78 (d, J = 9.0 Hz, 2H), 7.72 (ddd, J = 8.4, 6.9, 1.4 Hz, 1H), 7.58-7.47 (m, 4H), 7.37 (d, J = 8.3 Hz, 2H), 7.01 (s, 1H), 6.12 (q, J = 6.7 Hz, 1H), 1.76 (d, J = 6.7 Hz, 3H) |
| 37 | 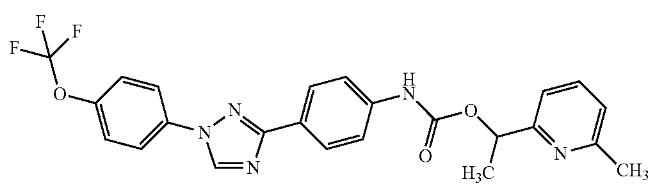 [SMILES: Cc1cccc(C(C)OC(=O)Nc2ccc(-c3ncn(-c4ccc(OC(F)(F)F)cc4)n3)cc2)n1] | | HRMS-FAB (m/z) [M + H]$^+$ calcd for C$_{24}$H$_{21}$F$_3$N$_5$O$_3$, 484.1591; found, 484.1589 | 152.5-155 | 8.54 (s, 1H), 8.11 (d, J = 8.8 Hz, 2H), 7.78 (d, J = 9.1 Hz, 2H), 7.57 (t, J = 7.7 Hz, 1H), 7.50 (d, J = 8.8 Hz, 2H), 7.37 (dd, J = 9.0, 0.7 Hz, 2H), 7.17 (d, J = 7.7 Hz, 1H), 7.07 (d, J = 7.7 Hz, 1H), 6.99 (s, 1H), 5.91 (q, J = 6.7 Hz, 1H), 2.57 (s, 3H), 1.65 (d, J = 6.7 Hz, 3H) |
| 38 | 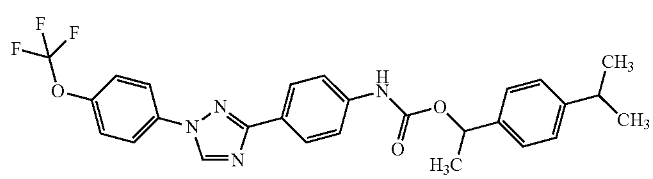 [SMILES: CC(C)c1ccc(C(C)OC(=O)Nc2ccc(-c3ncn(-c4ccc(OC(F)(F)F)cc4)n3)cc2)cc1] | | HRMS-FAB (m/z) [M + H]$^+$ calcd for C$_{27}$H$_{25}$F$_3$N$_4$O$_3$, 510.1879; found, 510.1889 | 149-151 | 8.52 (s, 1H), 8.12 (d, J = 8.8 Hz, 2H), 7.78 (d, J = 9.1 Hz, 2H), 7.49 (d, J = 8.7 Hz, 2H), 7.40-7.35 (m, 2H), 7.33 (d, J = 8.2 Hz, 2H), 7.23 (d, J = 8.1 Hz, 2H), 6.76 (s, 1H), 5.91 (q, J = 6.6 Hz, 1H), 2.97-2.85 (m, 1H), 1.62 (d, J = 6.6 Hz, 3H), 1.25 (d, J = 6.9 Hz, 6H) |

TABLE 1-continued

| # | Structure | IR (cm$^{-1}$) | MS | mp (° C.) | $^1$H NMR (CDCl$_3$, δ)$^1$ |
|---|---|---|---|---|---|
| 39 | 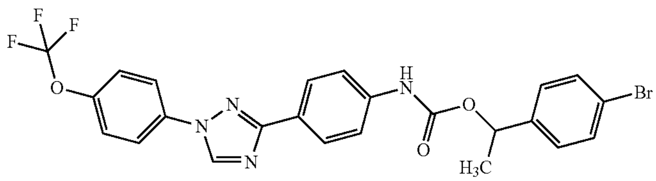 [SMILES: CC(OC(=O)Nc1ccc(-c2ncn(-c3ccc(OC(F)(F)F)cc3)n2)cc1)c1ccc(Br)cc1] | (thin film) 3317, 1723, 1518, 1263, 1224, 1071 | HRMS-FAB (m/z) [M + H]$^+$ calcd for C$_{24}$H$_{18}$BrF$_3$N$_4$O$_3$, 546.0514; found, 546.0513 | | 8.53 (s, 1H), 8.13 (d, J = 8.8 Hz, 2H), 7.78 (d, J = 9.1 Hz, 2H), 7.53-7.42 (m, 4H), 7.38 (dd, J = 9.0, 0.7 Hz, 2H), 7.28 (d, J = 8.4 Hz, 2H), 6.76 (s, 1H), 5.87 (q, J = 6.6 Hz, 1H), 1.60 (d, J = 6.6 Hz, 3H) |
| 40 | 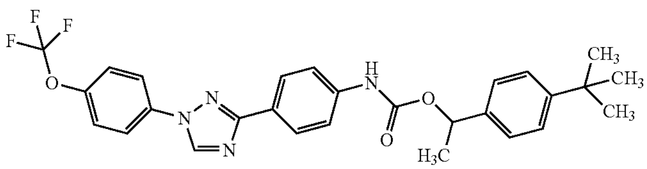 [SMILES: CC(OC(=O)Nc1ccc(-c2ncn(-c3ccc(OC(F)(F)F)cc3)n2)cc1)c1ccc(C(C)(C)C)cc1] | | HRMS-FAB (m/z) [M + H]$^+$ calcd for C$_{28}$H$_{27}$F$_3$N$_4$O$_3$, 524.2035; found, 524.2058 | 189-190.5 | 8.53 (s, 1H), 8.12 (d, J = 8.8 Hz, 2H), 7.78 (d, J = 9.1 Hz, 2H), 7.49 (d, J = 8.7Hz, 2H), 7.43-7.31 (m, 6H), 6.79 (s, 1H), 5.92 (q, J = 6.6 Hz, 1H), 1.62 (d, J = 6.6 Hz, 3H), 1.32 (s, 9H) |
| 41 | 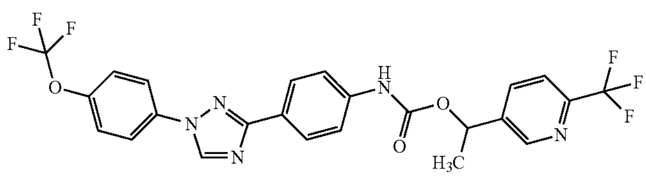 [SMILES: CC(OC(=O)Nc1ccc(-c2ncn(-c3ccc(OC(F)(F)F)cc3)n2)cc1)c1ccc(C(F)(F)F)nc1] | | HRMS-FAB (m/z) [M + H]$^+$ calcd for C$_{24}$H$_{17}$F$_6$N$_5$O$_3$, 537.124; found, 537.1235 | 154-156 | 8.78 (d, J = 1.8 Hz, 1H), 8.54 (s, 1H), 8.13 (d, J = 8.7 Hz, 2H), 7.89 (dd, J = 8.1, 2.0 Hz, 1H), 7.78 (d, J = 9.0 Hz, 2H), 7.69 (d, J = 8.1 Hz, 1H), 7.48 (d, J = 8.5 Hz, 2H), 7.37 (d, J = 8.4 Hz, 2H), 6.94 (s, 1H), 5.99 (q, J = 6.6 Hz, 1H), 1.66 (d, J = 6.7 Hz, 3H) |
| 42 | 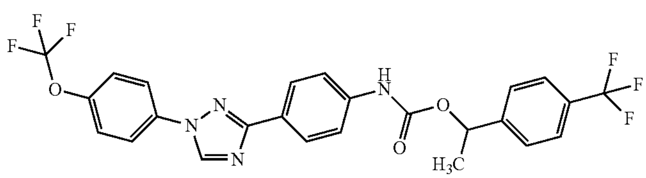 [SMILES: CC(OC(=O)Nc1ccc(-c2ncn(-c3ccc(OC(F)(F)F)cc3)n2)cc1)c1ccc(C(F)(F)F)cc1] | | HRMS-FAB (m/z) [M + H]$^+$ calcd for C$_{25}$H$_{18}$F$_6$N$_4$O$_3$, 536.128; found, 536.1284 | 128-131 | (400 MHz, DMSO-d$_6$) 10.11 (s, 1H), 9.36 (s, 1H), 8.05 (d, J = 9.1 Hz, 2H), 8.01 (d, J = 8.7 Hz, 2H), 7.77 (d, J = 8.2 Hz, 2H), 7.65 (d, J = 8.2 Hz, 2H), 7.60 (d, J = 8.6 Hz, 4H), 5.90 (q, J = 6.5 Hz, 1H), 1.57 (d, J = 6.6 Hz, 3H) |
| 43 | 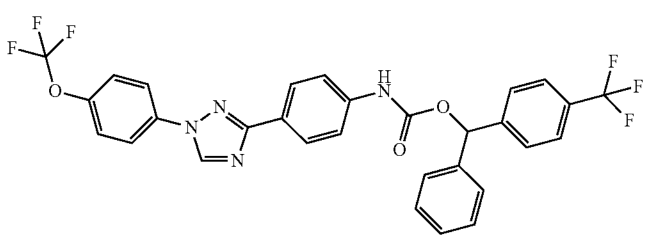 [SMILES: O=C(Nc1ccc(-c2ncn(-c3ccc(OC(F)(F)F)cc3)n2)cc1)OC(c1ccccc1)c1ccc(C(F)(F)F)cc1] | (thin film) 3318, 1734, 1519, 1327, 1265, 1220 | HRMS-FAB (m/z) [M + H]$^+$ calcd for C$_{30}$H$_{20}$F$_6$N$_4$O$_3$, 598.144; found, 598.1445 | | 8.54 (s, 1H), 8.14 (d, J = 8.8 Hz, 2H), 7.78 (d, J = 9.1 Hz, 2H), 7.63 (d, J = 8.2 Hz, 2H), 7.55-7.47 (m, 4H), 7.42-7.30 (m, 7H), 6.95 (s, 1H), 6.94 (s, 1H) |
| 44 | 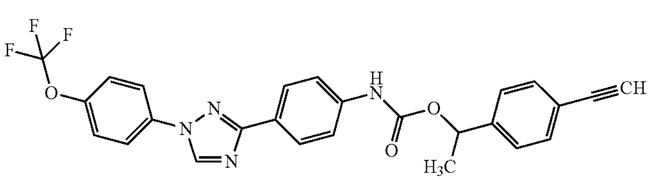 [SMILES: C#Cc1ccc(C(C)OC(=O)Nc2ccc(-c3ncn(-c4ccc(OC(F)(F)F)cc4)n3)cc2)cc1] | | 493 ([M + H]$^+$), 491 ([M − H]$^-$) | 132-134.5 | 8.53 (s, 1H), 8.13 (d, J = 8.8 Hz, 2H), 7.78 (d, J = 9.0 Hz, 2H), 7.53-7.43 (m, 4H), 7.41-7.32 (m, 4H), 6.78 (s, 1H), 5.90 (q, J = 6.6 Hz, 1H), 3.07 (s, 1H), 1.60 (d, J = 6.6 Hz, 3H) |

TABLE 1-continued

| # | Structure | IR (cm$^{-1}$) | MS | mp (° C.) | $^1$H NMR (CDCl$_3$, δ)$^1$ |
|---|---|---|---|---|---|
| 45 | 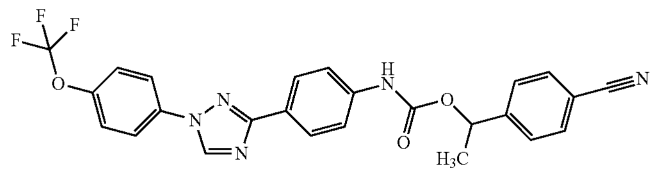 [SMILES: CC(OC(=O)Nc1ccc(-c2ncn(-c3ccc(OC(F)(F)F)cc3)n2)cc1)c1ccc(C#N)cc1] | | 494 ([M + H]$^+$), 492 ([M − H]$^-$) | 186.5-187.5 | 8.54 (s, 1H), 8.14 (d, J = 8.7 Hz, 2H), 7.78 (d, J = 9.0 Hz, 2H), 7.67 (d, J = 8.4 Hz, 2H), 7.55-7.43 (m, 4H), 7.38 (dd, J = 8.9, 0.6 Hz, 2H), 6.81 (s, 1H), 5.92 (q, J = 6.6 Hz, 1H), 1.61 (d, J = 6.7 Hz, 3H) |
| 46 | 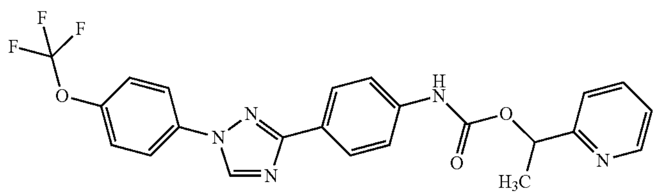 | | 470 ([M + H]$^+$), 468 ([M − H]$^-$) | 143-145 | 8.61 (ddd, J = 4.8, 1.6, 0.8 Hz, 1H), 8.54 (s, 1H), 8.11 (d, J = 8.7 Hz, 2H), 7.78 (d, J = 9.1 Hz, 2H), 7.69 (td, J = 7.7, 1.8 Hz, 1H), 7.49 (d, J = 8.8 Hz, 2H), 7.41-7.32 (m, 3H), 7.22 (ddd, J = 7.5, 4.9, 1.1 Hz, 1H), 7.08 (s, 1H), 5.95 (q, J = 6.6 Hz, 1H), 1.66 (d, J = 6.7 Hz, 3H) |
| 47 | 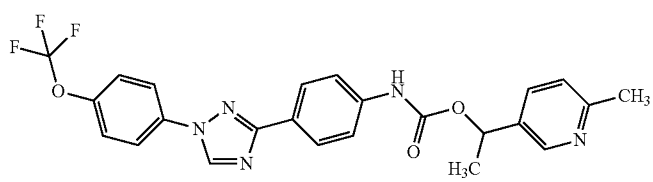 | | 484 ([M + H]$^+$), 482 ([M − H]$^-$) | 55-75 | 8.93 (d, J = 1.6 Hz, 1H), 8.55 (s, 1H), 8.14 (d, J = 8.8 Hz, 2H), 8.07 (dd, J = 8.2, 2.0 Hz, 1H), 7.79 (d, J = 9.0 Hz, 2H), 7.50 (app t, J = 8.9 Hz, 3H), 7.42-7.34 (m, 2H), 7.06 (s, 1H), 5.98 (q, J = 6.6 Hz, 1H), 2.80 (s, 3H), 1.67 (d, J = 6.7 Hz, 3H) |
| 48 | 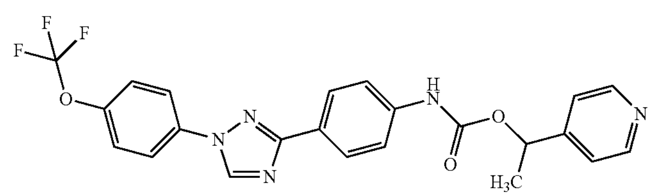 [SMILES: CC(OC(=O)Nc1ccc(-c2ncn(-c3ccc(OC(F)(F)F)cc3)n2)cc1)c1ccncc1] | (thin film) 3243, 1731, 1607, 1548, 1518, 1445, 1416, 1313, 1228 | 470 ([M + H]$^+$), 468 ([M − H]$^-$) | | (400 MHz, CD$_3$OD) 9.03 (s, 1H), 8.51 (dd, J = 4.6, 1.6 Hz, 2H), 8.02 (d, J = 8.9 Hz, 2H), 7.94 (d, J = 9.1 Hz, 2H), 7.54 (d, J = 8.8 Hz, 2H), 7.45 (ddd, J = 9.6, 6.8, 1.0 Hz, 4H), 5.86 (q, J = 6.6 Hz, 1H), 1.58 (d, J = 6.7 Hz, 3H) |
| 49 | 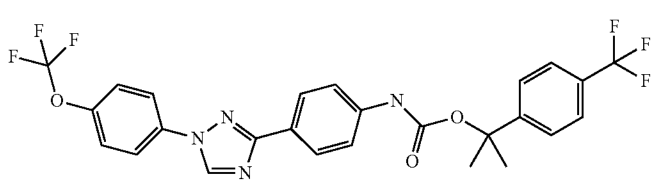 [SMILES: CC(C)(OC(=O)Nc1ccc(-c2ncn(-c3ccc(OC(F)(F)F)cc3)n2)cc1)c1ccc(C(F)(F)F)cc1] | | HRMS-FAB (m/z) [M + H]$^+$ calcd for C$_{26}$H$_{20}$F$_6$N$_4$O$_3$, 550.144; found, 550.146 | 168.5-171 | 8.51 (s, 1H), 8.10 (d, J = 8.8 Hz, 2H), 7.76 (d, J = 9.0 Hz, 2H), 7.60 (d, J = 8.3 Hz, 2H), 7.52 (d, J = 8.3 Hz, 2H), 7.44 (d, J = 8.8 Hz, 2H), 7.39-7.31 (m, 2H), 6.89 (s, 1H), 1.84 (s, 6H) |
| 50 | 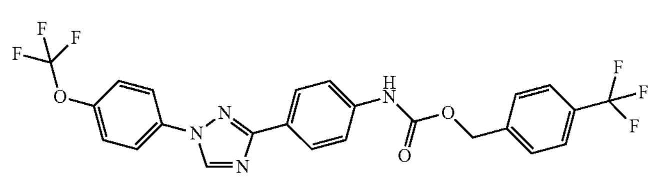 [SMILES: O=C(Nc1ccc(-c2ncn(-c3ccc(OC(F)(F)F)cc3)n2)cc1)OCc1ccc(C(F)(F)F)cc1] | | HRMS-FAB (m/z) [M + H]$^+$ calcd for C$_{24}$H$_{16}$F$_6$N$_4$O$_3$, 522.1127; found, 522.1139 | 166.5-168 | 8.53 (s, 1H), 8.15 (d, J = 8.8 Hz, 2H), 7.78 (d, J = 9.1 Hz, 2H), 7.64 (d, J = 8.1 Hz, 2H), 7.57-7.45 (m, 4H), 7.37 (dd, J = 9.0, 0.8 Hz, 2H), 6.92 (s, 1H), 5.27 (s, 2H) |

| # | Structure | IR (cm$^{-1}$) | MS | mp (° C.) | $^1$H NMR (CDCl$_3$, δ)$^1$ |
|---|---|---|---|---|---|
| 51 | 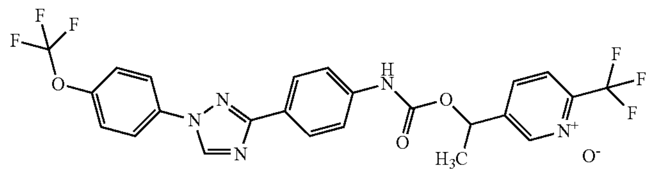 | | HRMS-FAB (m/z) [M + H]$^+$ calcd for C$_{24}$H$_{17}$F$_6$N$_5$O$_4$, 553.1185; found, 553.1191 | 199-202.5 | (300 MHz, DMSO-d$_6$) 10.16 (s, 1H), 9.36 (s, 1H), 8.59 (s, 1H), 8.10-7.95 (m, 5H), 7.68-7.50 (m, 5H), 5.86 (q, J = 6.5 Hz, 1H), 1.58 (d, J = 6.6 Hz, 3H) |
| 52 | 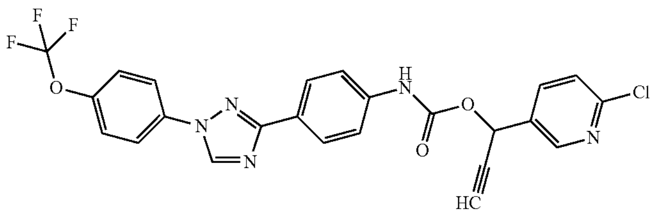 [SMILES: C#CC(OC(=O)Nc1ccc(-c2ncn(-c3ccc(OC(F)(F)F)cc3)n2)cc1)c1ccc(Cl)nc1] | | HRMS-FAB (m/z) [M + H]$^+$ calcd for C$_{24}$H$_{15}$ClF$_3$N$_5$O$_3$, 513.0816; found, 513.0832 | 156.5-158 | (300 MHz, acetone-d$_6$) 9.18 (s, 1H), 9.13 (s, 1H), 8.66 (d, J = 2.4 Hz, 1H), 8.16 (d, J = 8.8 Hz, 2H), 8.13-8.06 (m, 3H), 7.71 (d, J = 8.7 Hz, 2H), 7.63-7.52 (m, 3H), 6.63 (d, J = 2.3 Hz, 1H), 3.46 (d, J = 2.3 Hz, 1H) |
| 53 | 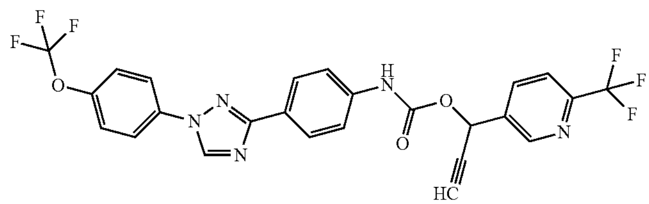 [SMILES: C#CC(OC(=O)Nc1ccc(-c2ncn(-c3ccc(OC(F)(F)F)cc3)n2)cc1)c1ccc(C(F)(F)F)nc1] | | HRMS-FAB (m/z) [M + H]$^+$ calcd for C$_{25}$H$_{15}$ClF$_6$N$_5$O$_3$, 547.1079; found, 547.1098 | 177-179 | (300 MHz, acetone-d$_6$) 9.24 (s, 1H), 9.13 (s, 1H), 9.02 (d, J = 1.9 Hz, 1H), 8.33 (dd, J = 8.1, 2.1 Hz, 1H), 8.16 (d, J = 8.8 Hz, 2H), 8.10 (d, J = 9.1 Hz, 2H), 7.97 (d, J = 8.2 Hz, 1H), 7.72 (d, J = 8.8 Hz, 2H), 7.63-7.52 (m, 2H), 6.74 (d, J = 2.3 Hz, 1H), 3.51 (d, J = 2.3 Hz, 1H) |
| 54 | 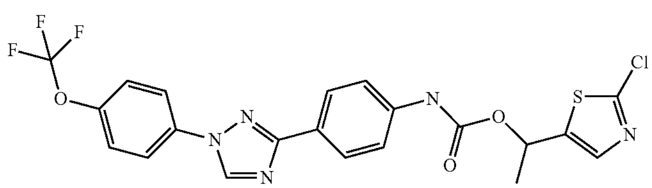 [SMILES: CC(OC(=O)Nc1ccc(-c2ncn(-c3ccc(OC(F)(F)F)cc3)n2)cc1)c1cnc(Cl)s1] | (thin film) 3248, 3111, 3062, 1728, 1608, 1518, 1445, 1417, 1262, 1223, 1053 | HRMS-FAB (m/z) [M + H]$^+$ calcd for C$_{21}$H$_{15}$ClF$_3$N$_5$O$_3$S, 509.054; found, 509.0531 | | 8.54 (s, 1H), 8.14 (d, J = 8.7 Hz, 2H), 7.78 (d, J = 9.0 Hz, 2H), 7.55 (s, 1H), 7.49 (d, J = 8.6 Hz, 2H), 7.38 (d, J = 8.8 Hz, 2H), 6.83 (s, 1H), 6.09 (q, J = 6.6 Hz, 1H), 1.71 (d, J = 6.6 Hz, 3H) |
| 55 | 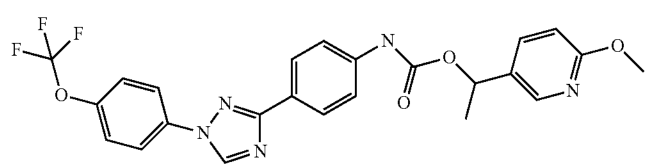 [SMILES: COc1ccc(C(C)OC(=O)Nc2ccc(-c3ncn(-c4ccc(OC(F)(F)F)cc4)n3)cc2)cn1] | (thin film) 3307, 3119, 2986, 2950, 1725, 1611, 1517, 1495, 1445, 1416, 1257, 1215 | HRMS-FAB (m/z) [M + H]$^+$ calcd for C$_{24}$H$_{20}$F$_3$N$_5$O$_4$, 499.147; found, 499.1463 | | 8.53 (s, 1H), 8.22 (d, J = 2.4 Hz, 1H), 8.12 (d, J = 8.7 Hz, 2H), 7.78 (d, J = 9.0 Hz, 2H), 7.63 (dd, J = 8.6, 2.5 Hz, 1H), 7.48 (d, J = 8.7 Hz, 2H), 7.42-7.32 (m, 2H), 6.81 (s, 1H), 6.75 (d, J = 8.6 Hz, 1H), 5.89 (q, J = 6.6 Hz, 1H), 3.93 (s, 3H), 1.61 (d, J = 6.6 Hz, 3H) |
| 56 | 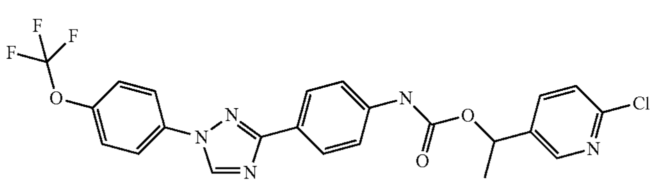 [SMILES: CC(OC(=O)Nc1ccc(-c2ncn(-c3ccc(OC(F)(F)F)cc3)n2)cc1)c1ccc(Cl)nc1] | (thin film) 3259, 3117, 3062, 2986, 1729, 1597, 1518, 1445, 1417, 1263, 1225 | HRMS-FAB (m/z) [M + H]$^+$ calcd for C$_{23}$H$_{17}$ClF$_3$N$_5$O$_3$, 503.097; found, 503.0970 | | 8.54 (s, 1H), 8.45 (d, J = 2.5 Hz, 1H), 8.13 (d, J = 8.8 Hz, 2H), 7.78 (d, J = 9.1 Hz, 2H), 7.68 (dd, J = 8.3, 2.5 Hz, 1H), 7.48 (d, J = 8.5 Hz, 2H), 7.37 (dd, J = 8.9, 0.6 Hz, 2H), 7.33 (d, J = 8.3 Hz, 1H), 6.97 (s, 1H), 5.91 (q, J = 6.6 Hz, 1H), 1.62 (d, J = 6.7 Hz, 3H) |

TABLE 1-continued

| # | Structure | IR (cm⁻¹) | MS | mp (° C.) | ¹H NMR (CDCl₃, δ)¹ |
|---|---|---|---|---|---|
| 57 | 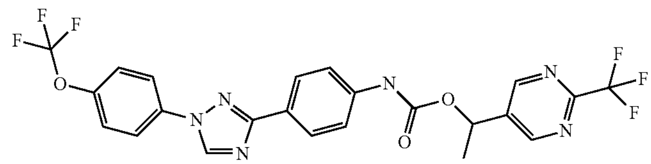 [SMILES: CC(OC(=O)Nc1ccc(-c2ncn(-c3ccc(OC(F)(F)F)cc3)n2)cc1)c1cnc(C(F)(F)F)nc1] | | 539 ([M + H]⁺), 537 ([M − H]⁻) | 185-187 | 8.94 (s, 2H), 8.55 (s, 1H), 8.15 (d, J = 8.8 Hz, 2H), 7.78 (d, J = 9.0 Hz, 2H), 7.48 (d, J = 8.6 Hz, 2H), 7.36 (d, J = 0.7 Hz, 2H), 6.91 (s, 1H), 6.01 (q, J = 6.7 Hz, 1H), 1.71 (d, J = 6.8 Hz, 3H) |
| 58 | 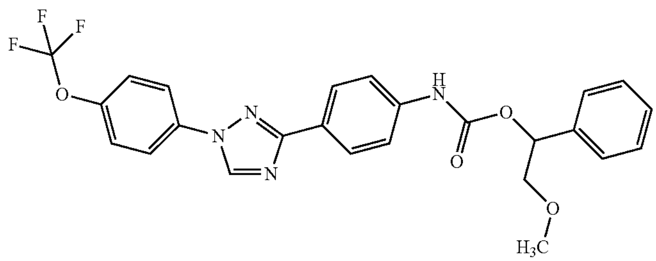 [SMILES: COCC(OC(=O)Nc1ccc(-c2ncn(-c3ccc(OC(F)(F)F)cc3)n2)cc1)c1ccccc1] | (thin film) 3295, 3120, 3066, 3036, 2934, 2894, 1728, 1597, 1518, 1493, 1445, 1263, 1223 | HRMS-FAB (m/z) [M + H]⁺ calcd for C₂₅H₂₁F₃N₄O₄, 498.152; found, 498.1511 | | 8.54 (s, 1H), 8.11 (d, J = 8.7 Hz, 2H), 7.78 (d, J = 9.0 Hz, 2H), 7.49 (d, J = 8.8 Hz, 2H), 7.44-7.31 (m, 7H), 6.97 (s, 1H), 5.99 (dd, J = 8.0, 3.6 Hz, 1H), 3.80 (dd, J = 10.9, 8.0 Hz, 1H), 3.63 (dd, J = 10.9, 3.7 Hz, 1H), 3.43 (s, 3H) |
| 59 | 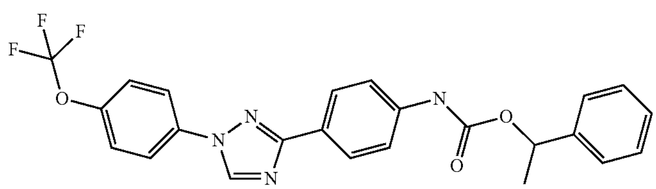 | | HRMS-FAB (m/z) [M + H]⁺ calcd for C₂₄H₁₉F₃N₄O₃, 468.140; found, 468.141 | 136-138 | 8.53 (s, 1H), 8.12 (d, J = 8.7 Hz, 2H), 7.78 (d, J = 9.0 Hz, 2H), 7.49 (d, J = 8.6 Hz, 2H), 7.45-7.34 (m, 6H), 7.34-7.28 (m, 1H), 6.82 (s, 1H), 5.92 (q, J = 6.6 Hz, 1H), 1.62 (d, J = 6.6 Hz, 3H) |
| 60 | 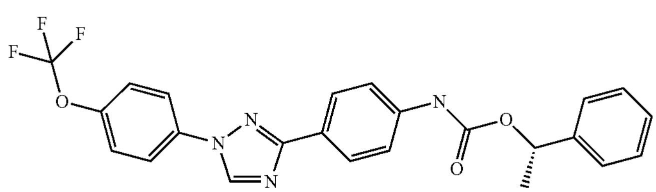 [SMILES: C[C@H](OC(=O)Nc1ccc(-c2ncn(-c3ccc(OC(F)(F)F)cc3)n2)cc1)c1ccccc1] | | 469 ([M + H]⁺) | 122.5-125.0 | 8.54 (s, 1H), 8.12 (d, J = 8.7 Hz, 2H), 7.78 (d, J = 9.0 Hz, 2H), 7.50 (d, J = 8.6 Hz, 2H), 7.46-7.34 (m, 6H), 7.34-7.28 (m, 1H), 6.78 (s, 1H), 5.92 (q, J = 6.6 Hz, 1H), 1.63 (d, J = 6.6 Hz, 3H) |
| 61 | 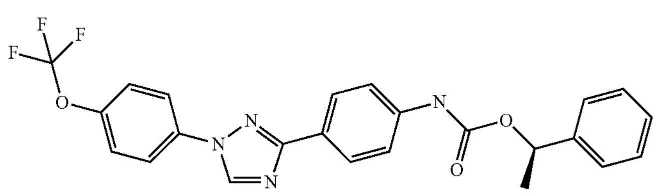 [SMILES: C[C@@H](OC(=O)Nc1ccc(-c2ncn(-c3ccc(OC(F)(F)F)cc3)n2)cc1)c1ccccc1] | | 469 ([M + H]⁺) | 123.5-125.0 | 8.53 (s, 1H), 8.12 (d, J = 8.7 Hz, 2H), 7.78 (d, J = 9.0 Hz, 2H), 7.49 (d, J = 8.7 Hz, 2H), 7.44-7.34 (m, 6H), 7.34-7.28 (m, 1H), 6.81 (s, 1H), 5.92 (q, J = 6.6 Hz, 1H), 1.62 (d, J = 6.6 Hz, 3H) |
| 62 | 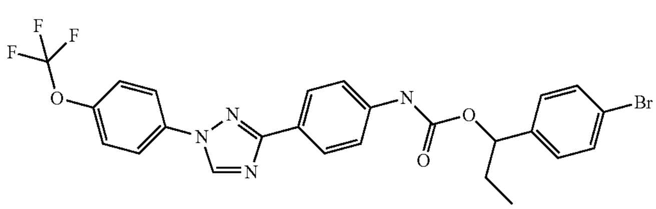 [SMILES: CCC(OC(=O)Nc1ccc(-c2ncn(-c3ccc(OC(F)(F)F)cc3)n2)cc1)c1ccc(Br)cc1] | (thin film) 3320, 3120, 2973, 2938, 1722, 1596, 1518, 1490, 1445, 1416, 1314, 1263, 1222, 1051, 732 | 562 ([M + H]⁺) | | 8.53 (s, 1H), 8.12 (d, J = 8.8 Hz, 2H), 7.78 (d, J = 9.2 Hz, 2H), 7.58-7.40 (m, 4H), 7.37 (dd, J = 9.0, 0.8 Hz, 2H), 7.28-7.14 (m, 2H), 6.85 (s, 1H), 5.62 (t, J = 6.9 Hz, 1H), 2.11-1.73 (m, 2H), 0.93 (t, J = 7.4 Hz, 3H) |

TABLE 1-continued

| # | Structure | IR (cm⁻¹) | MS | mp (° C.) | ¹H NMR (CDCl₃, δ)¹ |
|---|-----------|-----------|-----|----------|--------------------|
| 63 | 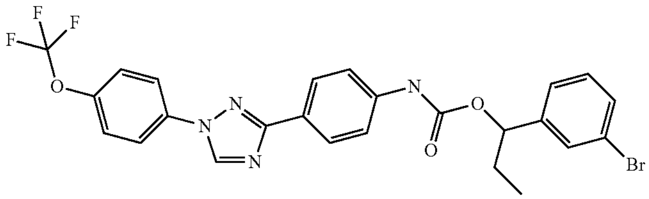 [SMILES: CCC(OC(=O)Nc1ccc(-c2ncn(-c3ccc(OC(F)(F)F)cc3)n2)cc1)c1cccc(Br)c1] | (thin film) 3318, 3121, 3064, 2973, 2938, 1720, 1596, 1518, 1491, 1445, 1416, 1313, 1263, 1222, 1051, 909, 732 | HRMS-FAB (m/z) [M + H]⁺ calcd for C₂₅H₂₀BrF₃N₄O₃, 560.067; found, 560.0672 | | 8.54 (s, 1H), 8.12 (d, J = 8.8 Hz, 2H), 7.78 (d, J = 9.0 Hz, 2H), 7.54-7.47 (m, 3H), 7.43 (ddd, J = 7.7, 1.9, 1.4 Hz, 1H), 7.37 (dd, J = 9.0, 0.8 Hz, 2H), 7.29 (dt, J = 7.9, 1.5 Hz, 1H), 7.22 (t, J = 7.7 Hz, 1H), 6.90 (s, 1H), 5.62 (t, J = 6.8 Hz, 1H), 2.08-1.74 (m, 2H), 0.94 (t, J = 7.4 Hz, 3H) |
| 64 | 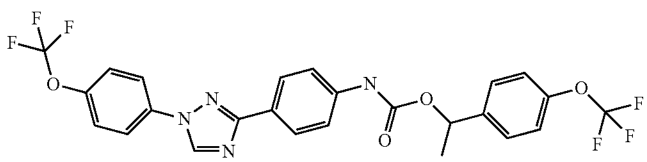 [SMILES: CC(OC(=O)Nc1ccc(-c2ncn(-c3ccc(OC(F)(F)F)cc3)n2)cc1)c1ccc(OC(F)(F)F)cc1] | | HRMS-FAB (m/z) [M + H]⁺ calcd for C₂₅H₁₈F₆N₄O₄, 552.123; found, 552.1230 | 110-113 | 8.54 (s, 1H), 8.13 (d, J = 8.8 Hz, 2H), 7.78 (d, J = 9.0 Hz, 2H), 7.49 (d, J = 8.7 Hz, 2H), 7.43 (d, J = 8.6 Hz, 2H), 7.38 (dd, J = 9.0, 0.8 Hz, 2H), 7.22 (dd, J = 8.7, 0.8 Hz, 2H), 6.81 (s, 1H), 5.91 (q, J = 6.6 Hz, 1H), 1.61 (d, J = 6.6 Hz, 3H) |
| 65 | 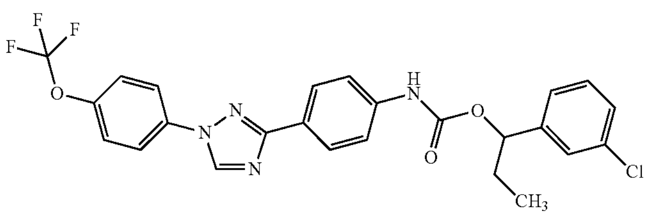 [SMILES: CCC(OC(=O)Nc1ccc(-c2ncn(-c3ccc(OC(F)(F)F)cc3)n2)cc1)c1cccc(Cl)c1] | (thin film) 3229, 3181, 3108, 3048, 1742, 1600, 1541, 1519, 1441, 1417, 1310, 1248, 1222, 1083, 985, 843 | HRMS-FAB (m/z) [M + H]⁺ calcd for C₂₅H₂₀ClF₃N₄O₃, 516.118; found, 516.1174 | | 8.54 (s, 1H), 8.13 (d, J = 8.8 Hz, 2H), 7.78 (d, J = 9.0 Hz, 2H), 7.50 (d, J = 8.8 Hz, 2H), 7.40-7.34 (m, 3H), 7.31-7.19 (m, 3H), 6.86 (s, 1H), 5.64 (t, J = 6.9 Hz, 1H), 2.08-1.74 (m, 2H), 0.94 (t, J = 7.4 Hz, 3H) |
| 66 | 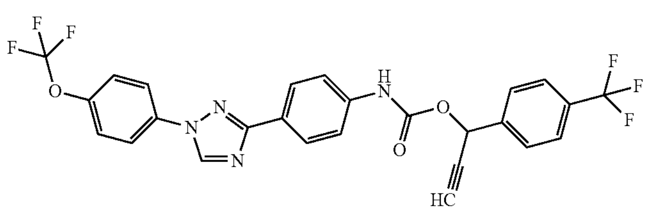 [SMILES: C#CC(OC(=O)Nc1ccc(-c2ncn(-c3ccc(OC(F)(F)F)cc3)n2)cc1)c1ccc(C(F)(F)F)cc1] | (thin film) 3250, 3117, 3061, 2126, 1735, 1610, 1549, 1519, 1492, 1445, 1417, 1328, 1263, 1220, 1068, 1050, 848 | HRMS-FAB (m/z) [M + H]⁺ calcd for C₂₆H₁₆F₆N₄O₃, 546.113; found, 546.1125 | | 8.55 (s, 1H), 8.15 (d, J = 8.8 Hz, 2H), 7.83-7.75 (m, 2H), 7.75-7.64 (m, 4H), 7.51 (d, J = 8.7 Hz, 2H), 7.43-7.34 (m, 2H), 6.90 (s, 1H), 6.56 (d, J = 2.2 Hz, 1H), 2.76 (d, J = 2.4 Hz, 1H) |

TABLE 1-continued

| # | Structure | IR (cm$^{-1}$) | MS | mp (° C.) | $^1$H NMR (CDCl$_3$, δ)$^1$ |
|---|---|---|---|---|---|
| 67 | 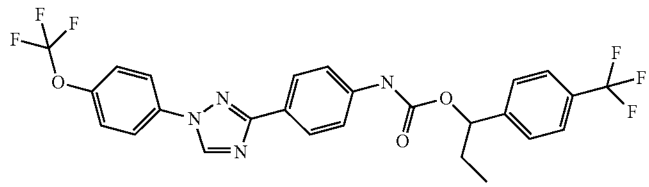 [SMILES: CCC(OC(=O)Nc1ccc(-c2ncn(-c3ccc(OC(F)(F)F)cc3)n2)cc1)c1ccc(C(F)(F)F)cc1] | | HRMS-FAB (m/z) [M + H]$^+$ calcd for C$_{26}$H$_{20}$F$_6$N$_4$O$_3$, 550.144; found, 550.1440 | 161.5-163.0 | 8.54 (s, 1H), 8.13 (d, J = 8.7 Hz, 2H), 7.78 (d, J = 9.0 Hz, 2H), 7.63 (d, J = 8.2 Hz, 2H), 7.49 (d, J = 8.5 Hz, 2H), 7.48 (d, J = 8.5 Hz, 2H), 7.43-7.27 (m, 2H), 6.85 (s, 1H), 5.71 (t, J = 6.8 Hz, 1H), 2.11-1.73 (m, 2H), 0.96 (t, J = 7.4 Hz, 3H) |
| 68 | 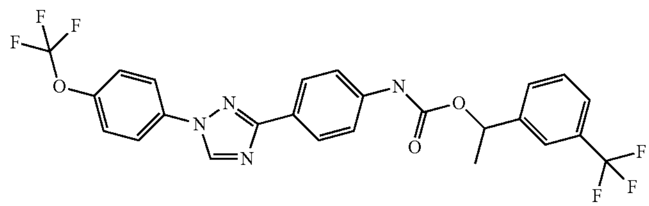 [SMILES: CC(OC(=O)Nc1ccc(-c2ncn(-c3ccc(OC(F)(F)F)cc3)n2)cc1)c1cccc(C(F)(F)F)c1] | | HRMS-FAB (m/z) [M + H]$^+$ calcd for C$_{25}$H$_{18}$F$_6$N$_4$O$_3$, 536.128; found, 536.1282 | 118-119.5 | 8.54 (s, 1H), 8.13 (d, J = 8.7 Hz, 2H), 7.78 (d, J = 9.0 Hz, 2H), 7.67 (s, 1H), 7.63-7.55 (m, 2H), 7.54-7.46 (m, 3H), 7.38 (dd, J = 9.0, 0.7 Hz, 2H), 6.85 (s, 1H), 5.96 (q, J = 6.6 Hz, 1H), 1.63 (d, J = 6.6 Hz, 3H) |
| 69 | 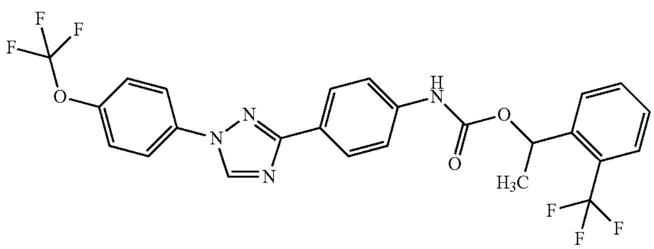 [SMILES: CC(OC(=O)Nc1ccc(-c2ncn(-c3ccc(OC(F)(F)F)cc3)n2)cc1)c1ccccc1C(F)(F)F] | | HRMS-FAB (m/z) [M + H]$^+$ calcd for C$_{25}$H$_{18}$F$_6$N$_4$O$_3$, 536.128; found, 536.1282 | 171.5-173.5 | 8.53 (s, 1H), 8.11 (d, J = 8.8 Hz, 2H), 7.78 (d, J = 9.1 Hz, 2H), 7.67 (app t, J = 7.0 Hz, 2H), 7.58 (dd, J = 11.3, 3.9 Hz, 1H), 7.49 (d, J = 8.7 Hz, 2H), 7.44-7.32 (m, 3H), 6.85 (s, 1H), 6.27 (q, J = 6.5 Hz, 1H), 1.61 (d, J = 6.5 Hz, 3H) |
| 70 | 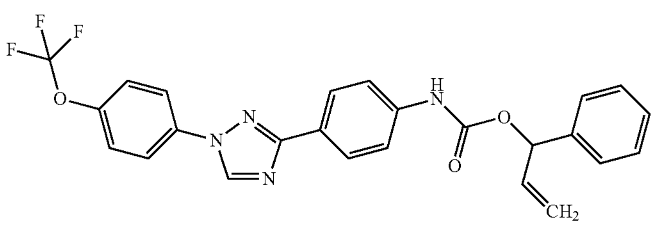 [SMILES: C=CC(OC(=O)Nc1ccc(-c2ncn(-c3ccc(OC(F)(F)F)cc3)n2)cc1)c1ccccc1] | | HRMS-FAB (m/z) [M + H]$^+$ calcd for C$_{25}$H$_{19}$F$_3$N$_4$O$_3$, 480.141; found, 480.1411 | 118-121 | 8.54 (s, 1H), 8.13 (d, J = 8.7 Hz, 2H), 7.78 (d, J = 9.0 Hz, 2H), 7.51 (d, J = 8.7 Hz, 2H), 7.46-7.30 (m, 7H), 6.89 (s, 1H), 6.29 (d, J = 5.9 Hz, 1H), 6.09 (ddd, J = 17.0, 10.4, 5.9 Hz, 1H), 5.38 (dt, J = 17.2, 1.3 Hz, 1H), 5.31 (dt, J = 10.5, 1.2 Hz, 1H) |
| 71 | 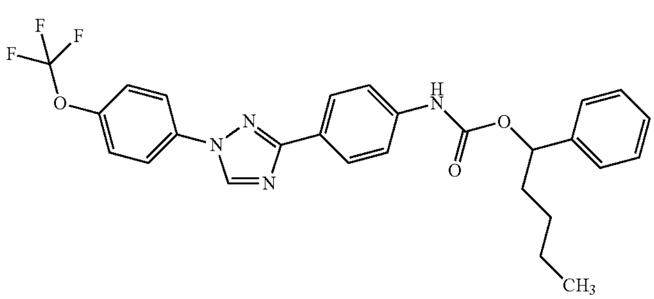 [SMILES: CCCCC(OC(=O)Nc1ccc(-c2ncn(-c3ccc(OC(F)(F)F)cc3)n2)cc1)c1ccccc1] | | HRMS-FAB (m/z) [M + H]$^+$ calcd for C$_{27}$H$_{25}$F$_3$N$_4$O$_3$, 510.188; found, 510.1884 | 146.5-148.5 | 8.53 (s, 1H), 8.11 (d, J = 8.7 Hz, 2H), 7.78 (d, J = 9.0 Hz, 2H), 7.49 (d, J = 8.7 Hz, 2H), 7.41-7.33 (m, 6H), 7.32-7.27 (m, 1H), 6.83 (s, 1H), 5.74 (dd, J = 7.5, 6.5 Hz, 1H), 2.09-1.91 (m, 1H), 1.91-1.71 (m, 1H), 1.59-1.02 (m, 4H), 0.89 (t, J = 7.0 Hz, 3H) |

TABLE 1-continued

| # | Structure | IR (cm$^{-1}$) | MS | mp (° C.) | $^1$H NMR (CDCl$_3$, δ)$^1$ |
|---|---|---|---|---|---|
| 72 | 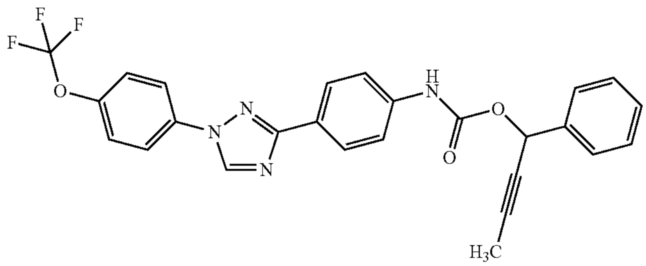 [SMILES: CC#CC(OC(=O)Nc1ccc(-c2ncn(-c3ccc(OC(F)(F)F)cc3)n2)cc1)c1ccccc1] | (thin film) 3317, 3123, 3066, 3036, 2246, 1731, 1598, 1518, 1492, 1445, 1416, 1263, 1217, 1039, 986, 909, 850, 732 | HRMS-FAB (m/z) [M + H]$^+$ calcd for C$_{26}$H$_{19}$F$_3$N$_4$O$_3$, 492.141; found, 492.1413 | | 8.53 (s, 1H), 8.13 (d, J = 8.7 Hz, 2H), 7.77 (d, J = 9.0 Hz, 2H), 7.58 (dd, J = 7.9, 1.6 Hz, 2H), 7.50 (d, J = 8.6 Hz, 2H), 7.44-7.32 (m, 5H), 6.91 (s, 1H), 6.49 (q, J = 2.1 Hz, 1H), 1.93 (d, J = 2.2 Hz, 3H) |
| 73 | 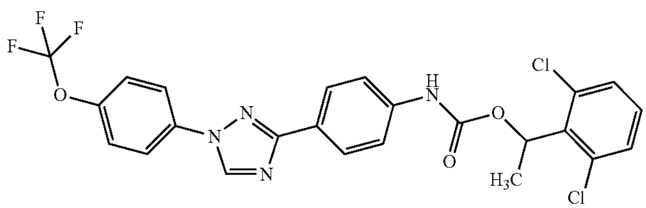 [SMILES: CC(OC(=O)Nc1ccc(-c2ncn(-c3ccc(OC(F)(F)F)cc3)n2)cc1)c1c(Cl)cccc1Cl] | | HRMS-FAB (m/z) [M + H]$^+$ calcd for C$_{24}$H$_{17}$Cl$_2$F$_3$N$_4$O$_3$, 536.063; found, 536.0634 | 196-198 | 8.69 (s, 1H), 8.11 (d, J = 8.7 Hz, 2H), 7.80 (d, J = 9.0 Hz, 2H), 7.51 (d, J = 8.7 Hz, 2H), 7.37 (d, J = 8.6 Hz, 2H), 7.30 (d, J = 8.0 Hz, 2H), 7.14 (dd, J = 8.4, 7.7 Hz, 1H), 6.90 (s, 1H), 6.56 (q, J = 6.9 Hz, 1H), 1.73 (d, J = 6.9 Hz, 3H) |
| 74 | 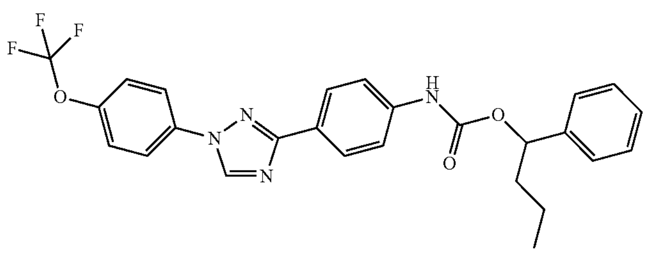 [SMILES: CCCC(OC(=O)Nc1ccc(-c2ncn(-c3ccc(OC(F)(F)F)cc3)n2)cc1)c1ccccc1] | (thin film) 3251, 3111, 3064, 2962, 2874, 1724, 1607, 1518, 1493, 1445, 1416, 1313, 1262, 1225, 1179, 1107, 1058 | HRMS-FAB (m/z) [M + H]$^+$ calcd for C$_{26}$H$_{23}$F$_3$N$_4$O$_3$, 496.172; found, 496.1727 | | 8.98 (s, 1H), 8.08 (d, J = 8.1 Hz, 2H), 7.86-7.74 (m, 2H), 7.44 (d, J = 7.8 Hz, 2H), 7.36-7.26 (m, 6H), 7.26-7.20 (m, 1H), 6.80 (s, 1H), 5.69 (dd, J = 7.4, 6.5 Hz, 1H), 1.96-1.83 (m, 1H), 1.80-1.66 (m, 1H), 1.46-1.19 (m, 2H), 0.88 (t, J = 7.4 Hz, 3H) |
| 75 | 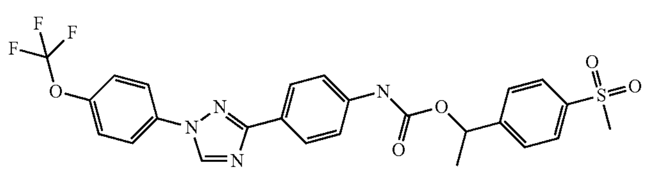 [SMILES: CC(OC(=O)Nc1ccc(-c2ncn(-c3ccc(OC(F)(F)F)cc3)n2)cc1)c1ccc(S(C)(=O)=O)cc1] | | HRMS-FAB (m/z) [M + H]$^+$ calcd for C$_{25}$H$_{21}$F$_3$N$_4$O$_5$S, 546.118; found, 546.1187 | 131-135 | 8.56 (s, 1H), 8.14 (d, J = 8.7 Hz, 2H), 7.95 (d, J = 8.4 Hz, 2H), 7.79 (d, J = 9.0 Hz, 2H), 7.60 (d, J = 8.4 Hz, 2H), 7.49 (d, J = 8.6 Hz, 2H), 7.38 (d, J = 8.4 Hz, 2H), 6.87 (s, 1H), 5.95 (q, J = 6.6 Hz, 1H), 3.05 (s, 3H), 1.63 (d, J = 6.7 Hz, 3H) |

TABLE 1-continued

| # | Structure | IR (cm⁻¹) | MS | mp (° C.) | ¹H NMR (CDCl₃, δ)¹ |
|---|---|---|---|---|---|
| 76 | 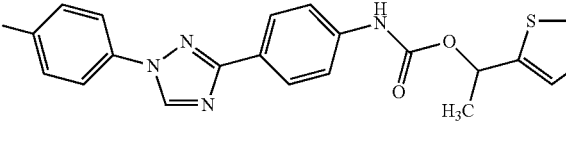 | | HRMS-FAB (m/z) [M + H]⁺ calcd for $C_{22}H_{17}F_3N_4O_3S$, 474.097; found, 474.0976 | 158-160 | (400 MHz, DMSO-d₆) 10.00 (s, 1H), 9.37 (s, 1H), 8.06 (d, J = 9.0 Hz, 2H), 8.01 (d, J = 8.7 Hz, 2H), 7.67-7.56 (m, 4H), 7.53 (dd, J = 5.1, 1.2 Hz, 1H), 7.19 (d, J = 3.4 Hz, 1H), 7.03 (dd, J = 5.1, 3.5 Hz, 1H), 6.11 (q, J = 6.5 Hz, 1H), 1.66 (d, J = 6.6 Hz, 3H) |
| 77 | 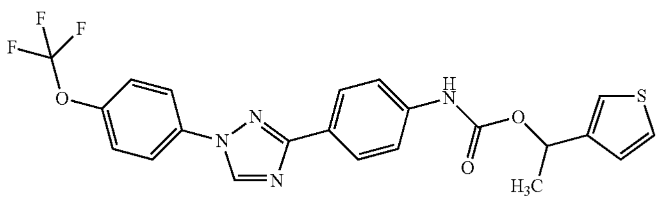 [SMILES: CC(OC(=O)Nc1ccc(-c2ncn(-c3ccc(OC(F)(F)F)cc3)n2)cc1)c1ccsc1] | | HRMS-FAB (m/z) [M + H]⁺ calcd for $C_{22}H_{17}F_3N_4O_3S$, 474.097; found, 474.0979 | 135-137 | (400 MHz, DMSO-d₆) 9.96 (s, 1H), 9.36 (s, 1H), 8.05 (d, J = 9.0 Hz, 2H), 8.01 (d, J = 8.7 Hz, 2H), 7.62 (d, J = 8.6 Hz, 2H), 7.60 (d, J = 8.6 Hz, 2H), 7.57-7.51 (m, 2H), 7.20 (dd, J = 4.8, 1.5 Hz, 1H), 5.93 (q, J = 6.5 Hz, 1H), 1.59 (d, J = 6.6 Hz, 3H) |
| 78 | 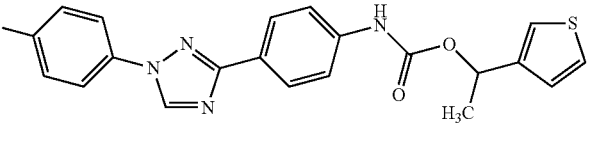 | (thin film) 3251, 3064, 2960, 1724, 1608, 1518, 1493, 1445, 1416, 1313, 1262, 1224, 1179, 1056, 849 | HRMS-FAB (m/z) [M + H]⁺ calcd for $C_{27}H_{25}F_3N_4O_3$, 510.1883; found, 510.187 | | 8.93 (s, 1H), 8.14 (d, J = 8.7 Hz, 2H), 7.84 (d, J = 9.0 Hz, 2H), 7.50 (d, J = 8.7 Hz, 2H), 7.44-7.32 (m, 6H), 7.30 (ddd, J = 6.7, 3.8, 1.7 Hz, 1H), 6.86 (s, 1H), 5.83 (dd, J = 8.6, 5.3 Hz, 1H), 2.03-1.80 (m, 1H), 1.75-1.52 (m, 2H), 0.98 (d, J = 6.3 Hz, 3H), 0.97 (d, J = 6.2 Hz, 3H) |
| 79 | 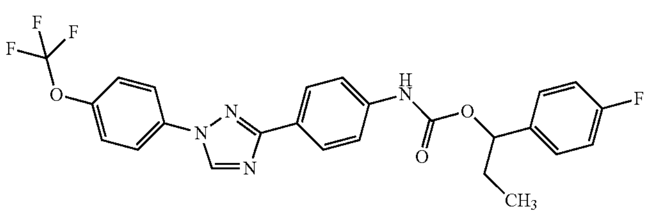 [SMILES: CCC(OC(=O)Nc1ccc(-c2ncn(-c3ccc(OC(F)(F)F)cc3)n2)cc1)c1ccc(F)cc1] | | HRMS-FAB (m/z) [M + H]⁺ calcd for $C_{25}H_{20}F_4N_4O_3$, 500.147; found, 500.1475 | 123-126 | 8.88 (s, 1H), 8.14 (d, J = 8.7 Hz, 2H), 7.83 (d, J = 9.0 Hz, 2H), 7.50 (d, J = 8.6 Hz, 2H), 7.43-7.30 (m, 4H), 7.04 (t, J = 8.7 Hz, 2H), 6.91 (s, 1H), 5.64 (t, J = 7.0 Hz, 1H), 2.07-1.91 (m, 1H), 1.91-1.75 (m, 1H), 0.92 (t, J = 7.4 Hz, 3H) |
| 80 | 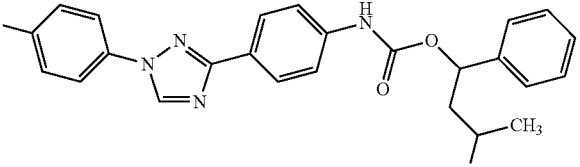 | | HRMS-FAB (m/z) [M + H]⁺ calcd for $C_{22}H_{14}F_6N_4O_4$, 512.092; found, 512.0919 | 97-99 | 8.71 (s, 1H), 8.17 (d, J = 8.7 Hz, 2H), 7.81 (d, J = 9.0 Hz, 2H), 7.66 (s, 1H), 7.51 (d, J = 8.4 Hz, 2H), 7.46 (t, J = 1.7 Hz, 1H), 7.39 (d, J = 8.5 Hz, 2H), 7.05 (s, 1H), 6.55 (s, 1H), 6.22 (q, J = 6.8 Hz, 1H) |

TABLE 1-continued

| # | Structure | IR (cm⁻¹) | MS | mp (° C.) | ¹H NMR (CDCl₃, δ)¹ |
|---|-----------|-----------|-----|-----------|--------------------|
| 81 | 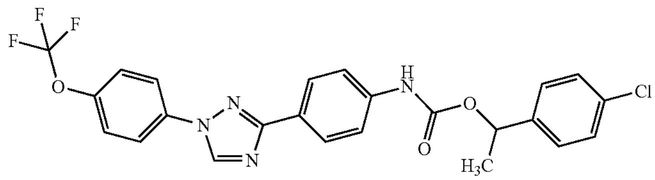 | | HRMS-FAB (m/z) [M + H]⁺ calcd for C$_{24}$H$_{18}$F$_3$N$_4$O$_3$Cl, 502.102; found, 502.1020 | 144-147 | 8.58 (s, 1H), 8.13 (d, J = 8.7 Hz, 2H), 7.79 (d, J = 9.0 Hz, 2H), 7.49 (d, J = 8.6 Hz, 2H), 7.38 (d, J = 8.3 Hz, 2H), 7.34 (app s, 4H), 6.80 (s, 1H), 5.87 (q, J = 6.6 Hz, 1H), 1.59 (d, J = 6.6 Hz, 3H) |
| 82 | 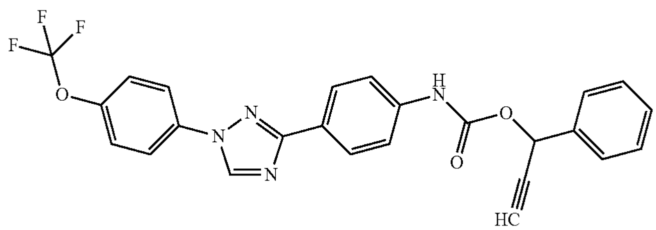 [SMILES: C#CC(OC(=O)Nc1ccc(-c2ncn(-c3ccc(OC(F)(F)F)cc3)n2)cc1)c1ccccc1] | | HRMS-FAB (m/z) [M + H]⁺ calcd for C$_{25}$H$_{17}$F$_3$N$_4$O$_3$, 478.125; found, 478.1256 | 142-144 | (400 MHz, DMSO-d$_6$) 10.19 (s, 1H), 9.37 (s, 1H), 8.04 (dd J = 10.4 8.9 Hz, 4H), 7.68-7.56 (m, 6H), 7.51-7.29 (m, 3H), 6.47 (d, J = 2.2 Hz, 1H), 3.88 (d, J = 2.2 Hz, 1H) |
| 83 | 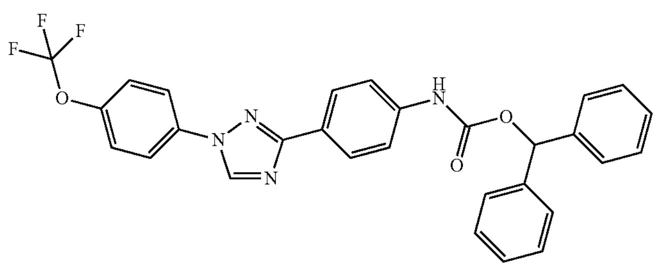 [SMILES: O=C(Nc1ccc(-c2ncn(-c3ccc(OC(F)(F)F)cc3)n2)cc1)OC(c1ccccc1)c1ccccc1] | | HRMS-FAB (m/z) [M + H]⁺ calcd for C$_{29}$H$_{21}$F$_3$N$_4$O$_3$, 530.157; found, 530.1564 | 158-160 | 8.99 (s, 1H), 8.18 (d, J = 8.7 Hz, 2H), 7.87 (d, J = 9.0 Hz, 2H), 7.56 (d, J = 8.7 Hz, 2H), 7.47-7.30 (m, 12H), 7.09 (s, 1H), 6.94 (s, 1H) |
| 84 | 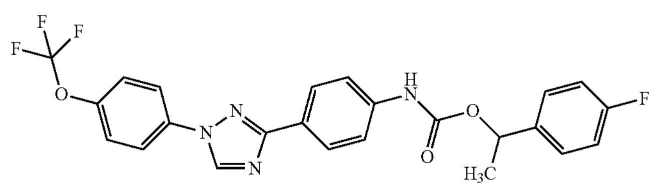 [SMILES: CC(OC(=O)Nc1ccc(-c2ncn(-c3ccc(OC(F)(F)F)cc3)n2)cc1)c1ccc(F)cc1] | | HRMS-FAB (m/z) [M + H]⁺ calcd for C$_{24}$H$_{18}$F$_4$N$_4$O$_3$, 486.131; found, 486.1318 | 142-144 | 8.56 (s, 1H), 8.12 (d, J = 8.4 Hz, 2H), 7.78 (d, J = 8.6 Hz, 2H), 7.49 (d, J = 8.2 Hz, 2H), 7.38 (dd, J = 8.6, 5.4 Hz, 4H), 7.05 (t, J = 8.7 Hz, 2H), 6.85 (s, 1H), 5.89 (q, J = 6.6 Hz, 1H), 1.60 (d, J = 6.6 Hz, 3H) |
| 85 | 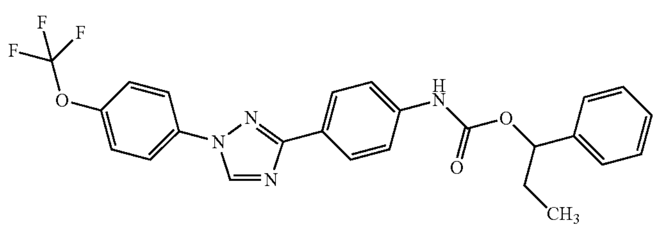 | | HRMS-FAB (m/z) [M + H]⁺ calcd for C$_{25}$H$_{21}$F$_3$N$_4$O$_3$, 482.156; found, 482.1568 | 127-131 | 8.53 (s, 1H), 8.12 (d, J = 8.7 Hz, 2H), 7.76 (d, J = 9.0 Hz, 2H), 7.50 (d, J = 8.6 Hz, 2H), 7.42-7.15 (m, 7H), 6.97 (s, 1H), 5.68 (t, J = 6.9 Hz, 1H), 2.07-1.75 (m, 2H), 0.94 (t, J = 7.4 Hz, 3H) |
| 86 | 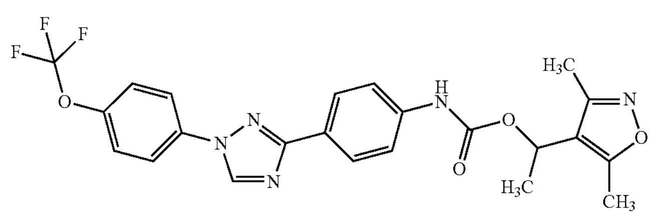 [SMILES: Cc1noc(C)c1C(C)OC(=O)Nc1ccc(-c2ncn(-c3ccc(OC(F)(F)F)cc3)n2)cc1] | | HRMS-FAB (m/z) [M + H]⁺ calcd for C$_{23}$H$_{20}$F$_3$N$_5$O$_4$, 487.146; found, 487.1468 | | 8.55 (s, 1H), 8.13 (d, J = 8.7 Hz, 2H), 7.79 (d, J = 9.0 Hz, 2H), 7.49 (d, J = 8.4 Hz, 2H), 7.38 (d, J = 8.3 Hz, 2H), 6.91 (s, 1H), 5.82 (q, J = 6.8 Hz, 1H), 2.46 (s, 3H), 2.36 (s, 3H), 1.60 (d, J = 6.9 Hz, 3H) |

TABLE 1-continued

| # | Structure | IR (cm⁻¹) | MS | mp (° C.) | ¹H NMR (CDCl₃, δ)¹ |
|---|---|---|---|---|---|
| 87 | 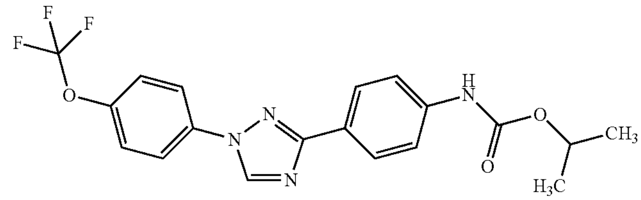 [SMILES: CC(C)OC(=O)Nc1ccc(-c2ncn(-c3ccc(OC(F)(F)F)cc3)n2)cc1] | | HRMS-FAB (m/z) [M + H]⁺ calcd for $C_{19}H_{17}F_3N_4O_3$, 406.125; found, 406.1252 | 193-195 | 8.54 (s, 1H), 8.13 (d, J = 8.7 Hz, 2H), 7.79 (d, J = 9.0 Hz, 2H), 7.50 (d, J = 8.5 Hz, 2H), 7.37 (d, J = 8.5 Hz, 2H), 6.71 (s, 1H), 5.23-4.88 (m, 1H), 1.31 (d, J = 6.3 Hz, 6H) |
| 88 | 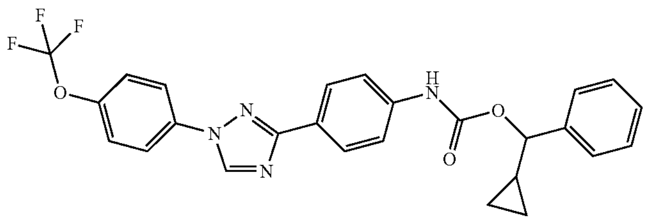 [SMILES: O=C(Nc1ccc(-c2ncn(-c3ccc(OC(F)(F)F)cc3)n2)cc1)OC(c1ccccc1)C1CC1] | | HRMS-FAB (m/z) [M + H]⁺ calcd for $C_{26}H_{21}F_3N_4O_3$, 494.156; found, 494.1567 | | 8.54 (s, 1H), 8.12 (d, J = 8.8 Hz, 2H), 7.79 (d, J = 9.1 Hz, 2H), 7.50 (d, J = 8.8 Hz, 2H), 7.46-7.28 (m, 7H), 6.82 (s, 1H), 5.21 (d, J = 8.9 Hz, 1H), 1.45-1.29 (m, 1H), 0.76-0.56 (m, 3H), 0.51-0.38 (m, 1H) |
| 89 | 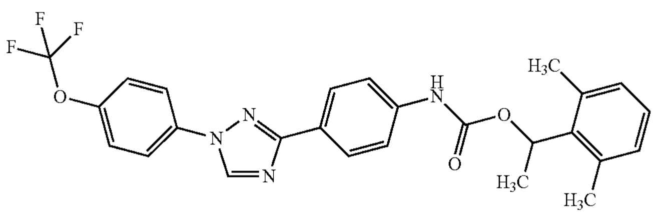 [SMILES: Cc1cccc(C)c1C(C)OC(=O)Nc1ccc(-c2ncn(-c3ccc(OC(F)(F)F)cc3)n2)cc1] | | HRMS-FAB (m/z) [M + H]⁺ calcd for $C_{26}H_{23}F_3N_4O_3$, 496.172; found, 496.1726 | 181-183 | 8.53 (s, 1H), 8.11 (d, J = 8.4 Hz, 2H), 7.78 (d, J = 9.0 Hz, 2H), 7.49 (d, J = 8.5 Hz, 2H), 7.37 (d, J = 8.5 Hz, 2H), 7.07 (dd, J = 8.5, 6.3 Hz, 1H), 7.01 (d, J = 7.4 Hz, 2H), 6.79 (s, 1H), 6.34 (q, J = 6.9 Hz, 1H), 2.50 (s, 6H), 1.65 (d, J = 7.0 Hz, 3H) |
| 90 | 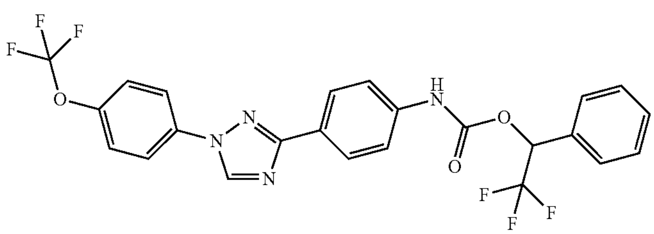 [SMILES: O=C(Nc1ccc(-c2ncn(-c3ccc(OC(F)(F)F)cc3)n2)cc1)OC(c1ccccc1)C(F)(F)F] | | HRMS-FAB (m/z) [M + H]⁺ calcd for $C_{24}H_{16}F_6N_4O_3$, 522.112; found, 522.1128 | | 8.55 (s, 1H), 8.15 (d, J = 8.7 Hz, 2H), 7.78 (d, J = 9.0 Hz, 2H), 7.58-7.46 (m, 4H), 7.48-7.34 (m, 5H), 7.11 (s, 1H), 6.17 (q, J = 6.9 Hz, 1H) |
| 91 | 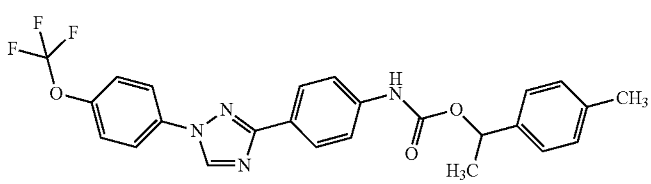 [SMILES: Cc1ccc(C(C)OC(=O)Nc2ccc(-c3ncn(-c4ccc(OC(F)(F)F)cc4)n3)cc2)cc1] | | HRMS-FAB (m/z) [M + H]⁺ calcd for $C_{25}H_{21}F_3N_4O_3$, 482.156; found, 482.156 | 160-162 | 8.53 (s, 1H), 8.11 (d, J = 8.7 Hz, 2H), 7.77 (d, J = 9.0 Hz, 2H), 7.49 (d, J = 8.6 Hz, 2H), 7.37 (d, J = 8.4 Hz, 2H), 7.30 (d, J = 8.1 Hz, 2H), 7.18 (d, J = 7.9 Hz, 2H), 6.84 (s, 1H), 5.89 (q, J = 6.6 Hz, 1H), 2.34 (s, 3H), 1.61 (d, J = 6.6 Hz, 3H) |
| 92 | 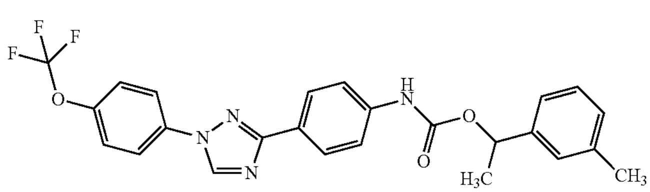 | | HRMS-FAB (m/z) [M + H]⁺ calcd for $C_{25}H_{21}F_3N_4O_3$, 482.156; found, 482.157 | 94-97 | 8.53 (s, 1H), 8.12 (d, J = 8.7 Hz, 2H), 7.78 (d, J = 9.0 Hz, 2H), 7.50 (d, J = 8.6 Hz, 2H), 7.37 (d, J = 8.4 Hz, 2H), 7.30-7.17 (m, 3H), 7.12 (d, J = 7.5 Hz, 1H), 6.86 (s, 1H), 5.88 (q, J = 6.6 Hz, 1H), 2.37 (s, 3H), 1.61 (d, J = 6.6 Hz, 3H) |

TABLE 1-continued

| # | Structure | IR (cm$^{-1}$) | MS | mp (° C.) | $^1$H NMR (CDCl$_3$, δ)$^1$ |
|---|---|---|---|---|---|
| 93 | 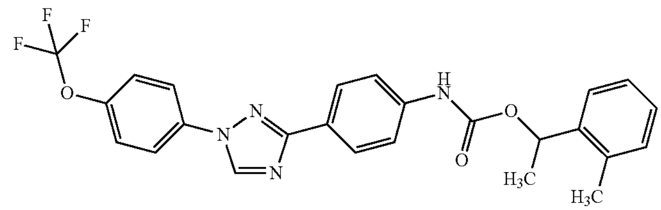 [SMILES: Cc1ccccc1C(C)OC(=O)Nc1ccc(-c2ncn(-c3ccc(OC(F)(F)F)cc3)n2)cc1] | | HRMS-FAB (m/z) [M + H]$^+$ calcd for C$_{25}$H$_{21}$F$_3$N$_4$O$_3$, 482.156; found, 482.157 | 147-149 | 8.53 (s, 1H), 8.12 (d, J = 8.7 Hz, 2H), 7.77 (d, J = 9.0 Hz, 2H), 7.49 (d, J = 8.6 Hz, 2H), 7.45-7.39 (m, 1H), 7.37 (d, J = 8.7 Hz, 2H), 7.27-7.11 (m, 3H), 6.90 (s, 1H), 6.13 (q, J = 6.5 Hz, 1H), 2.43 (s, 3H),1.59 (d, J = 6.6 Hz, 3H) |
| 94 | 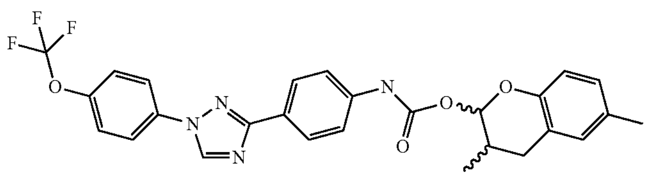 [SMILES: Cc1ccc2c(c1)CC(C)C(OC(=O)Nc1ccc(-c3ncn(-c4ccc(OC(F)(F)F)cc4)n3)cc1)O2] | | 525 ([M + H]$^+$) | >150 | (3:2 mixture of diastereomers) 8.52 (s, 1H), 8.11 (d, J = 8.6 Hz, 2H), 7.77 (d, J = 9.0 Hz, 2H), 7.59-7.43 (m, 2H), 7.37 (d, J = 8.4 Hz, 2H), 6.98-6.89 (m, 2H), 6.82-6.63 (m, 2H), 6.39 (d, J = 2.2 Hz, 0.6H), 6.25 (d, J = 3.0 Hz, 0.4H), 3.76-3.62 (m, 0.6H), 3.09 (dd, J = 16.4, 5.9 Hz, 0.4H), 2.67 (d, J = 9.0 Hz, 1.2H), 2.33-2.20 (m, 0.8H), 2.27 (s, 3H), 1.14 (d, J = 6.8 Hz, 1.5H), 1.08 (d, J = 7.1 Hz, 1.5H) |
| 95 | 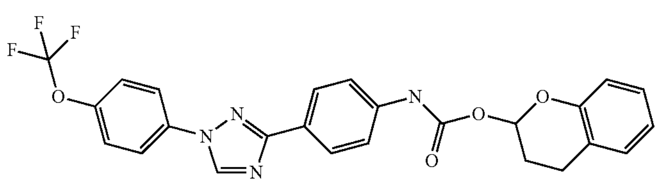 [SMILES: O=C(Nc1ccc(-c2ncn(-c3ccc(OC(F)(F)F)cc3)n2)cc1)OC1CCc2ccccc2O1] | | HRMS-FAB (m/z) [M + H]$^+$ calcd for C$_{25}$H$_{19}$F$_3$N$_4$O$_4$, 496.135; found, 496.136 | 171-173 | 8.54 (s, 1H), 8.13 (d, J = 8.7 Hz, 2H), 7.79 (d, J = 9.2 Hz, 2H), 7.50 (d, J = 8.5 Hz, 2H), 7.38 (dd, J = 9.1, 0.8 Hz, 2H), 7.13 (dd, J = 15.8, 7.8 Hz, 2H), 6.94 (ddd, J = 9.7, 7.6, 1.7 Hz, 2H), 6.76 (s, 1H), 6.62 (t, J = 2.5 Hz, 1H), 3.03 (ddd, J = 17.4, 12.3, 5.9 Hz, 1H), 2.77 (ddd, J = 17.0, 6.2, 3.1 Hz, 1H), 2.33-1.98 (m, 2H) |
| 96 | 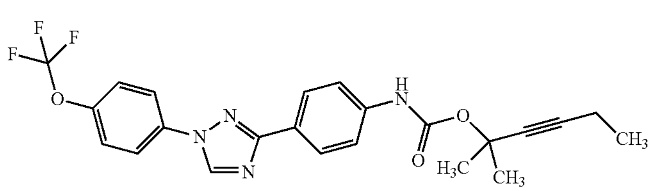 [SMILES: CCC#CC(C)(C)OC(=O)Nc1ccc(-c2ncn(-c3ccc(OC(F)(F)F)cc3)n2)cc1] | | HRMS-FAB (m/z) [M + H]$^+$ calcd for C$_{23}$H$_{21}$F$_3$N$_4$O$_3$, 458.156; found, 458.157 | 158-159 | 8.53 (s, 1H), 8.11 (d, J = 8.7 Hz, 2H), 7.78 (d, J = 9.0 Hz, 2H), 7.51 (d, J = 8.6 Hz, 2H), 7.36 (d, J = 8.4 Hz, 2H), 6.77 (s, 1H), 2.23 (q, J = 7.5 Hz, 2H), 1.73 (s, 6H), 1.13 (t, J = 7.5 Hz, 3H) |

TABLE 1-continued

| # | Structure | IR (cm$^{-1}$) | MS | mp (° C.) | $^1$H NMR (CDCl$_3$, δ)$^1$ |
|---|---|---|---|---|---|
| 97 | 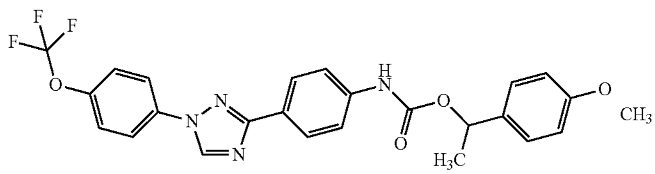 | (thin film) 3317, 3122, 2981, 2933, 2839, 1724, 1615, 1518, 1492, 1445, 1416, 1249, 1225, 1179, 1111, 1064, 986, 847 | HRMS-FAB (m/z) [M + H]$^+$ calcd for C$_{25}$H$_{21}$F$_3$N$_4$O$_4$, 498.151; found, 498.151 | | 8.53 (s, 1H), 8.11 (d, J = 8.7 Hz, 2H), 7.78 (d, J = 8.9 Hz, 2H), 7.48 (d, J = 8.6 Hz, 2H), 7.37 (d, J = 8.9 Hz, 2H), 7.35 (d, J = 8.8 Hz, 2H), 6.90 (d, J = 8.7 Hz, 2H), 6.79 (s, 1H), 5.88 (q, J = 6.6 Hz, 1H), 3.80 (s, 3H), 1.61 (d, J = 6.6 Hz, 3H) |
| 98 | 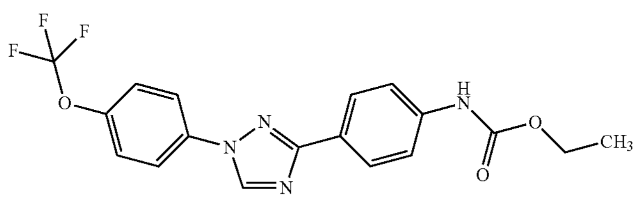 [SMILES: CCOC(=O)Nc1ccc(-c2ncn(-c3ccc(OC(F)(F)F)cc3)n2)cc1] | | HRMS-FAB (m/z) [M + H]$^+$ calcd for C$_{18}$H$_{15}$F$_3$N$_4$O$_3$, 392.109; found, 392.109 | 182-184 | 8.55 (s, 1H), 8.12 (d, J = 8.7 Hz, 2H), 7.78 (d, J = 9.0 Hz, 2H), 7.50 (d, J = 8.5 Hz, 2H), 7.37 (d, J = 8.5 Hz, 2H), 6.81 (s, 1H), 4.25 (q, J = 7.1 Hz, 2H), 1.32 (t, J = 7.1 Hz, 3H) |
| 99 | 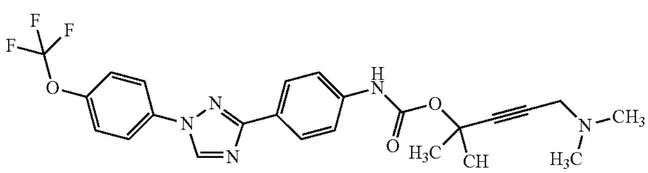 [SMILES: CN(C)CC#CC(C)(C)OC(=O)Nc1ccc(-c2ncn(-c3ccc(OC(F)(F)F)cc3)n2)cc1] | | HRMS-FAB (m/z) [M + H]$^+$ calcd for C$_{24}$H$_{24}$F$_3$N$_5$O$_3$, 487.183; found, 487.183 | 130-133 | (300 MHz, CDCl$_3$-CD$_3$OD) 8.60 (s, 1H), 7.97 (d, J = 8 Hz, 2H), 7.75 (d, J = 8 Hz, 2H), 7.44 (d, J = 8 Hz, 2H), 7.30 (d, J = 8 Hz, 2H), 3.83 (br, 1H), 3.21 (s, 2H), 2.22 (s, 6H), 1.65 (s, 6H) |
| 100 | 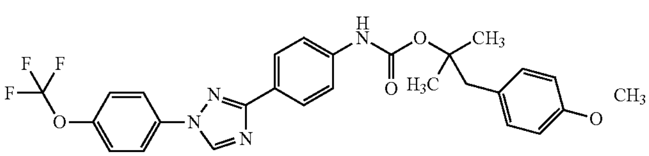 | | HRMS-FAB (m/z) [M + H]$^+$ calcd for C$_{27}$H$_{25}$F$_3$N$_4$O$_4$, 526.182; found, 526.183 | 173-176 | 8.53 (s, 1H), 8.13 (d, J = 8.7 Hz, 2H), 7.77 (d, J = 9.0 Hz, 2H), 7.50 (d, J = 8.2 Hz, 2H), 7.37 (d, J = 8.4 Hz, 2H), 7.14 (d, J = 8.6 Hz, 2H), 6.83 (d, J = 8.7 Hz, 2H), 6.77 (s, 1H), 3.78 (s, 3H), 3.12 (s, 2H), 1.50 (s, 6H) |
| 101 | 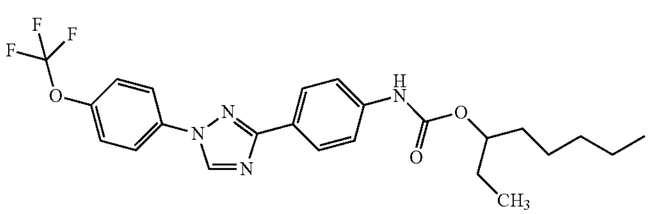 [SMILES: CCCCCC(CC)OC(=O)Nc1ccc(-c2ncn(-c3ccc(OC(F)(F)F)cc3)n2)cc1] | | HRMS-FAB (m/z) [M + H]$^+$ calcd for C$_{24}$H$_{27}$F$_3$N$_4$O$_3$, 476.203; found, 476.204 | 111-115 | 8.54 (s, 1H), 8.13 (d, J = 8.7 Hz, 2H), 7.78 (d, J = 9.1 Hz, 2H), 7.52 (d, J = 8.6 Hz, 2H), 7.37 (d, J = 8.3 Hz, 2H), 6.79 (s, 1H), 4.86-4.76 (m, 1H), 1.71-1.50 (m, 4H), 1.47-1.16 (m, 6H), 0.94 (t, J = 7.4 Hz, 3H), 0.88 (t, J = 6.7 Hz, 3H) |

TABLE 1-continued

| # | Structure | IR (cm$^{-1}$) | MS | mp (° C.) | $^1$H NMR (CDCl$_3$, δ)$^1$ |
|---|---|---|---|---|---|
| 102 | 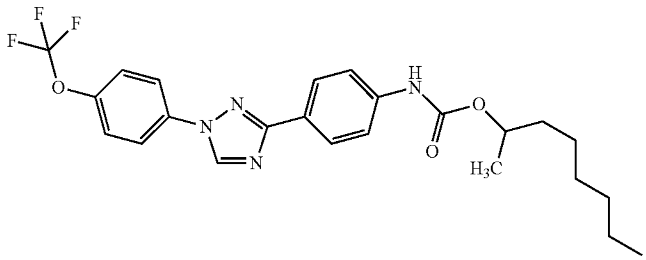 [SMILES: CCCCCCC(C)OC(=O)Nc1ccc(-c2ncn(-c3ccc(OC(F)(F)F)cc3)n2)cc1] | | HRMS-FAB (m/z) [M + H]$^+$ calcd for C$_{24}$H$_{27}$F$_3$N$_4$O$_3$, 476.203; found, 476.204 | 123-124 | 8.54 (s, 1H), 8.13 (d, J = 8.7 Hz, 2H), 7.78 (d, J = 9.0 Hz, 2H), 7.51 (d, J = 8.5 Hz, 2H), (7.37 (d, J = 8.5 Hz, 2H), 6.76 (s, 1H), 5.07-4.81 (m, 1H), 1.96-1.58 (m, 1H), 1.58-1.47 (m, 1H), 1.47-1.17 (m, 8H), 1.29 (d, J = 6.2 Hz, 3H), 0.88 (t, J = 6.7 Hz, 3H) |
| 103 | 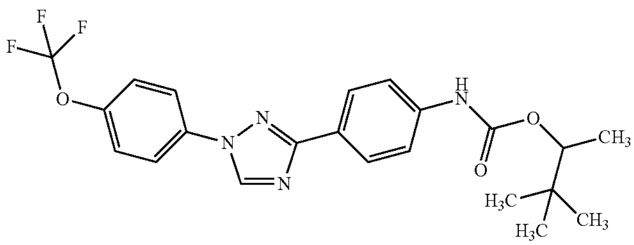 [SMILES: CC(OC(=O)Nc1ccc(-c2ncn(-c3ccc(OC(F)(F)F)cc3)n2)cc1)C(C)(C)C] | | HRMS-FAB (m/z) [M + H]$^+$ calcd for C$_{22}$H$_{23}$F$_3$N$_4$O$_3$, 448.172; found, 448.172 | 165-166 | 8.54 (s, 1H), 8.13 (d, J = 8.7 Hz, 2H), 7.78 (d, J = 9.0 Hz, 2H), 7.52 (d, J = 8.4 Hz, 2H), 7.37 (d, J = 8.6 Hz, 2H), 6.77 (s, 1H), 4.71 (q, J = 6.4 Hz, 1H), 1.22 (d, J = 6.4 Hz, 3H), 0.95 (s, 9H) |
| 104 | 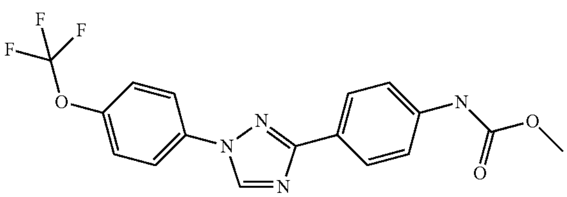 [SMILES: COC(=O)Nc1ccc(-c2ncn(-c3ccc(OC(F)(F)F)cc3)n2)cc1] | | HRMS-FAB (m/z) [M + H]$^+$ calcd for C$_{17}$H$_{13}$F$_3$N$_4$O$_3$, 378.093; found, 378.094 | 171-173 | 8.54 (s, 1H), 8.13 (d, J = 8.7 Hz, 2H), 7.78 (d, J = 9.0 Hz, 2H), 7.50 (d, J = 8.5 Hz, 2H), 7.37 (d, J = 8.4 Hz, 2H), 6.85 (s, 1H), 3.80 (s, 3H) |
| 105 | 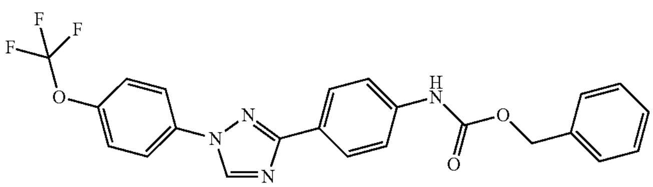 [SMILES: O=C(Nc1ccc(-c2ncn(-c3ccc(OC(F)(F)F)cc3)n2)cc1)OCc1ccccc1] | | HRMS-FAB (m/z) [M + H]$^+$ calcd for C$_{23}$H$_{17}$F$_3$N$_4$O$_3$, 454.125; found, 454.125 | 155-157 | 8.54 (s, 1H), 8.13 (d, J = 8.7 Hz, 2H), 7.78 (d, J = 9.0 Hz, 2H), 7.51 (d, J = 8.5 Hz, 2H), 7.46-7.32 (m, 7H), 6.89 (s, 1H), 5.22 (s, 2H) |
| 106 | 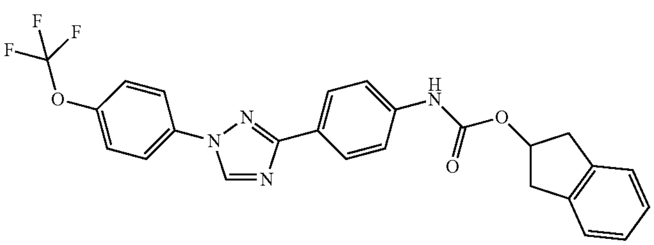 [SMILES: O=C(Nc1ccc(-c2ncn(-c3ccc(OC(F)(F)F)cc3)n2)cc1)OC1Cc2ccccc2C1] | | HRMS-FAB (m/z) [M + H]$^+$ calcd for C$_{22}$H$_{19}$F$_3$N$_4$O$_3$, 480.140; found, 480.141 | 196-197 | 8.52 (s, 1H), 8.11 (d, J = 8.6 Hz, 2H), 7.77 (d, J = 8.9 Hz, 2H), 7.47 (d, J = 8.2 Hz, 2H), 7.37 (d, J = 8.7 Hz, 2H), 7.30-7.24 (m, 2H), 7.24-7.16 (m, 2H), 6.78 (s, 1H), 5.63-5.58 (m, 1H), 3.35 (dd, J = 17.0, 6.1 Hz, 2H), 3.11 (dd, J = 17.0, 2.3 Hz, 2H) |
| 107 | 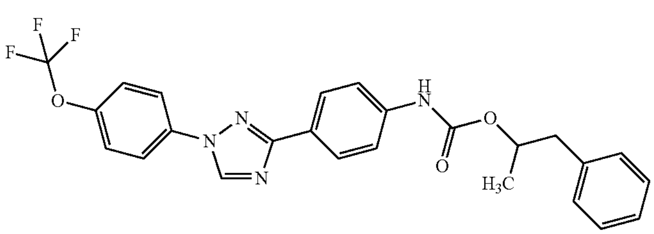 [SMILES: CC(Cc1ccccc1)OC(=O)Nc1ccc(-c2ncn(-c3ccc(OC(F)(F)F)cc3)n2)cc1] | | HRMS-FAB (m/z) [M + H]$^+$ calcd for C$_{25}$H$_{21}$F$_3$N$_4$O$_3$, 482.156; found, 482.1567 | 143-145 | 8.54 (s, 1H), 8.13 (d, J = 8.7 Hz, 2H), 7.78 (d, J = 9.0 Hz, 2H), 7.48 (d, J = 8.4 Hz, 2H), 7.37 (d, J = 8.4 Hz, 2H), 7.34-7.27 (m, 2H), 7.27-7.19 (m, 3H), 6.76 (s, 1H), 5.16 (h, J = 6.3 Hz, 1H), 3.02 (dd, J = 13.7, 6.4 Hz, 1H), 2.83 (dd, J = 13.7, 6.7 Hz, 1H), 1.30 (d, J = 6.3 Hz, 3H) |

TABLE 1-continued

| # | Structure | IR (cm$^{-1}$) | MS | mp (° C.) | $^1$H NMR (CDCl$_3$, δ)$^1$ |
|---|---|---|---|---|---|
| 108 | 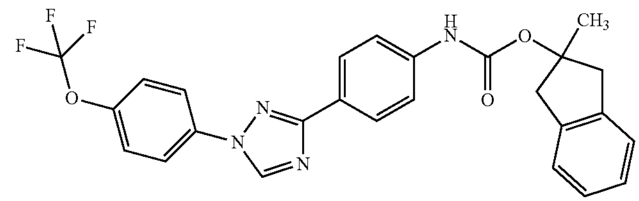 [SMILES: CC1(OC(=O)Nc2ccc(-c3ncn(-c4ccc(OC(F)(F)F)cc4)n3)cc2)Cc2ccccc2C1] | | HRMS-FAB (m/z) [M + H]$^+$ calcd for C$_{26}$H$_{21}$F$_3$N$_4$O$_3$, 494.156; found, 494.157 | 197-201 | 8.54 (s, 1H), 8.12 (d, J = 8.7 Hz, 2H), 7.79 (d, J = 9.0 Hz, 2H), 7.47 (d, J = 8.2 Hz, 2H), 7.38 (d, J = 8.3 Hz, 2H), 7.23-7.11 (m, 4H), 6.68 (s, 1H), 3.51 (d, J = 16.5 Hz, 2H), 3.20 (d, J = 16.5 Hz, 2H), 1.78 (s, 3H) |
| 109 | 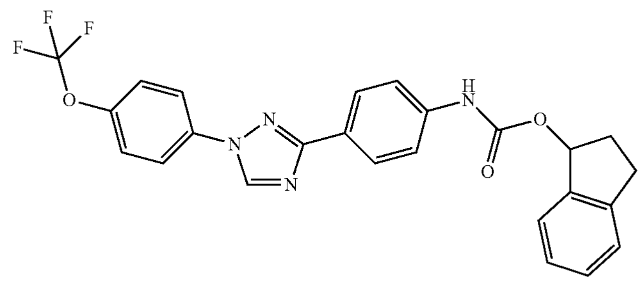 [SMILES: O=C(Nc1ccc(-c2ncn(-c3ccc(OC(F)(F)F)cc3)n2)cc1)OC1CCc2ccccc21] | | HRMS-FAB (m/z) [M + H]$^+$ calcd for C$_{25}$H$_{19}$F$_3$N$_4$O$_3$, 480.140; found 480.1415 | 187-190 | 8.54 (s, 1H), 8.14 (d, J = 8.7 Hz, 2H), 7.78 (d, J = 9.0 Hz, 2H), 7.51 (d, J = 7.0 Hz, 3H), 7.38 (d, J = 8.4 Hz, 2H), 7.35-7.21 (m, 3H), 6.77 (s, 1H), 6.26 (dd, J = 6.9, 3.5 Hz, 1H), 3.19-3.10 (m, 1H), 2.92 (ddd, J = 16.1, 8.6, 4.6 Hz, 1H), 2.62-2.49 (m, 1H), 2.21 (dddd, J = 14.0, 8.3, 4.5, 3.7 Hz, 1H) |
| 110 | 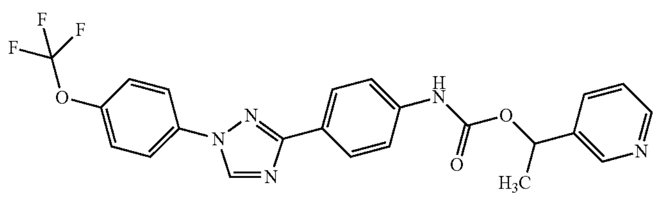 [SMILES: CC(OC(=O)Nc1ccc(-c2ncn(-c3ccc(OC(F)(F)F)cc3)n2)cc1)c1cccnc1] | | HRMS-FAB (m/z) [M + H]$^+$ calcd for C$_{23}$H$_{18}$F$_3$N$_5$O$_3$, 469.136; found, 469.1366 | 147-150 | 8.70 (s, 1H), 8.58 (d, J = 4.1 Hz, 1H), 8.54 (s, 1H), 8.13 (d, J = 8.7 Hz, 2H), 7.78 (d, J = 9.0 Hz, 2H), 7.73 (dt, J = 7.9, 1.7 Hz, 1H), 7.50 (d, J = 8.6 Hz, 2H), 7.37 (d, J = 8.5 Hz, 2H), 7.32 (dd, J = 7.8, 4.9 Hz, 1H), 7.11 (s, 1H), 5.95 (q, J = 6.6 Hz, 1H), 1.65 (d, J = 6.7 Hz, 3H) |
| 111 | 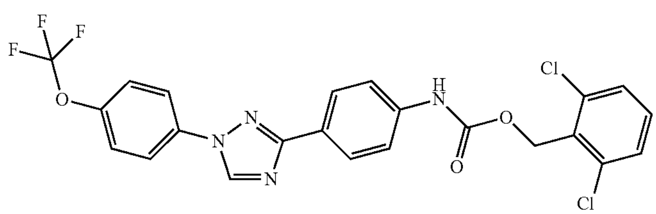 [SMILES: O=C(Nc1ccc(-c2ncn(-c3ccc(OC(F)(F)F)cc3)n2)cc1)OCc1c(Cl)cccc1Cl] | | HRMS-FAB (m/z) [M + H]$^+$ calcd for C$_{23}$H$_{15}$F$_3$N$_4$O$_3$Cl$_2$, 522.047; found, 522.0480 | 171-173 | 8.54 (s, 1H), 8.13 (d, J = 8.7 Hz, 2H), 7.78 (d, J = 9.0 Hz, 2H), 7.51 (d, J = 8.4 Hz, 2H), 7.43-7.32 (m, 4H), 7.24 (dd, J = 8.7, 7.3 Hz, 1H), 6.92 (s, 1H), 5.51 (s, 2H) |
| 112 | 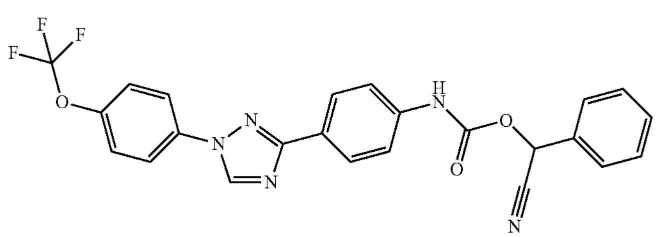 [SMILES: N#CC(OC(=O)Nc1ccc(-c2ncn(-c3ccc(OC(F)(F)F)cc3)n2)cc1)c1ccccc1] | | HRMS-FAB (m/z) [M + H]$^+$ calcd for C$_{24}$H$_{16}$F$_3$N$_5$O$_3$, 479.120; found, 479.1206 | 134-136 | 8.56 (s, 1H), 8.16 (d, J = 8.6 Hz, 2H), 7.78 (d, J = 9.0 Hz, 2H), 7.58 (dd, J = 6.8, 2.9 Hz, 2H), 7.55-7.43 (m, 5H), 7.38 (d, J = 8.4 Hz, 2H), 7.08 (s, 1H), 6.53 (s, 1H) |
| 113 | 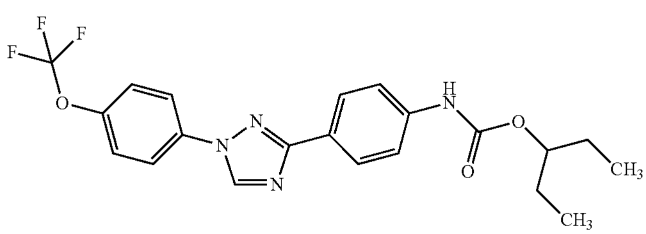 [SMILES: CCC(CC)OC(=O)Nc1ccc(-c2ncn(-c3ccc(OC(F)(F)F)cc3)n2)cc1] | | HRMS-FAB (m/z) [M + H]$^+$ calcd for C$_{21}$H$_{21}$F$_3$N$_4$O$_3$, 434.156; found, 434.1568 | 161-162 | 9.05 (s, 1H), 8.17 (d, J = 8.7 Hz, 2H), 7.87 (d, J = 8.9 Hz, 2H), 7.54 (d, J = 8.5 Hz, 2H), 7.39 (d, J = 8.5 Hz, 2H), 6.80 (s, 1H), 4.80-4.71 (m, 1H), 1.72-1.53 (m, 4H), 0.95 (t, J = 7.4 Hz, 6H) |

TABLE 1-continued

| # | Structure | IR (cm$^{-1}$) | MS | mp (° C.) | $^1$H NMR (CDCl$_3$, δ)$^1$ |
|---|---|---|---|---|---|
| 114 | 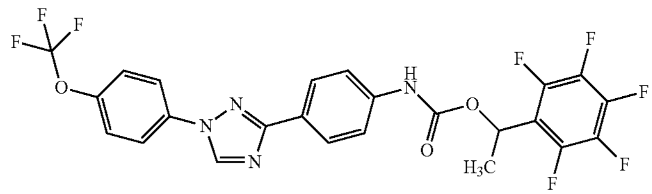 [SMILES: CC(OC(=O)Nc1ccc(-c2ncn(-c3ccc(OC(F)(F)F)cc3)n2)cc1)c1c(F)c(F)c(F)c(F)c1F] | | HRMS-FAB (m/z) [M + H]$^+$ calcd for C$_{24}$H$_{14}$F$_3$N$_4$O$_3$, 558.094; found, 558.0937 | 185-188 | 8.54 (s, 1H), 8.13 (d, J = 8.8 Hz, 2H), 7.79 (d, J = 9.0 Hz, 2H), 7.48 (d, J = 8.7 Hz, 2H), 7.38 (dd, J = 9.0, 0.8 Hz, 2H), 6.84 (s, 1H), 6.18 (q, J = 6.7 Hz, 1H), 1.72 (d, J = 6.9 Hz, 3H) |
| 115 | 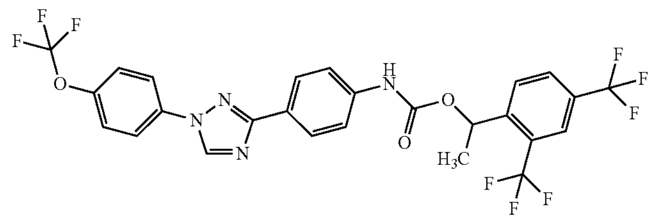 [SMILES: CC(OC(=O)Nc1ccc(-c2ncn(-c3ccc(OC(F)(F)F)cc3)n2)cc1)c1ccc(C(F)(F)F)cc1C(F)(F)F] | | HRMS-FAB (m/z) [M + H]$^+$ calcd for C$_{26}$H$_{17}$F$_9$N$_4$O$_3$, 604.116; found, 604.1154 | 212.5-214.5 | 10.20 (s, 1H), 9.35 (s, 1H), 8.20 (d, J = 8.3 Hz, 1H), 8.10-7.95 (m, 6H), 7.58 (app t, J = 9.2 Hz, 4H), 6.09 (q, J = 6.4 Hz, 1H), 1.59 (d, J = 6.5 Hz, 3H) |
| 116 | 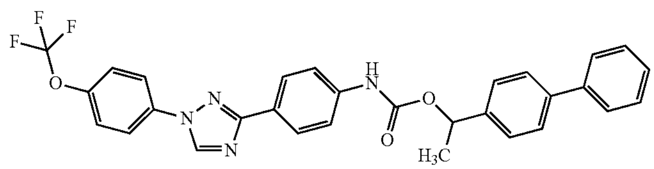 [SMILES: CC(OC(=O)Nc1ccc(-c2ncn(-c3ccc(OC(F)(F)F)cc3)n2)cc1)c1ccc(-c2ccccc2)cc1] | | HRMS-FAB (m/z) [M + H]$^+$ calcd for C$_{30}$H$_{23}$F$_3$N$_4$O$_3$, 544.1722; found, 544.1722 | 174.5-177.5 | 8.54 (s, 1H), 8.13 (d, J = 8.7 Hz, 2H), 7.79 (d, J = 9.0 Hz, 2H), 7.64-7.55 (m, 4H), 7.54-7.31 (m, 9H), 6.81 (s, 1H), 5.97 (q, J = 6.5 Hz, 1H), 1.67 (d, J = 6.6 Hz, 3H) |
| 117 | 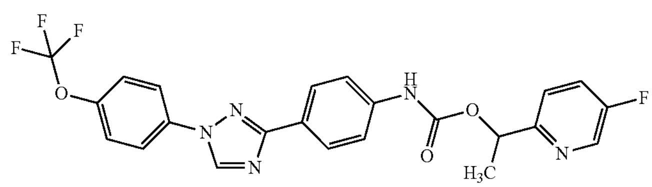 [SMILES: CC(OC(=O)Nc1ccc(-c2ncn(-c3ccc(OC(F)(F)F)cc3)n2)cc1)c1ccc(F)cn1] | | 488 ([M + H]$^+$), 486 ([M − H]$^-$) | 153.5-156 | 8.54 (s, 1H), 8.46 (t, J = 1.6 Hz, 1H), 8.12 (d, J = 8.8 Hz, 2H), 7.78 (d, J = 9.0 Hz, 2H), 7.49 (d, J = 8.7 Hz, 2H), 7.44-7.33 (m, 4H), 6.93 (s, 1H), 5.95 (q, J = 6.6 Hz, 1H), 1.66 (d, J = 6.7 Hz, 3H) |
| 118 | 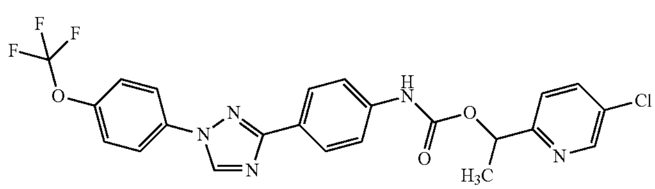 [SMILES: CC(OC(=O)Nc1ccc(-c2ncn(-c3ccc(OC(F)(F)F)cc3)n2)cc1)c1ccc(Cl)cn1] | | 504 ([M + H]$^+$), 502 ([M − H]$^-$) | 181-184.5 | 8.57 (dd, J = 2.4, 0.5 Hz, 1H), 8.54 (s, 1H), 8.13 (d, J = 8.8 Hz, 2H), 7.79 (d, J = 9.0 Hz, 2H), 7.68 (dd, J = 8.4, 2.5 Hz, 1H), 7.49 (d, J = 8.7 Hz, 2H), 7.38 (dd, J = 9.1, 0.8 Hz, 2H), 7.37-7.33 (m, 1H), 6.90 (s, 1H), 5.93 (q, J = 6.6 Hz, 1H), 1.65 (d, J = 6.7 Hz, 3H) |
| 119 | 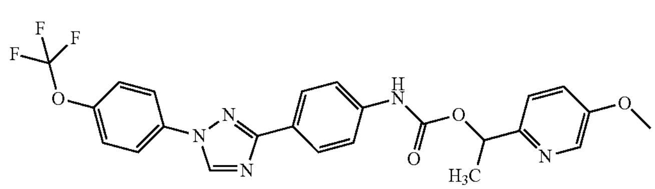 [SMILES: COc1ccc(C(C)OC(=O)Nc2ccc(-c3ncn(-c4ccc(OC(F)(F)F)cc4)n3)cc2)nc1] | | 500 ([M + H]$^+$), 498 ([M − H]$^-$) | 143-148 | 8.54 (s, 1H), 8.34-8.28 (m, 1H), 8.11 (d, J = 8.8 Hz, 2H), 7.78 (d, J = 9.1 Hz, 2H), 7.48 (d, J = 8.8 Hz, 2H), 7.42-7.34 (m, 2H), 7.32 (d, J = 8.5 Hz, 1H), 7.19 (dd, J = 8.6, 2.9 Hz, 1H), 6.94 (s, 1H), 5.93 (q, J = 6.6 Hz, 1H), 3.85 (s, 3H), 1.66 (d, J = 6.7 Hz, 3H) |

TABLE 1-continued

| # | Structure | IR (cm⁻¹) | MS | mp (° C.) | ¹H NMR (CDCl₃, δ)¹ |
|---|---|---|---|---|---|
| 120 | 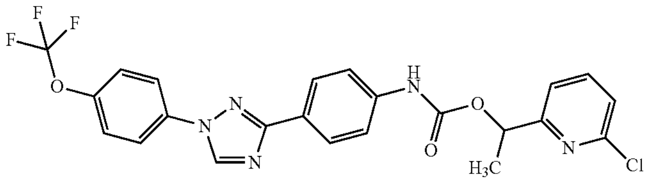 [SMILES: CC(OC(=O)Nc1ccc(-c2ncn(-c3ccc(OC(F)(F)F)cc3)n2)cc1)c1cccc(Cl)n1] | (thin film) 3301, 3119, 3061, 2987, 1721, 1596, 1517, 1491, 1439, 1311, 1220, 1163, 1078, 985, 914, 846, 756, 732 | 504 ([M + H]⁺), 502 ([M − H]⁻) | | 8.54 (s, 1H), 8.13 (d, J = 8.8 Hz, 2H), 7.79 (d, J = 9.1 Hz, 2H), 7.66 (t, J = 7.8 Hz, 1H), 7.50 (d, J = 8.8 Hz, 2H), 7.41-7.35 (m, 2H), 7.32 (d, J = 7.5 Hz, 1H), 7.28-7.24 (m, 1H), 6.92 (s, 1H), 5.90 (q, J = 6.7 Hz, 1H), 1.66 (d, J = 6.7 Hz, 3H) |
| 121 | 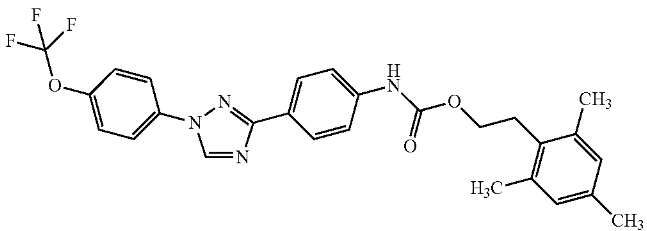 [SMILES: Cc1cc(C)c(CCOC(=O)Nc2ccc(-c3ncn(-c4ccc(OC(F)(F)F)cc4)n3)cc2)c(C)c1] | | HRMS-FAB (m/z) [M + H]⁺ calcd for C₂₇H₂₅F₃N₄O₃, 510.188; found, 510.1876. | 172-173 | 8.54 (s, 1H), 8.14 (d, J = 8.7 Hz, 2H), 7.79 (d, J = 9.0 Hz, 2H), 7.51 (d, J = 8.6 Hz, 2H), 7.38 (dd, J = 9.0, 0.7 Hz, 2H), 6.87 (s, 2H), 6.77 (s, 1H), 4.31-4.19 (m, 2H), 3.10-2.97 (m, 2H), 2.37 (s, 6H), 2.26 (s, 3H) |
| 122 | 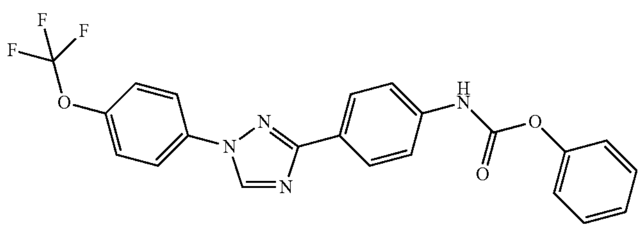 [SMILES: O=C(Nc1ccc(-c2ncn(-c3ccc(OC(F)(F)F)cc3)n2)cc1)Oc1ccccc1] | | HRMS-FAB (m/z) [M + H]⁺ calcd for C₂₂H₁₅F₃N₄O₃, 440.109; found, 440.110 | 186-188 | (400 MHz, DMSO-d₆) 10.49 (s, 1H), 9.37 (s, 1H), 8.08 (d, J = 3.4 Hz, 2H), 8.05 (d, J = 3.7 Hz, 2H), 7.67 (d, J = 8.7 Hz, 2H), 7.61 (d, J = 8.7 Hz, 2H), 7.45 (t, J = 7.9 Hz, 2H), 7.32-7.19 (m, 3H) |
| 123 | 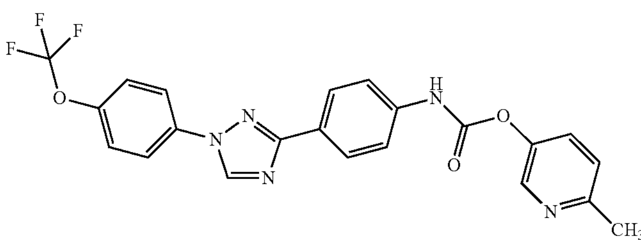 [SMILES: Cc1ccc(OC(=O)Nc2ccc(-c3ncn(-c4ccc(OC(F)(F)F)cc4)n3)cc2)cn1] | | HRMS-FAB (m/z) [M + H]⁺ calcd for C₂₂H₁₆F₃N₅O₃, 455.121; found, 455.1206 | 219-221 | (300 MHz, DMSO-d₆) 10.59 (s, 1H), 9.38 (d, J = 0.4 Hz, 1H), 8.39 (d, J = 2.7 Hz, 1H), 8.09 (d, J = 2.6 Hz, 2H), 8.06 (d, J = 2.9 Hz, 2H), 7.69-7.59 (m, 4H), 7.34 (d, J = 8.7 Hz, 1H), 7.07-7.00 (m, 1H), 2.49 (s, 3H) |
| 124 | 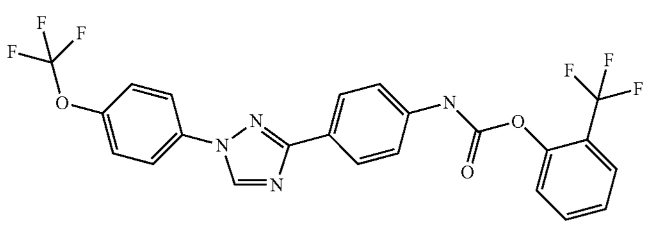 [SMILES: O=C(Nc1ccc(-c2ncn(-c3ccc(OC(F)(F)F)cc3)n2)cc1)Oc1ccccc1C(F)(F)F] | | 509 ([M + H]⁺) | 153-168 | 8.56 (s, 1H), 8.19 (d, J = 8.8 Hz, 2H), 7.80 (d, J = 9.1 Hz, 2H), 7.70 (d, J = 8.9 Hz, 1H), 7.63 (d, J = 8.1 Hz, 1H), 7.59 (d, J = 8.9 Hz, 2H), 7.45-7.35 (m, 4H), 7.21 (s, 1H) |
| 125 | 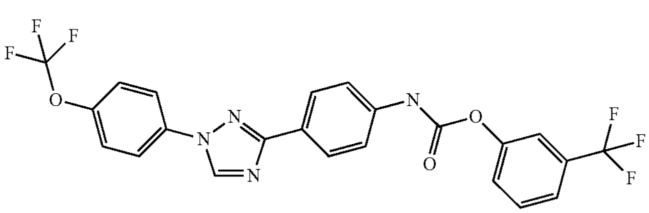 [SMILES: O=C(Nc1ccc(-c2ncn(-c3ccc(OC(F)(F)F)cc3)n2)cc1)Oc1cccc(C(F)(F)F)c1] | | 509 ([M + H]⁺) | 161-169 | 8.56 (s, 1H), 8.19 (d, J = 8.8 Hz, 2H), 7.80 (d, J = 9.1 Hz, 2H), 7.70 (d, J = 8.9 Hz, 1H), 7.61 (dd, J = 18.0, 8.6 Hz, 3H), 7.40 (dd, J = 15.7, 7.7 Hz, 4H), 7.20 (s, 1H) |

TABLE 1-continued

| # | Structure | IR (cm⁻¹) | MS | mp (°C.) | ¹H NMR (CDCl₃, δ)[1] |
|---|---|---|---|---|---|
| 126 | [structure] | | 509 ([M + H]⁺) | 183-188 | 8.56 (s, 1H), 8.19 (d, J = 8.7 Hz, 2H), 7.80 (d, J = 9.0 Hz, 2H), 7.68 (d, J = 8.6 Hz, 2H), 7.57 (d, J = 8.6 Hz, 2H), 7.37 (dd, J = 15.2, 8.3 Hz, 4H), 7.13 (s, 1H) |
| 127 | [structure] | | 459 ([M + H]⁺), 457 ([M − H]⁻) | 184-188 | 8.56 (s, 1H), 8.18 (d, J = 8.8 Hz, 2H), 7.80 (d, J = 9.1 Hz, 2H), 7.58 (d, J = 8.7 Hz, 2H), 7.38 (d, J = 9.7 Hz, 2H), 7.29 (dd, J = 7.9, 1.5 Hz, 1H), 7.24-7.13 (m, 4H) |
| 128 | [structure] | | 489 ([M + H]⁺) | 179-182.5 | 8.56 (s, 1H), 8.18 (d, J = 8.8 Hz, 2H), 7.80 (d, J = 9.1 Hz, 2H), 7.57 (d, J = 8.5 Hz, 2H), 7.39 (d, J = 8.3 Hz, 2H), 7.25 (d, J = 2.4 Hz, 1H), 7.22-7.20 (m, 1H), 7.20-7.18 (m, 1H), 7.11 (br s, 1H), 7.09 (d, J = 8.5 Hz, 1H), 2.26 (s, 3H) |
| 129 | [structure] | | 517 ([M + H]⁺) | 172-180 | 8.55 (s, 1H), 8.19 (d, J = 8.8 Hz, 2H), 7.80 (d, J = 9.1 Hz, 2H), 7.64-7.56 (m, 4H), 7.46 (qd, J = 7.7, 4.5 Hz, 5H), 7.37 (dd, J = 12.4, 7.8 Hz, 3H), 7.29 (d, J = 8.7 Hz, 1H), 7.20 (dd, J = 9.0, 2.4 Hz, 1H), 7.13 (s, 1H) |

TABLE 2

| Compound Number | % Mortality CEW 50 μg/cm² | % Mortality BAW 50 μg/cm² | % Mortality GPA 200 ppm |
|---|---|---|---|
| 1 | A | A | B |
| 2 | B | A | B |
| 3 | B | A | B |
| 4 | B | B | B |
| 5 | A | A | B |
| 6 | B | A | B |
| 7 | B | B | B |
| 8 | A | A | B |
| 9 | A | A | B |
| 10 | B | A | B |
| 11 | A | A | B |
| 12 | A | A | B |
| 13 | A | A | B |
| 14 | B | B | C |
| 15 | A | A | B |
| 16 | B | B | B |
| 17 | A | A | B |
| 18 | A | A | B |
| 19 | A | A | B |
| 20 | A | A | B |
| 21 | A | A | B |
| 22 | A | A | B |
| 23 | B | B | B |
| 24 | A | A | B |
| 25 | A | A | B |
| 26 | A | A | C |
| 27 | A | A | B |
| 28 | A | A | B |
| 29 | A | A | B |
| 30 | A | A | B |
| 31 | A | A | B |
| 32 | A | A | B |
| 33 | A | A | B |
| 34 | A | A | B |
| 35 | A | A | B |
| 36 | A | A | B |
| 37 | A | A | B |
| 38 | A | A | B |
| 39 | A | A | B |
| 40 | A | A | B |
| 41 | A | A | B |
| 42 | A | A | B |
| 43 | A | A | B |
| 44 | A | A | B |

TABLE 2-continued

| Compound Number | % Mortality CEW 50 μg/cm² | % Mortality BAW 50 μg/cm² | % Mortality GPA 200 ppm |
|---|---|---|---|
| 45 | A | A | B |
| 46 | A | A | B |
| 47 | A | A | B |
| 48 | A | A | B |
| 49 | A | A | B |
| 50 | B | B | B |
| 51 | A | A | B |
| 52 | A | A | B |
| 53 | A | A | B |
| 54 | A | A | B |
| 55 | A | A | B |
| 56 | A | A | B |
| 57 | A | A | B |
| 58 | A | A | B |
| 59 | A | A | B |
| 60 | A | A | C |
| 61 | A | A | C |
| 62 | A | A | C |
| 63 | A | A | B |
| 64 | A | A | B |
| 65 | A | A | B |
| 66 | A | A | B |
| 67 | A | A | B |
| 68 | A | A | B |
| 69 | A | A | B |
| 70 | A | A | B |
| 71 | A | A | B |
| 72 | A | A | B |
| 73 | A | A | B |
| 74 | A | A | B |
| 75 | A | A | B |
| 76 | A | A | B |
| 77 | A | A | B |
| 78 | A | A | B |
| 79 | A | A | B |
| 80 | A | A | B |
| 81 | A | A | B |
| 82 | A | A | B |
| 83 | A | A | B |
| 84 | A | A | B |
| 85 | A | A | B |
| 86 | A | A | B |
| 87 | B | A | B |
| 88 | A | A | B |
| 89 | A | A | B |
| 90 | A | A | B |
| 91 | A | A | B |
| 92 | A | A | B |
| 93 | A | A | B |
| 94 | A | A | B |
| 95 | A | A | B |
| 96 | A | A | B |
| 97 | A | A | B |
| 98 | A | A | B |
| 99 | B | B | B |
| 100 | B | B | B |
| 101 | A | A | B |
| 102 | B | B | B |
| 103 | B | A | B |
| 104 | A | A | B |
| 105 | A | A | B |
| 106 | A | B | B |
| 107 | A | A | B |
| 108 | B | B | B |
| 109 | A | B | B |
| 110 | A | A | B |
| 111 | A | B | B |
| 112 | A | A | B |
| 113 | A | A | B |
| 114 | B | A | B |
| 115 | B | B | B |
| 116 | A | B | B |
| 117 | A | A | B |
| 118 | A | A | B |
| 119 | A | A | B |
| 120 | A | A | B |
| 121 | A | B | B |
| 122 | A | A | B |
| 123 | B | B | B |
| 124 | A | A | B |
| 125 | C | C | B |
| 126 | C | C | B |
| 127 | C | C | B |
| 128 | A | A | B |
| 129 | A | A | B |
| 130 | A | A | B |
| 131 | A | A | B |
| 132 | B | A | B |
| 133 | A | A | B |
| 134 | B | B | B |
| 135 | A | A | B |
| 136 | B | B | B |

We claim:

1. A process comprising applying a composition comprising a carrier and a molecule of the following formula:

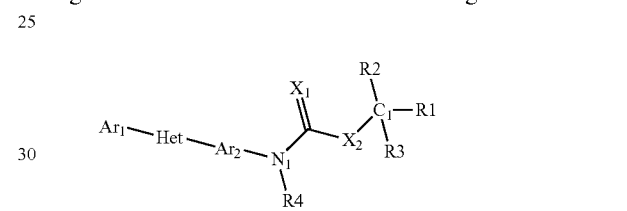

wherein:

(a) $Ar_1$ is substituted phenyl wherein said substituted phenyl has one or more substituents independently selected from $C_1$-$C_6$ haloalkyl and $C_1$-$C_6$ haloalkoxy;

(b) Het is a triazolyl;

(c) $Ar_2$ is phenyl;

(d) $X_1$ is O or S;

(e) $X_2$ is O or S;

(f) R4 is H or a $C_1$-$C_6$ alkyl;

(g) R1, R2, and R3 are independently selected from H, CN, $C_1$-$C_6$ alkyl, $C_1$-$C_6$ haloalkyl, $C_3$-$C_6$ cycloalkyl, $C_2$-$C_6$ alkenyl, $C_2$-$C_6$ alkynyl, C(=O)O($C_1$-$C_6$ alkyl), phenyl, and Het-1 wherein Het-1 is a 5- or 6-membered, saturated or unsaturated, heterocyclic ring, containing one or more heteroatoms independently selected from nitrogen, sulfur or oxygen, wherein each Het-1 is optionally substituted with one or more substituents independently selected from F, Cl, Br, I, and $C_1$-$C_6$ alkoxy;

to a locus to control a pest, in an amount sufficient to control such pest.

2. A process according to claim 1 wherein said molecule has one of the following structures

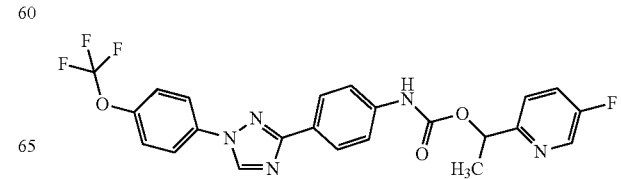

-continued
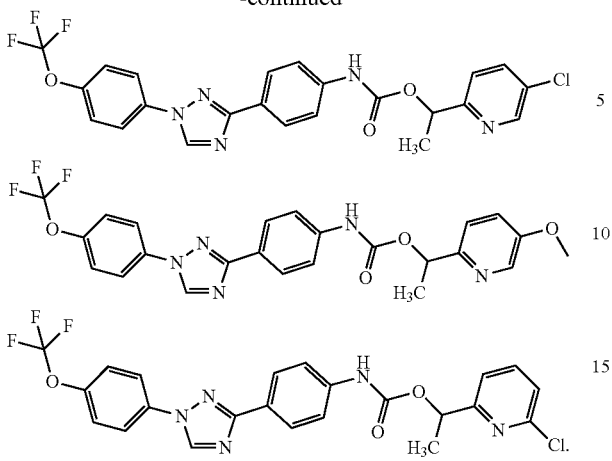
3. A process according to claim 1 or 2 wherein said pest is BAW, CEW, or GPA.
4. A process according to claim 1 wherein said composition further comprises at least one other compound having insecticidal, herbicidal, acaricidal, nematicidal, or fungicidal activity.
* * * * *